(12) United States Patent
Katamreddy et al.

(10) Patent No.: US 8,222,261 B2
(45) Date of Patent: Jul. 17, 2012

(54) CHEMICAL COMPOUNDS

(75) Inventors: Subba R Katamreddy, Durham, NC (US); Richard Dama Caldwell, Durham, NC (US); Dennis Heyer, Durham, NC (US); Vincente Samano, Durham, NC (US); James Benjamin Thompson, Durham, NC (US); Andrew J Carpenter, Durham, NC (US); Christopher R Conlee, Durham, NC (US); Eric Eugene Boros, Durham, NC (US); Brian D Thompson, Durham, NC (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 652 days.

(21) Appl. No.: 12/373,524

(22) Filed: Jan. 13, 2009

(65) Prior Publication Data

US 2009/0318477 A1    Dec. 24, 2009

Related U.S. Application Data

(60) Provisional application No. 60/807,225, filed on Jul. 13, 2006.

(51) Int. Cl.
*A61K 31/519* (2006.01)
(52) U.S. Cl. .................................................. 514/265.1
(58) Field of Classification Search ................ 514/265.1
See application file for complete search history.

(56) References Cited

U.S. PATENT DOCUMENTS

2004/0176400 A1 * 9/2004 Capelli et al. ............ 514/264.11

OTHER PUBLICATIONS

Fyfe et al 'GPR 119 agonists as potential new oral agents for the treatment of type 2 diabetes and obesity' Expert Opin. Drug Discov., 3(4), p. 403-413, 2008.*
Padwal et al 'A Systematic Review of Drug Therapy to Delay of Prevent Type 2 Diabetes' Diabetes Care, 28(3), p. 736-744, 2005.*
Stella et al 'Prodrugs: Challenges and Rewards, Part 1' Biotechnology: Pharmaceutical Aspects, p. 24, 2007.*
Vippagunta et al 'Crystalline Solids' Advanced Drug Delivery Reviews, vol. 48, p. 3-26, 2001.*
Mayet, S., et al, "GPR119 activation increases glucose-dependent insulin secretion in insulin-producing cells and isolated rat islets," *Diabetologia*, V48 NSuppl, 2005 p. A166.
Fyfe, Matthew, et al, "Discovery of novel, orally active, synthetic GPR119 agonists as potential agents for treatment of obesity and associated metabolic disorders," *Diabetes*, V55, NSuppl, Jun. 2006, p. A81.
Soga, T, et al., "Lysophosphatidylcholine enhances glucose-dependent insulin secretion via an orphan G-protein-coupled receptor," *Biochemical and Biophysical Research Communications*, V326, N4, Jan. 28, 2005, pp. 744-751.
Overton, Hilary, et al., "Deorphanization of a G protein-coupled receptor for eleoylethanoamide and its use in the discovery of small-molecule hypophagic agents," *Cell Metabolism*, V3, N3, Mar. 2006, pp. 167-175.

* cited by examiner

*Primary Examiner* — Brandon Fetterolf
*Assistant Examiner* — Christopher R Stone
(74) *Attorney, Agent, or Firm* — Bonnie L. Deppenbrock

(57) ABSTRACT

The present invention relates to novel compounds that are useful in the treatment of metabolic disorders, particularly Type II diabetes mellitus and related disorders, and also to the methods for the making and use of such compounds.

32 Claims, 22 Drawing Sheets

CHEMICAL COMPOUNDS

Figure 1:
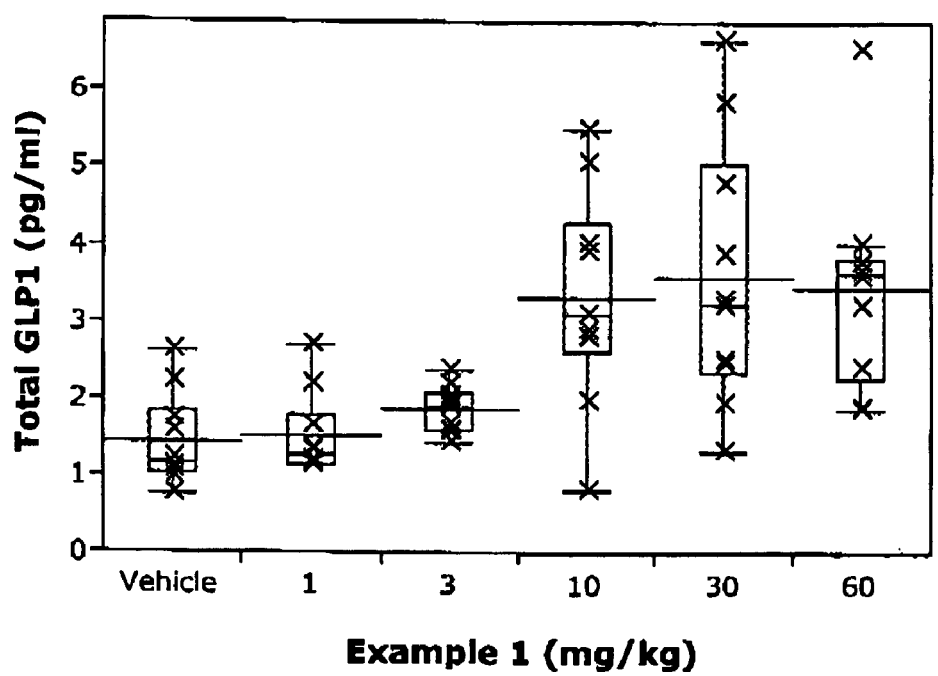

This application is filed pursuant to 35 U.S.C. §371 as a United States National Phase Application of International Application No. PCT/US2007/073352 filed Jul. 12, 2007, which claims priority from U.S. 60/807,225 filed Jul. 13, 2006.

FIELD OF THE INVENTION

The present invention relates to novel compounds that are useful in the treatment and prevention of metabolic disorders, including diabetes mellitus (Type I and Type II), obesity, and related disorders, and also includes methods for making, pharmaceutical compositions containing, and therapeutic uses for such compounds.

BACKGROUND OF THE INVENTION

Diabetes mellitus is an ever-increasing threat to human health. For example, in the United States current estimates maintain that about 16 million people suffer from diabetes mellitus.

Type I diabetes, also known as insulin-dependent diabetes mellitus (IDDM), is caused by the autoimmune destruction of the insulin producing pancreatic β-cells, and necessitates regular administration of exogenous insulin. Without insulin, cells cannot absorb sugar (glucose), which they need to produce energy. Symptoms of Type I diabetes usually start in childhood or young adulthood. People often seek medical help because they are seriously ill from sudden symptoms of high blood sugar (hyperglycemia).

Type II diabetes, also known as non-insulin-dependent diabetes mellitus (NIDDM), manifests with an inability to adequately regulate blood-glucose levels. Type II diabetes may be characterized by a defect in insulin secretion or by insulin resistance, namely those that suffer from Type II diabetes have too little insulin or cannot use insulin effectively. Insulin resistance refers to the inability of body tissues to respond properly to endogenous insulin. Insulin resistance develops because of multiple factors, including genetics, obesity, increasing age, and having high blood sugar over long periods of time. Type II diabetes, sometimes called mature or adult onset diabetes, can develop at any age, but most commonly becomes apparent during adulthood. The incidence of Type II diabetes in children, however, is rising.

In diabetics, glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes accounts for approximately 90-95% of diabetes cases, killing about 193,000 U.S. residents each year. Type II diabetes is the seventh leading cause of all deaths. In Western societies, Type II diabetes currently affects 6% of the adult population with world-wide frequency expected to grow by 6% per annum. Although there are certain inheritable traits that may predispose particular individuals to developing Type II diabetes, the driving force behind the current increase in incidence of the disease is the increased sedentary lifestyle, diet, and obesity now prevalent in developed countries. About 80% of diabetics with Type II diabetes are significantly overweight. As noted above, an increasing number of young people are developing the disease. Type II diabetes is now internationally recognized as one of the major threats to human health in the 21$^{st}$ century.

Type II diabetes currently is treated at several levels. A first level of therapy is through the use of diet and/or exercise, either alone or in combination with therapeutic agents. Such agents may include insulin or pharmaceuticals that lower blood glucose levels. About 49% of individuals with Type II diabetes require oral medication(s), about 40% of individuals require insulin injections or a combination of insulin injections and oral medication(s), and about 10% of individuals may use diet and exercise alone.

Current therapies for diabetes mellitus include: insulin; insulin secretagogues, such as sulphonylureas, which increase insulin secretion from pancreatic β-cells; glucose-lowering effectors, such as mefformin which reduce glucose production from the liver; activators of the peroxisome proliferator-activated receptor-γ(PPAR-γ), such as the thiazolidinediones, which enhances insulin action; and α-glucosidase inhibitors which interfere with gut glucose production. There are, however, deficiencies associated with currently available treatments, including hypoglycemic episodes, weight gain, loss in responsiveness to therapy over time, gastrointestinal problems, and edema.

There are several areas at which research is being targeted in order to bring new, more effective, therapies to the marketplace. For example, on-going research includes exploring a reduction in excessive hepatic glucose production, enhancing the pathway by which insulin transmits its signal to the cells such that they take up glucose, enhancing glucose-stimulated insulin secretion from the pancreatic β-cells, and targeting obesity and associated problems with fat metabolism and accumulation.

GIP and GLP-1 are peptides, known as incretins, secreted from enteroendocrine K and L cells respectively in response to ingestion of nutrients, and have a wide variety of physiological effects that have been described in numerous publications over the past two decades. See, for example, Bojanowska, E. et al., *Med. Sci. Monit.*, 2005, August 11(8): RA271-8; Perry, T. et al., *Curr. Alzheimer Res.*, 2005, July 2(3): 377-85; and Meier, J. J. et al., *Diabetes Metab. Res. Rev.*, 2005, March-April; 21(2); 91-117 (each herein incorporated by reference with regard to a background understanding of incretins). Moreover, although the mechanisms regulating GLP-1 secretion remain unclear, the initial rapid rise in GLP-1 following a meal may be a result of hormonal stimulation of neuronal afferents involving GIP. See, for example, J. N. Roberge and P. L. Brubaker, *Endocrinology* 133 (1993), pp. 233-240 (herein incorporated by reference with regard to such teaching). Furthermore, later increases in GLP-1 may involve direct activation of L-cells by nutrients in the distal small-intestine and the colon. GIP and GLP-1 are potent stimulators of the body's ability to produce insulin in response to elevated levels of blood sugar.

In Type II diabetes the action of GLP-1 on the β-cell is maintained, although GLP-1 secretion, itself, is reduced. More recently, therefore, much research has been focused on GLP-1. Studies show glucose-lowering effects in addition to GLP-1's ability to stimulate glucose-dependent insulin secretion including, but not limited to, an inhibition of the release of the hormone glucagon following meals, a reduction in the rate at which nutrients are absorbed into the bloodstream, and a reduction of food intake. Studies demonstrate that treatments to increase GLP-1, therefore, may be used for a variety of conditions and disorders including but not limited to metabolic disorders, gastrointestinal disorders, inflammatory diseases, psychosomatic, depressive, and neuropsychiatric disease including but not limited to diabetes mellitus (Type 1 and Type 2), metabolic syndrome, obesity, appetite control and satiety, weight loss, stress, inflammation, myocardial ischemia/reperfusion injury, Alzheimer's Disease, and other diseases of the central nervous system. In Type II diabetes, patients display a decreased responsiveness to GIP but not GLP-1, with respect to its ability to stimulate insulin secretion. The mechanism behind the decreased responsiveness to GIP remains unclear since Type II diabetics retain sensitivity to a bolus administration of GIP but not to a continuous infusion (Meier et al. 2004 Diabetes 53 S220-S224). Moreover recent studies with a long-acting fatty-acid derivative of GIP showed beneficial effects on glucose homeostasis in ob/ob mice following 14 days of treatment (Irwin N. et al. (2006) J. Med. Chem. 49, 1047-1054).

The use of exogenous GLP-1 in clinical treatment is severely limited, however, due to its rapid degradation by the protease DPP-IV. There are multiple GLP-1 mimetics in development for type 2 diabetes that are reported in the literature, all are modified peptides, which display longer half-lives than endogenous GLP-1. For example, the product sold under the tradename BYETTA® is the first FDA-approved agent of this new class of medications. These mimetics, however, require injection. An oral medication that is able to elevate GLP-1 secretion is desirable. Orally available inhibitors of DPP-IV, which result in elevation in intact GLP-1, are now available, such as sitagliptin, marketed under the brand name JANUVIA®. Nevertheless, a molecule which may stimulate GLP-1 secretion would provide a therapeutic benefit. A molecule which could stimulate both GLP-1 secretion and insulin secretion through effects on the L-cell and direct effects on the β-cell would hold much promise for Type II diabetes therapy.

One particular target is GPR119. GPR119 is a member of the rhodopsin family of G-protein-coupled receptors. In addition to the "GPR119" identifier, several other identifiers exist, including but not limited to RUP 3, Snorf 25, 19 AJ, GPR116 (believed to be erroneous), AXOR20, and PS1. GPR119 is expressed in human gastrointestinal regions and in human islets. Activation of GPR119 has been demonstrated to stimulate intracellular cAMP and lead to glucose-dependent GLP-1 and insulin secretion. See, T. Soga et al., *Biochemical and Biophysical Research Communications* 326 (2005) 744-751, herein incorporated by reference with regard to a background understanding of GPR119.

Agonists to GPR119 may be of therapeutic value for diabetes and associated conditions, particularly Type II diabetes, obesity, glucose intolerance, insulin resistance, metabolic syndrome X, hyperlipidemia, hypercholesterolemia, and atherosclerosis.

SUMMARY OF THE PRESENT INVENTION

The present invention identifies agonists of GPR119 which increase glucose-disposal in part through elevation of GIP and GLP-1, and augmentation of glucose stimulated insulin secretion. Studies also demonstrate that GPR119 agonists such as the compounds of the present invention can increase GLP-1 and GIP independently of circulating blood glucose levels, Moreover, studies demonstrate that GPR119 agonists enhance insulin stimulated glucose disposal, thus increasing whole body insulin sensitivity.

The present invention includes a compound of Formula (I):

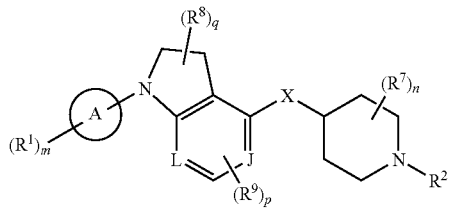

(I)

or a salt, solvate, or prodrug thereof, wherein
ring A is an aryl or heteroaryl;
m is 1, 2, or 3;
each $R^1$ independently is acyl; acylsulfonamide; acyloxy; $C_2$-$C_6$ alkenyl; $C_1$-$C_6$ alkoxy; $C_1$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio; $C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl; heteroaryl substituted with one or more $C_1$-$C_6$ alkyl, $C_1$-$C_6$ alkoxy, cyano, halogen, or $C_1$-$C_6$ haloalkyl; hydroxyl; nitro; sulfonamide; or thiol;
L and J each independently is CH or N;
n is 0, 1, 2, 3, or 4;
each $R^7$ independently is $C_1$-$C_6$ alkyl;
q is 0, 1, or 2;
each $R^8$ independently is $C_1$-$C_6$ alkyl, amino, $C_1$-$C_6$ alkylamino, $C_1$-$C_6$ dialkylamino, halogen, or $C_1$-$C_6$ haloalkyl;
p is 0, 1, or 2;
when p is 1 or 2, then $R^9$ is substituted from a carbon atom on the depicted ring;
each $R^9$ independently is $C_1$-$C_6$ alkyl, $C_1$-$C_6$ alkoxy, amino, $C_1$-$C_6$ alkylamino, $C_1$-$C_6$ dialkylamino, halogen, $C_1$-$C_6$ haloalkyl, or cyano;
X is —$NR^4$—, —O—, —S—, —S(O)—, or —S(O)$_2$—;
wherein $R^4$ is H or $C_1$-$C_6$ alkyl;
$R^2$ is —$Y_t$—$R^5$;
wherein Y is —C(O)—, —C(O)O—, —C(S)—, —C(S)S—, —C(S)O—, or —C(O)S—;
t is 0 or 1; and
$R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro.

Preferably when A is aryl, then A is phenyl; and when A is heteroaryl, then A is pyridyl or pyrimidinyl.

Preferably m is 1 or 2. Preferably, $R^1$ is $C_1$-$C_6$ alkylsulfonyl, cyano, halogen, or heteroaryl. In an embodiment m is 1 and $R^1$ is $C_1$-$C_3$ alkylsulfonyl. In an embodiment m is 2 and one $R^1$ is $C_1$-$C_3$ alkylsulfonyl and the other $R^1$ is halogen. Preferably one $R^1$ is methylsulfonyl and one $R^1$ is fluorine. Preferably the methylsulfonyl is located para to the depicted N atom and the fluorine is located ortho to the depicted N atom. In an embodiment m is 2 and one $R^1$ is cyano and the other $R^1$ is halogen.

In an embodiment L and J are the same. Preferably, both L and J are N.

In an embodiment p is 0 or 1.

In an embodiment q is 0.

In an embodiment X is —O—.

In an embodiment t is 0. Preferably $R^5$ is heteroaryl or heteroaryl substituted with one or more of $C_1$-$C_6$ alkyl, $C_1$-$C_6$ alkoxy, aryl, $C_1$-$C_6$ aralkyl, cyano, halogen, or $C_1$-$C_6$ haloalkyl. Preferably the heteroaryl is pyrimidinyl or oxadiazolyl.

In an embodiment t is 1. Preferably Y is C(O)O. Preferably $R^5$ is $C_1$-$C_6$ alkyl; aryl; aryl substituted with one or more of $C_1$-$C_6$ alkyl, $C_1$-$C_6$ alkoxy, aryl, $C_1$-$C_6$ aralkyl, cyano, halogen, or $C_1$-$C_6$ haloalkyl; $C_3$-$C_7$ cycloalkyl. Preferably $R^5$ is $C_1$-$C_6$ alkyl.

One embodiment of the present invention includes a compound of Formula (II):

(II)

or a salt, solvate, or prodrug thereof, wherein ring A is an aryl or heteroaryl;

m is 1, 2, or 3;

each $R^1$ independently is acyl; acylsulfonamide; acyloxy; $C_2$-$C_6$ alkenyl; $C_1$-$C_6$ alkoxy; $C_1$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio; $C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl; heteroaryl substituted with one or more $C_1$-$C_6$ alkyl, $C_1$-$C_6$ alkoxy, cyano, halogen, or $C_1$-$C_6$ haloalkyl; hydroxyl; nitro; sulfonamide; or thiol;

n is 0, 1, 2, 3, or 4;

each $R^7$ independently is $C_1$-$C_6$ alkyl;

q is 0, 1, or 2;

each $R^8$ independently is $C_1$-$C_6$ alkyl, amino, $C_1$-$C_6$ alkylamino, $C_1$-$C_6$ dialkylamino, halogen, or $C_1$-$C_6$ haloalkyl;

p is 0, 1, or 2;

when p is 1 or 2, then $R^9$ is substituted from a carbon atom on the depicted ring;

each $R^9$ independently is $C_1$-$C_6$ alkyl, $C_1$-$C_6$ alkoxy, amino, $C_1$-$C_6$ alkylamino, $C_1$-$C_6$ dialkylamino, halogen, $C_1$-$C_6$ haloalkyl, or cyano;

X is —$NR^4$—, —O—, —S—, —S(O)—, or —$S(O)_2$—;

wherein $R^4$ is H or $C_1$-$C_6$ alkyl;

$R^2$ is —$Y_t$—$R^5$;

wherein Y is —C(O)—, —C(O)O—, —C(S)—, —C(S)S—, —C(S)O—, or —C(O)S—;

t is 0 or 1; and $R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro;

One embodiment of the present invention includes a compound of Formula (III):

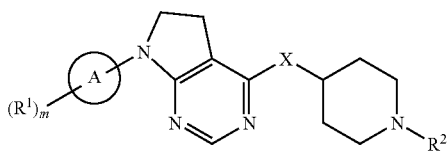

or a salt, solvate, or prodrug thereof, wherein
ring A is an aryl or heteroaryl;
m is 1, 2, or 3;
each $R^1$ independently is acyl; acylsulfonamide; acyloxy; $C_2$-$C_6$ alkenyl; $C_1$-$C_6$ alkoxy; $C_1$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio; $C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl; heteroaryl substituted with one or more of $C_1$-$C_6$ alkyl, $C_1$-$C_6$ alkoxy, cyano, halogen, or $C_1$-$C_6$ haloalkyl; hydroxyl; nitro; sulfonamide; or thiol;
X is —$NR^4$—, —O—, —S—, —S(O)—, or —S(O)$_2$—;
wherein $R^4$ is H or $C_1$-$C_6$ alkyl;
$R^2$ is —$Y_t$—$R^5$;
wherein Y is —C(O)—, —C(O)O—, —C(S)—, —C(S)S—, —C(S)O—, or —C(O)S—;
t is 0 or 1; and
$R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro.

One embodiment of the present invention includes a compound selected from:

1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

1,1-Dimethylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2,2-Dimethylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

4-{[1-(5-Bromo-2-pyrimidinyl)-4-piperidinyl]oxy}-7-[2-fluoro-4-(methylsulfonyl)phenyl]-6,7-dihydro-5H-pyrrolo[2,3-d]pyrimidine;

7-[2-Fluoro-4-(methylsulfonyl)phenyl]-4-({1-[5-(2-methylpropyl)-2-pyrimidinyl]-4-piperidinyl}oxy)-6,7-dihydro-5H-pyrrolo[2,3-d]pyrimidine;

7-[2-Fluoro-4-(methylsulfonyl)phenyl]-4-{[1-(2-pyrimidinyl)-4-piperidinyl]oxy}-6,7-dihydro-5H-pyrrolo[2,3-d]pyrimidine;

4-{[1-(5-Ethyl-2-pyrimidinyl)-4-piperidinyl]oxy}-7-[2-fluoro-4-(methylsulfonyl)phenyl]-6,7-dihydro-5H-pyrrolo[2,3-d]pyrimidine;

7-[2-Fluoro-4-(methylsulfonyl)phenyl]-4-{[1-(5-fluoro-2-pyrimidinyl)-4-piperidinyl]oxy}-6,7-dihydro-5H-pyrrolo[2,3-d]pyrimidine;

1-Methylethyl 4-{[7-(4-cyano-2-fluorophenyl)-6,7-dihydro-5H-pyrrolo[2,3-d]pyrimidin-4-yl]oxy}-1-piperidinecarboxylate;

1-Methylethyl 4-({7-[2-fluoro-4-(1,3-thiazol-2-yl)phenyl]-6,7-dihydro-5H-pyrrolo[2,3-d]pyrimidin-4-yl}oxy)-1-piperidinecarboxylate;

1-Methylethyl 4-({7-[4-(methylsulfonyl)phenyl]-6,7-dihydro-5H-pyrrolo[2,3-d]pyrimidin-4-yl}thio)-1-piperidinecarboxylate;

1-Methylethyl 4-({7-[2-fluoro-4-(methylsulfonyl)phenyl]-6,7-dihydro-5H-pyrrolo[2,3-d]pyrimidin-4-yl}sulfonyl)-1-piperidinecarboxylate;

1,1-Dimethylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate;

1-Methylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate;

7-[2-Fluoro-4-(methylsulfonyl)phenyl]-2-methyl-4-({1-[3-(1-methylethyl)-1,2,4-oxadiazol-5-yl]-4-piperidinyl}oxy)-6,7-dihydro-5H-pyrrolo[2,3-d]pyrimidine;

2,5-Difluoro-4-[4-({1-[3-(1-methylethyl)-1,2,4-oxadiazol-5-yl]-4-piperidinyl}oxy)-5,6-dihydro-7H-pyrrolo[2,3-d]pyrimidin-7-yl]benzonitrile;

7-[2-Fluoro-4-(methylsulfonyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

7-(4-Bromo-2,5-difluorophenyl)-4-({1-[3-(1-methylethyl)-1,2,4-oxadiazol-5-yl]-4-piperidinyl}oxy)-6,7-dihydro-5H-pyrrolo[2,3-d]pyrimidine;

1,1-Dimethylethyl 4-{[7-(4-bromo-2,5-difluorophenyl)-6,7-dihydro-5H-pyrrolo[2,3-d]pyrimidin-4-yl]oxy}-1-piperidinecarboxylate;

1,1-Dimethylethyl 4-({1-[4-(methylsulfonyl)phenyl]-2,3-dihydro-1H-indol-4-yl}oxy)-1-piperidinecarboxylate;

1-Methylethyl 4-({1-[4-(methylsulfonyl)phenyl]-2,3-dihydro-1H-indol-4-yl}oxy)-1-piperidinecarboxylate;

1-Methylethyl 4-{[1-(4-cyanophenyl)-2,3-dihydro-1H-indol-4-yl]oxy}-1-piperidinecarboxylate;

1-Methylethyl 4-({1-[4-(1,3-thiazol-2-yl)phenyl]-2,3-dihydro-1H-indol-4-yl}oxy)-1-piperidinecarboxylate;

1,1-Dimethylethyl 4-({1-[5-(methylsulfonyl)-2-pyrimidinyl]-2,3-dihydro-1H-indol-4-yl}oxy)-1-piperidinecarboxylate;

1-Methylethyl 4-({1-[5-(methylsulfonyl)-2-pyrimidinyl]-2,3-dihydro-1H-indol-4-yl}oxy)-1-piperidinecarboxylate;

1-Methylethyl 4-[(1-{4-[bis(butyloxy)phosphoryl]phenyl}-2,3-dihydro-1H-indol-4-yl)oxy]-1-piperidinecarboxylate;

4-Fluorophenyl 4-({1-[4-(methylsulfonyl)phenyl]-2,3-dihydro-1H-indol-4-yl}oxy)-1-piperidinecarboxylate;

1,1-Dimethylethyl 4-({1-[2-fluoro-4-(methylsulfonyl)phenyl]-2,3-dihydro-1H-indol-4-yl}oxy)-1-piperidinecarboxylate;

1-Methylethyl 4-({1-[2-fluoro-4-(methylsulfonyl)phenyl]-2,3-dihydro-1H-indol-4-yl}oxy)-1-piperidinecarboxylate;

(±)-1,1-Dimethylethyl 4-({1-[4-(methylsulfinyl)phenyl]-2,3-dihydro-1H-indol-4-yl}oxy)-1-piperidinecarboxylate;

(+)-1,1-Dimethylethyl 4-({1-[4-(methylsulfinyl)phenyl]-2,3-dihydro-1H-indol-4-yl}oxy)-1-piperidinecarboxylate;

(−)-1,1-Dimethylethyl 4-({1-[4-(methylsulfinyl)phenyl]-2,3-dihydro-1H-indol-4-yl}oxy)-1-piperidinecarboxylate;

1,1-Dimethylethyl 4-[(1-{4-[(ethyloxy)carbonyl]phenyl}-2,3-dihydro-1H-indol-4-yl)oxy]-1-piperidinecarboxylate;

4-{4-[(1-{[(1,1-Dimethylethyl)oxy]carbonyl}-4-piperidinyl)oxy]-2,3-dihydro-1H-indol-1-yl}benzoic acid;

1,1-Dimethylethyl 4-({1-[4-({[2-(methyloxy)ethyl]amino}carbonyl)phenyl]-2,3-dihydro-1H-indol-4-yl}oxy)-1-piperidinecarboxylate;

1,1-Dimethylethyl 4-[(1-{4-[(methylamino)carbonyl]phenyl}-2,3-dihydro-1H-indol-4-yl)oxy]-1-piperidinecarboxylate;

1,1-Dimethylethyl 4-{[1-(4-{[(3-hydroxypropyl)amino]carbonyl}phenyl)-2,3-dihydro-1H-indol-4-yl]oxy}-1-piperidinecarboxylate;

1,1-Dimethylethyl 4-{[1-(4-cyanophenyl)-2,3-dihydro-1H-indol-4-yl]oxy}-1-piperidinecarboxylate;

1,1-Dimethylethyl 4-{[1-(4-formylphenyl)-2,3-dihydro-1H-indol-4-yl]oxy}-1-piperidinecarboxylate;

1-[2-Fluoro-4-(methylsulfonyl)phenyl]-4-{[1-(2-pyrimidinyl)-4-piperidinyl]oxy}-2,3-dihydro-1H-indole;

4-{[1-(5-Fluoro-2-pyrimidinyl)-4-piperidinyl]oxy}-1-[4-(methylsulfonyl)phenyl]-2,3-dihydro-1H-indole;

1-[4-(Methylsulfonyl)phenyl]-4-{[1-(5-propyl-2-pyrimidinyl)-4-piperidinyl]oxy}-2,3-dihydro-1H-indole;

1-[4-(Methylsulfonyl)phenyl]-4-({1-[5-(phenylmethyl)-2-pyrimidinyl]-4-piperidinyl}oxy)-2,3-dihydro-1H-indole;

1-[4-(Methylsulfonyl)phenyl]-4-{[1-(5-phenyl-2-pyrimidinyl)-4-piperidinyl]oxy}-2,3-dihydro-1H-indole;

4-{[1-(5-Bromo-2-pyrimidinyl)-4-piperidinyl]oxy}-1-[4-(methylsulfonyl)phenyl]-2,3-dihydro-1H-indole;

2-[4-({1-[4-(Methylsulfonyl)phenyl]-2,3-dihydro-1H-indol-4-yl}oxy)-1-piperidinyl]-5-pyrimidinecarbonitrile;

4-{[1-(Cyclopentylacetyl)-4-piperidinyl]oxy}-1-[4-(methylsulfonyl)phenyl]-2,3-dihydro-1H-indole;

4-({1-[3-(1-Methylethyl)-1,2,4-oxadiazol-5-yl]-4-piperidinyl}oxy)-1-[4-(methylsulfonyl)phenyl]-2,3-dihydro-1H-indole;

1-Methylethyl 4-({1-[4-(3,5-dimethyl-4-isoxazolyl)phenyl]-2,3-dihydro-1H-indol-4-yl}oxy)-1-piperidinecarboxylate;

1-Methylethyl 4-({1-[4-(3-furanyl)phenyl]-2,3-dihydro-1H-indol-4-yl}oxy)-1-piperidinecarboxylate;

1-Methylethyl 4-({1-[4-(1-methyl-1H-pyrazol-4-yl)phenyl]-2,3-dihydro-1H-indol-4-yl}oxy)-1-piperidinecarboxylate;

(1R,2S,5R)-5-Methyl-2-(1-methylethyl)cyclohexyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

1-Methylethyl 4-({7-[4-(methylsulfonyl)phenyl]-6,7-dihydro-5H-pyrrolo[2,3-d]pyrimidin-4-yl}oxy)-1-piperidinecarboxylate;

1-Methylethyl 4-{[7-(4-cyanophenyl)-6,7-dihydro-5H-pyrrolo[2,3-d]pyrimidin-4-yl]oxy}-1-piperidinecarboxylate;

1-Methyl ethyl 4-({7-[2-fluoro-4-(1-methyl-1H-pyrrol-2-yl)phenyl]-6,7-dihydro-5H-pyrrolo[2,3-d]pyrimidin-4-yl}oxy)-1-piperidinecarboxylate;

(±)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;

(+)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;

(−)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;

Methyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

Ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

Propyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

n-Butyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-Fluoroethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

3-Chloropropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-(Methyloxy)ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-Propen-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;

3-Buten-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-Butyn-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;

Pentyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

Hexyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

1-Methylethyl 4-{[7-(2-methyl-3-pyridinyl)-6,7-dihydro-5H-pyrrolo[2,3-d]pyrimidin-4-yl]oxy}-1-piperidinecarboxylate;

1-Methylethyl 4-{[7-(4-cyano-3-fluorophenyl)-6,7-dihydro-5H-pyrrolo[2,3-d]pyrimidin-4-yl]oxy}-1-piperidinecarboxylate;

S-Ethyl 4-({7-[2-fluoro-4-(methylsulfonyl)phenyl]-6,7-dihydro-5H-pyrrolo[2,3-d]pyrimidin-4-yl}oxy)-1-piperidinecarbothioate;

S-Methyl 4-({7-[2-fluoro-4-(methylsulfonyl)phenyl]-6,7-dihydro-5H-pyrrolo[2,3-d]pyrimidin-4-yl}oxy)-1-piperidinecarbothioate;

S-(1-Methylethyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

S-(2-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

(±)-S-(1,2-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

(±)-S-(1-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

S-(1,1-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

(±)-S-(2-Methylbutyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

S-2-Propen-1-yl 4-({7-[2-fluoro-4-(methylsulfonyl)phenyl]-6,7-dihydro-5H-pyrrolo[2,3-d]pyrimidin-4-yl}oxy)-1-piperidinecarbothioate;

S-(3-Chloropropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

S-Cyclopentyl 4-({7-[2-fluoro-4-(methylsulfonyl)phenyl]-6,7-dihydro-5H-pyrrolo[2,3-d]pyrimidin-4-yl}oxy)-1-piperidinecarbothioate;

S-Cyclohexyl 4-({7-[2-fluoro-4-(methylsulfonyl)phenyl]-6,7-dihydro-5H-pyrrolo[2,3-d]pyrimidin-4-yl}oxy)-1-piperidinecarbothioate;

S-(2,4-Difluorophenyl)4-({7-[2-fluoro-4-(methylsulfonyl)phenyl]-6,7-dihydro-5H-pyrrolo[2,3-d]pyrimidin-4-yl}oxy)-1-piperidinecarbothioate;

1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarbodithioate;

2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarbodithioate; Phenyl 4-({7-[2-fluoro-4-(methylsulfonyl)phenyl]-6,7-dihydro-5H-pyrrolo[2,3-d]pyrimidin-4-yl}oxy)-1-piperidinecarbodithioate;

7-[2-Fluoro-4-(methylsulfonyl)phenyl]-4-{[1-(2-pyridinylmethyl)-4-piperidinyl]oxy}-6,7-dihydro-5H-pyrrolo[2,3-d]pyrimidine trifluoroacetate;

N-(1,1-Dimethylethyl)-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate;

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-[5-(2-pyridinyl)-2-thienyl]ethanone trifluoroacetate;

4-{[1-(Ethylsulfonyl)-4-piperidinyl]oxy}-7-[2-fluoro-4-(methylsulfonyl)phenyl]-6,7-dihydro-5H-pyrrolo[2,3-d]pyrimidine;

7-[2-Fluoro-4-(methylsulfonyl)phenyl]-4-({1-[(1-methylethyl)sulfonyl]-4-piperidinyl}oxy)-6,7-dihydro-5H-pyrrolo[2,3-d]pyrimidine;

4-({7-[2-Fluoro-4-(methylsulfonyl)phenyl]-6,7-dihydro-5H-pyrrolo[2,3-d]pyrimidin-4-yl}oxy)-N,N-dimethyl-1-piperidinesulfonamide;

N,N-Diethyl-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate;

2-[4-({7-[2-Fluoro-4-(methylsulfonyl)phenyl]-6,7-dihydro-5H-pyrrolo[2,3-d]pyrimidin-4-yl}oxy)-1-piperidinyl]-N-(phenylmethyl)acetamide;

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-methyl-2-thienyl)ethanone;

1-(5-Ethyl-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate;

1-(5-Chloro-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate;

7-[2-Fluoro-4-(methylsulfonyl)phenyl]-4-{[1-({5-[4-(methyloxy)phenyl]-1,2,4-oxadiazol-3-yl}methyl)-4-piperidinyl]oxy}-6,7-dihydro-5H-pyrrolo[2,3-d]pyrimidine;

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(1-methyl-1H-pyrrol-2-yl)ethanone;

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-phenyl-2-thienyl)ethanone;

7-[2-Fluoro-4-(methylsulfonyl)phenyl]-4-({1-[5-(1-methylethyl)-1,2,4-oxadiazol-3-yl]-4-piperidinyl}oxy)-6,7-dihydro-5H-pyrrolo[2,3-d]pyrimidine;

7-[2-Fluoro-4-(methylsulfonyl)phenyl]-4-{[1-(1,4,5,6-tetrahydro-2-pyrimidinyl)-4-piperidinyl]oxy}-6,7-dihydro-5H-pyrrolo[2,3-d]pyrimidine;

1-Methyl ethyl 4-[(7-{4-[(dimethylamino)sulfonyl]phenyl}-6,7-dihydro-5H-pyrrolo[2,3-d]pyrimidin-4-yl)oxy]-1-piperidinecarboxylate;

1-Methylethyl 4-{[7-(5-cyano-2-pyridinyl)-6,7-dihydro-5H-pyrrolo[2,3-d]pyrimidin-4-yl]oxy}-1-piperidinecarboxylate;

1-Methylethyl 4-{[7-(5-fluoro-2-pyridinyl)-6,7-dihydro-5H-pyrrolo[2,3-d]pyrimidin-4-yl]oxy}-1-piperidinecarboxylate;

1,1-Dimethylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate;

1-Methylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate;

1-Methylethyl 4-[{7-[2-fluoro-4-(methylsulfonyl)phenyl]-6,7-dihydro-5H-pyrrolo[2,3-d]pyrimidin-4-yl}(methyl)amino]-1-piperidinecarboxylate trifluoroacetate;

7-[2-Fluoro-4-(methylsulfonyl)phenyl]-N-[1-(2-fluoro-5-pyrimidinyl)-4-piperidinyl]-6,7-dihydro-5H-pyrrolo[2,3-d]pyrimidin-4-amine trifluoroacetate;

7-[2-Fluoro-4-(methylsulfonyl)phenyl]-4-{[1-(methylsulfonyl)-4-piperidinyl]oxy}-6,7-dihydro-5H-pyrrolo[2,3-d]pyrimidine trifluoroacetate;

(±)-1-Methylethyl 4-({7-[5-(methylsulfinyl)-2-pyridinyl]-6,7-dihydro-5H-pyrrolo[2,3-d]pyrimidin-4-yl}oxy)-1-piperidinecarboxylate hydrochloride;

1-Methyl ethyl 4-({7-[5-(methylsulfonyl)-2-pyridinyl]-6,7-dihydro-5H-pyrrolo[2,3-d]pyrimidin-4-yl}oxy)-1-piperidinecarboxylate hydrochloride;

1-Methyl ethyl 4-({7-[6-(methylthio)-3-pyridinyl]-6,7-dihydro-5H-pyrrolo[2,3-d]pyrimidin-4-yl}oxy)-1-piperidinecarboxylate;

(±)-1-Methylethyl 4-({7-[6-(methylsulfinyl)-3-pyridinyl]-6,7-dihydro-5H-pyrrolo[2,3-d]pyrimidin-4-yl}oxy)-1-piperidinecarboxylate hydrochloride;

1-Methylethyl 4-({7-[6-(methylsulfonyl)-3-pyridinyl]-6,7-dihydro-5H-pyrrolo[2,3-d]pyrimidin-4-yl}oxy)-1-piperidinecarboxylate hydrochloride;

1-Methyl ethyl 4-({7-[2-fluoro-4-(methylthio)phenyl]-6,7-dihydro-5H-pyrrolo[2,3-d]pyrimidin-4-yl}oxy)-1-piperidinecarboxylate;

(±)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

(R)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

(S)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

7-[2-Fluoro-4-(methylthio)phenyl]-4-{[1-(5-fluoro-2-pyrimidinyl)-4-piperidinyl]oxy}-6,7-dihydro-5H-pyrrolo[2,3-d]pyrimidine;

(±)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

(R)-7-[2-fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

(S)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

7-[2-Fluoro-4-(methylthio)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(±)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(R)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(S)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

1-Methylethyl 4-({7-[4-(methylthio)phenyl]-6,7-dihydro-5H-pyrrolo[2,3-d]pyrimidin-4-yl}oxy)-1-piperidinecarboxylate;

(±)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

(+)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

(−)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

1-Methylethyl 4-({2-amino-7-[2-fluoro-4-(methylsulfonyl)phenyl]-6,7-dihydro-5H-pyrrolo[2,3-d]pyrimidin-4-yl}oxy)-1-piperidinecarboxylate;

1-Methylethyl 4-{[7-[2-fluoro-4-(methylsulfonyl)phenyl]-2-(methylamino)-6,7-dihydro-5H-pyrrolo[2,3-d]pyrimidin-4-yl]oxy}-1-piperidinecarboxylate;

7-(4-Bromo-2-fluorophenyl)-4-{[1-(5-fluoro-2-pyrimidinyl)-4-piperidinyl]oxy}-6,7-dihydro-5H-pyrrolo[2,3-d]pyrimidine;

3-Fluoro-4-(4-{[1-(5-fluoro-2-pyrimidinyl)-4-piperidinyl]oxy}-5,6-dihydro-7H-pyrrolo[2,3-d]pyrimidin-7-yl)benzonitrile;

3-Fluoro-4-[4-({1-[3-(1-methylethyl)-1,2,4-oxadiazol-5-yl]-4-piperidinyl}oxy)-5,6-dihydro-7H-pyrrolo[2,3-d]pyrimidin-7-yl]benzonitrile;

4-[4-({1-[3-(1-Methylethyl)-1,2,4-oxadiazol-5-yl]-4-piperidinyl}oxy)-5,6-dihydro-7H-pyrrolo[2,3-d]pyrimidin-7-yl]benzonitrile;

4-(4-{[1-(5-Fluoro-2-pyrimidinyl)-4-piperidinyl]oxy}-5,6-dihydro-7H-pyrrolo[2,3-d]pyrimidin-7-yl)benzonitrile;

4-{[1-(5-Fluoro-2-pyrimidinyl)-4-piperidinyl]oxy}-7-[4-(methylsulfonyl)phenyl]-6,7-dihydro-5H-pyrrolo[2,3-d]pyrimidine;

4-({1-[3-(1-Methylethyl)-1,2,4-oxadiazol-5-yl]-4-piperidinyl}oxy)-7-[4-(methylsulfonyl)phenyl]-6,7-dihydro-5H-pyrrolo[2,3-d]pyrimidine;

4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine;

(R)-4-({1-[3-(1-methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine;

(S)-4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine;

4-{[1-(5-fluoro-2-pyrimidinyl)-4-piperidinyl]oxy}-7-[4-(methylsulfinyl)phenyl]-6,7-dihydro-5H-pyrrolo[2,3-d]pyrimidine;

(R)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine;

(S)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine;

S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

(R)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

(S)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

(S)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(S)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate;

(S)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate; or a salt, solvate, or prodrug thereof.

One embodiment of the present invention includes a pharmaceutical composition comprising a compound of the present invention as herein described. One embodiment of the present invention includes a compound of the present invention as herein described for use as an active therapeutic substance.

One embodiment of the present invention includes a compound of the present invention as herein described for use in the treatment or prophylaxis of diseases and conditions mediated through GPR119.

One embodiment of the present invention includes a compound of the present invention as herein described for use in the treatment or prophylaxis of metabolic disorders or conditions. Preferably the condition or disease is diabetes or obesity.

One embodiment of the present invention includes using a compound of the present invention in the manufacture of a medicament for use in the treatment or prophylaxis of metabolic disorders or conditions. Preferably the disorder or condition is diabetes or obesity.

One embodiment of the present invention includes a method for the treatment or prophylaxis of metabolic disorders or conditions comprising the administration of a compound of the present invention as herein described. Preferably the condition or disorder is diabetes or obesity.

The present invention covers all combinations of embodiments, particular recitations, and preferred groups herein described.

DETAILED DESCRIPTION OF THE PREFERRED EMBODIMENTS

The present invention is described in terms known and appreciated by those skilled in the art. For ease of reference certain terms hereinafter are defined. The fact that certain terms are defined, however, should not be considered as indicative that defined terms are used in a manner inconsistent with the ordinary meaning or, alternatively, that any term that is undefined is indefinite or not used within the ordinary and accepted meaning. Rather, all terms used herein are believed to describe the invention such that one of ordinary skill can appreciate the scope of the present invention. The following definitions are meant to clarify, but not limit, the terms defined.

As used herein the term "alkyl" refers to a straight or branched chain hydrocarbon, preferably having from one to twelve carbon atoms. Examples of "alkyl" as used herein include, but are not limited to, methyl, ethyl, propyl, isopropyl, isobutyl, n-butyl, tert-butyl, isopentyl, n-pentyl, and the like.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds. Examples include, but are not limited to, vinyl, allyl, and the like As used herein the term "alkynyl" refers to a straight or branched chain aliphatic hydrocarbon containing one or more carbon-to-carbon triple bonds. Examples include, but are not limited to, ethynyl and the like.

As used herein, the term "alkylene" refers to a straight or branched chain divalent hydrocarbon radical, preferably having from one to ten carbon atoms. Examples of "alkylene" as used herein include, but are not limited to, methylene, ethylene, n-propylene, n-butylene, and the like. As used herein, when the term "alkylene" appears as a suffix on a named substituent group, the intention is to describe a divalent hydrocarbon linker. As a non-limiting example, "alkylcarboxamidealkylene" refers to an alkylcarboxamide group, or —C(O)NHR, attached through an alkylene linker, namely —(CH$_2$)$_n$C(O)NHR. When used herein the terminology $C_1$-$C_6$ refers to the substituent group rather than the linker. Thus, $C_1$-$C_6$ alkylcarboxamidealkylene refers to —(CH$_2$)$_n$C(O)NHR, where R is $C_1$-$C_6$ alkyl. As noted hereinabove, n preferably is an integer from 1 to 10.

As used herein, the term "cycloalkyl" refers to a non-aromatic cyclic hydrocarbon ring. Exemplary "cycloalkyl" groups include, but are not limited to, cyclopropyl, cyclobutyl, cyclopentyl, cyclohexyl, and cycloheptyl. As used herein, the term "cycloalkyl" includes a fused ring system where, for example, a cycloalkyl ring, such as a cyclopentyl ring, is fused with an aromatic ring, herein an "aryl" ring, such as a benzene ring, to form, for example, groups such as indane.

As used herein, the term "heterocycle" or "heterocyclyl" refers to a mono- or polycyclic non-aromatic ring system that may contain one or more degrees of unsaturation and also contains one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Such rings may be optionally fused to one or more of another "heterocyclic" ring(s) or cycloalkyl ring(s). Also, the terms include fused ring systems where, for example, a saturated heterocyclic ring (such as a pyrrolidine ring) is fused with an aromatic ring, herein an "aryl" ring, such as a benzene ring to form, for example, groups such as indoline. Further examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to a benzene ring or to a fused benzene ring system, for example anthracene, phenanthrene, or naphthalene ring systems. Examples of "aryl" groups include, but are not limited to, phenyl, 2-naphthyl, 1-naphthyl, and the like.

As used herein, the term "heteroaryl" refers to a monocyclic five to seven membered aromatic ring or to a fused bicyclic aromatic ring system comprising two of such aromatic rings that contain one or more nitrogen, sulfur, and/or oxygen atoms, where N-oxides, sulfur oxides, and dioxides are permissible heteroatom substitutions. Examples of "heteroaryl" groups as used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and the like.

As used herein the term "acyl" refers to a group —C(O)$R^a$, where $R^a$ is hydrogen, alkyl, cycloalkyl, aryl, heteroaryl, or heterocyclyl, as each is herein defined. For example, the term "acyl" encompasses a heteroarylcarbonyl group, such as —C(O)—Het, where "Het" refers to a heteroaryl group as defined herein. As used herein, the phrase "substituted acyl" refers to a group as herein defined wherein $R^a$ is capable of being substituted, namely alkyl, cycloalkyl, aryl, heteroaryl, or heterocyclyl, and excludes where $R^a$ is hydrogen. For example, the phrase "acyl substituted with one or more heteroaryl," encompasses a substituted heteroarylcarbonyl group, namely —C(O)Het-Het, where each "Het" refers to a heteroaryl group as defined herein.

As used herein the term "acylsulfonamide" refers to a group —S(O)$_2$NHC(O)$R^a$, where $R^a$ is alkyl, cycloalkyl, aryl, heteroaryl, or heterocyclyl, as each is herein defined.

As used herein the term "acyloxy" refers to a group —OC(O)$R^a$, where $R^a$ is alkyl, cycloalkyl, aryl, heteroaryl, or heterocyclyl, as each is herein defined.

As used herein the term "alkoxy" refers to a group —O$R^a$, where $R^a$ is alkyl, as herein defined.

As used herein the term "alkylamino" refers to a group —NH$R^a$, where $R^a$ is alkyl or substituted alkyl, where the alkyl group is substituted with an alkoxy group or a hydroxyl group as herein defined.

As used herein the term "alkylcarboxamide" refers to a group —C(O)NH$R^a$ or, alternatively, —NHC(O)$R^a$, where each $R^a$ independently is alkyl or substituted alkyl, where the alkyl group is substituted with an alkoxy group or a hydroxyl group as herein defined. The term, thus, includes groups such as alkoxyalkylcarboxamides (—C(O)—NH—(CH$_2$)$_x$—O—$R^a$) and hydroxyalkylcarboxamides (—C(O)—NH—(CH$_2$)$_x$—OH).

As used herein "alkoxycarbonyl" refers to a group —C(O)O$R^a$ where $R^a$ is alkyl, as herein defined.

As used herein the term "alkyloxyphosphoryl" refers to a group —P(O)(O$R^a$)(O$R^a$), where each $R^a$ independently is hydrogen, alkyl, or substituted alkyl, where the alkyl group is substituted with an alkoxy group or a hydroxyl group as herein defined.

As used herein the term "alkylthiocarboxamide" refers to a group —C(S)NH$R^a$ or alternatively —NHC(S)$R^a$, where each $R^a$ independently is alkyl or substituted alkyl, where the alkyl group is substituted with an alkoxy group or a hydroxyl group as herein defined.

As used herein the term "alkylsulfonamide" refers to a group —S(O)$_2$NH$R^a$, or alternatively —N$R^a$S(O)$_2$, where each $R^a$ independently is alkyl or substituted alkyl, and where the alkyl group is substituted with an alkoxy group or a hydroxyl group as herein defined.

As used herein the term "alkylsulfinyl" refers to a group —S(O)$R^a$ where $R^a$ is alkyl, as herein defined.

As used herein the term "alkylsulfonyl" refers to a group —S(O)$_2R^a$ where $R^a$ is alkyl, as herein defined.

As used herein the term "alkylsulfoximine" refers to a group —S(NH)(O)$R^a$, where $R^a$ is an alkyl group as herein defined.

As used herein the term "alkylthio" refers to a group —S$R^a$ where $R^a$ is alkyl, as herein defined.

As used herein the term "alkylthioureyl" refers to a group —N($R^a$)C(S)N($R^a$)($R^a$), where each $R^a$ independently is hydrogen or alkyl, as herein defined.

As used herein the term "alkylureyl" refers to a group —N($R^a$)C(O)N($R^a$)($R^a$), where each $R^a$ independently is hydrogen or alkyl, as herein defined.

As used herein the term "amino" refers to a group —NH$_2$.

As used herein the term "aralkyl" refers to a group —$R^bR^a$, where $R^b$ is an alkylene and $R^a$ is aryl, as each herein is defined. Preferably the alkylene group has one to ten carbon atoms, preferably one to six carbon atoms, and preferably is a methylene group, —CH$_2$—.

As used herein the term "carbamimidoyl" refers to a group —C(=N)N($R^a$)($R^a$), where each $R^a$ independently is hydrogen or alkyl, as herein defined.

As used herein "carboxy" refers to a group —C(O)OH.

As used herein the term "carboxamide" refers to a group —C(O)NH$_2$.

As used herein the term "cyano" refers to a group —CN.

As used herein the term "cycloalkylalkylene" refers to a group —$R^bR^a$, where $R^b$ is an alkylene and $R^a$ is cycloalkyl, as each herein is defined. As used herein "$C_1$-$C_6$ cycloalkylalkylene" refers to a cycloalkyl group linked through a $C_1$-$C_6$ alkylene group.

As used herein the term "dialkylamino" refers to a group —N($R^a$)($R^a$), where each $R^a$ independently is alkyl or substituted alkyl, where the alkyl group is substituted with an alkoxy group or a hydroxyl group as herein defined. The reference of $C_1$-$C_6$ refers to each alkyl group independently. Thus, $C_1$-$C_6$ dialkylamino refers to a group —N($R^a$)($R^a$), where each $R^a$ independently is $C_1$-$C_6$ alkyl as herein defined.

As used herein the term "dialkylcarboxamide" refers to a group —C(O)N($R^a$)($R^a$), where each $R^a$ independently is alkyl or substituted alkyl, where the alkyl group is substituted with an alkoxy group or a hydroxyl group as herein defined.

As used herein the term "dialkyloxyphosphoryl" refers to a group —P(O)(O$R^a$)(O$R^a$), where each $R^a$ independently is alkyl or substituted alkyl, where the alkyl group is substituted with an alkoxy group or a hydroxyl group as herein defined.

As used herein the term "dialkylsulfonamide" refers to a group —S(O)$_2$N($R^a$)($R^a$) where each $R^a$ independently is alkyl or substituted alkyl, where the alkyl group is substituted with an alkoxy group or a hydroxyl group as herein defined.

As used herein the term "dialkylthiocarboxamide" refers to a group —C(S)N($R^a$)($R^a$), where each $R^a$ independently is alkyl or substituted alkyl, where the alkyl group is substituted with an alkoxy group or a hydroxyl group as herein defined.

As used herein "haloalkoxy" refers to a group —O$R^a$, where $R^a$ is haloalkyl as herein defined.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents such as perfluoroalkyl groups and the like.

As used herein the term "haloalkylsulfonyl" refers to a group —S(O)$_2R^a$, where $R^a$ is haloalkyl as herein defined.

As used herein the term "haloalkylthio" refers to a group —S$R^a$, where $R^a$ is haloalkyl as herein defined.

As used herein the term "heteroaralkyl" refers to a group —$R^bR^a$, where $R^b$ is an alkylene and $R^a$ is heteroaryl, as each herein is defined. Preferably the alkylene group has one to ten carbon atoms, preferably one to six carbon atoms, and preferably is a methylene group, —CH$_2$—.

As used herein the term "hydroxyl" refers to a group —OH.

As used herein the term "nitro" refers to a group —$NO_2$.

As used herein the term "sulfonamide" refers to a group —$S(O)_2NH_2$, or alternatively —$NHS(O)_2$.

As used herein the term "thiol" refers to a group —SH.

The compounds of formula (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein may be capable of existing as stereoisomers. The scope of the present invention includes mixtures of stereoisomers as well as purified or enriched mixtures. Also included within the scope of the invention are the individual isomers of the compounds represented by formula (I), as well as any wholly or partially equilibrated mixtures thereof. Certain compounds of formula (I) contain a chiral center. Therefore, in particular, the scope of the present invention should be interpreted to include racemates, purified enantiomers, and enantiomerically enriched mixtures of the compounds of formula (I). As one example, the compounds of the present invention include racemic and chiral sulfones and sulfoxides.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "prodrug" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, 5$^{th}$ Edition, Vol 1: Principles and Practice, which is incorporated herein by reference to the extent that it teaches prodrugs.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from metabolic disorders such as diabetes and obesity, generally, should be in the range of 0.1 to 100 mg/kg body weight of recipient (mammal) per day. More usually the effective amount should be in the range of 0.1 to 10 mg/kg body weight per day. Thus, for a 70 kg adult mammal the actual amount per day would usually be from 7 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage, or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets.

The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions. As such, the compounds of the present invention may be used in combination with a variety of other therapeutic agents useful in the treatment or prophylaxis of those disorders or conditions. The compounds of the present invention may be used in combination with diet, exercise, insulin, an insulin sensitivity enhancer, a glucose absorption inhibitor, a biguanide, an insulin secretion enhancer, a SGLT2 inhibitor, an insulin or insulin analogue, a glucagon receptor antagonist, an insulin receptor kinase stimulant, a tripeptidyl peptidase 11 inhibitor, a dipeptidyl peptidase IV inhibitor, a protein tyrosine phosphatase-1B inhibitor, a glycogen phosphorylase inhibitor, anAXOR 109 agonist, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-1, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, antidiarrhoics, cathartics, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent, and a urinary alkalinizer.

Exemplary compounds are hereinafter described, however, a combination within the scope of the present invention should not be limited by this specific description. Rather, any combination within the perview of those skilled in the art is contemplated. In addition, this listing of exemplary compounds includes the free compounds, as well as salts, solvates, and physiologically functional derivatives.

As insulin sensitivity enhancers, peroxisome proliferator-activated receptor-γ agonists such as troglitazone, pioglitazone, rosiglitazone, darglitazone, GI-262570, isaglitazone, LG-100641, NC-2100, T-174, DRF-2189, CLX-0921, CS-011, GW-1929, ciglitazone, englitazone, and NIP-221, peroxisome proliferator-activated receptor-q agonists such as GW-9578 and BM-170744, peroxisome proliferator-activated receptor-α/γ agonists such as GW-409544, KRP-297, N,N-622, CLX-0940, LR-90, SB-219994, DRF-4158, and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers may be used for diabetes, impaired glucose tolerance, diabetic complications, obesity, hyperinsulinemia, hyperlipidemia, hypercholesterolemia, hypertriglyceridemia, lipid metabolism disorder or atherosclerosis, and more preferably for diabetes, impaired glucose tolerance or hyperinsulinemia. Such compounds are believed to improve the disturbance of insulin signal transduction in peripheral tissues and enhancing glucose uptake into the tissues from the blood, leading to lowering of blood glucose level.

As glucose absorption inhibitors, for example, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors may be used for diabetes, impaired glucose tolerance, diabetic complications, obesity or hyperinsulinemia, and more preferably for impaired glucose tolerance. Such compounds are beleived to inhibit the gastrointestinal enzymatic digestion of carbohydrates contained in foods, and inhibit and/or delay the absorption of glucose into the body.

As biguanides, phenformin, buformin, mefformin, or the like are illustrated. Biguanides may be used for diabetes, impaired glucose tolerance, diabetic complications or hyperinsulinemia, and more preferably for diabetes, impaired glucose tolerance or hyperinsulinemia. Such compounds are believed to lower blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide or the like are illustrated. In addition, the insulin secretion enhancers include glucokinase activators such as RO-28-1675. Insulin secretion enhancers may be used for diabetes, impaired glucose tolerance or diabetic complications, and more preferably for diabetes or impaired glucose tolerance. Such compounds are beleived to lower blood glucose level by acting on pancreatic β-cells and enhancing the insulin secretion.

As SGLT2 inhibitors, compounds described in Japanese patent publications Nos. Hei 10-237089 and 2001-288178, and International Publications Nos. WO01/16147, WO01/27128, WO01/68660, WO01/74834, WO01/74835, WO02/28872, WO02/36602, WO02/44192, WO02/53573, and WO 03/99836 are illustrated. In addition, inhibitors identified as dapagliflozin, GW869682, and/or GSK189075 are illustrated as well. SGLT2 inhibitors may be used for diabetes, impaired glucose tolerance, diabetic complications, obesity or hyperinsulinemia, and more preferably for diabetes, impaired glucose tolerance, obesity or hyperinsulinemia. Such compounds are beleived to lower blood glucose level by inhibiting the reabsorption of glucose at the kidney's proximal tubule.

As insulin or insulin analogues, human insulin, animal-derived insulin, human or animal-derived insulin analogues or the like are illustrated. These preparations may be used for diabetes, impaired glucose tolerance or diabetic complications, and more preferably for diabetes or impaired glucose tolerance.

AXOR 109, also known as TGR5, BG37, M-BAR, or hGPCR19, is a bile acid G-protein coupled receptor primarily expressed in monocytes/macrophages, lung, spleen, and the intestinal tract. AXOR 109 agonists may be used for diabetes mellitus, stress, obesity, appetite control and satiety, Alzheimers, inflammation, and diseases of the central nervous system. AXOR 109 agonists are believed to moderate blood glucose level by stimulating the release of GLP-1 from enteroendocrine cells.

As glucagon receptor antagonists, BAY-27-9955, NNC-92-1687 or the like are illustrated; as insulin receptor kinase stimulants, TER-17411, L-783281, KRx-613 or the like are illustrated; as tripeptidyl peptidase II inhibitors, UCL-1397 or the like are illustrated; as dipeptidyl peptidase IV inhibitors, vildagliptin, sitigliptin, denagliptin, saxagliptin, TSL-225, P-32/98 or the like are illustrated; as protein tyrosine phosphatase 1B inhibitors, PTP-112, OC-86839, PNU-177496 or the like are illustrated; as glycogen phosphorylase inhibitors, N,N-4201, CP-368296 or the like are illustrated; as fructose-bisphosphatase inhibitors, R-132917 or the like are illustrated; as pyruvate dehydrogenase inhibitors, AZD-7545 or the like are illustrated; as hepatic gluconeogenesis inhibitors, FR-225659 or the like are illustrated; as glucagon-like peptide-1 analogues, exendin-4, CJC-1131 or the like are illustrated; as glucagon-like peptide 1 agonists; AZM-134, LY-315902 or the like are illustrated; and as amylin, amylin analogues or amylin agonists, pramlintide acetate or the like are illustrated. These drugs, glucose-6-phosphatase inhibitors, D-chiroinsitol, glycogen synthase kinase-3 inhibitors and glucagon-like peptide-1 may be used for diabetes, impaired glucose tolerance, diabetic complications or hyperinsulinemia, and more preferably for diabetes or impaired glucose tolerance.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat or the like are illustrated. Aldose reductase inhibitors may be used for diabetic complications. Such compounds are beleived to inhibit aldose reductase and lowering excessive intracellular accumulation of sorbitol in accelated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride or the like are illustrated. Advanced glycation endproducts formation inhibitors may be used for diabetic complications. Such compounds are beleived to inhibit formation of advanced glycation endproducts which are accelated in continuous hyperglycemic condition in diabetes and declining of cellular damage.

As protein kinase C inhibitors, LY-333531, midostaurin or the like are illustrated. Protein kinase C inhibitors may be used for diabetic complications. Such compounds are beleived to inhibit protein kinase C activity, which is accelated in continuous hyperglycemic condition in diabetic patients.

As γ-aminobutyric acid receptor antagonists, topiramate or the like are illustrated; as sodium channel antagonists, mexiletine hydrochloride, oxcarbazepine or the like are illustrated; as transcrit factor NF-κB inhibitors, dexlipotam or the like are illustrated; as lipid peroxidase inhibitors, tirilazad mesylate or the like are illustrated; as N-acetylated-α-linked-acid-dipeptidase inhibitors, GPI-5693 or the like are illustrated; and as carnitine derivatives, carnitine, levacecamine hydrochloride, levocarnitine chloride, levocarnitine, ST-261 or the like are illustrated. These drugs, insulin-like growth factor-1, platelet-derived growth factor, platelet derived growth factor analogues, epidermal growth factor, nerve growth factor, uridine, 5-hydroxy-1-methylhidantoin, EGB-761, bimoclomol, sulodexide and Y-128 may be used for diabetic complications.

As antidiarrhoics or cathartics, polycarbophil calcium, albumin tannate, bismuth subnitrate or the like are illustrated. These drugs may be used for diarrhea, constipation or similar conditions that may accompany diabetes or other metabolic disorders.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin or the like are illustrated. Hydroxymethylglutaryl coenzyme A reductase inhibitors may be used for hyperlipidemia, hypercholesterolemia, hypertriglyceridemia, lipid metabolism disorder or atherosclerosis, and more preferably for hyperlipidemia, hypercholesterolemia, or atherosclerosis. Such compounds are believed to lower blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 or the like are illustrated. Fibric acid derivatives may be used for hyperinsulinemia, hyperlipidemia, hypercholesterolemia, hypertriglyceridemia, lipid metabolism disorder or atherosclerosis, and more preferably for hyperlipidemia, hypertriglyceridemia, or atherosclerosis. Such compounds are beleived to activate hepatic lipoprotein lipase and enhancing fatty acid oxidation, leading to a lowering of blood triglyceride levels.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353 (solabegron), N-5984, GW-2696, YM178 or the like are illustrated. $\beta_3$-Adrenoceptor agonists may be used for diabetes, obesity, hyperinsulinemia, hyperlipidemia, hypercholesterolemia, hypertriglyceridemia, lipid metabolism disorder, urinary incontinence, and IBS.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe or the like are illustrated. Acyl-coenzyme A cholesterol acyltransferase inhibitors may be used for hyperlipidemia, hypercholesterolemia, hypertriglyceridemia or lipid metabolism disorder, and more preferably for hyperlipidemia or hypercholesterolemia. Such compounds are beleived to lower blood cholesterol levels by inhibiting acyl-coenzyme A cholesterol acyltransferase.

As thyroid hormone recptor agonists, sodium liothyronine, sodium levothyroxine, KB-2611 or the like are illustrated; as cholesterol absorption inhibitors, ezetimibe, SCH-48461 or the like are illustrated; as lipase inhibitors, orlistat, ATL-962, AZM-131, RED-103004 or the like are illustrated; as carnitine palmitoyltransferase inhibitors, etomoxir or the like are illustrated; as squalene synthase inhibitors, SDZ-268-198, BMS-188494, A-87049, RPR-101821, ZD-9720, RPR-107393, ER-27856 or the like are illustrated; as nicotinic acid derivatives, nicotinic acid, nicotinamide, nicomol, niceritrol, acipimox, nicorandil or the like are illustrated; as bile acid sequestrants, colestyramine, colestilan, colesevelam hydrochloride, GT-102-279 or the like are illustrated; as sodium/bile acid cotransporter inhibitors, 264W94, S-8921, SD-5613 or the like are illustrated; and as cholesterol ester transfer protein inhibitors, PNU-107368E, SC-795, JTT-705, CP-529414 or the like are illustrated. Probcol, microsomal trigylceride transfer protein inhibitors, lipoxygenase inhibitors, and low-density lipoprotein receptor enhancers may be used for hyperlipidemia, hypercholesterolemia, hypertriglyceridemia, or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenaline reuptake inhibitors, noradrenaline releasing stimulants, $\alpha_1$-adrenoceptor agonists, $\beta_2$-adrenoceptor agonists, dopamine agonists, cannabinoid receptor antagonists, γ-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), α-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. As monoamine reuptake inhibitors, mazindol or the like are illustrated; as serotonin reuptake inhibitors, dexfenfluramine hydrochloride, fenfluramine, sibutramine hydrochloride, fluvoxamine maleate, sertraline hydrochloride or the like are illustrated; as serotonin agonists, inotriptan, (+)-norfenfluramine or the like are illustrated; as noradrenaline reuptake inhibitors, bupropion, GW-320659 or the like are illustrated; as noradrenaline releasing stimulants, rolipram, YM-992 or the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex or the like are illustrated; as dopamine agonists, ER-230, doprexin, bromocriptine mesylate or the like are illustrated; as cannabinoid receptor antagonists, rimonabant or the like are illustrated; as γ-aminobutyric acid receptor antagonists, topiramate or the like are illustrated; as $H_3$-histamine antagonists, GT-2394 or the like are illustrated; as leptin, leptin analogues or leptin receptor agonists, LY-355101 or the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 or the like are illustrated; and as neuropeptide Y antagonists, SR-120819-A, PD-160170, NGD-95-1, BIBP-3226, 1229-U-91, CGP-71683, BIBO-3304, CP-671906-01, J-115814 or the like are illustrated.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril or the like are illustrated. Angiotensin-converting enzyme inhibitors may be used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril or the like are illustrated. Neutral endopeptidase inhibitors may be used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 or the like are illustrated. Angiotensin II receptor antagonists may be used for diabetic complications or hypertension.

As endothelin-converting enzyme inhibitors, CGS-31447, CGS-35066, SM-19712 or the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 or the like are illustrated. Such drugs may be used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-γ, PNU-80873A, isosorbide, D-mannitol, D-sorbitol, fructose, glycerin, acetazolamide, methazolamide, FR-179544, OPC-31260, lixivaptan, conivaptan hydrochloride or the like are illustrated. Diuretic drugs may be used for diabetic complications, hypertension, congestive heart failure or edema, and more preferably for hypertension, congestive heart failure or edema. Such compounds are beleived to reduce blood pressure or improve edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride or the like are illustrated; as vasodilating antihypertensive agents, indapamide, todralazine hydrochloride, hydralazine hydrochloride, cadralazine, budralazine or the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin or the like are illustrated; as centrally acting antihypertensive agents, reserpine or the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride or the like are illustrated. These drugs may be used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin or the like are illustrated. Antiplatelets agents may be used for atherosclerosis or congestive heart failure.

As uric acid synthesis inhibitors, allopurinol, oxypurinol or the like are illustrated; as uricosuric agents, benzbromarone, probenecid or the like are illustrated; and as urinary alkalinizers, sodium hydrogen carbonate, potassium citrate, sodium citrate or the like are illustrated. These drugs may be used for hyperuricemia or gout.

As noted, the compounds of the present invention may be used alone or may be combined with other medical therapies to treat and/or prevent a variety of disorders and conditions. More particularly, the diseases and conditions metabolic disorders, such as diabetes, including but not limited to diabetes types I and II, obesity, glucose intolerance, insulin resistance, metabolic syndrome X, hyperlipidemia, hypercholesterolemia, artheroscelrosis, neurodegenerative diseases, and other indications such as stroke.

The compounds of this invention may be made by a variety of methods. Illustrative general synthetic methods are set out below followed by a description of exemplary synthesis of specific compounds of the invention as illustrated in the examples.

In the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protective Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be affected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

The compounds of this invention may be made by a variety of methods, including well-known standard synthetic methods. The novel compounds of the present invention should not be limited by any specific process herein described.

EXPERIMENTAL SECTION

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade). All reactions were conducted at room temperature unless otherwise noted.

¹H-NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on Micromass Platform or ZMD mass spectrometers from Micromass Ltd., Altricham, UK, using either Atmospheric Chemical Ionization (APCI) or Electrospray Ionization (ESI).

Ozone was generated from oxygen using a standard ozonolysis unit as is known in the art (Ozonology, Inc.).

The microwave reactions were conducted using Emrys™ Optimizer/SmithSynthesizer from Biotage using standard protocols that are know in the art.

The absolute stereochemistry of chiral enantiopure sulfoxides was determined using ab initio Vibrational Circular Dichroism (VCD) Spectroscopy. The experimental details are as follows:

Spectrometer: BioTools Chiral/R™ VCD spectrometer equipped with a dual photoelastic modulator (PEM) and operated at 4 cm⁻¹ resolution.

Frequency Range: 2000-800 cm⁻¹

PEM Calibration: dual PEM calibrated at 1400 cm⁻¹

PEM Retardation Settings: PEM1=0.250λ; PEM2=0.275λ

Scan Method: single 5 min. DC scan+single 75 min. AC scan per enantiomer.

Solvent: CDCl₃

Concentration: ~4 mg/100 μl

Absolute configurations were assigned by comparing the sign (+/−) of an intense VCD band at 954 cm⁻¹ in experimental VCD spectra to the corresponding band in reference spectra. The sign (+/−) of a VCD marker band was identified as highly diagnostic for the absolute configuration of the aromatic methyl sulfinyl group. For related work see: (1) Stephens, P. J. et al *J. Org. Chem.*, 2001, 66, 3671; (2) F. J. Devlin and Stephens P. J. et al *Chirality*, 2002, 14, 400.

Synthetic Schemes

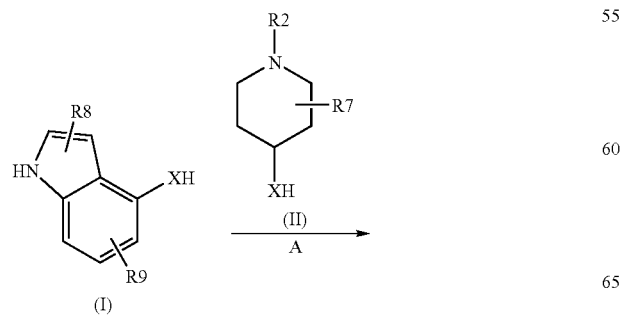

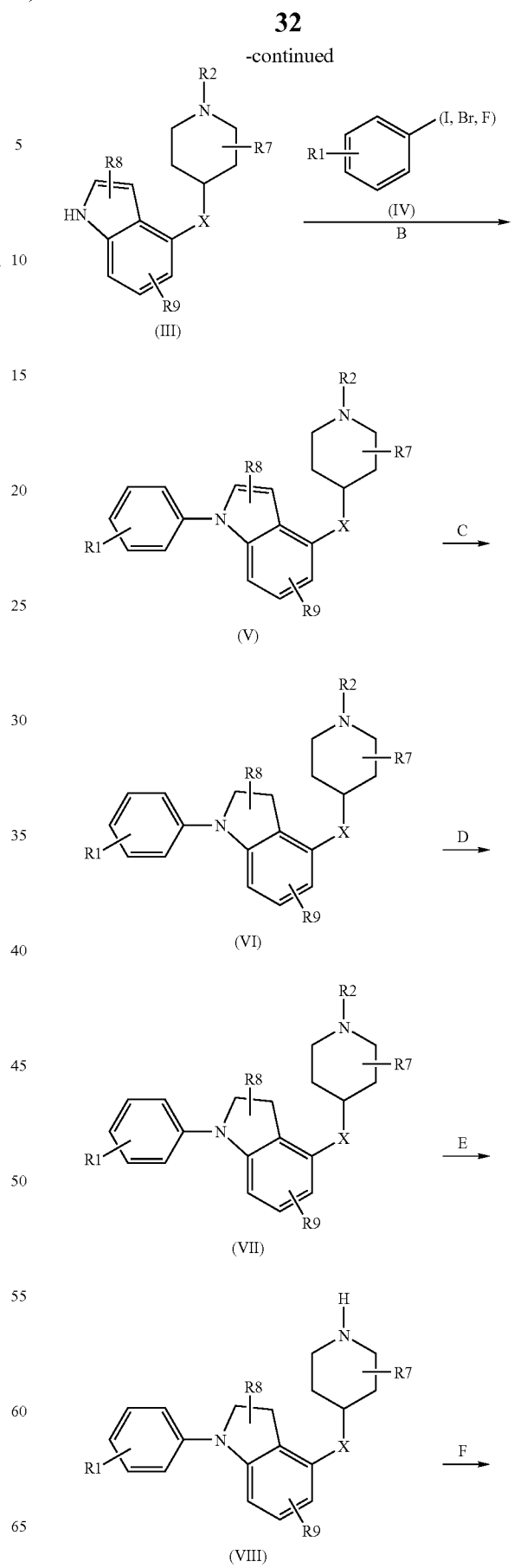

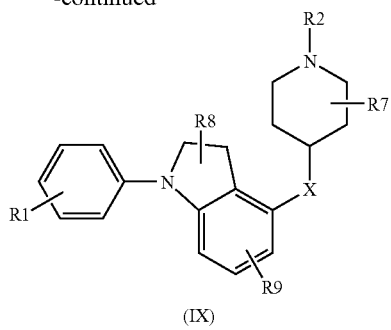

(IX)

Reagents and conditions: A) Ph$_3$P, DIAD, THF, RT; B) CuI, K$_3$PO$_4$, toluene, reflux, or 37% KF—Al$_2$O$_3$, 18-crown-6, DMSO, reflux; C) NaCNBH$_3$, AcOH, RT; D) (a) CuI, L-proline, NaOH, CH$_3$SO$_2$Na, DMSO, 110° C., or (b) CuCN, NMP, 150° C., or (c) HP(O)(OR)$_2$, CuI, Cs$_2$CO$_3$, toluene, reflux, or (d) PdCl$_2$(PPh$_3$)$_2$ or Pd(Ph$_3$P)$_4$, boronic acid, 2 N Na$_2$CO$_3$, THF, reflux, or (e) Sn(Bu)$_3$R, Pd catalyst, THF, reflux; E) (a) TFA, CH$_2$Cl$_2$, RT, or (b) Conc. HCl; F) (a) R$_2$OCOCl, Et$_3$N, CH$_2$Cl$_2$, RT, or (b) Substituted pyrimidine, DIPEA, ACN, reflux, or (c) R$_2$COCl, Et$_3$N, CH$_2$Cl$_2$, RT, or (d) i. NaHCO$_3$, H$_2$O, ii. CNBr, Na$_2$CO$_3$, iii. RC(NH$_2$)NOH, 1N ZnCl$_2$ in Et$_2$O, iv. EtOAc, H$_3$O$^+$, EtOH, reflux.

Indoline-based ligands can be prepared by following the general synthetic Scheme 1. A Mitsunobu reaction between substituted indole I and 4-OH piperidine derivative II can provide the compound of the formula III. For Mitsunobu reaction conditions, see Mitsunobu, *Synthesis*, 1981, 1, and for a Mitsunobu reaction review see D. L. Hughes *Organic Reactions* 42, 335, each herein incorporated by reference with regard to such synthetic teaching. The compound III upon N-arylation with variously substituted aryl halides using the standard reaction conditions can give the compound V. For N-arylation procedures, see S. L. Buchwald et al *J. Org. Chem.*, 2004, 69, 5578 and W. J. Smith et al *Tetrahedron Lett.*, 1996, 37, 299, each herein incorporated by reference with regard to such synthesis. Reduction of compound V with NaCNBH$_3$ in AcOH or CF$_3$CO$_2$H can give the indoline of formula VI. For reaction conditions, G. W. Gribble et al *Synthesis* 1977, 859 and also see G. W. Gribble *Chem. Soc. Rev.*, 1998, 27, 395, each herein incorporated by reference with regard to such synthesis. The intermediate VI (where R$^2$ preferably is BOC) can serve as a starting material for making a variety of analogues. Exploration of different functional groups at R$^2$ of formula VI can be accessed by a sequence involving deprotection of a suitable protecting group, such as a BOC group, with acid, like TFA or 4 N HCl in dioxane to yield a compound such as VIII. Reaction of compound VIII with a variety of electrophiles would yield compounds of IX, wherein R$^2$ represents part of a carbamate, urea, or pyrimidine moiety. For reaction conditions see Fyfe, M., et al WO 2006/067531A1 and WO2006/067532A1, each herein incorporated by reference with regard to such synthesis. Examples of electrophiles include chloroformates, isocyanates, and halopyrimidines that give carbamates, ureas, and piperidinopyrimidines, respectively. Reactions with electrophiles can be performed in a suitable solvent like dichloromethane, tetrahydrofuran, or acetonitrile under conditions known to those skilled in the art.

If R$^1$ is Br or I, sulfonylation of VI can provide the indoline VII (R$^1$ is SO$_2$R, where R is alkyl or aryl). For the conversion of aryl halides to the corresponding sulphones, see D. Ma., et al, *J. Org. Chem.* 2005, 70, 2696, herein incorporated by reference with regard to such synthesis. Metal catalyzed carbon-carbon bond forming reactions such as a Suzuki reaction with boronic acids or boronates or a Stille reaction with trialkyltin reagents can provide the corresponding indoline derivatives of VII. For reaction conditions of the Suzuki coupling reaction, see, N, Miyaura, A. Suzuki, *Chem. Rev.* 1995, 95, 2457-2483; A. Suzuki, A, *J. Organometallic Chem.* 1999, 576, 147-168; and A. Suzuki, in *Metal-catalyzed Cross-coupling Reactions*, F. Diederich., and P. J. Stang., Eds.; Wiley-VCH: New York, 1998, 49-97, each herein incorporated by reference with regard to such teaching. The compound VI (where R$^1$ is Br or I) under Rosunmund-von Braun conditions can give the corresponding nitrile compound VII (R$^1$ is CN). For related reaction conditions see, C. Liangzhen et al., *Synthetic Commun.* 2004, 34, 1215, herein incorporated by reference with regard to such synthesis. After transformation of R$^1$, the compound VII can also be treated with acid, like TFA or concentrated HCl to afford the compound of the formula VIII.

The nitrile of the compound VII can afford the carboxylic acid using standard reaction conditions appreciated in the art. The carboxylic acid can serve as a precursor for making several acyl amides. The carboxylic acid or sulfoxides can also be obtained by following a different synthetic strategy where the N-arylation of 11 with an appropriate aryl halide can give an indole V (where R$^1$ is —CO$_2$R, —SR). The compound VII (where R$^1$ is CN) can further be modified to give 1,3-thiazole derivatives to afford active ligands. For reaction conditions, see R. Olsson et al *J. Med. Chem.* 2005, 48, 7517, herein incorporated by reference with regard to such synthesis. The compound VII (where R$^1$ is —(O)P(OR)$_2$) can be prepared from compound VI (where R$^1$ is I) using literature protocol that is well-known to those skilled in the art. The compound VII (where R$^1$ is Br or I) can, in turn, be converted to the compound VII (where R$^1$=HOP(O)(OR)). For reaction conditions, S. L. Buchwald et al *Org. Lett.*, 2003, 5, 2315 and S. Gul et al *Biochem. J.* 2003, 376, 813, each herein incorporated by references with regard to such synthesis. For example if R$^1$ is a halogen in the compound VI, then alkyl or arylthiolation can afford the compound VII (where R$^1$ is SR), which in turn can be oxidized to give the sulfoxides VII (where R$^1$ is SOR). For the conversion of aryl or alkylhalides to the corresponding sulfides see, N. Taniguchi et al J. Org. Chem., 2004, 69, 6904, herein incorporated by reference with regard to such synthesis. The compound VI can be treated with oxidant such as 30% aqueous H$_2$O$_2$ in hexafluoroisopropanol to give the racemic sulfoxides of VII (where R$^1$ is SOR). For reaction conditions, see K. S. Ravikumar et al *Eur. J. Chem.* 1998, 2937, herein incorporated by reference with regard to such synthesis. The racemic sulfoxides can be separated using chiral HPLC analysis to give the pure or enriched (R and S) enantiomers. The compound IX can be derivatized further to give active compounds (herein also referred to as physiologically functional derivatives) by following the standard reaction conditions as are appreciated in the art.

For example, the compound VIII can further be derivatized by varying the substitution on the N atom of the depicted piperidine. The compound VIII (where R$^2$ is H), obtained upon treating the compound VII (where R$^2$ is BOC) with CF$_3$CO$_2$H, may be used to make a variety of analogues. For example compound VIII can be converted, under basic conditions, to pyrimidine derivatives via a reaction with a variety of 2-chloro 5-substituted pyrimidines using the protocols appreciated in art. For related reaction conditions see, Fyfe, M., et al WO2006/067532A1, herein incorporated by reference with regard to such teaching. Compound VIII can also be used for the synthesis of N-acyl or N-alkyl derivatives using basic conditions that are well-appreciated in the art.

Compound VIII can also be used to make a variety of carbamates. The compound VIII can serve as a precursor for making many heterocycles, including oxadiazoles. For reaction conditions, see R. M. Jones et al WO 2005/121121A2, herein incorporated by reference with regard to such synthesis. The compound VIII can be reacted with cyanogen bromide to give N—CN derivative which in turn can be converted to a heterocycle, including but not limited to an oxadiazole, of IX.

Alternatively, the indoline based-ligands can also be prepared by following the synthetic Scheme 2. Compound III can be converted to indoline X using a NaCNBH$_3$/AcOH reduction protocol. The indoline X can be transformed to the compound VI via an N-arylation protocol, as is known in the art. The compound VI may serve as an intermediate for making several derivatives, as described above, of the indoline-based ligands.

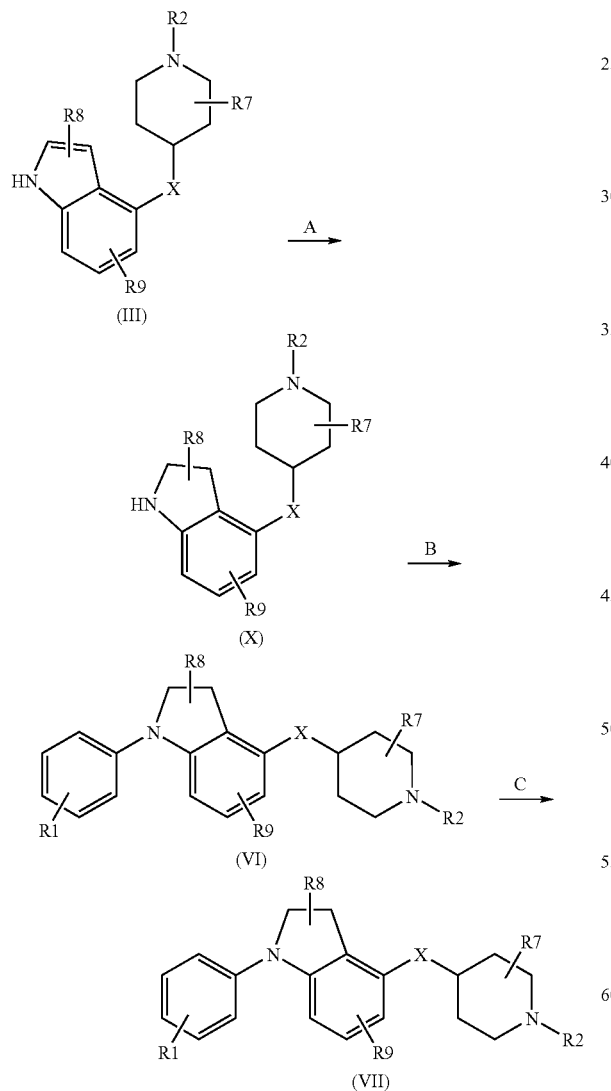

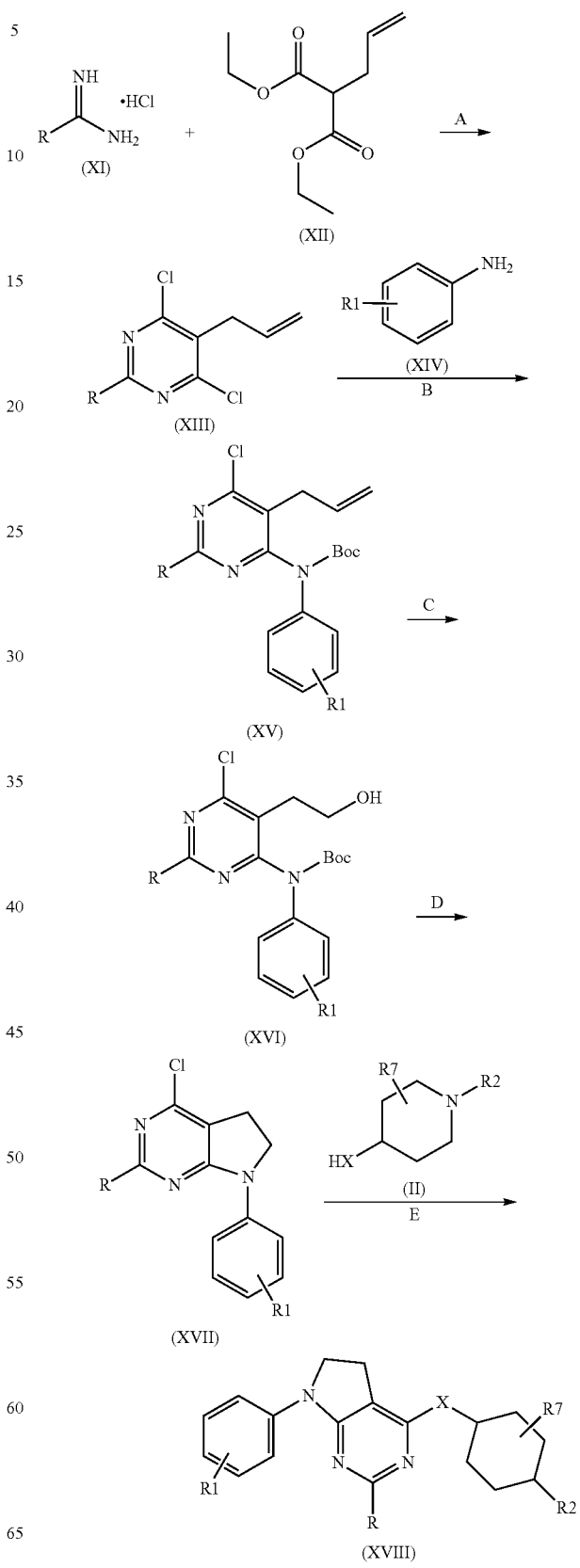

Reagents and conditions: A) NaCNBH$_3$, AcOH, RT; B) ArX (where X is I, Br), CuI, K$_3$PO$_4$, toluene or DMF, reflux; C) CuI, L-proline, NaOH, CH$_3$SO$_2$Na, DMSO, 110° C.

Reagents and conditions: A) (a) NaOMe, MeOH, RT, (b) POCl$_3$, reflux; B) (a) NaH, THF, reflux, (b) (BOC)$_2$O, DMAP (cat.), CH$_2$Cl$_2$, RT; C) (a) O$_3$, −78° C., CH$_2$Cl$_2$/MeOH, (b) NaBH$_4$, −78° C. to RT; D) (a) CH$_3$SO$_2$Cl or (CH$_3$SO$_2$)$_2$O, Et$_3$N, CH$_2$Cl$_2$, 5° C. to RT, (b) CF$_3$CO$_2$H, CH$_2$Cl$_2$, RT, (c) Et$_3$N, CH$_2$Cl$_2$, RT; E) (a) NaH, THF, reflux or K$_2$CO$_3$, solvent, (b) CuI, L-proline, NaOH, CH$_3$SO$_2$Na, DMSO, 110° C., heat; or (c) CuCN, NMP; 150° C.; or (d) HP(O)(OR)$_2$, CuI, Cs$_2$CO$_3$, toluene, reflux, or (e) PdCl$_2$(PPh$_3$)$_2$ or Pd(Ph$_3$P)$_4$, boronic acid or boronates, 2 N Na$_2$CO$_3$, THF, reflux; or (f) Sn(Bu)$_3$R, Pd catalyst, THF, reflux.

The dihydropyrrolopyrimidine-based ligands of XVIII can be prepared following the general Scheme 3. Substituted pyrimidine XIII can be obtained from a reaction between XI and XII. Compound XI can be reacted with XII to afford a 4,6-dihydroxy pyrimidine derivative. The intermediate 4,6-dihydroxypyrimidine derivative can be treated with POCl$_3$ to afford the compound XIII after work-up. Nucleophilic displacement reaction between the compound XIII and variously substituted anilines XIV can provide intermediate XV, which upon treating with (BOC)$_2$O in presence of catalytic amount of DMAP in dichloromethane can afford the compound XV. The oxidation of the compound XV by ozonolysis followed by reduction with NaBH$_4$ can give the alcohol XVI. The compound XVI upon mesylation can provide mesylate derivative of XVI. The mesylate derivative of XVI can afford, via two step sequence viz: removal of BOC with TFA followed by base treatment such as Et$_3$N or NaH, the bicyclic compound of formula XVII. For reaction conditions for these kinds of transformations, see, D. F. Romanao et al WO 2002/100863A1 incorporated by reference with regard to such synthesis.

The compound XVII can be used as an intermediate for making a variety of analogues. The compound XVII can react with the compound II to give the compound XVIII in presence of a base and solvent. The compound XVIII can be derivatized further using the standard organic reaction conditions. For example, if R$^1$ is Br or I, sulfonation can give the compound XVIII (where R$^1$ is SO$_2$R). Reaction with alkyl or aryl disulfides can give the compound XVIII (where R$^1$ is SR), and the sulfide can, in turn, be oxidized using H$_2$O$_2$ or Oxone to afford the corresponding sulfoxides. For reaction conditions, see Scheme 1 as herein described. Racemic sulfoxides of XIX (where R$^1$ is SOR) may be resolved using chiral HPLC analysis and the individual enantiomers or enantiomerically enriched mixtures can be isolated, as is appreciated in the art. The compound XVIII can be reacted with alkyl phosphonate to afford the compound where R is P(O)(OR)$_2$, and this compound, in turn, will provide the compound where R is HOP(O)(OR) via known synthetic transformations as are appreciated in the art. For reaction conditions, see S. L. Buchwald et al Org. Lett., 2003, 5, 2315 and S. Gul et al Biochem. J. 2003, 376, 813, each herein incorporated by references with regard to such synthesis. The compound XVIII can serve as a substrate for making a variety of active anlogues via known synthetic organic transformations as are appreciated in art. For example, the compound XVIII where R is CN can further be modified to give 1,3-thiazole derivatives to afford active ligands. For a related reaction conditions, see R. Olsson et al J. Med. Chem. 2005, 48, 7517, herein incorporated by references with regard to such teaching. The "R" group in the compound XVIII can serve as a "handle" to make a variety of substitutions at that position. For example, when R is halogen (preferably Cl, Br, or I) or SO$_2$R, a Suzuki reaction with alkyl, aryl, or heteroaryl boronic acids can give a variety of substitutions in that position. Likewise, if R is NH$_2$, the N-alkylation of the primary amine can give additional analogues of XVIII. If R is alkyl such as CH$_3$, oxidation can give the carboxylic acid that in turn can be used to make additional active analogues of the compound XVIII. For related reaction conditions see, Culshaw, A. J. et al J. Med. Chem. 2006, 49, 471, herein incorporated by references with regard to such teaching.

Alternatively, the bicyclic compound XVII can be prepared using the synthetic approach delineated in Scheme 4. The compound XIX can be subjected to ozonolysis conditions and the resultant product(s) reduced with NaBH$_4$ to afford the compound XX. For ozonolysis conditions see, Montgomery, J. A. et al J. Med. Chem. 1967, 10, 665; herein incorporated by reference with regard to such teachings. This compound XX, via an intermediate mesylate, can cyclize intramolecularly in basic conditions to afford the bicyclic compound XVII. For reaction conditions refer to the previous description regarding Scheme 3.

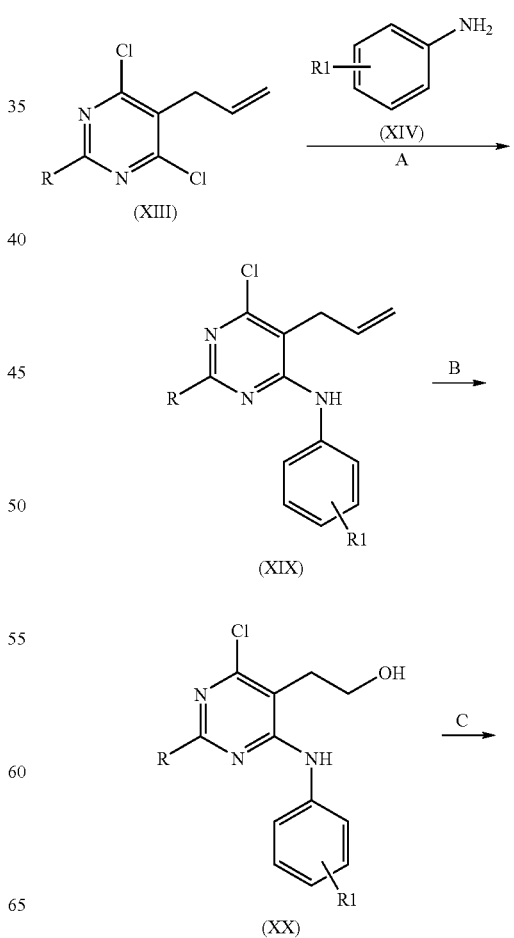

Scheme 4
Synthesis of Bicyclic Dihydropyrrolopyrimidine

-continued

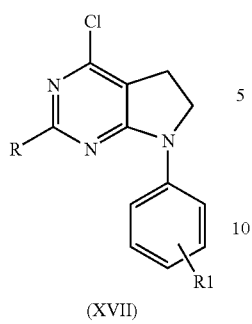

(XVII)

Reagents and conditions: A) NaH, THF, RT to reflux; B) (a) O$_3$, −78° C., CH$_2$Cl$_2$/MeOH, (b) NaBH$_4$, −78° C. to RT, C) (a) CH$_3$SO$_2$Cl or (CH$_3$SO$_2$)$_2$O, Et$_3$N, CH$_2$Cl$_2$, 5° C. to RT.

Scheme 5
Synthesis of Dihydropyrrolopyrimidine-based Ligands

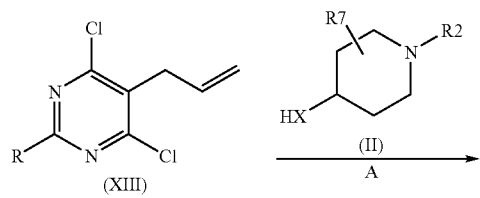

(XXIII)

R = Ms
(XXIV)

(XVIII)

Reagents and conditions: A) NaH, THF, RT to reflux; B) NaH, THF, reflux; C) (a) O$_3$, CH$_2$Cl$_2$, −70° C., (b) NaBH$_4$, MeOH, −70° C. to RT, iv) Et$_3$N, (CH$_3$SO$_2$)$_2$O, CH$_2$Cl$_2$, RT; D) CH$_3$SO$_2$Cl or (CH$_3$SO$_2$)$_2$O, Et$_3$N, CH$_2$Cl$_2$, 5° C. to RT.

In another approach, compound XIII can be converted to XXI using substituted piperidine derivative II under basic/acidic conditions to give the compound XXI. For related reaction conditions Jones, R. M. et al WO2005/5007647A1 and WO2005/121121A2, herein incorporated by reference with regard to such synthesis. Compound XXI can be reacted, under the conditions described for Scheme 3, with variously substituted anilines XIV to afford the compound XXII. The ozonolysis of XXII followed by reduction with NaBH$_4$ can give the alcohol XXIII. The compound of formula XXIII can cyclize intramolecularly via mesylate XXIV (where R is Ms) as an intermediate to afford the compound of formula XVIII. For reactions conditions and related literature references, see hereinabove Scheme 3.

Scheme 6
Synthetic Schemes for Intermediate

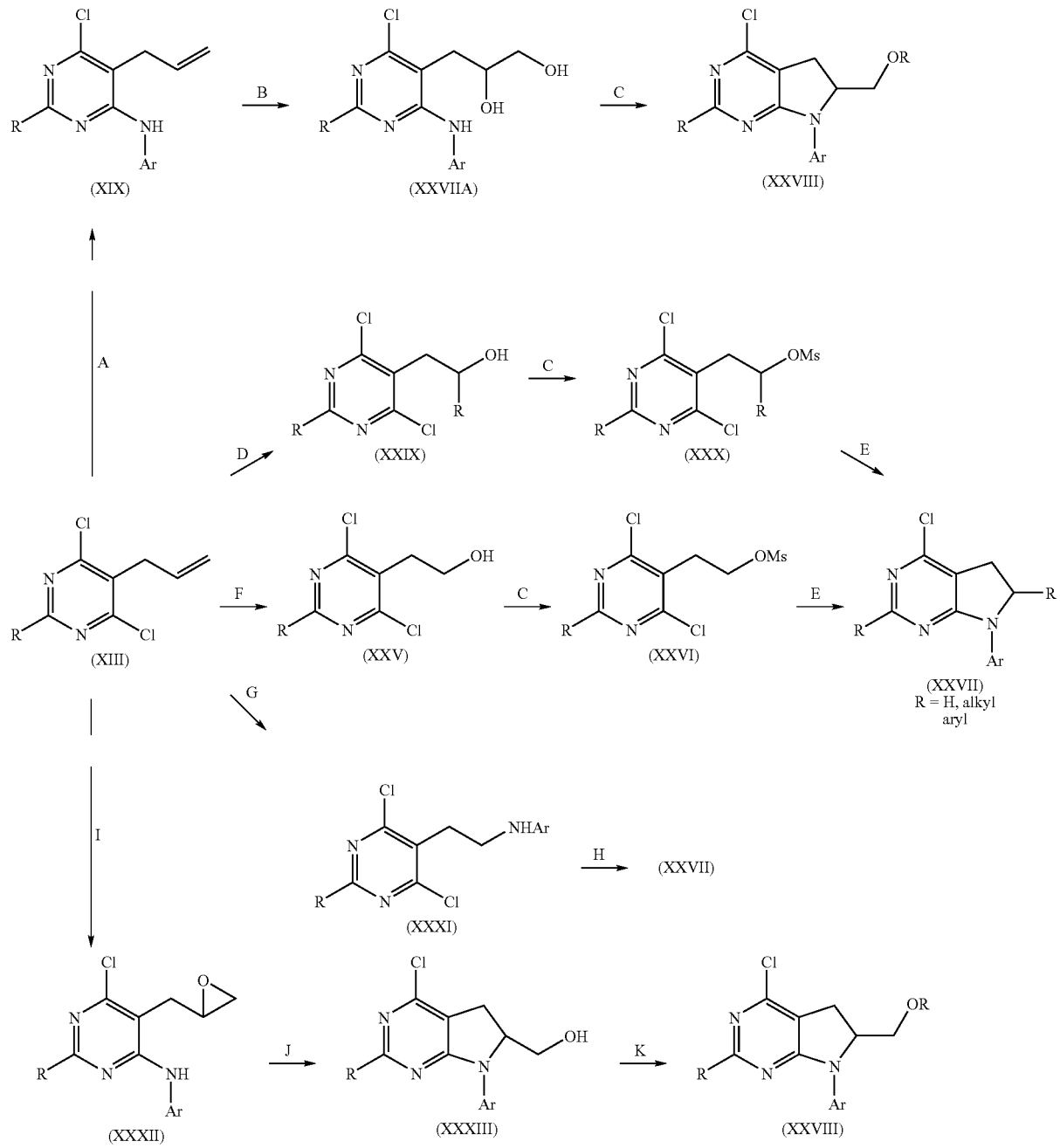

Reagents and conditions: A) NaH, THF, ArNH$_2$, THF, reflux; B) OsO$_4$, Solvent, RT; C) Et$_3$N, (CH$_3$SO$_2$)$_2$O, CH$_2$Cl$_2$, 5° C. to RT; D) (a) O$_3$, −78° C., CH$_2$Cl$_2$; (b) RMgX, THF, RT; NaBH$_4$, −78° C. to RT; E) ArNH$_2$, NaH, DMF, 0° C. to RT; F) (a) O$_3$, −78° C., CH$_2$Cl$_2$/MeOH, (b) NaBH$_4$, −78° C. to RT; G) (a) O$_3$, −78° C., CH$_2$Cl$_2$/MeOH, Me$_2$S (b) ArNH$_2$, NaC-NBH$_3$, AcOH, RT; H) CF$_3$CO$_2$H, RT; I) A, m-CPBA, CH$_2$Cl$_2$, 5° C. to RT; J) BF$_3$.Et$_2$O, CH$_2$Cl$_2$, 5° C. to RT; K) Rx, base, solvent.

The intermediates XXVII and XXVIII can be prepared using any one of the sequences delineated in Scheme 6. The compound XIII can be transformed to XIX via nucleophilic displacement reaction with substituted anilines using NaH in an aprotic solvent like THF or DMF. The compound XIX may give dihydroxy compound XXVII via dihydroxylation reaction. For reaction conditions Sharpless, K. B. et al *J. Org. Chem.*, 1992, 57, 2768., herein incorporated by reference with regard to such synthesis. The compound XXVIIA may cyclize to afford the compound of XXVIII.

The compound XIII upon ozonolysis followed by reduction with NaBH$_4$ can give the compound XXV. The compound XXV can be transformed using the same mesylation conditions described herein above to afford the bicyclic compound XXVII.

Alternatively, the compound XXVII can also be obtained via reductive amination as illustrated in Scheme 6. The aldehyde generated by oxidation of the compound XIII by ozonolysis can be coupled with a substituted aniline/substituted pyridinamine to form an imine that, in turn, can be reduced with NaCNBH₃ to give the amine compound XXXI. The amine, under acidic conditions and treated with TFA, can form the bicyclic compound XXVII. For related reaction conditions see, R. O. Hutchins et al *In Comprehensive Organic Synthesis*; B. M. Trost et al Eds.; Pergamon: Oxford, 1991; Vol. 8, p 25; and Hudlicky, M. *Reductions in Organic Chemistry*, 2nd ed.; ACS Monograph 188, 1996; p 187, each herein incorporated by reference with regard to such synthesis. The aldehyde from an olefin X111 can also be generated using K₂OsO₄.2H₂0/NaIO₄ in aqueous acetone. The aldehyde thus obtained was treated with substituted aniline or sunstituted pyridinamine in TFA or acetic acid in the presence of Na(OAc)₃BH to afford the bicyclic compound XXVII via an intermediacy of XXXI. For related reaction conditions see, Kempson, J. et al *Bioorg. Med. Chem.* 2005, 15, 1829, herein incorporated by reference with regard to such transformation.

The compound XIII can also be used to make 6-substituted compound XXVIII via the sequence delineated in Scheme 6. The compound XIII, upon treatment with m-CPBA, can give an epoxide XXXII. The epoxide XXXII may be opened intramolecularly under Lewis-acid catalyzed conditions to give the compound XXXIII. The depicted primary alcohol of compound XXXIII can be converted to a variety of functional groups by making use of reactions that are well appreciated in the art.

Another approach can be employed for the synthesis of dihydropyrrolopyrimidine ligands as shown in Scheme 7.

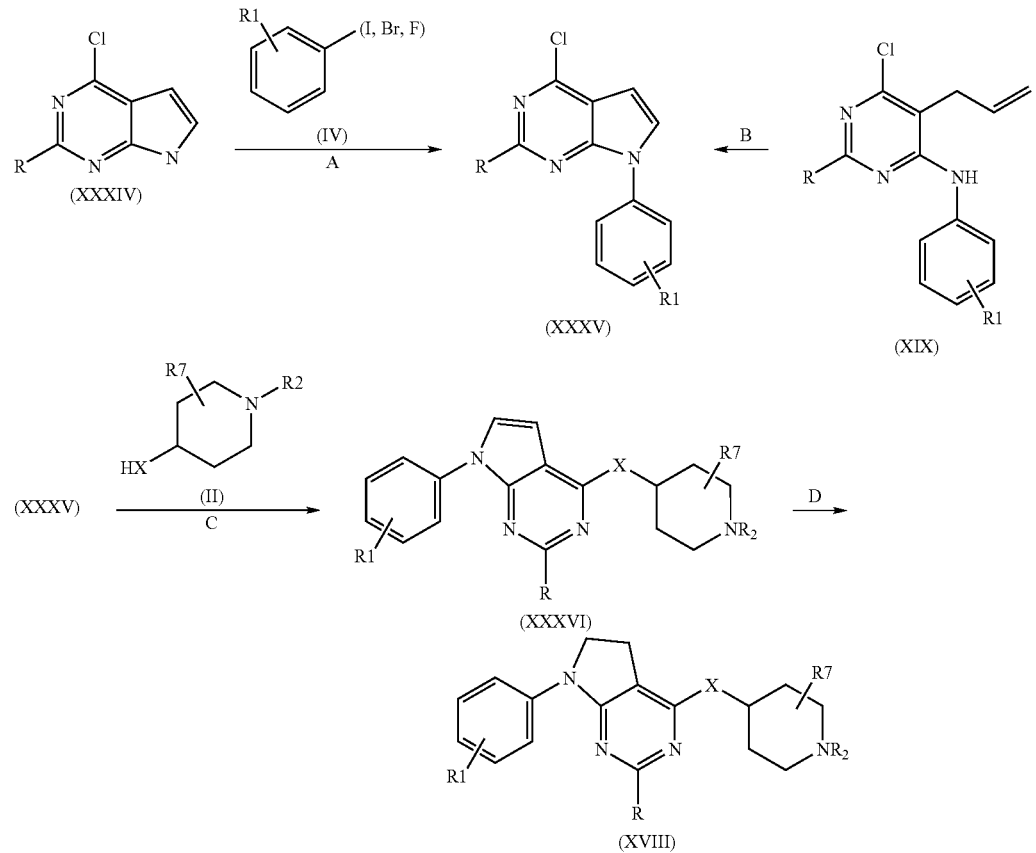

Reagents and conditions: A) CuI, K₃PO₄, toluene, Reflux; B) (a) O₃, −78° C., CH₂Cl₂; (b) Me₂S, H⁺; C) NaH, THF, reflux; D) Pd/C, H₂, ROH or EtOAc, autoclave.

The compound XXXV can be synthesized either by an N-arylation procedure using the compound XXXIV or the oxidation of the compound XIX by ozonolysis followed by intramolecular cyclization involving an aminol as an intermediate. For reaction conditions, refer herein above to Scheme 4. The compound XXXV can give the intermediate XXXVI using the reaction conditions described hereinabove for Scheme 3. The hydrogenation, under autoclave conditions, of the compound XXXVI can afford the compound XVIII. For reaction conditions see, S, Senda., Jpn. Kokai Tokkyo Koho (1972), 2 pp., JP 47025192 19721019; JP 71-14817 19710317, herein incorporated by reference with regard to such synthesis.

A variety of dihydropyrrolopyrimidines can be prepared by using the compound XVIII by following reaction conditions that are well appreciated in the art.

Scheme 8
Preparation of Dihydropyrrolopyrimidine-based Ligands

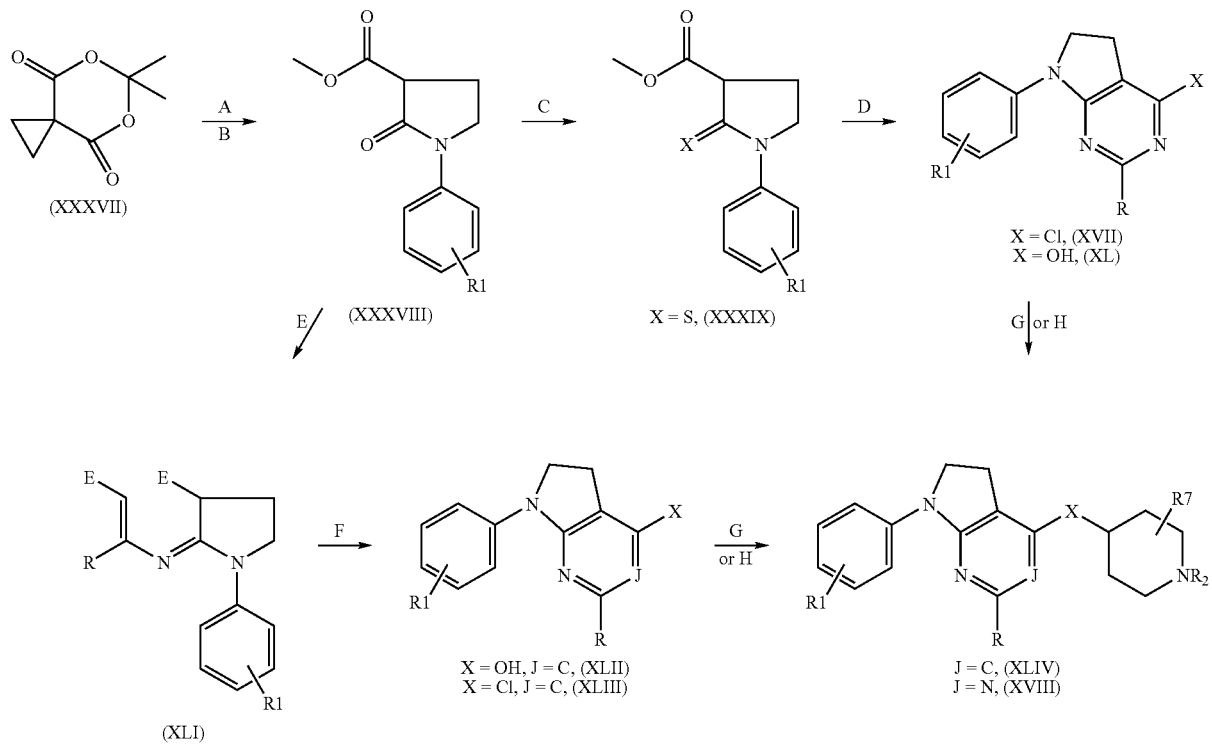

Reagents and conditions: A) ArNH$_2$, RT; B). MeOH, H$_2$SO$_4$ (cat.), reflux; C) P$_2$S$_5$ or Lawesson Reagent, THF, reflux; D) (a) R—C(NH$_2$)=NH, base, solvent, reflux; (b) POCl$_3$, reflux; E) RC(NH$_2$)=CH—CO$_2$R, POCl$_3$, reflux; F) NaOMe, MeOH, Reflux, H$^+$; G) II, NaH, THF, reflux; H) II, Mitsunobu conditions, hereinabove Scheme 1, A.

An alternative synthetic approach for making ligands of formulae XVIII and XLIV is delineated in Scheme 8. The cyclopropyl compound XXXVII can be treated with variously substituted anilines to afford 2-oxo-1-aryl-3-pyrrolidinecarboxylic acid, which upon esterification using Fisher esterification protocol, can afford the compound XXXVIII. For reaction conditions see, Organic Syntheses, Coll, Vol, 7, p. 411 (1990); Vol. 60, p. 66 (1981) and for Fischer-Speier esterification protocol Vogel's Textbook of Practical Organic Chemistry 5$^{th}$ Ed, 1989, p. 700, each herein incorporated by references with regard to such teaching. Thionation of XXXVIII using P$_2$S$_5$ or Lawesson reagent can give the compound XXXIX. For related reaction conditions and references, see J. B. Charles et al US1994/5302722, herein incorporated by reference with regard to such synthesis The compound XVII or XL can give the compound XVIII or XLIV respectively by following the reaction conditions illustrated in Scheme 8.

Alternatively, the compound XXXVIII can be converted to the compound of formula XLI using the reagents and conditions described in Scheme 8. The compound XLI can give the compound XLII via intramolecular cyclization under basic conditions. For the related reaction sequence and reaction conditions, see A. Daniele et al WO 2004/094420A1, herein incorporated by reference with regard to such synthesis. The hydroxyl compounds XXXX and XLII can be converted to the corresponding chloroderivatives XVII and XLIII, respectively, using POCl$_3$. The bicyclic compounds XVII or XL can be transformed to the desired product XVIII using either basic or Mitsunobu reaction conditions. Similarly XLII or XLIII can also be converted to the desired compounds XLIV.

The intermediate XXXVIII can also be synthesized using the methods shown in Scheme 9. In one approach, γ-butyrolacotone XLIV can be reacted with variously substituted anilines followed by carbomethoxylation procedure, using dimethylcarbonate, to afford the keto ester XXXVIII. For reaction conditions and literature references, see Lizuka Hajime EP 95/0668275A1, herein incorporated by reference with regard to such synthesis. Alternatively, the compound XXXVIII can also be obtained from 2-pyrrolidinone XLV by following N-arylation with substituted anilines and carbomethoxylation under basic conditions. For reaction conditions see, Deng, W., et al *Tetrahedron Lett.*, 2004, 45, 2311, herein incorporated by reference with regard to such synthesis.

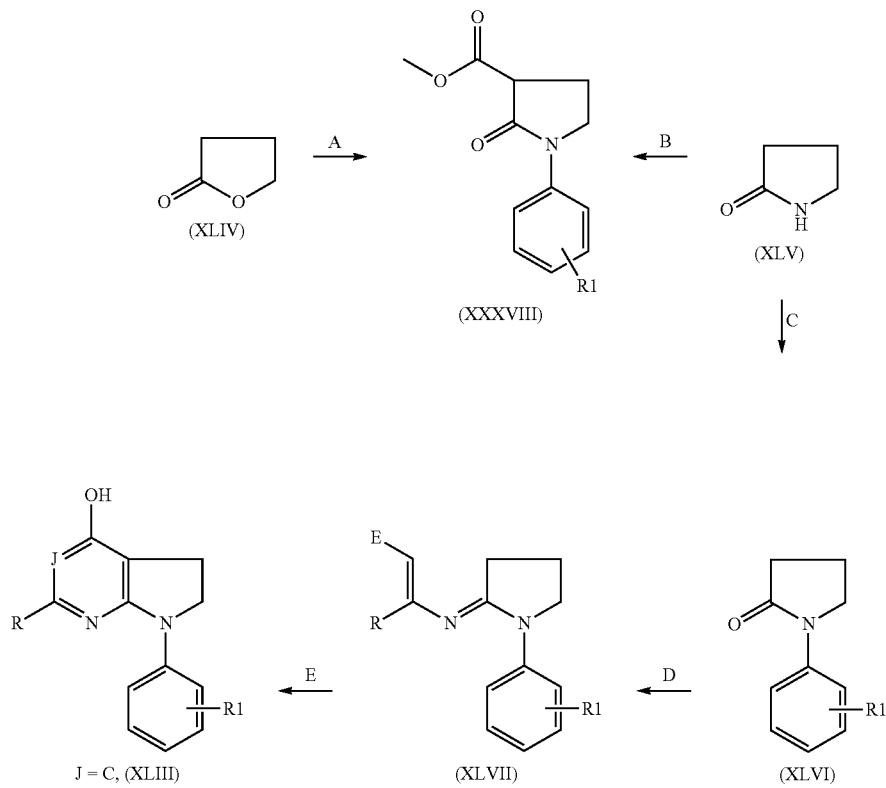

Reagents and Conditions: A) (a) ArNH$_2$, heat, (b) NaH, CO(OMe)$_2$, THF; B) (a) CuI, K$_3$PO$_4$, ArX, toluene, (b) NaH, CO(OMe)$_2$, THF; C) Step (a) in B; D) RC(NH$_2$)=NH, POCl$_3$, reflux; E) t-BuOK, t-BuOH or NaOMe, MeOH, reflux, H$^+$.

Ligands XLIII can also be prepared using the synthetic strategy as illustrated in Scheme 9. Intermediate XLVI can be prepared from 2-pyrrolidinone using an appropriate aryl halide as will be appreciated by those skilled in the art. For reaction conditions, see hereinabove Scheme 7. The compound XLVI can be transformed to the compound XLVII with a dehydrating agent such as POCl$_3$. The compound XLVII may be converted to the intermediate XLIII using basic conditions. For reaction conditions as well as a literature reference, refer hereinabove to Scheme 8.

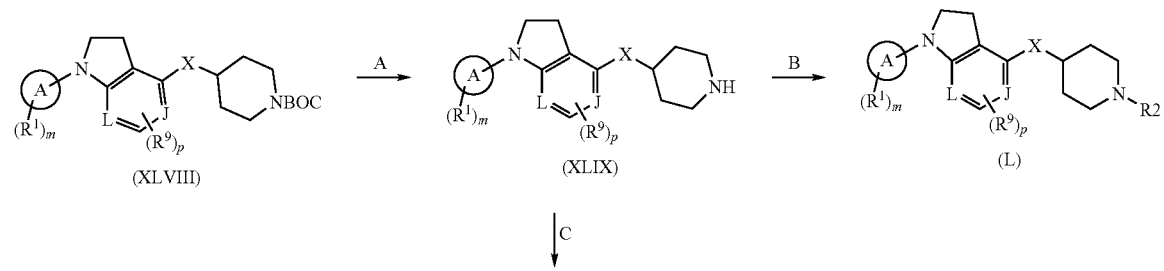

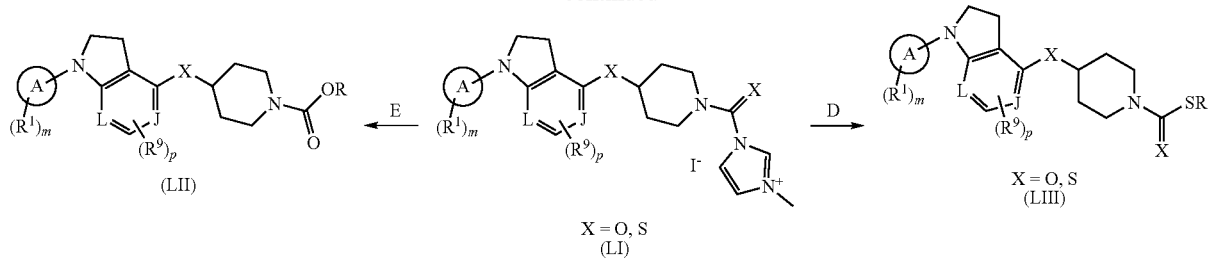

Reagents and conditions: A) CF$_3$CO$_2$H, CH$_2$Cl$_2$, RT, B) Et$_3$N, ClCO$_2$R or alkyl or aryl halides, CH$_2$Cl$_2$, RT, C) i. Im$_2$CO or Im$_2$CS, CH$_2$Cl$_2$, RT, ii. MeI, CH$_2$Cl$_2$/CH$_3$CN, RT, D) ArSH or RSH, Et$_3$N, CH$_2$Cl$_2$, RT, E) ArOH or ROH, Et$_3$N, CH$_2$Cl$_2$, RT The R2 substitution in the general formula can be changed by treating XLVIII with TFA in CH$_2$Cl$_2$ followed by reaction with an intermediate XLIX with appropriate acylating or alkylating or arylating reagents in the presence of a base and solvent to afford compound of the formula L (Scheme 10). The synthesis of carbamates LII and thiocarbamates LIII can be accomplished using carbamoyl imidazolium salts of the formula LI and the appropriate nucleophiles. For reaction conditions see Batey, R. A., *Tetrahedron Lett.*, 1999, 40, 2669, herein incorporated by reference with regard to such teachings.

Scheme 11
General Synthesis of Sulfides, Sulfoxides, Sulfoximines, and Sulfilimines
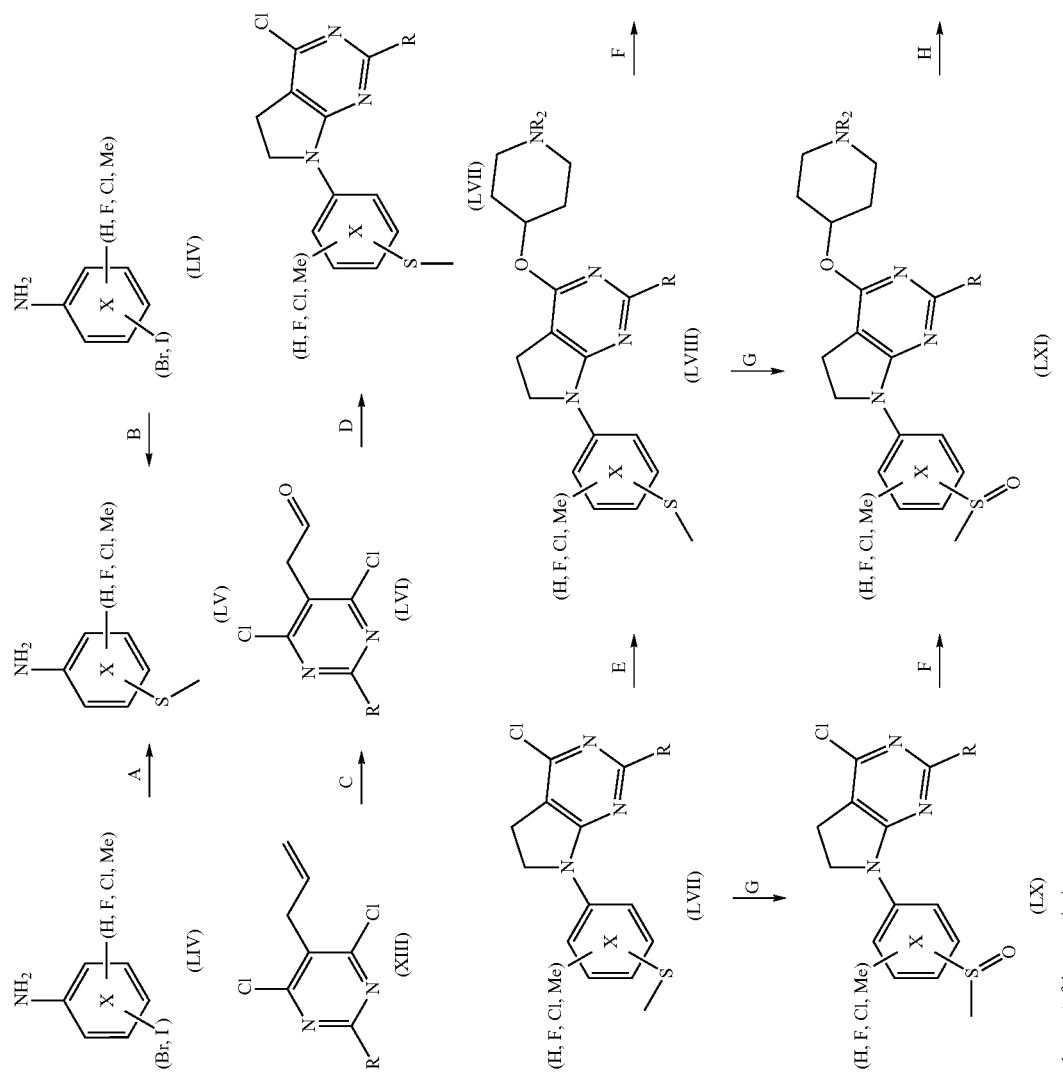
X can be a part of the aromatic ring
X = (N)$_n$
n = 1, 2, 3

Reagents and Conditions: A) NiBr$_2$, Zn, bpy, (MeS)$_2$, DMF, 110° C., B) MeSNa, Cu, MeOH, heat, C) K$_2$OsO$_4$.2H$_2$O or OsO$_4$/NMO, NaIO$_4$, aqueous acetone, RT, D) LV Na (OAc)$_3$BH, TFA, or CH$_3$CO$_2$H, −15° c. to RT, E) II, NaH, THF, reflux, F) MSH, CH$_2$Cl$_2$, RT, G) i. H$_2$O$_2$, HFIP, RT or ii Asymmetric sulfoxidation, Ti(O$^i$Pr)$_4$, D or L-diethyl tartrate, tBuOOH, toluene or any known procedures in the art, H) MSH, CH$_2$Cl$_2$, RT or racemic LXI, (S)-(+) or (R)-(−)-camphorsulfonic acid, acetone.

Compounds represented by LIV may include up to three heteroatoms, prefereably N. The synthesis of sulfide of the formula LVIII, sulfoxide of the formula LXI, sulfilimine of the formula LIX, and sulfoximines of the formula LXII can be synthesized by following the synthetic routes delinated in scheme 11. The required substituted sulfide LV can be prepared by following the procedures known in the art, for realated reaction conditions see Taniguchi, N. *J. Org. Chem.* 2004, 69, 6904 (route A), Wade, P. C. et al U.S. Pat. No. 4,221,796A (route B), herein incorporated by a reference with reagard to such teachings. The aldehyde LVI can be prepared either by ozonolysis or by reaction with K$_2$OsO$_4$.2H$_2$O and NaIO$_4$. The reductive amination between the aniline LV and an aldehyde LVI using the acidic conditions in the presence of Na(OAc)$_3$BH can give the bicyclic core LVII. For related reaction conditions see Kempson, J, et al *Bioorg. Chem. Lett.* 2005, 15, 1829, herein incorporated by reference with regard to such teachings. The compound LVII upon reaction with compound II in the presence of base and solvent afforded the sulfide of the formula LVIII. The sulfide LVIII would serve as a starting substrate for the preparation of a variety of analogues, for example sulfilimines LX can be prepared using the conditions that were reported in the art. For reaction conditions see, Tamura, Y. et al *Tetrahedron Lett.* 1972, 4137 and Bolm, C. et al *Org. Lett.* 2006, 8, 2349, herein incorporated by a references with regard to such teaching. The sulfides of the formulae LVII and LVIII can be oxidized using asymmetric sulfoxidation procedure to give enantiopure sulfoxides. In general enantiopure chiral sulfoxides can be prepared using any one of the known procedures: a) resolution of racemic mixtures, b) the asymmetric synthesis. For the details on the enantiopure sulfoxides synthesis and related references see, a review by Bolm, C. et al *Adv. Synth. Catal.* 2005, 347, 19-31. The enantiopure sulfoxides of the formulae LX and LXI can be prepared via a selective oxidation of prochiral sulfoxides LVII and LVIII using H$_2$O$_2$ and hexafluoroisopropanol (HFIP) followed by chiral HPLC analysis to afford entiopure or enriched R and S sulfoxides. The absolute stereochemistry of the enantiopure sulfoxides can be determined by VCD spectroscopy. For related analysis see, Stephens, P. J. et al *J. Org. Chem.* 2001, 66, 3671, herein incorporated by a reference for such analysis. The sulfoxide LX can be transformed to an advanced sulfoxide LXI using the compound 11 and base and solvent. The enantiopure sulfoximines can be prepared using the enatiopure sulfoxide of the formula LXI by following the procedure reported in the art using o-mesitylsulfonylhydroxylamine (MSH) or by resolution of racemic sulfoximines. For reaction conditions see Johnson, C. R. et al *J. Org. Chem.* 1974, 39, 2458, and Gaillard, S. et al *Tetrahedron* 2005, 61, 8138 and Brandt, J. et al *Tetrahedron: Asymmetry* 1997, 8, 909, Gaillard, S. et al *Tetrahedron* 2005, 61, 8138, herein incorporated by a references with regard to such teachings.

Examples

The following specific examples are included as illustrations and are not to be construed as limiting the scope of the present invention.

Example 1 (10)

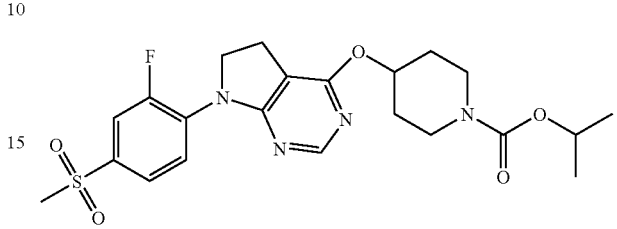

Step 1: 6-Hydroxy-5-(2-propen-1-yl)-4(1H)-pyrimidinone (1)

To a solution of sodium methoxide (0.5 M in MeOH, 1.89 L, 0.95 mol) was added formamidine hydrochloride (39.0 g, 0.48 mol) at ambient temperature under N$_2$. The mixture was stirred at RT for 1 h. Diethyl allylmalonate (91.5 mL, 0.46 mol) was added to the above mixture and the resulting reaction mixture was stirred at RT for 36 h. The reaction mixture was filtered and the filtrate was concentrated under reduced pressure to afford the crude solid material. The crude material was dissolved in H$_2$O (1000 mL) and acidified with concentrated HCl. The solid was filtered and dried to afford 62.8 g (90%) of the title compound 1 as a white solid. $^1$H NMR (400 MHz, DMSO-d$_6$): δ 11.65 (br s, 2H), 7.90 (s, 1H), 5.79-5.71 (m, 1H), 4.94-4.90 (app. dd, J$_1$=17.2 Hz, J$_2$=2.0 Hz, 2H), 2.96 (d, J=6.0 Hz, 2H); LCMS (ESI): m/z 153 (M+H)$^+$.

Step 2: 4,6-Dichloro-5-(2-propen-1-yl) pyrimidine (2)

A round-bottomed flask was charged, under N$_2$, with 6-hydroxy-5-(2-propen-1-yl)-4(1H)-pyrimidinone (1) (19.0 g, 125.0 mmol) and phosphorous oxychloride (200 mL). The mixture was refluxed for 4 h and then cooled to RT. The reaction mixture was poured very slowly into ice cold (5° C.) water (2000 mL) with vigorous stirring. The product was extracted with CH$_2$Cl$_2$ (4×250 mL). The combined organic layer was washed with sat. NaHCO$_3$ (1×100 mL), brine (1×50 mL), dried over Na$_2$SO$_4$, filtered, and the filtrate concentrated under reduced pressure to afford 22.70 g (96%) of the title compound 2 as a light yellow oil. $^1$H NMR (400 MHz, DMSO-d$_6$): δ 8.08 (s, 1H), 5.90-5.80 (m, 1H), 5.17-5.09 (app. m, 2H), 3.65 (app. d, J=6.4 Hz, 2H)); LCMS (ESI): m/z 190 (M+H)$^+$.

Step 3: 2-Fluoro-4-(methylsulfonyl)aniline (3)

As previously described hereinabove, the following example is a representative procedure for the conversion of an aryl halide to a corresponding sulphone derivative.

A mixture of 4-bromo-2-fluoroaniline (9.5 g, 50.0 mmol), sodium methanesulfinate (6.13 g, 60.0 mmol), copper iodide (0.95 g, 5.0 mmol), L-proline (1.15 g, 10.0 mmol), NaOH (0.40 g, 10.0 mmol), and DMSO (60 mL) in a sealed tube (pressure tube) was stirred at 95° C. for 60 h. The reaction was cooled to room temperature and then partitioned between EtOAc and water (1:1, 1000 mL). The layers were separated and the aqueous phase was further extracted with EtOAc (2×300 mL). The combined organic layer was washed with brine (1×100 mL), dried over $Na_2SO_4$, filtered, and the filtrate was concentrated under reduced pressure to afford the crude product. The product was purified by $SiO_2$ flash column chromatography to afford 7.41 g (78%) of the title product 3 as an off-white solid. $^1H$ NMR (400 MHz, DMSO-$d_6$): δ 7.47 and 7.44 (dd, $J_1$=11.2 Hz, $J_2$=2.0 Hz, 1H), 7.40 and 7.37 (dd, $J_1$=8.8 Hz, $J_2$=2.0 Hz, 1H), 6.84 (app. t, J=6.8 Hz, 1H), 6.17 (s, 2H), 3.07 (s, 3H); LCMS (ESI): m/z 190 (M+H)$^+$.

Step 4: 6-Chloro-N-[2-fluoro-4-(methylsulfonyl) phenyl]-5-(2-propen-1-yl)-4-pyrimidinamine (4)

To a mixture of NaH (7.94 g, 60% dispersion in mineral oil, washed with anhydrous toluene) and anhydrous THF (50 mL) was added, at RT under $N_2$, 2-fluoro-4-(methylsulfonyl) aniline (3) (12.51 g, 66.12 mmol) in THF (150 mL). The mixture was stirred at RT for 1 h and then compound 2 (12.50 g, 66.12 mmol) in THF (50 mL) was added. The resulting reaction mixture was refluxed for 3 h. The mixture was allowed to cool to room temperature and then poured slowly into $H_2O$ (600 mL) and the mixture was extracted with EtOAc (4×300 mL). The combined organic layer was washed with brine (1×50 mL), dried over $Na_2SO_4$, filtered, and the filtrate concentrated under reduced pressure. The crude product was crystallized from EtOAc to give 10.3 g of solid material. The mother liquor was concentrated and purified by $SiO_2$ flash column chromatography to give an additional 9.35 g of product. A total yield of 19.65 g (87%) of the title compound 4 was obtained as an off-white solid. $^1H$ NMR (400 MHz, DMSO-$d_6$): δ 9.10 (s, 1H), 8.29 (s, 1H), 7.84-7.82 (dd, $J_1$=9.2 Hz, $J_2$=1.6 Hz, 1H), 7.78-7.72 (m, 2H), 5.96-5.86 (m, 1H), 5.11 and 5.09 (dd, $J_1$=10.4 Hz, $J_2$=1.2 Hz, 1H), 5.07 and 5.03 (dd, $J_1$=16.0 Hz, $J_2$=1.6 Hz, 1H), 3.58 (d, J=5.6 Hz, 2H), 3.27 (s, 3H); LCMS (ESI): m/z 342 (M+H)$^+$.

Step 5: 1,1-Dimethylethyl[6-chloro-5-(2-propen-1-yl)-4-pyrimidinyl][2-fluoro-4-(methylsulfonyl)phenyl]carbamate (5)

To a solution of compound 4 (9.0 g, 26.3 mmol) and $CH_2Cl_2$ (200 mL) was added catalytic amount of DMAP (0.32 g, 2.63 mmol). Bis(1,1-dimethylethyl)dicarbonate (8.61 g, 39.5 mmol) was introduced to the above mixture slowly and the resulting mixture was stirred at RT for 15 h. The mixture was diluted with $CH_2Cl_2$ (250 mL), washed with $H_2O$ (2×40 mL), brine (1×30 mL), dried over $Na_2SO_4$, and filtered. The filtrate was concentrated under reduced pressure to afford the crude product, which was purified by $SiO_2$ flash column chromatography to give 10.46 g (90%) of the title product 5 as an off-white solid. $^1H$ NMR (400 MHz, DMSO-$d_6$): δ 8.84 (s, 1H), 7.96 and 7.94 (dd, $J_1$=10.0 Hz, $J_2$=2.0 Hz, 1H), 7.74 and 7.72 (dd, $J_1$=8.4 Hz, $J_2$=2.0 Hz, 1H), 7.48 (app. t, J=8.0 Hz, 1H), 5.84-5.74 (m, 1H), 5.07 (app. d, J=11.2 Hz, 1H), 4.97 (app. d, J=17.2 Hz, 1H), 3.47 (app. d, J=5.6 Hz, 2H), 3.29 (s, 3H), 1.39 (s, 9H); LCMS (ESI): m/z 442 (M+H)$^+$.

Step 6: 1,1-Dimethylethyl[6-chloro-5-(2-hydroxyethyl)-4-pyrimidinyl][2-fluoro-4-(methylsulfonyl)phenyl]carbamate (6)

A solution of 5 (10.35 g, 23.42 mmol) and $CH_2Cl_2$ (300 mL) was cooled to −70° C. and treated with a stream of ozone that was generated by an ozone generator for 2.5 h. The reaction mixture became light blue upon completion. Methanol (30 mL) and $NaBH_4$ (3.54 g, 93.68 mmol) were introduced to the cold reaction mixture. The mixture was stirred at −70° C. for 1 h and at RT for 2 h. The reaction mixture was poured into $H_2O$ (1000 mL) and then layers were separated. The aqueous phase was further extracted with $CH_2Cl_2$ (4×250 mL). The combined organic layer was washed with brine (1×50 mL), dried over $Na_2SO_4$, and then concentrated under reduced pressure to afford the crude material, which was purified by flash $SiO_2$ flash column chromatography to give 3.32 g (32%) of the title compound 6 as a white solid. $^1H$ NMR (400 MHz, DMSO-$d_6$): δ 8.75 (s, 1H), 7.97 and 7.95 (dd, $J_1$=9.6 Hz, $J_2$=2.0 Hz, 1H), 7.75 and 7.73 (dd, $J_1$=8.0 Hz, $J_2$=1.6 Hz, 1H), 7.67 and 7.65 (app. t, J=7.6 Hz, 1H), 4.99 (t, J=5.6 Hz, 1H), 3.68 (q, J=6.0 Hz, 2H), 3.31 (s, 3H), 2.89 (t, J=6.4 Hz, 2H), 1.38 (s, 9H); LCMS (ESI): m/z 446 (M+H)$^+$.

Step 7: 2-(4-Chloro-6-{{[(1,1-dimethylethyl)oxy]carbonyl}[2-fluoro-4-(methylsulfonyl)phenyl]amino}-5-pyrimidinyl)ethyl methanesulfonate (7)

To a solution of 6 (3.22 g, 7.22 mmol) and $CH_2Cl_2$ (50 mL) were added $Et_3N$ (3.0 mL, 21.66 mmol), and DMAP (88 mg, 0.72 mmol). The solution was cooled to 5° C. and then methanesulfonic anhydride (1.89 g, 10.83 mmol) was introduced in portions. The reaction mixture was stirred at RT for 15 h under $N_2$. The mixture was diluted with $CH_2Cl_2$ (150 mL) and then washed with water (2×30 mL), brine (1×30 mL), dried over $Na_2SO_4$, and filtered. The filtrate was concentrated under reduced pressure to afford the crude product that was purified by $SiO_2$ flash column chromatography to give 3.56 g (97%) of the title product 7 as a white solid. This material was used without further characterization in the next step.

Step 8: 4-Chloro-7-[2-fluoro-4-(methylsulfonyl)phenyl]-6,7-dihydro-5H-pyrrolo[2,3-d]pyrimidine (8)

To a solution of 7 (3.55 g, 7.02 mmol) and $CH_2Cl_2$ (38 mL) was added, at RT under $N_2$, $CF_3COOH$ (12 mL). The reaction mixture was stirred at RT for 3 h and then concentrated under reduced pressure to afford the crude reaction mixture. The mixture was redissolved in $CH_2Cl_2$ (50 mL) and then treated with $Et_3N$ (5 mL) at RT for 2 h. The reaction mixture was concentrated under reduced pressure and then subjected to $SiO_2$ column chromatography to give 2.05 g (89%) of the title product 8 as a light yellow solid. $^1H$ NMR (400 MHz, DMSO-$d_6$): δ 8.29 (s, 1H), 7.94 (app. t, J=7.6 Hz, 1H), 7.91 and 7.88 (dd, $J_1$=15.6 Hz, $J_2$=1.6 Hz, 1H), 7.80-7.78, (dd, $J_1$=8.4 Hz, $J_2$=2.0 Hz, 1H), 4.20 (t, J=8.4 Hz, 2H), 3.27 (s, 3H), 3.23 (t, J=8.8 Hz, 2H); LCMS (ESI): m/z 328 (M+H)$^+$.

The bicyclic compound 8 was also synthesized, in good yield, by following the synthetic process as described hereinabove in Scheme 4.

Step 9: 1-Methylethyl 4-hydroxy-1-piperidinecarboxylate (9)

To a cold (5° C.) solution of 4-hydroxypiperidine (40.46 g, 0.40 mol) and $CH_2Cl_2$ (500 mL) was added diisopropylethylamine (140 mL, 0.80 mol) under $N_2$. A 1 M solution of isopropyl chloroformate (500 mL, 0.50 mol) in toluene was added dropwise over a period of 4 h. The resulting reaction mixture was stirred at RT for 48 h. The reaction mixture was washed with water (2×100 mL) and brine (1×100 mL), dried over $Na_2SO_4$, filtered, and concentrated under reduced pressure. The crude product was purified by flash column chromatography to afford 64.60 g (86%) of the title product 9 as colorless oil. $^1$H NMR (400 MHz, DMSO-d$_6$): δ 4.72 (m, 1H), 3.68-3.62 (m, 2H), 3.60 (septuplet, J=4.4 Hz, 1H), 2.96 (br m, 2H), 1.68-1.62 (m, 2H), 1.26-1.18 (m, 2H), 1.14 (d, J=6.4 Hz, 6H).

Step 10: 1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate (10)

To a stirred solution of NaH (0.73 g, 60% dispersion in mineral oil, washed with anhydrous toluene) and anhydrous THF (15 mL) was added 9 (1.09 g, 5.80 mmol) in THF (15 mL). The mixture was refluxed for 0.5 h and then cooled to RT. Compound 8 (2.0 g, mmol) in THF (30 mL) was added and the reaction refluxed for 1.5 h. The reaction mixture was cooled to RT, poured into H$_2$O (150 mL) and then extracted with CH$_2$Cl$_2$ (4×60 mL). The combined organic layer was dried over Na$_2$SO$_4$, filtered, and then concentrated under reduced pressure. The crude product was purified by flash SiO$_2$ column chromatography using CHCl$_3$:MeOH (100:0 to 98:02) as eluent to afford 1.96 g (71%) of the title product 10 as a white solid. $^1$H NMR (400 MHz, DMSO-d$_6$): δ 8.22 (s, 1H), 7.96 (app. t, J=8.4 Hz, 1H), 7.85 and 7.82 (dd, J$_1$=11.2 Hz, J$_2$=2.0 Hz, 1H), 7.75-7.73 (dd, J$_1$=8.4 Hz, J$_2$=2.0 Hz, 1H), 5.30-5.24 (m, 1H), 4.76 (septuplet, J=6.0 Hz, 1H), 4.14 (t, J=8.4 Hz, 2H), 3.70-3.64 (m, 2H), 3.25 (s, 3H), 3.40-3.21 (m, 2H), 3.05 (t, J=8.8 Hz, 2H), 1.95-1.90 (m, 2H), 1.67-1.51 (m, 2H), 1.17 (d, J=206.0 Hz, 6H); LCMS (ESI): m/z 479 (M+H)$^+$.

Example 2 (11)

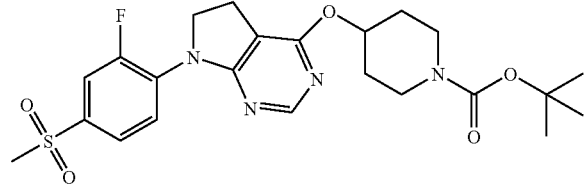

1,1-Dimethylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate (11)

The procedure described for 10 was employed using 1,1-dimethylethyl 4-hydroxy-1-piperidinecarboxylate (0.816 g, 4.1 mmol), NaH (0.51 g, 60% dispersion in mineral oil, 12.8 mmol), and compound 8 (1.40 g, 4.27 mmol). Aqueous work-up followed by purification gave 1.45 g (73%) of the title product 11 as a light yellow solid. $^1$H NMR (400 MHz, DMSO-d$_6$): δ 8.22 (s, 1H), 7.96 (app. t, J=7.6 Hz, 1H), 7.85 and 7.82 (dd, J$_1$=11.2 Hz, J$_2$=2.0 Hz, 1H), 7.75 and 7.73 (dd, J$_1$=8.4 Hz, J$_2$=2.0 Hz, 1H), 5.26 (m, 1H), 4.14 (t, J=8.0 Hz, 2H), 3.68-3.62 (m, 2H), 3.25 (s, 3H), 3.18-3.16 (m, 2H), 3.05 (t, J=9.2 Hz, 2H), 1.94-1.89 (m, 2H), 1.59-1.53 (m, 2H), 1.39 (s, 9H); LCMS (ESI): m/z 493 (M+H)$^+$.

Example 3 (13)

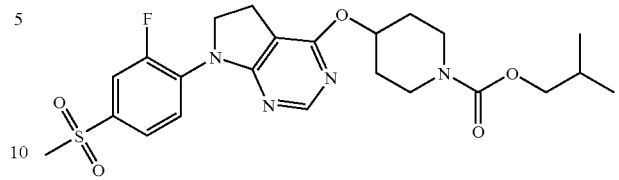

Step 1: 2-Methylpropyl 4-hydroxy-1-piperidinecarboxylate (12)

The procedure described for 9 was employed using 4-hydroxypiperidine (10.2 g, 100 mmol), diisopropylethylamine (35 mL, 200 mmol), and isobutyl chloroformate (17.1 g, 125 mmol). Standard aqueous work-up followed by purification gave 18.45 g (92%) of title product 12 as colorless oil. $^1$H NMR (400 MHz, DMSO-d$_6$): δ 4.70 (d, J=4.0 Hz, 1H), 3.74 (d, J=6.4 Hz, 2H), 3.69-3.65 (m, 2H), 3.61 (m, 1H), 3.00 (br s, 2H), 1.83 (app. septuplet, J=6.8 Hz, 1H), 1.69-1.65 (m, 2H), 1.26-1.21 (m, 2H), 0.85 (d, J=6.4 Hz, 6H).

Step 2: 2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate (13)

The procedure described for 10 was employed using the compound 8 (100 mg, 0.31 mmol), NaH (35 mg, 60% dispersion in mineral oil, 0.87 mmol), compound 12 (59 mg, 0.29 mmol) and THF (10 mL). Standard aqueous work-up followed by purification gave 118 mg (83%) of the title product 13 as a white solid. The product was lyophilized from acetonitrile to afford a white material. $^1$H NMR (400 MHz, DMSO-d$_6$): δ 8.22 (s, 1H), 7.96 (app. t, J=8.0 Hz, 1H), 7.85 and 7.82 (dd, J$_1$=10.8 Hz, J$_2$=1.6 Hz, 1H), 7.75 and 7.73 (dd, J$_1$=8.8 Hz, J$_2$=2.0 Hz, 1H), 5.28 (m, 1H), 4.14 (t, J=8.0 Hz, 2H), 3.78 (d, J=6.8 Hz, 2H), 3.71-3.68 (m, 2H), 3.25 (s, 3H), 3.30-3.27 (m, 2H), 3.05 (t, J=8.8 Hz, 2H), 1.97-1.91 (m, 2H), 1.88-1.80 (m, 1H), 1.63-1.54 (m, 2H), 0.87 (d, J=6.8 Hz, 6H); LCMS (ESI): m/z 493 (M+H)$^+$.

Example 4 (15)

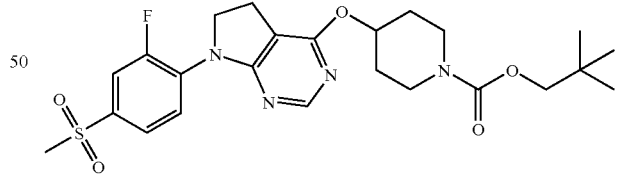

Step 1: 2,2-Dimethylpropyl 4-hydroxy-1-piperidinecarboxylate (14)

The procedure described for 9 was utilized using 4-hydroxypiperidine (3.32 g, 32.8 mmol), diisopropylethylamine (13.6 g, 98.5 mmol), and neopentyl chloroformate (5 mL, 32.84 mmol). The work-up followed by purification gave 5.85 g (83%) of the title product 14 as a white solid. $^1$H NMR (400 MHz, DMSO-d$_6$): δ 4.71 (app. d, J=4.4 Hz, 1H), 3.65 (s, 2H), 3.70-3.57 (m, 3H), 3.0 (br s, 2H), 1.69-1.65 (m, 2H), 1.28-1.20 (m, 2H), 0.87 (s, 9H).

Step 2: 2,2-Dimethylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate (15)

The procedure described for 10 was employed using compound 14 (33 mg, 0.145 mmol), NaH (19 mg, 0.46 mmol), and 8 (50 mg, 0.153 mmol). The aqueous work-up followed by flash SiO$_2$ column chromatography gave 53 mg (72%) of the title product 15 as a white solid. $^1$H NMR (400 MHz, DMSO-d$_6$): δ 8.23 (s, 1H), 7.96 (app. t, J=8.0 Hz, 1H), 7.85 and 7.82 (dd, J$_1$=10.8 Hz, J$_2$=1.6 Hz, 1H), 7.75 and 7.73 (dd, J$_1$=8.8 Hz, J$_2$=2.0 Hz, 1H), 5.29 (m, 1H), 4.14 (t, J=8.4 Hz, 2H), 3.70 (s, 2H), 3.73-3.64 (m, 2H), 3.25 (s, 3H), 3.30-3.27 (m, 2H), 3.06 (t, J=8.8 Hz, 2H), 1.97-1.90 (m, 2H), 1.62-1.52 (m, 2H), 0.89 (s, 9H); LCMS (ESI): m/z 507 (M+H)$^+$.

Example 5 (17)

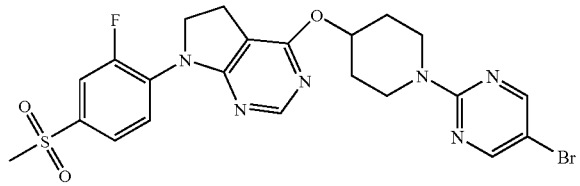

Step 1: 1-(5-Bromo-2-pyrimidinyl)-4-piperidinol (16)

A round-bottomed flask was charged, under N$_2$, with 4-hydroxypiperidine (1.93 g, 10 mmol), diisopropylethylamine (5.22 mL, 30 mmol), 5-bromo-2-chloropyrimidine (1.01 g, 10 mmol), and acetonitrile (50 mL). The mixture was refluxed for 15 h and then concentrated under reduced pressure. The crude product was redissolved in CH$_2$Cl$_2$ (150 ml), washed with H$_2$O (2×20 mL), brine (1×20 mL), dried over Na$_2$SO$_4$, and filtered. The filtrate was concentrated under reduced pressure and the crude material was purified by flash SiO$_2$ column chromatography to afford 2.55 g (99%) of the title compound 16 as a white solid. $^1$H NMR (400 MHz, DMSO-d$_6$): δ 8.34 (s, 2H), 4.73 (d, J=4.0 Hz, 1H), 4.17-4.12 (m, 2H), 3.74-3.68 (m, 1H), 3.28-3.22 (m, 2H), 1.76-1.70 (m, 2H), 1.33-1.25 (m, 2H); LCMS (ESI): m/z 260 (M+H)$^+$.

Step 2: 4-{[1-(5-Bromo-2-pyrimidinyl)-4-piperidinyl]oxy}-7-[2-fluoro-4-(methylsulfonyl)phenyl]-6,7-dihydro-5H-pyrrolo[2,3-d]pyrimidine (17)

The procedure described for 10 was utilized. 1-(5-Bromo-2-pyrimidinyl)-4-piperidinol 16 (0.968 g, 3.75 mmol) was allowed to react, under N$_2$, with 8 (0.98 g, 3 mmol) in the presence of NaH (360 mg, 9.0 mmol) and THF (40 mL). An aqueous work-up followed by purification gave 0.724 g (44%) of the title product 17 as a white solid. $^1$H NMR (400 MHz, DMSO-d$_6$): δ 8.45 (s, 2H), 8.24 (s, 1H), 7.96 (app. t, J=7.2 Hz, 1H), 7.85 and 7.82 (dd, J$_1$=10.8 Hz, J$_2$=2.0 Hz, 1H), 7.75 and 7.73 (dd, J$_1$=8.4 Hz, J$_2$=2.0 Hz, 1H), 5.37 (m, 1H), 4.16-4.09 (m, 4H), 3.25 (s, 3H), 3.06 (t, J=8.8 Hz, 2H), 2.03-1.97 (m, 2H), 1.65 (m, 2H); LCMS (ESI): m/z 550 (M+H)$^+$.

Example 6 (18)

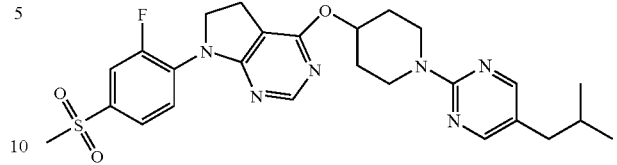

7-[2-Fluoro-4-(methylsulfonyl)phenyl]-4-({1-[5-(2-methylpropyl)-2-pyrimidinyl]-4-piperidinyl}oxy)-6,7-dihydro-5H-pyrrolo[2,3-d]pyrimidine (18)

A round-bottomed flask was charged with 17 (60 mg, 0.11 mmol), PdCl$_2$(dppf).CH$_2$Cl$_2$ (8.8 mg, 0.01 mmol), K$_2$CO$_3$ (75 mg, 0.55 mmol), (2-methylpropyl)boronic acid (34 mg, 0.33 mmol), THF (4 mL), and H$_2$O (1 mL) and the mixture was refluxed for 15 h. The reaction mixture was cooled to RT, diluted with H$_2$O (15 mL), and then extracted with EtOAc (4×20 mL). The combined organic layer was washed with brine (1×10 mL), dried over Na$_2$SO$_4$, filtered, and the filtrate was concentrated under reduced pressure to afford the crude product, which was subjected to SiO$_2$ flash column chromatography to isolate two products in near-equal proportion. The less polar compound 18 (5 mg) was identified as the desired product 18. $^1$H NMR (400 MHz, DMSO-d$_6$): δ 8.24 (s, 2H), 8.18 (s, 2H), 7.96 (app. t, J=8.0 Hz, 1H), 7.85 and 7.82 (dd, J$_1$=10.8 Hz, J$_2$=2.8 Hz, 1H), 7.75 and 7.73 (dd, J$_1$=8.4 Hz, J$_2$=1.6 Hz, 1H), 5.35 (m, 1H), 4.20-4.16 (m, 4H), 4.14 (app. t, J=8.4 Hz, 2H), 3.49 (m, 2H), 3.25 (s, 3H), 3.05 (t, J=8.4 Hz, 2H), 2.26 (d, J=7.2 Hz, 2H), 1.72 (m, 1H), 1.63 (m, 2H), 0.83 (d, J=6.4 Hz, 6H); LCMS (ESI): m/z 527 (M+H)$^+$.

Example 7 (19)

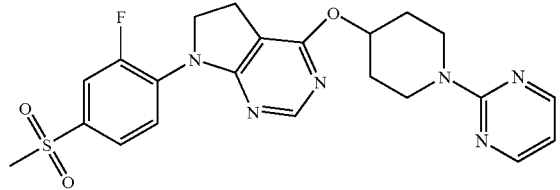

7-[2-Fluoro-4-(methylsulfonyl)phenyl]-4-{[1-(2-pyrimidinyl)-4-piperidinyl]oxy}-6,7-dihydro-5H-pyrrolo[2,3-d]pyrimidine (19)

The more polar compound 19 (5 mg) obtained as hereinabove described (Example 6) was identified as the compound resulting from debromination of the starting material. $^1$H NMR (400 MHz, DMSO-d$_6$): δ 8.35 (d, J=4.8 Hz, 2H), 8.24 (s, 1H), 7.96 (app. t, J=8.0 Hz, 1H), 7.85 and 7.82 (dd, J$_1$=10.8 Hz, J$_2$=2.0 Hz, 1H), 7.75 and 7.73 (dd, J$_1$=8.4 Hz, J$_2$=2.0 Hz, 1H), 6.61 (t, J=4.8 Hz, 1H), 5.37 (m, 1H), 4.23-4.18 (m, 1H), 4.14 (t, J=8.4 Hz, 2H), 3.56-3.49 (m, 2H), 3.31-3.28 (m, 2H), 3.25 (s, 3H), 3.06 (t, J=8.4 Hz, 2H), 2.03-1.98 (m, 2H); LCMS (ESI): m/z 471 (M+H)$^+$.

Example 8 (22)

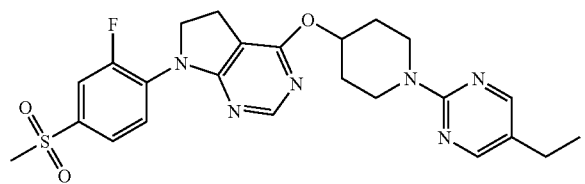

Step 1: 1-(5-Ethyl-2-pyrimidinyl)-4-piperidinol (21)

The procedure described for 16 was employed using 4-hydroxypiperidine (5.0 g, 35.1 mmol), diisopropylethylamine (19 mL, 105.2 mmol), 5-ethyl-2-chloropyrimidine (3.56 g, 35.1 mmol), and acetonitrile (100 mL) under $N_2$. The reaction mixture was refluxed for 36 h and concentrated under reduced pressure. The product was purified by $SiO_2$ flash column chromatography to afford 7.05 g (97%) of the title compound 21 product as oil. $^1$H NMR (400 MHz, DMSO-$d_6$): δ 8.19 (s, 1H), 4.67 (br s, 1H), 4.24-4.18 (m, 2H), 3.68 (m, 2H), 3.19-3.12 (m, 2H), 2.38 (q, J=7.6 Hz, 2H), 1.75-1.69 (m, 2H), 1.31-1.22 (m, 2H), 1.09 (t, J=7.2 Hz, 3H); LCMS (ESI): m/z 207 (M+H)$^+$.

Step 2: 4-{[1-(5-Ethyl-2-pyrimidinyl)-4-piperidinyl]oxy}-7-[2-fluoro-4-(methylsulfonyl)phenyl]-6,7-dihydro-5H-pyrrolo[2,3-d]pyrimidine (22)

The procedure described for 10 was employed using 8 (0.190 g, 0.58 mmol), NaH (70 mg, 1.74 mmol), 21 (114 mg, 0.55 mmol), and THF (10 mL). The aqueous work-up followed by purification gave 0.136 g (50%) of the title product 22 as a white solid. $^1$H NMR (400 MHz, DMSO-$d_6$): δ 8.24 (s, 3H), 7.96 (app. t, J=8.4 Hz, 1H), 7.85 and 7.82 (dd, $J_1$=10.8 Hz, $J_2$=2.0 Hz, 1H), 7.75 and 7.73 (dd, $J_1$=8.4 Hz, $J_2$=2.0 Hz, 1H), 5.36 (m, 1H), 4.20-4.18 (m, 2H), 4.14 (t, J=8.4 Hz, 2H), 3.51-3.45 (m, 2H), 3.25 (s, 3H), 3.05 (t, J=8.8 Hz, 2H), 2.41 (q, J=7.6 Hz, 2H), 2.01-1.97 (m, 2H), 1.65-1.48 (m, 2H), 1.11 (t, J=7.6 Hz, 3H); LCMS (ESI): m/z 499 (M+H)$^+$.

Example 9 (24)

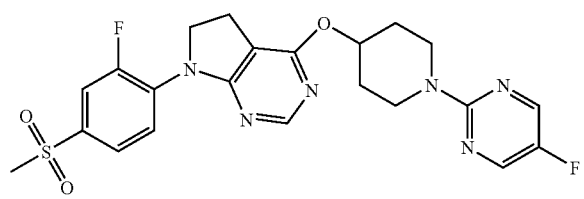

Step 1: 1-(5-Fluoro-2-pyrimidinyl)-4-piperidinol (23)

The procedure described for 16 was employed using 4-hydroxypiperidine (1.53 g, 15.1 mmol), diisopropylethylamine (7.9 mL, 45.3 mmol), 5-fluoro-2-chloropyrimidine (2.0 g, 15.1 mmol), and acetonitrile (50 mL) under $N_2$. The reaction mixture was refluxed for 10 h and then concentrated under reduced pressure. The crude product was purified by $SiO_2$ flash column chromatography to afford 2.46 g (83%) of the title 23 product as a white solid. $^1$H NMR (400 MHz, DMSO-$d_6$): δ 8.18 (s, 2H), 4.37-4.31 (m, 2H), 3.97-3.91 (m, 1H), 3.32-3.25 (m, 2H), 1.98-1.92 (m, 2H), 1.77 (br s, 1H), 1.57-1.48 (m, 2H); LCMS (ESI): m/z 198 (M+H)$^+$.

Step 2: 7-[2-Fluoro-4-(methylsulfonyl)phenyl]-4-{[1-(5-fluoro-2-pyrimidinyl)-4-piperidinyl]oxy}-6,7-dihydro-5H-pyrrolo[2,3-d]pyrimidine (24)

The procedure described for 10 was employed using 8 (358 mg, 1.09 mmol), NaH (131 mg, 3.28 mmol), and 23 (215 mg, 1.09 mmol). The work-up followed by purification gave 210 mg (39%) of the title product 24 as a white solid. $^1$H NMR (400 MHz, DMSO-$d_6$): δ 8.44 (s, 2H), 8.24 (s, 1H), 7.96 (app. t, J=7.6 Hz, 1H), 7.85 and 7.82 (dd, $J_1$=10.8 Hz, $J_2$=2.0 Hz, 1H), 7.75 and 7.73 (dd, J=8.4 Hz, $J_2$=1.6 Hz, 1H), 5.36 (m, 1H), 4.16-4.10 (m, 2H), 4.14 (t, J=8.4 Hz, 2H), 3.55-3.44 (m, 2H), 3.25 (s, 3H), 3.05 (t, J=8.8 Hz, 2H), 2.03-1.98 (m, 2H), 1.66-1.60 (m, 2H); LCMS (ESI): m/z 489 (M+H)$^+$.

Example 10 (31)

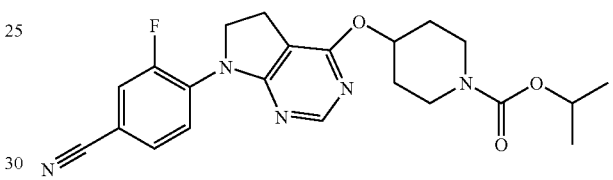

Step 1: N-(4-Bromo-2-fluorophenyl)-6-chloro-5-(2-propen-1-yl)-4-pyrimidinamine (25)

The procedure described for 10 (Example 1, Step 4) was employed. Compound 2 (4.7 g, 24.9 mmol) was allowed to react with 4-bromo-2-fluoroaniline (4.49 g, 23.6 mmol) in the presence of NaH (2.98 g, 74.6 mmol) in THF to give 6.21 g (73%) of the title compound 25 as a white solid. $^1$H NMR (400 MHz, CDCl$_3$): δ 8.40 (s, 1H), 8.31 (app. t, J=8.4 Hz, 1H), 7.31-7.26 (m, 2H), 7.02 (br s, 1H), 5.94-5.84 (m, 1H), 5.34-5.29 (m, 2H), 3.60 (app. d, J=6.4 Hz, 2H); LCMS (ESI): m/z 343 (M+H)$^+$.

Step 2: 1,1-Dimethylethyl (4-bromo-2-fluorophenyl)[6-chloro-5-(2-propen-1-yl)-4-pyrimidinyl]carbamate (26)

Following the procedure described for compound 10 (Example 1, Step 5), compound 25 (6.0 g, 17.5 mmol) was treated with (BOC)$_2$O (9.56 g, 43.8 mmol) in the presence of catalytic amount of DMAP (214 mg, 1.75 mmol) in CH$_2$Cl$_2$ (100 mL) at RT to give 6.56 g (85%) of the title compound 26 as a white solid. $^1$H NMR (400 MHz, DMSO-$d_6$): δ 8.81 (s, 1H), 7.73 and 7.71 (dd, $J_1$=10.0 Hz, $J_2$=2.0 Hz, 1H), 7.40 and 7.38 (dd, $J_1$=8.8 Hz, $J_2$=2.0 Hz, 1H), 7.16 (app. t, J=8.4 Hz, 1H), 5.82-5.75 (m, 1H), 5.09-5.06 (app. dd, $J_1$=10.0 Hz, $J_2$=1.6 Hz, 1H), 4.98 and 4.94 (app. dd, $J_1$=17.2 Hz, $J_2$=1.2 Hz, 1H), 3.47 (app. d, J=6.0 Hz, 2H), 1.36 (s, 9H); LCMS (ESI): m/z 443 (M+H)$^+$.

Step 3: 1,1-Dimethylethyl (4-bromo-2-fluorophenyl)[6-chloro-5-(2-hydroxyethyl)-4-pyrimidinyl]carbamate (27)

Following the procedure described for 10 (Example 1, Step 6), compound 26 (3.15 g, 7.12 mmol) was dissolved in $CH_2Cl_2$ (100 mL). To the cold (−70° C.) mixture ozone was bubbled for 2 h. The resulting mixture was treated with $NaBH_4$ (1.08 g, 28.5 mmol) and MeOH (10 mL) was added to the reaction mixture. Aqueous work-up followed by purification gave 1.40 g (44%) of the title product 27 as a white solid. $^1H$ NMR (400 MHz, DMSO-$d_6$): δ 8.81 (s, 1H), 7.74 and 7.71 (dd, $J_1$=9.6 Hz, $J_2$=2.4 Hz, 1H), 7.42 and 7.33 (m, 2H), 4.97 (app. t, J=5.2 Hz, 1H), 3.66 (q, J=4.8 Hz, 2H), 2.88 (app. t, J=6.4 Hz, 2H), 1.37 (s, 9H); LCMS (ESI): m/z 469 (M+Na)+.

Step 4: 2-[4-((4-Bromo-2-fluorophenyl){[(1,1-dimethylethyl)oxy]carbonyl}amino)-6-chloro-5-pyrimidinyl]ethyl methanesulfonate (28)

Following the procedure described for compound 10 (Example 1, Step 7), compound 27 (1.35 g, 3.02 mmol) was treated with methanesulfonic anhydride (0.79 g, 4.53 mmol) in the presence of $Et_3N$ (1.25 mL, 9.07 mmol) and a catalytic amount of DMAP (37 mg, 0.302 mmol) in $CH_2Cl_2$ (30 mL) to give 1.46 g (92%) of the title compound 28 as a white solid. LCMS (ESI): m/z 521 (M+H)+.

Step 5: 7-(4-Bromo-2-fluorophenyl)-4-chloro-6,7-dihydro-5H-pyrrolo[2,3-d]pyrimidine (29)

The procedure described for compound 10 (Example 1, Step 8) was employed. A solution of 27 (1.45 g, 2.76 mmol) and $CH_2Cl_2$ (19 mL) was added $CF_3COOH$ (6 mL) at RT. The mixture was stirred and concentrated under reduced pressure to give the crude product. The crude was redissolved in $CH_2Cl_2$ (40 mL) and then treated with $Et_3N$ (10 mL) for 2 h. The mixture was worked-up to give 0.75 g (80%) of the title product 29 as an off-white solid. $^1H$ NMR (400 MHz, DMSO-$d_6$): δ 8.20 (s, 1H), 7.70-7.68 (dd, $J_1$=10.4 Hz, $J_2$=2.4 Hz, 1H), 7.57 (app. t, J=8.4 Hz, 1H), 7.48 and 7.46 (dd, $J_1$=8.4 Hz, $J_2$=2.0 Hz, 1H), 4.09 (t, J=8.4 Hz, 2H), 3.19 (t, J=8.4 Hz, 2H); LCMS (ESI): m/z 329 (M+H)+.

Step 6: 1-Methylethyl 4-{[7-(4-bromo-2-fluorophenyl)-6,7-dihydro-5H-pyrrolo[2,3-d]pyrimidin-4-yl]oxy}-1-piperidinecarboxylate (30)

The procedure described for 10 (Example 1, Step 10) was utilized. Compound 29 (300 mg, 0.913 mmol) was reacted with compound 9 (162 mg, 0.87 mmol) in the presence of NaH (110 mg, 2.74 mmol) in THF (10 mL). The aqueous work-up followed by purification gave 410 g (94%) of the title product 30 as an off-white solid. $^1H$ NMR (400 MHz, DMSO-$d_6$): δ 8.13 (s, 1H), 7.64-7.61 (dd, $J_1$=10.8 Hz, $J_2$=2.0 Hz, 1H), 7.56 (app. t, J=8.4 Hz, 1H), 7.43 and 7.40 (dd, $J_1$=8.8 Hz, $J_2$=2.0 Hz, 1H), 5.25 (m, 1H), 4.75 (septuplet, J=6.4 Hz, 1H), 4.00 (t, J=9.2 Hz, 2H), 3.72-3.68 (m, 2H), 3.22 (m, 2H), 3.02 (t, J=8.8 Hz, 2H), 1.94-1.89 (m, 2H), 1.60-1.55 (m, 2H), 1.17 (d, J=6.4 Hz, 6H); LCMS (ESI): m/z 481 (M+H)+.

Step 7: 1-Methylethyl 4-{[7-(4-cyano-2-fluorophenyl)-6,7-dihydro-5H-pyrrolo[2,3-d]pyrimidin-4-yl]oxy}-1-piperidinecarboxylate (31)

A round-bottomed flask was charged with compound 30 (100 mg, 0.209 mmol), CuCN (42 mg, 0.47 mmol), and NMP (2 mL) under $N_2$. The resulting mixture was heated to 150° C. for 15 h. The mixture was cooled to RT, poured into $H_2O$ (25 mL) and the mixture was extracted with EtOAc (4×25 mL). The combined organic layer was washed with brine (1×10 mL), dried over $Na_2SO_4$, filtered and the filtrate was concentrated under reduced pressure. The crude product was purified by flash $SiO_2$ column chromatography to afford 76 mg (85%) of the title compound 31 as a white solid. $^1H$ NMR (400 MHz, DMSO-$d_6$): δ 8.23 (s, 2H), 7.95-7.89 (m, 2H), 7.69 and 7.67 (dd, $J_1$=8.0 Hz, $J_2$=2.0 Hz, 1H), 5.27 (m, J=4.0 Hz, 1H), 4.76 (septuplet, J=6.4 Hz, 1H), 4.14 (t, J=8.0 Hz, 2H), 3.70-3.64 (m, 2H), 3.25-3.21 (m, 2H), 3.04 (t, J=8.4 Hz, 2H), 1.95-1.90 (m, 2H), 1.61-1.53 (m, 2H), 1.17 (d, J=6.0 Hz, 6H); LCMS (ESI): m/z 426 (M+H)+.

Example 11 (32)

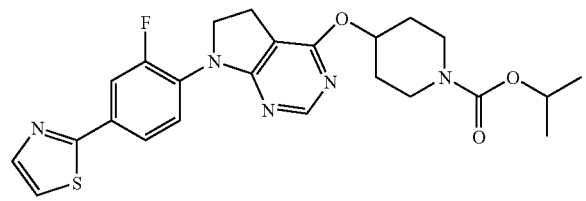

1-Methylethyl 4-({7-[2-fluoro-4-(1,3-thiazol-2-yl)phenyl]-6,7-dihydro-5H-pyrrolo[2,3-d]pyrimidin-4-yl}oxy)-1-piperidinecarboxylate (32)

A round-bottomed flask was charged with compound 30 (108 mg, 0.23 mmol), $PdCl_2(Ph_3P)_2$ (16 mg, 0.023 mmol), 2-(tributylstannanyl)-1,3-thiazole (85 mg, 0.23 mmol), and THF (4 mL) under $N_2$. The reaction mixture was refluxed for 12 h. Aqueous work-up followed by purification gave 66 mg (61%) of the title product 32 as an off-white solid. $^1H$ NMR (400 MHz, DMSO-$d_6$): δ 8.18 (s, 1H), 7.92 (d, J=3.2 Hz, 1H), 7.84-7.79 (m, 2H), 7.78-7.74 (m, 2H), 5.26 (m, 1H), 4.76 (septuplet, J=6.0 Hz, 1H), 4.10 (t, J=8.8 Hz, 1H), 3.71-3.65 (m, 2H), 3.25-3.21 (m, 2H), 3.05 (t, J=8.8 Hz, 2H), 1.95-1.91 (m, 2H), 1.61-1.53 (m, 2H), 1.17 (d, J=6.4 Hz, 6H); LCMS (ESI): m/z 484 (M+H)+.

Example 12 (36)

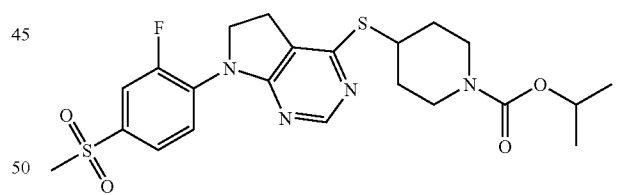

Step 1: 1-Methylethyl 4-bromo-1-piperidinecarboxylate (33)

A solution of 4-bromopiperidine hydrochloride (5.0 g, 20.4 mmol) in dichloromethane (100 mL) under $N_2$ at 0° C. was treated with diisopropylethylamine (7.8 mL, 44.9 mmol) followed by the dropwise addition of a solution of isopropyl chloroformate in toluene (20.4 mL of a 1.0 M solution). The mixture was stirred and allowed to warm to 25° C. over a 3 h period. The reaction was quenched by the addition of 1 N HCl and diluted with ethyl acetate. The aqueous layer was extracted with ethyl acetate (3 times) and the combined organic extracts were washed with saturated aqueous $NaHCO_3$ and brine, dried ($MgSO_4$) and concentrated to give a colorless oil 33 that was used without further purification. ¹H NMR (400 MHz, CDCl₃): δ 4.91 (septuplet, J=6.2 Hz, 1H), 4.35 (m, J=3.8 Hz, 1H), 3.71 (m, 2H), 3.36 (m, 2H), 2.09 (m, 2H), 1.93 (m, 2H), 1.24 (d, J=6.2 Hz, 6H).

Step 2: 1-Methylethyl 4-(acetylthio)-1-piperidinecarboxylate (34)

A solution of 1-methylethyl 4-bromo-1-piperidinecarboxylate (4.0 g, 16 mmol) in DMF (40 mL) under N₂ at 25° C. was treated with potassium thioacetate (3.4 g, 29.8 mmol) and the mixture was stirred and heated at 100° C. for 3.5 h. The reaction mixture was allowed to cool to 25° C. and was quenched by the addition of water and diluted with ethyl acetate. The aqueous layer was extracted with ethyl acetate (3 times) and the combined organic extracts were washed with water, saturated aqueous NaHCO₃ and brine, dried (Na₂SO₄) and concentrated to dark brown oil. Purification by flash chromatography (80 g silica column, 10→20% EtOAc/hexane) afforded 1-methylethyl 4-(acetylthio)-1-piperidinecarboxylate (34) (2.3 g, 59%) as a brown oil. ¹H NMR (400 MHz, CDCl₃): δ 4.91 (septuplet, J=6.2 Hz, 1H), 4.35 (m, J=3.8 Hz, 1H), 3.71 (m, 2H), 3.36 (m, 2H), 2.09 (m, 2H), 1.93 (m, 2H), 1.24 (d, J=6.2 Hz, 6H).

Step 3: 1-Methylethyl 4-mercapto-1-piperidinecarboxylate (35)

A solution of 1-methylethyl 4-(acetylthio)-1-piperidinecarboxylate (2.3 g, 9.4 mmol) in THF:water (1:1, 50 mL) under N₂ at 0° C. was treated with 1 N NaOH (11.2 mL, 11.2 mmol) and the mixture was stirred at 0° C. for 2 h. The reaction mixture was quenched by the addition of aqueous citric acid and the aqueous layer was extracted with ethyl acetate (4 times). The combined organic extracts were washed with saturated aqueous NaHCO₃ and brine; and were dried (MgSO₄) and concentrated to give a brown oil. Purification by flash chromatography (40 g silica column, 10→25% EtOAc/hexane) afforded the title product 35 (1.6 g, 89%) as an amber oil. ¹H NMR (400 MHz, DMSO-d₆): δ 4.72 (septuplet, J=6.4 Hz, 1H), 3.80 (overlapping br. s, 2H), 2.96-2.79 (br m, 3H), 2.64 (d, J=7.1 Hz, 1H), 1.90-1.82 (m, 2H), 1.38-1.27 (m, 2H), 1.15 (d, J=6.4 Hz, 6H).

Step 4: 1-Methylethyl 4-({7-[4-(methylsulfonyl)phenyl]-6,7-dihydro-5H-pyrrolo[2,3-d]pyrimidin-4-yl}thio)-1-piperidinecarboxylate (36)

A solution of 1-methylethyl 4-mercapto-1-piperidinecarboxylate (35) (82 mg, 0.43 mmol) in acetone (2 mL) was treated with compound 8 (refer hereinabove to Example 1, Step 8, 140 mg, 0.43 mmol) under N₂ at 25° C. followed by K₂CO₃ (89 mg, 0.64 mmol) and the mixture was stirred and heated in a sealed vial at 60° C. for 62 h. The reaction mixture was allowed to cool to 25° C. and was concentrated to ~⅓ volume and purified by flash chromatography (12 g silica column, 10→60% EtOAc/hexane, 35 min gradient) to afford the title product 36 (150 mg, 71%) as a white solid. ¹H NMR (400 MHz, DMSO-d₆): δ 8.35 (s, 1H), 7.96 (t, J=8.1 Hz, 1H), 7.85 (d, J=11.2 Hz, 1H), 7.75 (d, J=8.5 Hz, 1H), 4.74 (septuplet, J=6.2 Hz, 1H), 4.15 (app. t, J=8.5 Hz, 2H), 4.11 (obscured m, 1H), 3.82 (br d, J=12.7 Hz, 2H), 3.25 (s, 3H), 3.07 (br m, 2H), 2.99 (app. t, J=8.5 Hz, 2H), 2.01 (br d, J=12.7 Hz, 2H), 1.52 (m, 2H), 1.16 (d, J=6.2 Hz, 6H); LCMS (ESI): m/z 495 (M+H)⁺.

Example 13 (37)

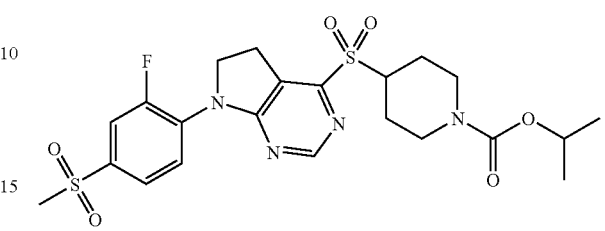

1-Methylethyl 4-({7-[2-fluoro-4-(methylsulfonyl)phenyl]-6,7-dihydro-5H-pyrrolo[2,3-d]pyrimidin-4-yl}sulfonyl)-1-piperidinecarboxylate (37)

A solution of 1-methylethyl 4-({7-[4-(methylsulfonyl)phenyl]-6,7-dihydro-5H-pyrrolo[2,3-d]pyrimidin-4-yl}thio)-1-piperidinecarboxylate (36) (145 mg, 0.29 mmol) in CH₂Cl₂ (5 mL) was treated with m-CPBA (77% maximum by weight, 105 mg, 0.47 mmol) under N₂ at 0° C. and the mixture was stirred at 0° C. for 1.5 h. The reaction mixture was quenched by the addition of methanol, concentrated to ~⅓ volume, and purified by reverse phase HPLC (10→100% CH₃CN/H₂O+0.5% trifluoroacetic acid, 10 min gradient, C18 column) to give the title product 37 (28 mg, 18%) as a white solid after lyophilization. ¹H NMR (400 MHz, DMSO-d₆): δ 8.57 (s, 1H), 8.02-7.97 (overlapping m, 2H), 7.88 (d, J=8.2 Hz, 1H), 4.79 (septuplet, J=6.0 Hz, 1H), 4.26 (app. t, J=8.0 Hz, 2H), 4.08 (br m, 2H), 3.84 (br m, 2H), 3.55 (app. t, J=8.0 Hz, 2H), 3.34 (s, 3H), 2.89 (br m, 2H), 1.95 (br d, J=11.4 Hz, 2H), 1.54 (m, 2H), 1.20 (d, J=6.0 Hz, 6H); LCMS (ESI): m/z 527 (M+H)⁺.

Example 14 (45)

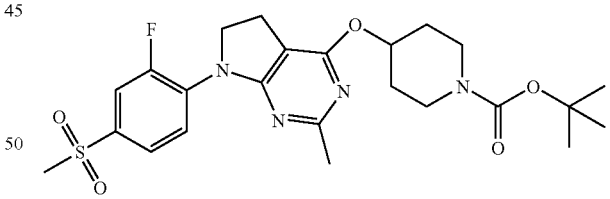

Step 1: 6-Hydroxy-2-methyl-5-(2-propen-1-yl)-4(1H)-pyrimidinone (38)

Ethanimidamide hydrochloride (25.0 g, 0.27 mol) was dissolved in 0.5 M sodium methoxide in methanol (1.1 L, 0.52 mol) and stirred for 1 h at ambient temperature. Diethyl 2-propen-1-yl propanedioate (50.0 g, 0.253 mol) was then added dropwise to the above solution and the resulting mixture stirred at room temperature for 15 h. The reaction mixture was then concentrated under reduced pressure and the crude residue dissolved in 500 mL cold water. The solution was acidified with 4 N aqueous HCl and a white precipitate formed. The precipitate was removed via filtration and air-dried on the filter plate for 48 hours to give 32.6 g (78%) of the title compound 38 as a white solid. $^1$H NMR (400 MHz, DMSO-$d_6$): δ 11.60 (s, 2H), 5.61-5.86 (m, 1H), 4.73-4.97 (m, 2H), 2.92 (d, J=6.1 Hz, 2H), 2.20 (s, 3H).

Step 2: 4,6-Dichloro-2-methyl-5-(2-propen-1-yl)pyrimidine (39)

Compound 38 (6.0 g, 36.1 mmol) was combined with 60 mL phosphorus oxychloride and the mixture was heated to reflux for 4 h. The reaction was then cooled to room temperature and poured very slowly into 500 mL of ice water. The reaction was then extracted three times with ethyl acetate (250 mL each). The combined organics were washed with 300 mL of saturated aqueous NaHCO$_3$, followed by 300 mL brine. The organics were dried over anhydrous magnesium sulfate, filtered and the solvent was removed under reduced pressure to give 6.1 g (85%) of the title compound 39 as a brown oil that was used without additional purification. $^1$H NMR (400 MHz, CDCl$_3$): δ 5.72-5.90 (m, 1H), 4.89-5.22 (m, 2H), 3.54 (d, J=6.1 Hz, 2H), 2.63 (s, 3H).

Step 3: 6-Chloro-N-[2-fluoro-4-(methylsulfonyl)phenyl]-2-methyl-5-(2-propen-1-yl)-4-pyrimidinamine (40)

NaH (60% oil dispersion, 936 mg, 23.4 mmol) was added to a 100 mL round bottom flask along with 5 mL anhydrous toluene. The suspension was stirred for 10 minutes and the toluene was decanted off. 2-Fluoro-4-(methylsulfonyl)aniline (2.2 g, 11.7 mmol) in 20 mL anhydrous THF was then added to the dry NaH dropwise over several minutes. The resulting mixture was stirred at ambient temperature for 15 minutes and then compound 39 (2.5 g, 12.3 mmol) in 30 mL anhydrous THF was added slowly over several minutes. The mixture was then heated to reflux for 2 h, cooled to room temperature and diluted with 100 mL water. The reaction was extracted three times with ethyl acetate (100 mL each) and the organics dried over anhydrous magnesium sulfate. The solids were removed via filtration and the solvent removed under reduced pressure to give 4.4 g (97%) of the title compound 40 which was used without additional purification. $^1$H NMR (400 MHz, CDCl$_3$): δ 2.60 (s, 3H), 3.09 (s, 3H), 3.61 (d, J=6.1 Hz, 2H), 5.22-5.42 (m, 2H), 5.79-5.98 (m, 1H), 7.31-7.41 (m, 1H), 7.64-7.73 (m, 1H), 7.74-7.81 (m, 1H), 7.64-7.73 (m, 1H), 8.83 (t, J=7.6 Hz, 1H).

Step 4: 1,1-Dimethylethyl[6-chloro-2-methyl-5-(2-propen-1-yl)-4-pyrimidinyl][2-fluoro-4-(methylsulfonyl)phenyl]carbamate (41)

Compound 40 (4.4 g, 13.2 mmol) was dissolved in methylene chloride (40 mL) and treated with (BOC)$_2$O (5.7 g, 26.5 mmol) and catalytic amount of DMAP (~50 mg). The resulting solution was stirred for 18 h at ambient temperature. The reaction was then diluted with 50 mL water and the phases were separated and the aqueous phase was extracted 3 times with ethyl acetate (100 mL each). The organics were then combined and dried over anhydrous magnesium sulfate. The solids were removed via filtration and the crude reaction was concentrated to dryness. The crude reaction was then purified via flash column chromatography (120 g of silica gel, 10→50% ethyl acetate/hexane) to give 3.0 g (50%) of the title compound 41 as a white solid. $^1$H NMR (400 MHz, CDCl$_3$): δ 1.47 (s, 9H), 2.61 (s, 3H), 3.10 (s, 3H) 3.43 (d, J=6.1 Hz, 2H), 4.89-5.10 (m, 2H), 5.62-5.83 (m, 1H), 7.36-7.49 (m, 1H), 7.60-7.77 (m, 2H).

Step 5: 1,1-Dimethylethyl[6-chloro-5-(2-hydroxyethyl)-2-methyl-4-pyrimidinyl][2-fluoro-4-(methylsulfonyl)phenyl]carbamate (42)

Compound 41 (3.0 g, 6.5 mmol) was dissolved in a mixture of methylene chloride (200 mL) and methanol (14 mL) and the resulting solution was cooled to −78° C. Ozone was bubbled through the reaction until a blue color persisted. The reaction was then purged with oxygen followed by nitrogen until the blue color dissipated. The reaction was allowed to warm to −15° C. at which time solid sodium borohydride (962 mg, 26.0 mmol) was added. The reaction was allowed to stir for 5 h while warming to room temperature.

The reaction was diluted with 50 mL water and the phases were separated. The aqueous phase was extracted with methylene chloride (2×50 mL) and the organics were combined and dried over anhydrous magnesium sulfate. The solids were removed via filtration and the crude reaction concentrated to dryness to give 2.4 g (82%) of the title compound 42 as a white solid. $^1$H NMR (400 MHz, CDCl$_3$): δ 1.46 (s, 9H), 2.58 (s, 3H), 3.01 (t, J=6.1 Hz, 2H), 3.10 (s, 3H), 3.86-3.99 (m, 2H), 7.54-7.83 (m, 3H).

Step 6: 2-(4-Chloro-6-{{[(1,1-dimethylethyl)oxy]carbonyl}[2-fluoro-4-(methylsulfonyl)phenyl]amino}-2-methyl-5-pyrimidinyl)ethyl methanesulfonate (43)

Compound 42 (2.4 g, 5.22 mmol) was dissolved in methylene chloride (40 mL) and treated with DIPEA (2.7 mL, 15.6 mmol) followed by methanesulfonyl chloride (804 μL, 10.45 mmol). The solution was stirred at ambient temperature for 4 h. The reaction was then diluted with 50 mL water and the phases were separated and the aqueous phase was extracted 3 times with methylene chloride (40 mL each). The organics were then combined and dried over anhydrous magnesium sulfate. The solids were removed via filtration and the crude reaction was concentrated to dryness to give 3.1 g of the title product 43 that was used without additional purification. $^1$H NMR (400 MHz, DMSO-$d_6$): δ 1.38 (s, 9H), 2.50 (s, 3H), 3.10 (t, J=6.1 Hz, 2H), 3.16 (s, 3H), 3.29 (s, 3H), 3.42 (t, J=6.1 Hz, 2H), 7.60 (t, J=7.8 Hz, 1H), 7.67-7.78 (m, 1H), 7.92-8.01 (m, 1H).

Step 7: 4-Chloro-7-[2-fluoro-4-(methylsulfonyl)phenyl]-2-methyl-6,7-dihydro-5H-pyrrolo[2,3-d]pyrimidine (44)

Compound 43 (500 mg, 0.93 mmol) was treated with 25 mL of a solution of 20% TFA in methylene chloride (v/v). The solution was stirred at room temperature for 3 h then concentrated under reduced pressure. The residue was redissolved in 20 mL of methylene chloride and Et$_3$N (450 μL, 2.53 mmol) added. The mixture was stirred at room temperature for 18 h, the solvent removed and the crude reaction purified via flash column chromatography (40 g of silica gel, 10→50% ethyl acetate/hexane) to give 298 mg (94%) of the title compound 44 as a white solid. $^1$H NMR (400 MHz, CDCl$_3$): δ 2.48 (s, 3H), 3.10 (s, 3H), 3.24 (t, J=7.3 Hz, 2H), 4.24 (t, J=7.3 Hz, 2H), 7.57-7.84 (m, 2H), 7.91-8.20 (m, 1H); LCMS (ESI): m/z 342 (M+H)$^+$.

Step 8: 1,1-Dimethylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate (45)

1,1-Dimethylethyl 4-hydroxy-1-piperidinecarboxylate (122 mg, 0.609 mmol) was dissolved in 5 mL anhydrous THF.

NaH (60% dispersion in oil, 70 mg, 1.74 mmol) was added to the solution and the mixture was stirred at room temperature for 0.5 h. Compound 44 (198 mg, 0.581 mmol) was dissolved in 5 mL THF and added dropwise to the above solution. The mixture was then refluxed for 3 h. The heating bath was removed and the reaction stirred overnight at room temperature. The reaction was then treated with 5 mL of 1 M aqueous HCl followed by 20 mL water. The crude reaction was then extracted 3 times with methylene chloride (20 mL each) and the organics were dried over anhydrous magnesium sulfate, filtered, and the crude reaction was concentrated to dryness. The reaction was purified via flash column chromatography using a gradient of (25 g of silica gel, 0→50% ethyl acetate/hexane) to give 170 mg (60%) of the title compound 45 as a white solid. $^1$H NMR (400 MHz, CDCl$_3$): δ 1.46 (s, 9H), 1.62-1.83 (m, 2H), 1.86-2.11 (m, 2H), 2.48 (s, 3H), 2.86-3.18 (m, 5H), 3.21-3.44 (m, 2H), 3.57-3.87 (m, 2H), 4.25 (t, J=7.3 Hz, 2H), 5.30-5.47 (m, 1H), 7.59-7.78 (m, 2H), 7.06-8.22 (m, 1H); LCMS (ESI): m/z 507 (M+H)$^+$.

Example 15 (47)

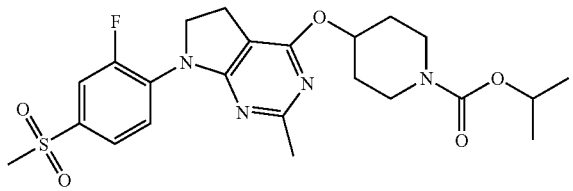

Step 1: 7-[2-Fluoro-4-(methylsulfonyl)phenyl]-2-methyl-4-(4-piperidinyloxy)-6,7-dihydro-5H-pyrrolo[2,3-d]pyrimidine trifluoroacetate (46)

Compound 45 (101 mg, 0.19 mmol) was treated with 10 mL of a solution of 20% TFA in methylene chloride (v/v). The solution was stirred at room temperature for 3 h. The solvent was then removed under reduced pressure and the crude residue was placed on a high vacuum pump for 0.5 h to give 100 mg of the crude TFA salt 46 that was used without purification.

Step 2: 1-Methylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate (47)

Compound 46 (50 mg, 0.10 mmol) was dissolved in methylene chloride (5 mL). A 1 M solution of isopropyl chloroformate in toluene (96 μL, 0.10 mmol) was added to the above solution followed by diisopropylethylamine (61 μL, 0.35 mmol) and the reaction mixture was stirred at room temperature for 18 h. The solvents were then removed under reduced pressure and the crude reaction purified via flash column chromatography (15→50% ethyl acetate/hexane) to give 48 mg (98%) of the title compound 47 as a white solid. $^1$H NMR (400 MHz, CDCl$_3$): δ1.17 (d, J=6.8 Hz, 6H), 1.60-1.82 (m, 2H), 1.89-2.01 (m, 2H), 2.47 (s, 3H), 2.94-3.15 (m, 5H), 3.25-3.46 (m, 2H), 3.63-3.87 (m, 2H), 4.19 (t, J=7.3 Hz, 2H), 4.83-5.02 (m, 1H), 5.30-5.47 (m, 1H), 7.59-7.78 (m, 2H), 7.06-8.22 (m, 1H); LCMS (ESI): m/z 493 (M+H)$^+$.

Example 16 (50)

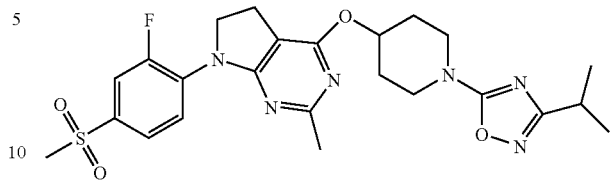

Step 1: 4-Hydroxy-1-piperidinecarbonitrile (48)

NaHCO$_3$ (41 g, 0.494 mol) was combined with 20 mL water and cooled to 0° C. on an ice bath. 4-Hydroxypiperidine (25 g, 0.25 mol) in 75 mL of methylene chloride was added to the above solution with vigorous stirring. Cyanogen bromide (28 g, 0.27 mol) in 25 mL of methylene chloride was then added and the ice bath was removed. The mixture was then stirred at ambient temperature for 18 h. Na$_2$CO$_3$ (75 g) was then added until pH≅7 and MgSO$_4$ (25 g) was added to remove water. The solids were removed via filtration and the solids were washed several times with methylene chloride. The filtrate was then removed under reduced pressure and the title product 48 (24.8 g) was used without purification.

Step 2: 1-[3-(1-Methylethyl)-1,2,4-oxadiazol-5-yl]-4-piperidinol (49)

A solution of compound 48 (12.9 g, 0.102 mol) and compound 106 (see, Example 48, Step 1) (12.8 g, 0.125 mol) in a mixture of ethyl acetate (500 mL) and ether (100 mL) was treated with a 1 N solution of ZnCl$_2$ (120 mL, 0.120 mol) in ether. The mixture was stirred for 15 min and the supernatant was decanted off. The residue was washed 2 times with 250 mL of ether, which was decanted off after each wash. The residue was then dissolved in a mixture of 4 N HCl (50 mL) and EtOH (100 mL). The resulting solution was refluxed for 1 h and the solvent was reduced under reduced pressure to about 25 mL and 25 g Na$_2$CO$_3$ was added along with 100 mL methylene chloride. The solids were removed via filtration and phases were separated. The organic phase was dried over MgSO$_4$, filtered, and concentrated to dryness to give 16 g of the desired compound 49 as a tan oil and the material was used without purification. $^1$H NMR (400 MHz, CDCl$_3$): δ1.13-1.38 (m, 6H), 1.49-1.74 (m, 2H), 1.80-2.05 (m, 2H), 2.78 (m, 1H), 3.20-3.44 (m, 2H), 3.74-4.04 (m, 3H).

Step 3: 7-[2-Fluoro-4-(methylsulfonyl)phenyl]-2-methyl-4-({1-[3-(1-methylethyl)-1,2,4-oxadiazol-5-yl]-4-piperidinyl}oxy)-6,7-dihydro-5H-pyrrolo[2,3-d]pyrimidine (50)

Compound 49 (100 mg, 0.292 mmol) was dissolved in 5 mL anhydrous THF. NaH (60% dispersion in oil, 35 mg, 0.876 mmol) was added to the solution and the mixture was stirred at room temperature for 0.5 h. Compound 44 (55 mg, 0.262 mmol) was dissolved in 5 mL THF and added dropwise to the above solution. The mixture was then refluxed for 3 hours. The crude reaction mixture was then concentrated in vacuo and the resulting residue was purified using the Gilson semi-preparative HPLC (Sunfire C18, 5 microns, 30/50 mm)

using a gradient of 10-100% CH₃CN/H₂O/0.1% TFA to give 76 mg (56%) of the title compound 50 as a white solid. ¹H NMR (400 MHz, CDCl₃): δ 1.27 (d, J=6.8 Hz, 6H), 1.81-1.97 (m, 2H), 2.01-2.13 (m, 2H), 2.49 (s, 3H), 2.80-2.95 (m, 1H), 2.99-3.14 (m, 5H), 3.54-3.66 (m, 2H), 3.79-3.92 (m, 2H), 4.19 (t, J=7.3 Hz, 2H), 5.39-5.54 (m, 1H), 7.62-7.79 (m, 2H), 7.92-8.13 (m, 1H); LCMS (ESI): m/z 517 (M+H)⁺.

Example 17 (56)

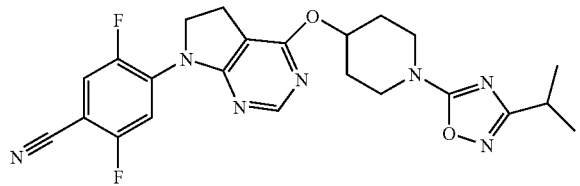

Step 1: 4-{[6-Chloro-5-(2-propen-1-yl)-4-pyrimidinyl]amino}-2,5-difluorobenzonitrile (51)

NaH (60% dispersion in oil, 967 mg, 24.2 mmol) was added to a 100 mL round bottom flask along with 5 mL anhydrous toluene. The suspension was stirred for 10 min and the toluene was decanted off. 4-Amino-2,5-difluorobenzonitrile (1.9 g, 12.2 mmol) in 40 mL anhydrous THF was then added to the NaH slurry dropwise over several minutes. The resulting mixture was stirred at ambient temperature for 15 min at which time compound 2 (2.4 g, 12.7 mmol) in 10 mL anhydrous THF was added slowly over several minutes. The mixture was then heated to reflux for 2 h. The reaction was then cooled to room temperature and diluted with 100 mL water and a white precipitate (1.62 g) formed which was removed via filtration and dried under reduced pressure. The filtrate was then transferred to a separatory funnel and was extracted with methylene chloride (3×100 mL). The combined organic extracts were then dried over anhydrous magnesium sulfate, filtered, and concentrated to dryness. The crude residue was then recrystallized from MeOH to give an additional 0.57 g of the desired product 51 as a white solid; 2.19 g total (51%). ¹H NMR (400 MHz, CDCl₃): δ 3.67 (d, J=6.0 Hz, 2H), 5.21-5.50 (m, 2H), 5.77-6.02 (m, 1H), 7.29-7.41 (m, 1H), 7.41-7.53 (s, 1H), 8.50 (s, 1H), 8.67-8.85 (m, 1H).

Step 2: 1,1-Dimethylethyl[6-chloro-5-(2-propen-1-yl)-4-pyrimidinyl](4-cyano-2,5-difluorophenyl)carbamate (52)

Compound 51 (2.2 g, 6.8 mmol) was dissolved in methylene chloride (40 mL) and treated with (BOC)₂O (3.0 g, 13.6 mmol) and a catalytic amount of DMAP. The resulting solution was stirred for 18 h at ambient temperature. The reaction was then diluted with 50 mL water and the aqueous phase was extracted 3 times with methylene chloride (50 mL each). The organics were then combined and dried over anhydrous magnesium sulfate. The solids were removed via filtration and the crude reaction was concentrated to dryness. The crude reaction was then purified via flash column chromatography (120 g of silica gel, 10→50% ethyl acetate/hexane) to give 2.4 g (83%) of the desired compound 52 as a white solid. ¹H NMR (400 MHz, CDCl₃): δ 1.44 (s, 9H), 3.52 (d, J=6.1 Hz, 2H), 4.89-5.21 (m, 2H), 5.63-5.98 (m, 1H), 7.06-7.20 (m, 1H), 7.32-7.52 (m, 1H), 8.70 (s, 1H).

Step 3: 1,1-Dimethylethyl[6-chloro-5-(2-hydroxyethyl)-4-pyrimidinyl](4-cyano-2,5-difluorophenyl)carbamate (53)

Compound 52 (2.4 g, 5.69 mmol) was dissolved in a mixture of methylene chloride (200 mL) and methanol (10 mL) and the resulting solution was cooled to −78° C. Ozone was then bubbled through the solution until a blue color persisted. The reaction was then purged with oxygen followed by nitrogen until blue color dissipated. The reaction was then allowed to warm to −15° C. at which time solid sodium borohydride (841 mg, 22.74 mmol) was added. The reaction was allowed to stir for 5 h while warming to room temperature. The reaction was then diluted with 50 mL water and the aqueous phase was extracted 2 times with methylene chloride (50 mL each). The organics were then combined and dried over anhydrous magnesium sulfate. The solids were removed via filtration and the crude reaction was concentrated to dryness. The reaction was then purified via flash column chromatography (20→50% ethyl acetate/hexane) to give 810 mg (33%) of the desired compound 53. ¹H NMR (400 MHz, CDCl₃): δ 1.49 (s, 9H), 3.08 (t, J=7.3 Hz, 2H), 3.98 (t, J=7.3 Hz, 2H), 7.29-7.46 (m, 2H), 8.50 (s, 1H).

Step 4: 2-[4-Chloro-6-((4-cyano-2,5-difluorophenyl){[(1,1-dimethylethyl)oxy]carbonyl}amino)-5-pyrimidinyl]ethyl methanesulfonate (54)

Compound 53 (810 mg, 1.90 mmol) was dissolved in methylene chloride (20 mL) and treated with DIPEA (1.0 mL, 5.7 mmol) followed by methanesulfonyl chloride (433 mg, 3.8 mmol). The solution was stirred at ambient temperature for 4 h. The reaction was then diluted with 50 mL water and the aqueous phase was extracted 3 times with methylene chloride (40 mL each). The organics were then combined and dried over anhydrous magnesium sulfate. The solids were removed via filtration and the crude reaction was concentrated to dryness to give 1.0 g of the crude title product 54 that was used without additional purification. ¹H NMR (400 MHz, CDCl₃): δ 1.40 (s, 9H), 2.89 (s, 3H), 3.25 (t, J=7.3 Hz, 2H), 4.50 (t, J=7.3 Hz, 2H), 7.29-7.46 (m, 2H), 8.63 (s, 1H).

Step 5: 4-(4-Chloro-5,6-dihydro-7H-pyrrolo[2,3-d]pyrimidin-7-yl)-2,5-difluorobenzonitrile (55)

Compound 54 (1.0 g, 2.05 mmol) was treated with 10 mL of a solution of 20% TFA in methylene chloride (v/v). The solution was stirred at room temperature for 3 hours. The solvent was then removed in vacuo and the crude residue was placed on a high vacuum pump for 0.5 h. The residue was then redissolved in 10 mL of methylene chloride and TEA (3 mL, 16.8 mmol) was added to the solution. The mixture was stirred at room temperature for 18 h. Solvent was removed to give 594 mg (98%) of the title compound 55 that was used without additional purification. ¹H NMR (400 MHz, CDCl₃): δ 3.35 (t, J=7.3 Hz, 2H), 4.35 (t, J=7.3 Hz, 2H), 7.32-7.51 (m, 1H), 7.89-8.13 (m, 1H), 8.44 (s, 1H).

Step 6: 2,5-Difluoro-4-[4-({1-[3-(1-methylethyl)-1,2,4-oxadiazol-5-yl]-4-piperidinyloxy}-5,6-dihydro-7H-pyrrolo[2,3-d]pyrimidin-7-yl]benzonitrile (56)

Compound 49 (162 mg, 0.770 mmol) was dissolved in 5 mL anhydrous THF. NaH (60% dispersion in oil, 102 mg, 2.57 mmol) was added to the solution and the mixture was stirred at room temperature for 0.5 h. Compound 55 (250 mg, 0.856 mmol) was dissolved in 5 mL THF and added dropwise to the above solution. The mixture was then refluxed for 3 h. The crude reaction mixture was then concentrated in vacuo and the resulting residue was purified via flash column chromatography (10→50% ethyl acetate/hexane) to give 50 mg (13%) of the title compound 56 as a white solid. $^1$H NMR (400 MHz, CDCl$_3$): δ 1.29 (d, J=6.8 Hz, 6H), 1.82-1.97 (m, 2H), 2.06-2.17 (m, 2H), 2.81-2.97 (m, 1H), 3.09 (t, J=7.3 Hz, 2H), 3.47-3.62 (m, 2H), 3.79-3.95 (m, 2H), 4.25 (t, J=7.3 Hz, 2H), 5.33-5.52 (m, 1H), 7.27-7.40 (m, 1H), 8.00-8.19 (m, 1H), 8.31 (s, 1H); LC); LCMS (ESI): m/z 468 (M+H)$^+$.

Example 18 (57)

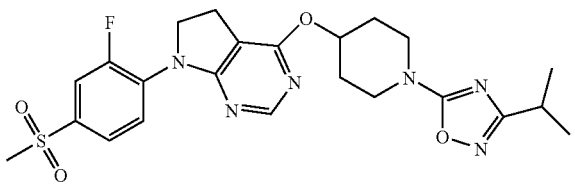

7-[2-Fluoro-4-(methylsulfonyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine (57)

The protocol described for 10 (Example 1, Step 10) was followed. Compound 8 (540 mg, 1.65 mmol) was allowed to react with compound 49 (332 mg, 1.57 mmol) in presence of NaH (60% dispersion in oil, 200 mg, 4.94 mmol) and THF (20 mL) for 2.5 h. Work-up followed by purification gave 460 mg (55%) of the title product 57 as a white solid. $^1$H NMR (400 MHz, DMSO-d$_6$): δ 8.27 (s, 1H), 7.99 (app. t, J=7.6 Hz, 1H), 7.87 (app. br d, J=10.8 Hz, 1H), 7.78 (app. br t, J=8.4 Hz, 1H), 5.36 (br m, 1H), 4.18 (t, J=8.8 Hz, 2H), 3.82-3.78 (m, 2H), 3.56-3.50 (m, 2H), 3.28 (s, 3H), 3.10 (t, J=8.4 Hz, 2H), 2.83 (septuplet, J=6.8 Hz, 1H), 2.09 (m, 2H), 1.78 (m, 2H), 1.20 (d, J=6.8 Hz, 6H); LCMS (ESI): m/z 503 (M+H)$^+$.

Example 19 (62)

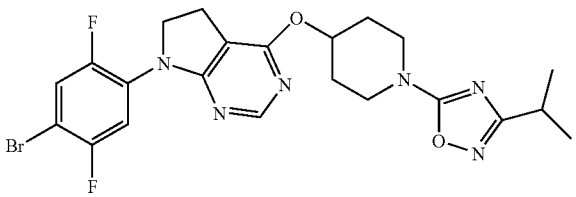

Step 1: (4-Bromo-N-[2-(4,6-dichloro-5-pyrimidinyl)ethyl]-2,5-difluoroaniline (58)

Compound 2 (1.71 g, 9.0 mmol) was dissolved in methylene chloride (200 mL) and methanol (10 mL) and the resulting solution was cooled to −78° C. Ozone was then bubbled through the solution until a blue color persisted. The reaction was then purged with oxygen followed by nitrogen until blue color dissipated. The reaction was then treated with dimethylsulfide (589 mg, 9.5 mmol) and the mixture was stirred for 1.5 h while warming to room temperature. The reaction was then concentrated to dryness. 4-Bromo-2,5-difluoroaniline (1.79 g, 8.6 mmol) was then added to the crude residue and the mixture was dissolved in 50 mL methylene chloride. MeOH (10 mL) was then added to the above solution along with 1 mL of glacial acetic acid. The resulting solution was then stirred for 1 h at which time solid sodium cyanoborohydride (1.6 g, 25.8 mmol) was added. The reaction was then left to stir at room temperature for 18 h. The reaction was then diluted with 50 mL water and the aqueous phase was extracted 3 times with methylene chloride (50 mL each). The organics were then combined and dried over anhydrous magnesium sulfate. The solids were removed via filtration and the crude reaction was concentrated to dryness. The reaction was then treated with MeOH and allowed to stand for 48 h. A yellow precipitate formed which was removed via filtration to give 510 mg (16%) of the title compound 58. $^1$H NMR (400 MHz, CDCl$_3$): δ 3.23 (t, J=6.8 Hz, 2H), 3.54 (t, J=6.8 Hz, 2H), 4.11-4.37 (br, 1H), 6.39-6.68 (m, 1H), 7.00-7.18 (m, 1H), 8.64 (s, 1H).

Step 2: 7-(4-Bromo-2,5-difluorophenyl)-4-chloro-6,7-dihydro-5H-pyrrolo[2,3-d]pyrimidine (59)

Compound 58 (367 mg) was dissolved in 10 mL methylene chloride and 1 mL TFA was added slowly. The resulting solution was allowed to stir at room temperature for 17 h. The reaction was then diluted with 10 mL of a saturated solution of NaHCO$_3$ and aqueous phase was extracted 2 times with methylene chloride. The organics were then combined and dried over anhydrous magnesium sulfate. The solids were removed via filtration and the crude reaction was concentrated to dryness to give 310 mg (94%) of the crude product 59 that was used without additional purification. $^1$H NMR (400 MHz, CDCl$_3$): δ 3.26 (t, J=6.8 Hz, 2H), 4.21 (t, J=6.8 Hz, 2H), 7.30-7.44 (m, 1H), 7.47-7.66 (m, 1H), 8.36 (s, 1H).

Step 3: 7-(4-Bromo-2,5-difluorophenyl)-4-({1-[3-(1-methylethyl)-1,2,4-oxadiazol-5-yl]-4-piperidinyl}oxy)-6,7-dihydro-5H-pyrrolo[2,3-d]pyrimidine (60)

Compound 49 (54 mg, 0.26 mmol) was dissolved in 5 mL anhydrous THF. NaH (60% dispersion in oil, 34 mg, 0.87 mmol) was added to the solution and the mixture was stirred at room temperature for 0.5 h. Compound 59 (100 mg, 0.29 mmol) was dissolved in 5 mL THF and added dropwise to the above solution. The mixture was then refluxed for 3 h. The crude reaction mixture was then diluted with 10 mL water and extracted 3 times with 10 mL methylene chloride. The combined organic extracts were dried over anhydrous magnesium sulfate, filtered, and concentrated to dryness. The resulting residue was purified via flash column chromatography (10→50% ethyl acetate/hexane) to give 100 mg (66%) of the title compound 60 as a white solid. $^1$H NMR (400 MHz, CDCl$_3$): δ1.21-1.38 (m, 6H), 1.83-1.99 (m, 2H), 2.02-2.19 (m, 2H), 2.79-2.97 (m, 1H), 3.10 (t, J=9.0 Hz, 2H), 3.51-3.73 (m, 2H), 3.78-3.99 (m, 2H), 4.09 (t, J=9.0 Hz, 2H), 5.25-5.52 (m, 1H), 7.27-7.39 (m, 1H), 7.44-7.66 (m, 1H), 8.21 (s, 1H); LCMS (ESI): m/z 522 (M+H)$^+$.

Example 20 (61)

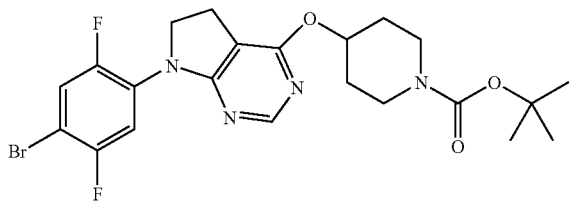

1,1-Dimethylethyl 4-{[7-(4-bromo-2,5-difluorophenyl)-6,7-dihydro-5H-pyrrolo[2,3-d]pyrimidin-4-yl]oxy}-1-piperidinecarboxylate (62)

1,1-Dimethylethyl 4-hydroxy-1-piperidinecarboxylate (109 mg, 0.546 mmol) was dissolved in 5 mL anhydrous THF. NaH (60% dispersion in oil, 72 mg, 1.8 mmol) was added to the solution and the mixture was stirred at room temperature for 0.5 h. Compound 59 (210 mg, 0.607 mmol) was dissolved in 5 mL THF and added dropwise to the above solution. The mixture was then refluxed for 3 h. The crude reaction mixture was then diluted with 10 mL water and extracted 3 times with 10 mL methylene chloride. The combined organic extracts were dried over anhydrous magnesium sulfate, filtered, and concentrated to dryness. The resulting residue was purified via flash column chromatography (10→50% ethyl acetate/hexane) to give 176 mg (60%) of the title compound 62 as a white solid. $^1$H NMR (400 MHz, CDCl$_3$): δ 1.46 (s, 9H), 1.65-1.80 (m, 2H), 1.90-2.03 (m, 2H), 3.11 (t, J=8.8 Hz, 2H), 3.21-3.35 (m, 2H), 3.68-3.82 (m, 2H), 4.10 (t, J=8.3 Hz, 2H), 5.23-5.37 (m, 1H), 7.28-7.37 (m, 1H), 7.54-7.68 (m, 1H), 8.19 (s, 1H); LCMS (ESI): m/z 512 (M+H)$^+$.

Example 21 (66)

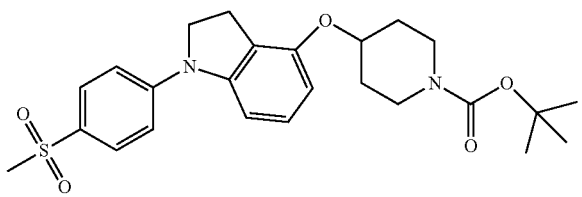

Step 1: 1,1-Dimethylethyl 4-(1H-indol-4-yloxy)-1-piperidinecarboxylate (63)

To a solution of 4-hydroxyindole (9.98 g, 75 mmol), Ph$_3$P (39.4 g, 150 mmol), 4-hydroxypiperidine (22.25 g, 113 mmol) and THF (600 mL) was added, dropwise at RT under N$_2$, diisopropyl azodicarboxylate (26.0 mL, 135 mmol). The reaction mixture was stirred at RT for 15 h and concentrated to give the crude material. The crude product was purified by flash chromatography over SiO$_2$ (0→20% ethyl acetate/hexanes) to afford 17.6 g (74%) of the title compound 63 as a white solid. $^1$H NMR (400 MHz, DMSO-d$_6$): δ 11.03 (br s, 1H), 7.19 (t, J=2.8 Hz, 1H), 6.99-6.93 (m, 2H), 6.54 and 6.53 (dd, J$_1$=7.2 Hz, J$_2$=1.2 Hz, 1H), 6.41 (app. t, J=2.4 Hz, 1H), 4.63 (m, 1H), 3.67-3.61 (m, 2H), 3.26-3.21 (m, 2H), 1.94-1.87 (m, 2H), 1.64-1.52 (m, 2H), 1.40 (s, 9H); LCMS (ESI): m/z 339 (M+Na)$^+$.

Step 2: 1,1-Dimethylethyl 4-{[1-(4-iodophenyl)-1H-indol-4-yl]oxy}-1-piperidinecarboxylate (64)

A round-bottomed flask was charged, at RT under N$_2$, with compound 63 (4.20 g, 13.3 mmol), CuI (253 mg, 1.3 mmol), K$_3$PO$_4$ (5.92 g, 27.9 mmol), 1,4-diiodobenzene (5.47 g, 16.6 mmol), trans-N,N'-dimethyl-1,2-cyclohexanediamine (378 mg, 2.7 mmol), and anhydrous DMF (15 mL). The reaction mixture was stirred at 140° C. for 36 h. The reaction mixture was diluted with EtOAc (50 mL) and filtered through a pad of Celite (washed with EtOAc). The filtrate was concentrated under reduced pressure to afford the crude material. The product was purified by flash column chromatography (0→20% ethyl acetate/hexanes) to give 4.72 g (69%) of a title product 64 as an off-white solid. $^1$H NMR (400 MHz, DMSO-d$_6$): δ 7.88 (t, J=8.8 Hz, 2H), 7.51 (d, J=3.2 Hz, 1H), 7.39 (d, J=8.8 Hz, 2H), 7.12 (t, J=5.6 Hz, 1H), 7.09 (t, J=8.0 Hz, 1H), 6.72 (d, J=7.2 Hz, 1H), 6.70 (d, J=3.2 Hz, 1H), 4.70 (m, 1H), 3.66-3.60 (m, 2H), 3.28-3.24 (m, 2H), 1.94-1.89 (m, 2H), 1.66-1.58 (m, 2H), 1.39 (s, 9H); LCMS (ESI): m/z 518 (M+H)$^+$.

Step 3: 1,1-Dimethylethyl 4-{[1-(4-iodophenyl)-2,3-dihydro-1H-indol-4-yl]oxy}-1-piperidinecarboxylate (65)

To a solution of 64 (330 mg, 0.64 mmol) in acetic acid (10 mL) at RT was added NaCNBH$_3$ (322 mg, 5.12 mmol). The mixture was stirred at RT for 15 h and then poured slowly into H$_2$O (40 mL) and stirred for 10 min. The solid was filtered and dried to afford 310 mg (93%) of the title product 65 as an off-white solid. $^1$H NMR (400 MHz, DMSO-d$_6$): δ 7.59 (t, J=8.4 Hz, 2H), 7.02 (d, J=8.8 Hz, 2H), 6.99 (app. t, J=8.0 Hz, 1H), 6.71 (d, J=8.0 Hz, 1H), 6.49 (d, J=8.4 Hz, 1H), 4.54 (m, 1H), 3.88 (t, J=8.4 Hz, 2H), 3.59-3.46 (m, 2H), 3.24-3.19 (m, 2H), 2.96 (t, J=8.4 Hz, 2H), 1.87-1.82 (m, 2H), 1.57-1.49 (m, 2H), 1.38 (s, 9H); LCMS (ESI): m/z 521 (M+H)$^+$.

Step 4: 1,1-Dimethylethyl 4-({1-[4-(methylsulfonyl)phenyl]-2,3-dihydro-1H-indol-4-yl}oxy)-1-piperidinecarboxylate (66)

A 10 mL glass tube was charged with 65 (260 mg, 0.50 mmol), MeSO$_2$Na (102 mg, 1.0 mmol), L-proline (12 mg, 0.104 mmol), NaOH (5 mg, 0.104 mmol) and DMSO (3 mL). The tube was sealed and then stirred at 120° C. for 18 h. The reaction mixture was cooled, the tube was opened, and the contents of the tube were poured into H$_2$O (40 mL). The mixture was stirred for 10 min, filtered the solid material, and the was purified by flash SiO$_2$ column chromatography gave dried to afford 222 mg (94%) of the title product 66 as an off-white solid. $^1$H NMR (400 MHz, DMSO-d$_6$): δ 7.79 (t, J=8.8 Hz, 2H), 7.35 (d, J=8.8 Hz, 2H), 7.08 (app. t, J=8.4 Hz, 1H), 6.93 (d, J=8.0 Hz, 1H), 6.60 (d, J=8.0 Hz, 1H), 4.60-4.52 (m, 1H), 4.01 (t, J=8.8 Hz, 2H), 3.61-3.55 (m, 2H), 3.30-3.21 (m, 2H), 3.13 (s, 3H), 3.01 (t, J=8.4 Hz, 2H), 1.89-1.84 (m, 2H), 1.39 (s, 9H); LCMS (ESI): m/z 495 (M+Na)$^+$.

Example 22 (69)

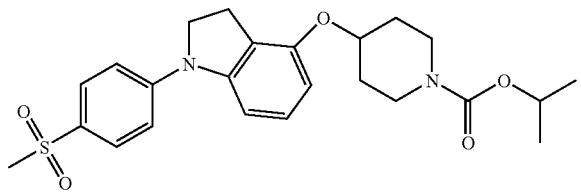

Step 1: 1-Methylethyl 4-{[1-(4-iodophenyl)-1H-indol-4-yl]oxy}-1-piperidinecarboxylate (67)

To a solution of 64 (3.150 g, 6.08 mmol) in CH$_2$Cl$_2$ (20 mL) at RT under N$_2$ was added CF$_3$CO$_2$H (5 mL). The reaction mixture was stirred at RT for 2.5 h and then concentrated under reduced pressure to afford the crude material. The crude material was redissolved in CH$_2$Cl$_2$ (100 mL) and cooled to 5° C. To the above mixture, DIPEA (3.2 mL, 18.2 mmol), DMAP (74 mg, 0.61 mmol), and a 1 M solution of isopropyl chloroformate in toluene (12.2 mL, 12.16 mmol) were added sequentially. The mixture was stirred at RT for 15 h. The reaction mixture was diluted with CH$_2$Cl$_2$ (150 mL) and then washed with water (2×20 mL), brine (1×20 mL), dried over Na$_2$SO$_4$, filtered, and the filtrate was concentrated under reduced pressure to afford the crude material. The product was purified by SiO$_2$ column chromatography (0→20% ethyl acetate/hexanes) to afford 2.56 g (83%) of the title product 67 as white solid. $^1$H NMR (400 MHz, DMSO-d$_6$): δ 7.88 (d, J=8.8 Hz, 2H), 7.51 (d, J=3.2 Hz, 1H), 7.39 (d, J=8.4 Hz, 2H), 7.12 (app. t, J=8.0 Hz, 1H), 7.10 (app. t, J=8.0 Hz, 1H), 6.72 (d, J=7.2 Hz, 1H), 6.70 (d, J=3.2 Hz, 1H), 4.76 (septuplet, J=6.4 Hz, 1H), 4.72 (m, 1H), 3.69-3.63 (m, 2H), 3.33-3.29 (m, 2H), 1.99-1.90 (m, 2H), 1.68-1.60 (m, 2H), 1.18 (d, J=6.4 Hz, 6H); LCMS (ESI): m/z 505 (M+Na)$^+$.

Step 2: 1-Methylethyl 4-{[1-(4-iodophenyl)-2,3-dihydro-1H-indol-4-yl]oxy}-1-piperidinecarboxylate (68)

To a solution of 67 (2.41 g, 4.78 mmol) and acetic acid (40 mL) at RT was added NaCNBH$_3$ (3.00 mg, 47.8 mmol). The mixture was stirred at RT for 15 h and then H$_2$O (150 mL) was added. The mixture was extracted with EtOAc (4×125 mL). The combined organic layer was washed with brine (1×50 mL), dried over Na$_2$SO$_4$, filtered, and the filtrate was concentrated under reduced pressure. The crude material was purified by flash SiO$_2$ column chromatography using (0→20% ethyl acetate/hexanes) to afford 2.31 mg (95%) of the title product 68 as a white solid. $^1$H NMR (400 MHz, DMSO-d$_6$): δ 7.59 (t, J=8.4 Hz, 2H), 7.02 (d, J=8.8 Hz, 2H), 6.99 (app. t, J=8.0 Hz, 1H), 6.71 (d, J=8.0 Hz, 1H), 6.49 (d, J=8.4 Hz, 1H), 4.75 (septuplet, J=5.6 Hz, 1H), 4.56 (m, 1H), 3.88 (t, J=8.4 Hz, 2H), 3.62-3.57 (m, 2H), 3.31-3.20 (m, 2H), 2.95 (t, J=8.8 Hz, 2H), 1.88-1.83 (m, 2H), 1.58-1.50 (m, 2H), 1.17 (d, J=6.4 Hz, 6H); LCMS (ESI): m/z 507 (M+H)$^+$.

Step 3: 1-Methylethyl 4-({1-[4-(methylsulfonyl)phenyl]-2,3-dihydro-1H-indol-4-yl}oxy)-1-piperidinecarboxylate (69)

The procedure described for 3 was employed. A 10 mL glass tube was charged with 68 (720 mg, 1.42 mmol), MeSO$_2$Na (290 mg, 2.84 mmol), L-proline (33 mg, 0.284 mmol), NaOH (12 mg, 0.284 mmol) and DMSO (5 mL). The tube was sealed and then heated to 120° C. and stirred for 24 h. The reaction mixture was cooled, opened, and then poured into H$_2$O. The mixture was stirred for 10 min, the solid material filtered and purified by flash SiO$_2$ column chromatography to afford 632 mg (97%) of the title product 69 as an off-white solid. $^1$H NMR (400 MHz, DMSO-d$_6$): δ 7.79 (t, J=8.8 Hz, 2H), 7.35 (d, J=8.8 Hz, 2H), 7.08 (app. t, J=8.4 Hz, 1H), 6.93 (d, J=8.0 Hz, 1H), 6.60 (d, J=8.4 Hz, 1H), 4.75 (septuplet, J=6.0 Hz, 1H), 4.60 (m, 1H), 4.01 (t, J=8.8 Hz, 2H), 3.60-3.55 (m, 2H), 3.28-3.26 (m, 2H), 3.13 (s, 3H), 3.01 (t, J=8.4 Hz, 2H), 1.89-1.60 (m, 2H), 1.59-1.52 (m, 2H), 1.17 (d, J=6.4 Hz, 6H); LCMS (ESI): m/z 458 (M+H)$^+$.

Example 23 (70)

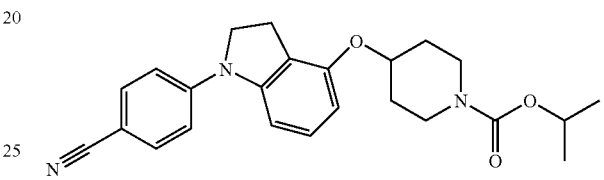

1-Methylethyl 4-{[1-(4-cyanophenyl)-2,3-dihydro-1H-indol-4-yl]oxy}-1-piperidinecarboxylate (70)

The procedure described for 31 (Example 10, Step 7) was followed by using 68 (507 mg, 1 mmol) and CuCN (202 mg, 2.25 mmol) in NMP (10 mL) at 150° C. for 15 h. The mixture was purified by SiO$_2$ flash column chromatography to give 388 mg (96%) of the title product 70 as a white solid. $^1$H NMR (400 MHz, DMSO-d$_6$): δ 7.70 (t, J=8.8 Hz, 2H), 7.28 (d, J=8.8 Hz, 2H), 7.08 (app. t, J=8.4 Hz, 1H), 6.91 (d, J=8.0 Hz, 1H), 6.61 (d, J=8.4 Hz, 1H), 4.75 (septuplet, J=6.4 Hz, 1H), 4.59 (m, 1H), 3.99 (t, J=8.4 Hz, 2H), 3.60-3.57 (m, 2H), 3.30-3.26 (m, 2H), 3.00 (t, J=8.8 Hz, 2H), 1.89-1.84 (m, 2H), 1.60-1.50 (m, 2H), 1.38 (d, J=6.4 Hz, 6H); LCMS (ESI): m/z 406 (M+H)$^+$.

Example 24 (71)

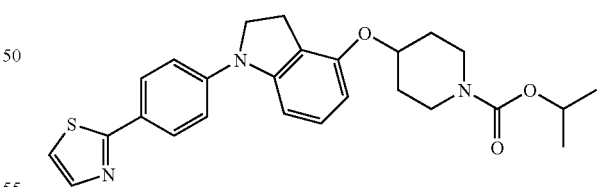

1-Methylethyl 4-({1-[4-(1,3-thiazol-2-yl)phenyl]-2,3-dihydro-1H-indol-4-yl}oxy)-1-piperidinecarboxylate (71)

The procedure described for 32 (Example 11) was utilized. A round-bottomed flask at RT under N$_2$ was charged with 68 (100 mg, 0.20 mmol), PdCl$_2$(Ph$_3$P)$_2$ (7 mg, 0.001 mmol), 2-(tributylstannanyl)-1,3-thiazole (110 mg, 0.296 mmol), and THF (3 mL). The reaction mixture was refluxed for 15 h. The reaction mixture was cooled to RT and then chromatographed to afford 52 mg (57%) of the title product 71 as a white solid. $^1$H NMR (400 MHz, DMSO-d$_6$): δ 7.88 (t, J=8.8 Hz, 2H), 7.83 (d, J=3.2 Hz, 2H), 7.65 (app. t, J=3.2 Hz, 1H), 7.28 (d, J=8.8 Hz, 1H), 7.05 (d, J=8.0 Hz, 1H), 6.86 (d, J=8.4 Hz, 1H), 7.05 (t, J=8.4 Hz, 1H), 6.86 (d, J=8.4 Hz, 1H), 6.54 (d, J=8.4 Hz, 1H), 4.76 (septuplet, J=6.4 Hz, 1H), 4.58 (m, 1H), 3.99 (t, J=8.8 Hz, 2H), 3.64-3.58 (m, 2H), 3.29-3.25 (m, 2H), 3.00 (t, J=8.8 Hz, 2H), 1.89-1.85 (m, 2H), 1.59-1.50 (m, 2H), 1.17 (d, J=6.4 Hz, 6H); LCMS (ESI): m/z 464 (M+H)$^+$.

Example 25 (74)

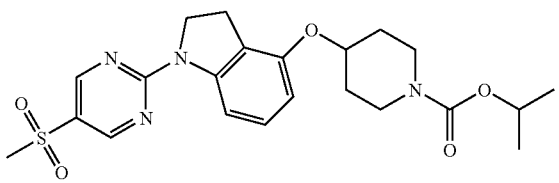

Step 1: 1,1-Dimethylethyl 4-(2,3-dihydro-1H-indol-4-yloxy)-1-piperidinecarboxylate (72)

The reduction procedure described for 65 (Example 21, Step 3) was followed using compound 63 (1.30 g, 4.11 mmol), NaCNBH$_3$ (2.58 g, 41.0 mmol) and AcOH (40 mL) at ambient temperature. Aqueous work-up followed by purification gave 0.84 g (64%) of the title product 72 as an off-white solid. LCMS (ESI): m/z 319 (M+H)$^+$.

Step 2: 1,1-Dimethylethyl 4-{[1-(5-bromo-2-pyrimidinyl)-2,3-dihydro-1H-indol-4-yl]oxy}-1-piperidinecarboxylate (73)

To a solution of 72 (637 mg, 2 mmol) in acetonitrile (40 mL) were added, under N$_2$ at ambient temperature, DIPEA (1.1 mL) and 5-bromo-2-chloropyrimidine (483 mg, 2.5 mmol). The mixture was refluxed for 15 h and then concentrated under reduced pressure. The crude product was purified by SiO$_2$ flash column chromatography to afford 60 mg (6%) of the title product 73 as a white solid. $^1$H NMR (400 MHz, DMSO-d$_6$): δ 8.67 (s, 2H), 7.84 (d, J=8.0 Hz, 1H), 7.13 (t, J=8.4 Hz, 1H), 6.68 (d, J=8.4 Hz, 1H), 4.58 (m, 1H), 4.13 (t, J=8.8 Hz, 2H), 3.60-3.54 (m, 2H), 3.30-3.19 (m, 2H), 3.04 (t, J=8.8 Hz, 2H), 1.89-1.80 (m, 2H), 1.60-1.51 (m, 2H), 1.38 (s, 9H); LCMS (ESI): m/z 498 (M+Na)$^+$.

Step 3: 1,1-Dimethylethyl 4-({1-[5-(methylsulfonyl)-2-pyrimidinyl]-2,3-dihydro-1H-indol-4-yl}oxy)-1-piperidinecarboxylate (74)

The procedure described for 3 (Example 1, Step 3) was employed using 73 (45 mg, 0.095 mmol), CuI (2 mg, 0.01 mmol), L-proline (3 mg, 0.02 mmol), NaOH (1 mg, 0.02 mmol), CH$_3$SO$_2$Na (20 mg, 0.19 mmol), and DMSO (2 mL). The mixture was heated to 110° C. for 24 h and then poured into H$_2$O (20 mL). The solid was filtered and dried to afford 44 mg (98%) of the title product 74 as a light yellow solid. $^1$H NMR (400 MHz, DMSO-d$_6$): δ 8.91 (s, 2H), 7.97 (d, J=8.4 Hz, 1H), 7.19 (t, J=8.4 Hz, 1H), 6.78 (d, J=8.0 Hz, 1H), 4.62 (m, 1H), 4.25 (t, J=8.4 Hz, 2H), 3.62-3.53 (m, 2H), 3.28 (s, 3H), 3.27-3.23 (m, 2H), 3.08 (t, J=8.8 Hz, 2H), 3.89-3.82 (m, 2H), 1.60-1.52 (m, 2H), 1.39 (s, 9H); LCMS (ESI): m/z 497 (M+Na)$^+$.

Example 26 (75)

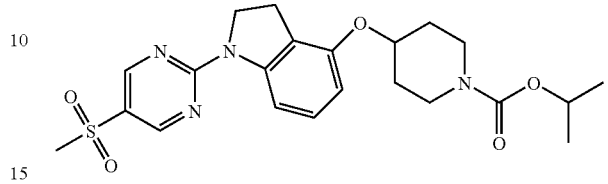

1-Methylethyl 4-({1-[5-(methylsulfonyl)-2-pyrimidinyl]-2,3-dihydro-1H-indol-4-yl}oxy)-1-piperidinecarboxylate (75)

To a mixture of 74 (30 mg, 0.063 mmol) and CH$_2$Cl$_2$ (8 mL) was added CF$_3$COOH (2 mL). The mixture was stirred at RT under N$_2$ for 2 h and then concentrated under reduced pressure. The crude material was redissolved in CH$_2$Cl$_2$ (4 mL) and DIPEA (50 μL, 0.38 mmol), DMAP (8 mg, 0.006 mmol), and a 1 M solution of isopropyl chloroformate (250 μL, 0.252 mmol) in toluene were introduced sequentially. The mixture was stirred at RT for 15 h. Standard work-up followed by purification gave 28 mg (96%) of the title product 75 as a white solid. $^1$H NMR (400 MHz, DMSO-d$_6$): δ 8.91 (s, 2H), 7.97 (d, J=8.4 Hz, 1H), 7.20 (t, J=8.0 Hz, 1H), 6.78 (d, J=8.4 Hz, 1H), 4.76 (septuplet, J=6.4 Hz, 1H), 4.63 (m, 1H), 4.25 (t, J=8.8 Hz, 2H), 3.65-3.56 (m, 2H), 3.29-3.23 (m, 2H), 3.28 (s, 3H), 3.08 (t, J=8.4 Hz, 2H), 1.92-1.84 (m, 2H), 1.60-1.52 (m, 2H), 1.17 (d, J=6.0 Hz, 6H); LCMS (ESI): m/z 461 (M+H)$^+$.

Example 27 (76)

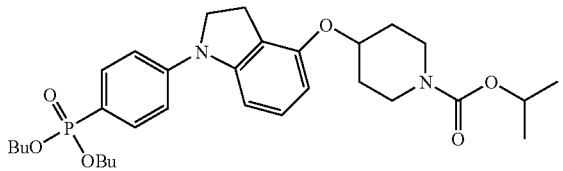

1-Methylethyl 4-[(1-{4-[bis(butyloxy)phosphoryl]phenyl}-2,3-dihydro-1H-indol-4-yl)oxy]-1-piperidinecarboxylate (76)

An oven dried 10 mL round-bottomed flask was evacuated and refilled with N$_2$ and then charged with CuI (4 mg, 0.02 mmol) followed by anhydrous toluene (3 mL), dibutyl phosphonate (48 mg, 0.248 mmol), N,N-dimethylethylenediamine (4 μL, 0.04 mmol), and compound 68 (100 mg, 0.197 mmol). The sealed tube was stirred at 110° C. for 24 h. The resulting suspension was cooled to RT, diluted with H$_2$O, and the mixture was extracted with EtOAC. The combined organic extracts were dried and then concentrated under reduced pressure. The product was purified by SiO$_2$ flash column chromatography to afford 78 mg (69%) of the title product 76 as a white solid. $^1$H NMR (400 MHz, DMSO-d$_6$):

δ 7.61 (d, J=8.4 Hz, 1H), 7.58 (d, J=8.8 Hz, 1H), 7.30 (d, J=3.2 Hz, 1H), 7.27 (d, J=3.2 Hz, 1H), 7.06 (app. t, J=8.0 Hz, 1H), 6.89 (d, J=8.0 Hz, 1H), 6.57 (d, J=8.0 Hz, 1H), 4.75 (m, 1H), 4.58 (m, 1H), 3.98 (t, J=8.8 Hz, 2H), 3.93-3.85 (m, 4H), 3.62-3.57 (m, 2H), 3.30-3.25 (m, 2H), 2.99 (t, J=8.4 Hz, 2H), 1.89-1.84 (m, 2H), 1.58-1.51 (m, 6H), 1.31 (m, J=7.6 Hz, 4H), 1.17 (d, J=6.0 Hz, 6H), 0.84 (t, J=7.6 Hz, 6H); LCMS (ESI): m/z 573 (M+H)$^+$.

Example 28 (77)

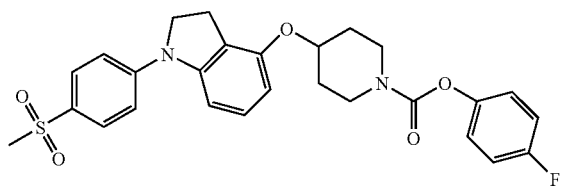

4-Fluorophenyl 4-({1-[4-(methylsulfonyl)phenyl]-2,3-dihydro-1H-indol-4-yl}oxy)-1-piperidinecarboxylate (77)

Compound 66 (42 mg, 0.089 mmol) was treated with concentrated HCl (5 mL) and was stirred at RT for 5 h. The mixture was poured into a 26% aqueous NH$_4$OH solution (25 mL) and the mixture was extracted with EtOAC (4×20 mL). The combined organic layer was washed with brine (1×12 mL), dried over Na$_2$SO$_4$, filtered and then the filtrate was concentrated under reduced pressure. The crude material was dissolved in CH$_2$Cl$_2$ and then DIPEA (47 μL, 0.27 mmol) and 4-fluorophenyl chloroformate (88 mg, 0.45 mmol) were added sequentially. The mixture was stirred at RT for 15 h. Aqueous work-up followed by purification gave 29 mg (64%) of the title product 77 as a white solid. $^1$H NMR (400 MHz, DMSO-d$_6$): δ 7.80 (d, J=8.8 Hz, 2H), 7.36 (d, J=9.2 Hz, 2H), 7.22-7.14 (m, 4H), 7.10 (t, J=8.0 Hz, 1H), 6.94 (d, J=8.0 Hz, 1H), 6.64 (d, J=8.4 Hz, 1H), 4.68 (m, 1H), 4.03 (t, J=8.4 Hz, 2H), 3.79 (app. br s, 1H), 3.65 (app. br s, 1H), 3.54 (app. br s, 1H), 3.40 (app. br s, 1H), 3.13 (s, 3H), 3.05 (t, J=8.4 Hz, 2H), 1.96 (app. br s, 2H), 1.71 (app. br s, 2H); LCMS (ESI): m/z 511 (M+H)$^+$.

Example 29 (80)

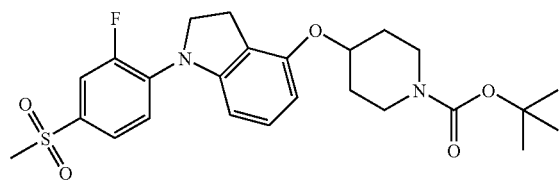

Step 1: 1,1-Dimethylethyl 4-{[1-(4-bromo-2-fluorophenyl)-1H-indol-4-yl]oxy}-1-piperidinecarboxylate (78)

A round-bottomed flask was charged under N$_2$ with compound 63 (1.90 g, 6.0 mmol), CuI (171 mg, 0.9 mmol), K$_2$CO$_3$ (1.66 g, 12 mmol), 4-bromo-2-fluoro-1-iodobenzene (3.61 g, 12 mmol) and anhydrous DMSO (20 mL). The reaction mixture was stirred at 110° C. for 60 h. The mixture was cooled to RT, diluted with EtOAC, filtered and the filtrate was concentrated under reduced pressure to afford the crude product, which was purified by flash column chromatography to give 1.96 g (75%) of the title product 78 as a mixture of two products. This material was used directly in the next step without purification.

Step 2: 1,1-Dimethylethyl 4-({1-[2-fluoro-4-(methylsulfonyl)phenyl]-1H-indol-4-yl}oxy)-1-piperidinecarboxylate (79)

The procedure described for 3 (Example 1, Step 3) was employed using 78 (1.34 g, 3.08 mmol), CuI (58 mg, 0.30 mmol), L-proline (71 mg, 0.60 mmol), NaOH (24 mg, 0.60 mmol), CH$_3$SO$_2$Na (471 mg, 4.6 mmol), and DMSO (4 mL). Aqueous work-up followed by purification gave 630 mg (42%) of the title product 79 as a white solid. $^1$H NMR (400 MHz, DMSO-d$_6$): δ 8.10 (app. d, J=10.8 Hz, 1H), 7.92 (m, 2H), 7.51 (app. t, J=2.0 Hz, 1H), 7.12 (app. t, J=8.0 Hz, 1H), 6.92 and 6.90 (dd, J$_1$=8.0 Hz, J$_2$=2.4 Hz, 1H), 6.78-6.76 (m, 2H), 4.72 (m, 1H), 3.67-3.62 (m, 2H), 3.45 (s, 3H), 3.30-3.22 (m, 2H), 1.97-1.91 (m, 2H), 1.67-1.60 (m, 2H), 1.40 (s, 9H); LCMS (ESI): m/z 511 (M+Na)$^+$.

Step 3: 1,1-Dimethylethyl 4-({1-[2-fluoro-4-(methylsulfonyl)phenyl]-2,3-dihydro-1H-indol-4-yl}oxy)-1-piperidinecarboxylate (80)

The procedure described for 65 (Example 21, Step 3) was followed using 79 (70 mg, 0.14 mmol), NaCNBH$_3$ (45 mg, 0.72 mmol), and acetic acid (2 mL). Aqueous work-up gave the crude mixture which was a 3:1 mixture (~50 mg) of product and starting material. An 18 mg portion of this mixture was again treated at RT with NaCNBH$_3$ (37 mg) in AcOH (3 mL) for 48 h. Aqueous work-up followed by purification by SiO$_2$ flash column chromatography gave 13 mg of the title product 80 as a white solid. $^1$H NMR (400 MHz, DMSO-d$_6$): δ 7.81 and 7.78 (dd, J$_1$=11.6 Hz, J$_2$=2.4 Hz, 1H), 7.69 and 7.67 (dd, J$_1$=8.4 Hz, J$_2$=2.0 Hz, 1H), 7.59 (app. t, J=8.4 Hz, 1H), 7.03 (app. t, J=8.4 Hz, 1H), 6.56 (d, J=8.4 Hz, 1H), 6.37 and 6.35 (dd, J$_1$=7.6 Hz, J$_2$=4.4 Hz, 1H), 4.60-4.52 (m, 1H), 4.0 (t, J=8.0 Hz, 2H), 3.62-3.53 (m, 2H), 3.22 (s, 3H), 3.29-3.19 (m, 2H), 3.02 (t, J=8.4 Hz, 3H), 1.89-1.84 (m, 2H), 1.56-1.50 (m, 2H), 1.51 (s, 9H); LCMS (ESI): m/z 513 (M+Na)$^+$.

Example 30 (82)

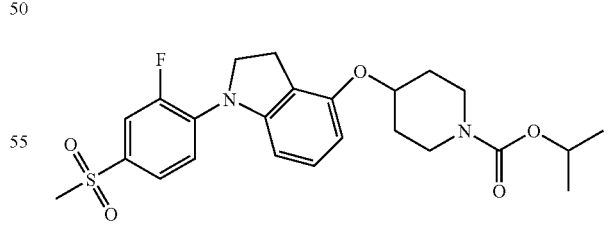

Step 1: 1-Methylethyl 4-({1-[2-fluoro-4-(methylsulfonyl)phenyl]-1H-indol-4-yl}oxy)-1-piperidinecarboxylate (81)

To a solution of 79 (200 mg, 0.409 mmol) in CH$_2$Cl$_2$ (20 mL) at RT under N$_2$ was added CF$_3$COOH (5 mL) and resulting reaction mixture was stirred for 2 h. The mixture was concentrated under reduced pressure and dried. The crude material was redissolved in $CH_2Cl_2$ and cooled to 5° C. To the above mixture DIPEA (213 μL, 1.22 mmol) and a 1 M solution of isopropyl chloroformate (~1 mL) in toluene were added. The mixture was allowed to stir at RT for 1 h. Standard work-up followed by purification gave 155 mg (80%) of the title product 81 as white solid. $^1$H NMR (400 MHz, DMSO-$d_6$): δ 8.10 (app. d, J=10.8 Hz, 1H), 7.93-7.92 (m, 2H), 7.51 (t, J=2.0 Hz, 1H), 7.12 (t, J=8.0 Hz, 1H), 6.93 and 6.91 (dd, $J_1$=8.4 Hz, $J_2$=2.4 Hz, 1H), 6.78-6.76 (m, 2H), 4.80-4.70 (m, 2H), 3.70-3.65 (m, 2H), 3.35 (s, 3H), 3.32-3.29 (br m, 2H), 1.97-1.92 (m, 2H), 1.69-1.61 (m, 2H), 1.18 (d, J=6.0 Hz, 2H); LCMS (ESI): m/z 475 (M+H)$^+$.

Step 2: 1-Methylethyl 4-({1-[2-fluoro-4-(methylsulfonyl)phenyl]-2,3-dihydro-1H-indol-4-yl}oxy)-1-piperidinecarboxylate (82)

The procedure described for 65 (Example 21, Step 3) was followed using 81 (110 mg, 0.23 mmol), $NaCNBH_3$ (300 mg, 4.8 mmol), and AcOH (12 mL). The mixture was stirred for 60 h. Aqueous work gave a 3:1 mixture (~110 mg) of product and starting material favoring the desired product. A 110 mg sample of the mixture obtained above, was treated again with $NaCNBH_3$ (291 mg, 4.6 mmol) in $CF_3CO_2H$ (10 mL) at RT for 15 h. Aqueous work-up followed by purification gave 43 mg (39%) of the title product 82 as a white solid. $^1$H NMR (400 MHz, DMSO-$d_6$): δ 7.81 and 7.78 (dd, $J_1$=11.6 Hz, $J_2$=2.0 Hz, 1H), 7.69 and 7.67 (dd, $J_1$=8.4 Hz, $J_2$=2.0 Hz, 1H), 7.59 (app. t, J=8.4 Hz, 1H), 7.03 (t, J=8.0 Hz, 1H), 6.56 (d, J=8.4 Hz, 2H), 6.37-6.35 (dd, $J_1$=7.6 Hz, $J_2$=4.4 Hz, 1H), 4.76 (septuplet, J=6.4 Hz, 1H), 4.58 (m, 1H), 4.0 (t, J=8.4 Hz, 1H), 3.68-3.57 (m, 2H), 3.30-3.21 (m, 2H), 3.22 (s, 3H), 3.02 (t, J=8.8 Hz, 2H), 1.92-1.82 (m, 2H), 1.61-1.52 (m, 2H), 1.17 (d, J=6.4 Hz, 6H); LCMS (ESI): m/z 477 (M+H)$^+$.

Example 31 (85)

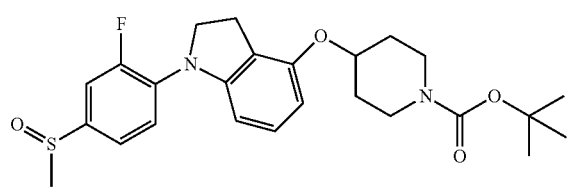

Step 1: 1,1-Dimethylethyl 4-({1-[4-(methylthio)phenyl]-1H-indol-4-yl}oxy)-1-piperidinecarboxylate (83)

The N-arylation procedure described for 64 (Example 21, Step 2) was followed using compound 63 (3.40 g, 10.8 mmol), CuI (204 mg, 1.1 mmol), $K_3PO_4$ (3.42 g, 16.1 mmol), 1-iodo-4-(methylthio)benzene (4.03 g, 16.1 mmol), trans-N,N'-dimethyl-1,2-cyclohexanediamine (323 μL, 2.7 mmol), and anhydrous 1,4-dioxane (25 mL). The reaction mixture was stirred at 110° C. for 48 h. Work-up followed by purification gave 2.56 g (54%) of a title product 83 as an off-white solid. $^1$H NMR (400 MHz, DMSO-$d_6$): δ 7.50-7.47 (m, 3H), 7.43-7.41 (m, 2H), 7.09-7.07 (m, 2H), 6.71 and 6.69 (dd, $J_1$=6.0 Hz, $J_2$=2.4 Hz, 1H), 6.67 (d, J=3.2 Hz, 1H), 4.70 (m, 1H), 3.67-3.61 (m, 2H), 3.28-3.24 (m, 2H), 2.52 (s, 3H), 1.95-1.90 (m, 2H), 1.66-1.58 (m, 2H), 1.39 (s, 9H); LCMS (ESI): m/z 439 (M+H)$^+$.

Step 2: 1,1-Dimethylethyl 4-({1-[4-(methylthio)phenyl]-2,3-dihydro-1H-indol-4-yl}oxy)-1-piperidinecarboxylate (84)

The reduction procedure described for 65 (Example 21, Step 3) was employed using compound 83 (600 mg, 1.37 mmol), $NaCNBH_3$ (515 mg, 8.20 mmol), and acetic acid (10 mL). The aqueous work-up followed by purification by column chromatography afforded 528 mg (88%) of the title product 84 as a white solid. $^1$H NMR (400 MHz, DMSO-$d_6$): δ 7.26 (t, J=8.8 Hz, 2H), 7.15 (d, J=8.8 Hz, 2H), 6.98 (app. t, J=8.0 Hz, 1H), 6.65 (d, J=7.6 Hz, 1H), 6.45 (d, J=8.0 Hz, 1H), 4.53 (septuplet, J=3.2 Hz, 1H), 3.88 (t, J=8.4 Hz, 2H), 3.60-3.54 (m, 2H), 3.24-3.20 (m, 2H), 2.95 (t, J=8.8 Hz, 2H), 2.42 (s, 3H), 1.87-1.82 (m, 2H), 1.57-1.49 (m, 2H), 1.38 (s, 9H); LCMS (ESI): m/z 441 (M+H)$^+$.

Step 3: (±)-1,1-Dimethylethyl 4-({1-[4-(methylsulfinyl)phenyl]-2,3-dihydro-1H-indol-4-yl}oxy)-1-piperidinecarboxylate (85)

To a solution of 84 (200 mg, 0.454 mmol) and hexafluoroisopropanol (2.5 mL) was added 30% aqueous $H_2O_2$ (100 μL). The mixture was stirred at RT for 0.5 h. A saturated sodium sulfide solution (8 mL) was introduced to the above mixture and stirred for 5 min. Layers were separated and the organic layer was subjected to column chromatography (0→20% ethyl acetate/hexanes) to afford 178 mg (86%) of the title product 85 as an off-white solid. $^1$H NMR (400 MHz, DMSO-$d_6$): δ 7.61 (t, J=8.8 Hz, 2H), 7.34 (d, J=8.8 Hz, 2H), 7.04 (app. t, J=8.0 Hz, 1H), 6.83 (d, J=8.0 Hz, 1H), 6.54 (d, J=8.4 Hz, 1H), 4.56 (septuplet, J=3.2 Hz, 1H), 3.98 (t, J=8.8 Hz, 2H), 3.60-3.55 (m, 2H), 3.25-3.22 (m, 2H), 2.99 (t, J=8.4 Hz, 2H), 2.69 (s, 3H), 1.88-1.83 (m, 2H), 1.58-1.49 (m, 2H), 1.39 (s, 9H); LCMS (ESI): m/z 457 (M+H)$^+$.

Example 32

The racemic sulfoxide 85 (150 mg) was subjected to Chiral HPLC [column: Chiralpak AS (analytical), Chiralpak (prep.), mobile phase: 78% $CO_2$: 22% MeOH (14 mL/min), pressure 140 bar, temperature 40° C., 240 nm)] analysis and then was separated into its two (R and S) enantiomers. The absolute stereochemistry was not assigned.

Example 32A (86)

Tr (retention time) was 11.57 min, 33 mg (% ee>98%), and the spectral data are essentially the same to that of Example 31 (85).

Example 32B (87)

Tr was 14.04 min, 38 mg (% ee>97%), and the spectral data are essentially the same to that of Example 31 (85).

Example 33 (89)

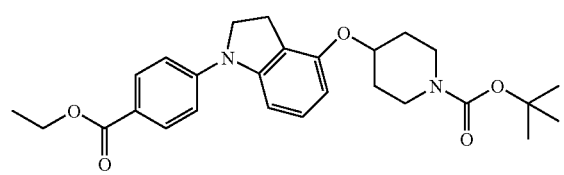

Step 1: 1,1-Dimethylethyl 4-[(1-{4-[(ethyloxy)carbonyl]phenyl}-1H-indol-4-yl)oxy]-1-piperidinecarboxylate (88)

A mixture of 1,1-dimethylethyl 4-(1H-indol-4-yloxy)-1-piperidinecarboxylate (63) (1.00 g, 3.16 mmol), ethyl 4-fluorobenzoate (3.00 g, 17.84 mmol)18-crown-6 (0.33 g, 1.23 mmol), KF/Al$_2$O$_3$ (2.86 g, 19.69 mmol) and DMSO (30 mL) was heated at 130° C. for 7 h in a Biotage Initiator microwave apparatus. The reaction was diluted with 150 mL each water and EtOAc. The EtOAc fraction was washed with water (150 mL) and brine (150 mL), dried (Na$_2$SO$_4$) and concentrated to give an yellow oil. The crude product was purified by column chromatography on silica gel with 15% EtOAc/hexanes to afford 560 mg (38%) of compound 88 as white foam. $^1$H NMR (400 MHz, DMSO-d$_6$): δ 1.33 (t, J=7.1 Hz, 3H), 1.39 (s, 9H), 1.60-1.66 (m, 2H), 1.91-1.95 (m, 2H), 3.27-3.31 (m, 2H), 3.62-3.66 (m, 2H), 4.35 (q, J=7.1 Hz, 2H), 4.70-4.72 (m, 1H), 6.75 (s, 1H), 6.77 (d, J=5.2 Hz, 1H), 7.13 (t, J=8.0 Hz, 1H), 7.25 (d, J=8.4 Hz, 1H), 7.62 (d, J=3.3 Hz, 1H), 7.73 (d, J=8.5 Hz, 2H), 8.11 (d, J=8.5 Hz, 2H); LCMS (ESI): m/z 487 (M+Na)$^+$.

Step 2: 1,1-Dimethylethyl 4-[(1-{4-[(ethyloxy)carbonyl]phenyl}-2,3-dihydro-1H-indol-4-yl)oxy]-1-piperidinecarboxylate (89)

To a stirring solution of compound 88 (0.11 g, 0.24 mmol) in glacial AcOH (3 mL) was added, in a single portion, NaCNBH$_3$ (0.15 g, 2.40 mmol). Gas evolution was observed over ~5 min and the reaction turned from light yellow to colorless. After 22 h the reaction was diluted with 50 mL each saturated aqueous NaHCO$_3$ and EtOAc. The EtOAc layer was rinsed with saturated aqueous NaHCO$_3$ (50 mL) and brine (50 mL) dried (Na$_2$SO$_4$) and concentrated to a pale yellow oil. The crude product was purified by column chromatography on silica gel with 10% EtOAc/hexanes to afford the 84 mg (75%) of the title compound 89 as colorless oil. $^1$H NMR (400 MHz, DMSO-d$_6$): δ 1.28 (t, J=7.1 Hz, 3H), 1.39 (s, 9H), 1.51-1.57 (m, 2H), 1.82-1.88 (m, 2H), 3.00 (t, J=8.5 Hz, 2H), 3.21-3.26 (m, 2H), 3.54-3.60 (m, 2H), 3.99 (t, J=8.5 Hz, 2H), 4.25 (q, J=7.1 Hz, 2H), 4.55-4.59 (m, 1H), 6.58 (d, J=8.3 Hz, 1H), 6.91 (d, J=8.0 Hz, 1H), 7.06 (t, J=8.1 Hz, 1H), 7.25 (d, J=8.9 Hz, 2H), 7.88 (d, J=8.8 Hz, 2H); LCMS (ESI): m/z 467 (M+H)$^+$, m/z 489 (M+Na)$^+$.

Example 34 (90)

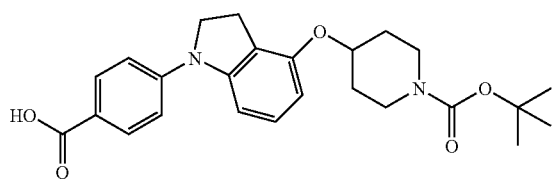

4-{4-[(1-{[(1,1-Dimethylethyl)oxy]carbonyl}-4-piperidinyl)oxy]-2,3-dihydro-1H-indol-1-yl}benzoic acid (90)

To a stirring solution of compound 88 (84 mg, 0.18 mmol) in 10 mL 1:1 v/v THF/EtOH was added 2.8 mL 1 N aq. NaOH and the colorless solution was heated at reflux. After 4 h the reaction was poured onto 30 mL 1 N aqueous HCl (30 mL) followed by EtOAc (50 mL). The EtOAc layer was washed with brine (30 mL), dried (Na$_2$SO$_4$) and concentrated to a white solid. The solid was triturated with 25 mL hexanes (25 mL), filtered and air-dried to yield 73 mg (93%) of the title compound 90 as a white solid. $^1$H NMR (400 MHz, DMSO-d$_6$): δ 1.39 (s, 9H), 1.50-1.58 (m, 2H), 1.83-1.88 (m, 2H), 3.00 (t, J=8.4 Hz, 2H), 3.21-3.25 (m, 2H), 3.55-3.60 (m, 2H), 3.99 (t, J=8.4 Hz, 2H), 4.55-4.58 (m, 1H), 6.56 (d, J=8.2 Hz, 1H), 6.90 (d, J=8.0 Hz, 1H), 7.06 (t, J=8.2 Hz, 1H), 7.23 (d, J=8.9 Hz, 2H), 7.87 (d, J=8.8 Hz, 2H), 12.46 (br s, 1H); LCMS (APCI): m/z 439 (M+H)$^+$, m/z 437 (M–H)$^-$.

As illustrated herein, a general procedure for amide formation is applicable for compounds of the present invention. The following provides a synthetic description applicable to the examples that follow. The specific examples provide appropriate characterizing data.

To a solution of 4-{4-[(1-{[(1,1-dimethylethyl)oxy]carbonyl}-4-piperidinyl)oxy]-2,3-dihydro-1H-indol-1-yl}benzoic acid (90, 75 mg, 0.17 mmol) and DIEA (78 mg, 0.60 mmol) in DMF (2 mL) was added a primary or secondary amine (0.60 mmol), the selection of which will be apparent to a person of ordinary skill in the art upon review of the examples, followed by a solution of HATU (91 mg, 0.24 mmol) in DMF (0.5 mL). The resulting solution was stirred at RT overnight. After 48 h the reaction was diluted with 30 mL each EtOAc and 1 N aqueous HCl. The EOAc layer was washed with saturated aqueous NaHCO$_3$ (25 mL) and brine (25 mL), dried (Na$_2$SO$_4$) and concentrated to a crude product which was subsequently triturated with a few mL EtOAc.

Example 35 (91)

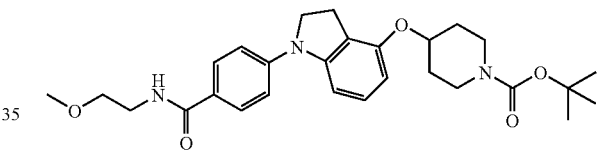

1,1-Dimethylethyl 4-({1-[4-({[2-(methyloxy)ethyl]amino}carbonyl)phenyl]-2,3-dihydro-1H-indol-4-yl}oxy)-1-piperidinecarboxylate (91)

Trituration with EtOAc yielded a white solid that was further purified by column chromatography on silica gel with 50% EtOAc/hexane. The title compound, 91, was isolated as a white solid (15 mg, 25%). $^1$H NMR (400 MHz, DMSO-d$_6$): δ 1.38 (s, 9H), 1.50-1.58 (m, 2H), 1.64 (quintuplet, J=6.7 Hz, 2H), 1.83-1.88 (m, 2H), 2.98 (t, J=8.2 Hz, 2H), 3.21-3.25 (m, 2H), 3.24 (s, 3H), 3.26-3.45 (m, 4H), 3.55-3.58 (m, 2H), 3.96 (t, J=8.4 Hz, 2H), 4.54-4.57 (m, 1H), 6.53 (d, J=8.4 Hz, 1H), 6.84 (d, J=8.1 Hz, 1H), 7.03 (t, J=8.1 Hz, 1H), 7.20 (d, J=8.8 Hz, 2H), 7.83 (d, J=8.8 Hz, 2H), 8.33 (t, J=4.8 Hz, 1H); LCMS (ESI): m/z 496 (M+H)$^+$, m/z 518 (M+Na)$^+$.

Example 36 (92)

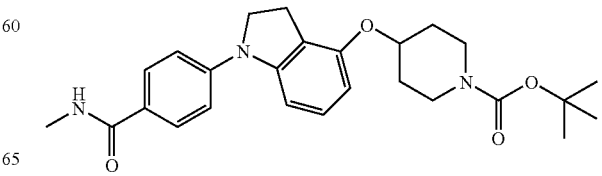

1,1-Dimethylethyl 4-[(1-{4-[(methylamino)carbonyl]phenyl}-2,3-dihydro-1H-indol-4-yl)oxy]-1-piperidinecarboxylate (92)

Trituration with EtOAc yielded 35 mg (46%) of the title compound, 92, as a white solid. $^1$H NMR (400 MHz, DMSO-d$_6$): δ 1.39 (s, 9H), 1.50-1.58 (m, 2H), 1.83-1.88 (m, 2H), 2.75 (d, J=4.6 Hz, 3H), 2.99 (t, J=8.4 Hz, 2H), 3.23-3.31 (m, 2H), 3.56-3.60 (m, 2H), 3.97 (t, J=8.3 Hz, 2H), 4.54-4.57 (m, 1H), 6.53 (d, J=8.2 Hz, 1H), 6.84 (d, J=8.1 Hz, 1H), 7.04 (t, J=8.2 Hz, 1H), 7.21 (d, J=8.8 Hz, 2H), 7.80 (d, J=8.7 Hz, 2H), 8.24 (br q, J=4.5 Hz, 1H); LCMS (ESI): m/z 452 (M+H)$^+$, m/z 474 (M+Na)$^+$.

Example 37 (93)

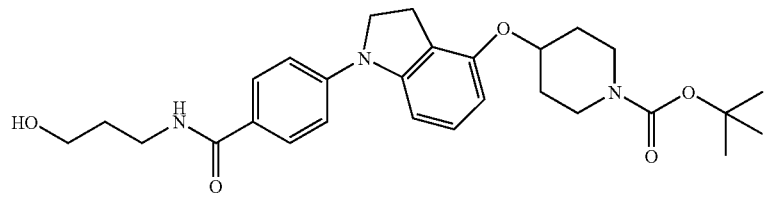

1,1-Dimethylethyl 4-{[1-(4-{[(3-hydroxypropyl)amino]carbonyl}phenyl)-2,3-dihydro-1H-indol-4-yl]oxy}-1-piperidinecarboxylate (93)

Trituration with EtOAc yielded 32 mg (38%) of the title compound, 93, as a pale yellow solid. $^1$H NMR (400 MHz, DMSO-d$_6$): δ 1.38 (s, 9H), 1.52-1.58 (m, 2H), 1.64 (quintuplet, J=6.7 Hz, 2H), 1.83-1.87 (m, 2H), 2.98 (t, J=8.4 Hz, 2H), 2.99 (t, J=8.4 Hz, 2H), 3.23-3.30 (m, 2H), 3.27 (m, 2H), 3.43 (t, J=6.2 Hz, 2H), 3.55-3.58 (m, 2H), 3.96 (t, J=8.6 Hz, 2H), 4.46 (t, J=5.1 Hz, 2H), 4.54-4.57 (m, 1H), 6.52 (d, J=8.5 Hz, 1H), 6.83 (d, J=7.9 Hz, 1H), 7.03 (t, J=8.2 Hz, 1H), 7.20 (d, J=8.8 Hz, 2H), 7.80 (d, J=8.7 Hz, 2H), 8.25 (t, J=4.5 Hz, 1H); LCMS (ESI): m/z 496 (M+H)$^+$, m/z 518 (M+Na)$^+$.

Example 38 (95)

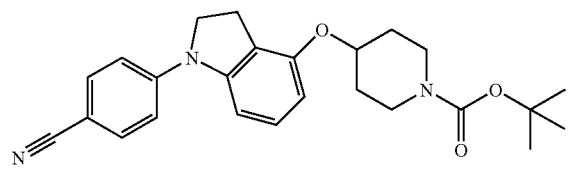

Step 1: 1,1-Dimethylethyl 4-{[1-(4-cyanophenyl)-1H-indol-4-yl]oxy}-1-piperidinecarboxylate (94)

A mixture of 1,1-dimethylethyl 4-(1H-indol-4-yloxy)-1-piperidinecarboxylate (63, 1.00 g, 3.16 mmol), 4-fluorobenzonitrile (1.72 g, 14.14 mmol), 18-crown-6 (0.32 g, 1.34 mmol), KF/Al$_2$O$_3$ (2.86 g, 19.70 mmol) and DMSO (25 mL) was heated at 130° C. in a Biotage Initiator microwave for 7 h. The reaction was diluted with 150 mL each of water and EtOAc. Brine (100 mL) was added to disperse an emulsion and the EtOAc fraction was washed with water (1×150 mL) and brine (1×150 mL), dried (Na$_2$SO$_4$), and concentrated to pale yellow, viscous oil. The crude material was purified by column chromatography on silica gel with a gradient of 10→20% EtOAc/hexanes. The product was isolated as a white solid (1.14 g) contaminated with ~20% of the starting indole 63. The white solid was recrystallized from 220 mL of EtOAc:hexanes (10:1 v/v) to yield 720 mg (55%) of the title compound 94 as a white crystalline solid. $^1$H NMR (400 MHz, DMSO-d$_6$): δ 1.39 (s, 9H), 1.61-1.67 (m, 2H), 1.90-1.95 (m, 2H), 3.24-3.29 (m, 2H), 3.60-3.66 (m, 2H), 4.69-4.74 (m, 1H), 6.76 (s, 1H), 6.77 (d, J=4.9 Hz, 1H), 7.14 (t, J=8.1 Hz, 1H), 7.25 (d, J=8.3 Hz, 1H), 7.65 (d, J=3.4 Hz, 1H), 7.80 (d, J=8.5 Hz, 2H), 8.01 (d, J=8.7 Hz, 2H); LCMS (ESI): m/z 440 (M+Na)$^+$.

Step 2: 1,1-Dimethylethyl 4-{[1-(4-cyanophenyl)-2,3-dihydro-1H-indol-4-yl]oxy}-1-piperidinecarboxylate (95)

To a stirring solution of 1,1-dimethylethyl 4-{[1-(4-cyanophenyl)-1H-indol-4-yl]oxy}-1-piperidinecarboxylate (94, 0.59 g, 1.41 mmol) and glacial AcOH (20 mL) was added, as a single portion, NaCNBH$_3$ (2.67 g, 42.45 mmol). Gas evolution was observed over 5 min and the reaction turned from colorless to light yellow. After 72 h the reaction was carefully poured onto 150 mL each saturated aqueous NaHCO$_3$ and EtOAc. The EtOAc layer was washed with brine (150 mL), dried (Na$_2$SO$_4$) and concentrated to reddish oil. The crude product was purified by column chromatography on silica gel with 15% EtOAc/hexane to yield 430 mg (73%) of compound 95 as a white solid. $^1$H NMR (400 MHz, DMSO-d$_6$): δ 1.38 (s, 9H), 1.50-1.58 (m, 2H), 1.83-1.88 (m, 2H), 3.00 (t, J=8.4 Hz, 2H), 3.21-3.25 (m, 2H), 3.54-3.60 (m, 2H), 3.99 (t, J=8.4 Hz, 2H), 4.56-4.60 (m, 1H), 6.61 (d, J=8.2 Hz, 1H), 6.91 (d, J=7.9 Hz, 1H), 7.08 (t, J=8.1 Hz, 1H), 7.25 (d, J=8.7 Hz, 2H), 7.70 (d, J=8.7 Hz, 2H); LCMS (ESI): m/z 442 (M+Na)$^+$.

Example 39 (96)

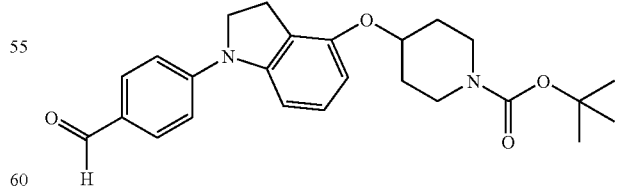

1,1-Dimethylethyl 4-{[1-(4-formylphenyl)-2,3-dihydro-1H-indol-4-yl]oxy}-1-piperidinecarboxylate (96)

A stirring solution of 1,1-dimethylethyl 4-{[1-(4-cyanophenyl)-2,3-dihydro-1H-indol-4-yl]oxy}-1-piperidinecarboxylate (95, 0.41 g, 0.98 mmol) in anhydrous toluene (15 mL) was chilled to −78° C., and DIBAL-H (1.5 M in toluene) added via syringe. The reaction was allowed to slowly warm to 0° C. After 3 h the clear yellow reaction was quenched by addition of MeOH (3 mL) followed by 1 N HCl (10 mL) then stirred for 2 h while slowly warming from 0° C. to room temperature. The reaction was diluted with EtOAc (100 mL) and the organic fraction washed with brine (2×50 mL), dried ($Na_2SO_4$) and concentrated to viscous yellow oil. The crude product was chromatographed on silica gel with 15% EtOAc/hexane to yield 320 mg (78%) of the title compound 96 as a yellow solid. $^1$H NMR (400 MHz, DMSO-$d_6$): δ 1.39 (s, 9H), 1.51-1.59 (m, 2H), 1.84-1.89 (m, 2H), 3.02 (t, J=8.4 Hz, 2H), 3.21-3.28 (m, 2H), 3.55-3.61 (m, 2H), 4.04 (t, J=8.4 Hz, 2H), 4.56-4.63 (m, 1H), 6.62 (d, J=8.2 Hz, 1H), 6.97 (d, J=8.0 Hz, 1H), 7.09 (t, J=8.1 Hz, 1H), 7.32 (d, J=8.8 Hz, 2H), 7.82 (d, J=8.8 Hz, 2H), 9.79 (s, 1H); LCMS (ESI): m/z 445 (M+Na)$^+$.

Example 40 (98)

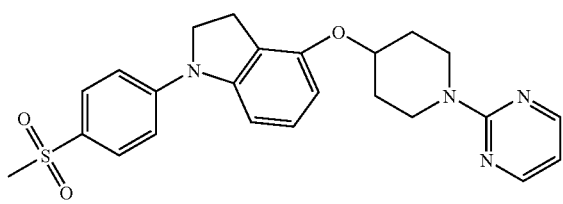

Step 1: 1-[4-(Methylsulfonyl)phenyl]-4-(4-piperidinyloxy)-2,3-dihydro-1H-indole hydrochloride (97)

Compound 66 (3.2 g, 6.7 mmol, prepared as a separate batch using the procedure hereinabove of Steps 1-4 of Example 21) was dissolved in 25 mL of a 4 N solution of HCl in Dioxane. The resulting solution was then stirred at ambient temperature for 2 h. The solvent was then removed under reduced pressure and the material was dried on the high vacuum to give 2.6 g of the HCl salt 97 that was used without purification.

Step 2: 1-[2-Fluoro-4-(methylsulfonyl)phenyl]-4-{[1-(2-pyrimidinyl)-4-piperidinyl]oxy}-2,3-dihydro-1H-indole (98)

Compound 97 (50 mg, 0.12 mmol) was dissolved in 5 mL methylene chloride and treated with 2 mL of DIPEA followed by 2-chloropyrimidine (100 mg, 0.88 mmol). The reaction was then heated at 40° C. for 48 h while stirring. The reaction was cooled to room temperature and all the solvents were removed under reduced pressure. The crude reaction was then purified via reverse phase chromatography (C18, 10-100% $CH_3CN/H_2O$/0.05% TFA) to give 26 mg of the desired product 98 as a white solid (48%). $^1$H NMR (400 MHz, CDCl$_3$): δ 1.78-1.94 (m, 2H), 1.94-2.04 (m, 2H), 3.02 (s, 3H), 3.15 (t, J=8.0 Hz, 2H), 3.70-3.88 (m, 2H), 3.95-4.19 (m, 4H), 4.54-4.74 (m, 1H), 6.42-6.59 (m, 2H), 6.90 (d, J=8.0 Hz, 1H), 7.15 (t, J=8.0 Hz, 1H), 7.25 (d, J=9.0 Hz, 2H), 7.82 (d, J=9.0 Hz, 2H), 8.30 (d, J=4.0 Hz, 2H); LCMS (ESI): m/z 451 (M+H)$^+$.

Example 41 (99)

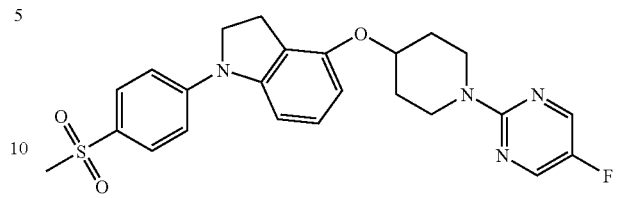

4-{[1-(5-Fluoro-2-pyrimidinyl)-4-piperidinyl]oxy}-1-[4-(methylsulfonyl)phenyl]-2,3-dihydro-1H-indole (99)

Compound 97 (50 mg, 0.12 mmol) was dissolved in 5 mL methylene chloride and treated with 2 mL of DIPEA followed by 2-chloro-5-fluoropyrimidine (100 mg, 0.76 mmol). The reaction was then heated at 40° C. for 48 h while stirring. The reaction was cooled to room temperature and all the solvents were removed under reduced pressure. The crude reaction was then purified via reverse phase chromatography (C18, 10-100% $CH_3CN/H_2O$/0.05% TFA) to give 35 mg (61%) of the title product 99 as a white solid. $^1$H NMR (400 MHz, CDCl$_3$): δ 1.77-1.93 (m, 2H), 1.94-2.07 (m, 2H), 3.01 (s, 3H), 3.15 (t, J=8.0 Hz, 2H), 3.65-3.83 (m, 2H), 3.95-4.19 (m, 4H), 4.54-4.74 (m, 1H), 6.50 (d, J=8.0 Hz, 2H), 6.90 (d, J=8.0 Hz, 1H), 7.11 (t, J=8.0 Hz, 1H), 7.25 (d, J=9.0 Hz, 2H), 7.82 (d, J=9.0 Hz, 2H), 8.16 (s, 2H); LCMS (ESI): m/z 469 (M+H)$^+$.

Example 42 (100)

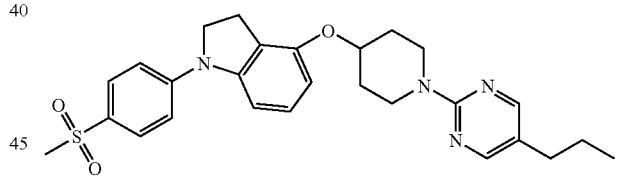

1-[4-(Methylsulfonyl)phenyl]-4-{[1-(5-propyl-2-pyrimidinyl)-4-piperidinyl]oxy}-2,3-dihydro-1H-indole (100)

Compound 97 (50 mg, 0.12 mmol) was dissolved in 5 mL methylene chloride and treated with 5 mL of DIPEA followed by 2-chloro-5-propylpyrimidine (100 mg, 0.64 mmol). The reaction was then heated at 40° C. for 48 h while stirring. The reaction was cooled to room temperature and all the solvents were removed under reduced pressure. The crude reaction was then purified via reverse phase chromatography (C18, 10-100% $CH_3CN/H_2O$/0.05% TFA) to give 9 mg (15%) of the title product 100 as a white solid. $^1$H NMR (400 MHz, CDCl$_3$): δ 0.87-1.01 (t, J=7.0 Hz, 3H), 1.43-1.55 (m, 2H), 1.86-1.94 (m, 2H), 1.98-2.14 (m, 2H), 2.38-2.51 (t, J=7.0 Hz, 2H), 3.13 (s, 3H), 3.18 (t, J=8.0 Hz, 2H), 3.70-3.88 (m, 2H), 3.98-4.10 (m, 4H), 4.61-4.69 (m, 1H), 6.50 (d, J=8.0 Hz, 1H), 6.91 (d, J=9.0 Hz, 1H), 7.10 (t, J=8.0 Hz, 1H), 7.29 (d, J=9.0 Hz, 2H), 7.82 (d, J=9.0 Hz, 2H), 8.20 (s, 2H); LCMS (ESI): m/z 493 (M+H)⁺.

Example 43 (101)

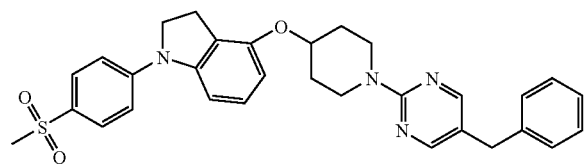

1-[4-(Methylsulfonyl)phenyl]-4-({1-[5-(phenyl methyl)-2-pyrimidinyl]-4-piperidinyl}oxy)-2,3-dihydro-1H-indole (101)

Compound 97 (50 mg, 0.12 mmol) was dissolved in 2 mL methylene chloride and treated with 2 mL of DIPEA followed by 2-chloro-5-(phenylmethyl)pyrimidine (100 mg, 0.49 mmol). The reaction was then heated at 50° C. for 48 h while stirring. The reaction was cooled to room temperature and all the solvents were removed under reduced pressure. The crude reaction was then purified via column chromatography (5→50% ethyl acetate/hexane) to give 10 mg (15%) of the title product 101 as a white solid (15%). ¹H NMR (400 MHz, CDCl₃): δ 1.88-1.93 (m, 2H), 1.97-2.12 (m, 2H), 3.07 (s, 3H), 3.18 (t, J=8.0 Hz, 2H), 3.67-3.83 (m, 4H), 3.96-4.10 (m, 4H), 4.50-4.69 (m, 1H), 6.51 (d, J=8.0 Hz, 1H), 6.91 (d, J=8.0 Hz, 1H), 7.06-7.35 (m, 8H), 7.83 (d, J=9.0 Hz, 2H), 8.19 (s, 2H); LCMS (ESI): m/z 541 (M+H)⁺.

Example 44 (102)

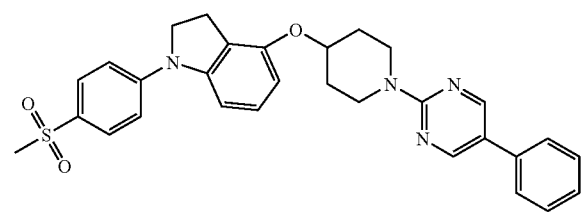

1-[4-(Methylsulfonyl)phenyl]-4-{[1-(5-phenyl-2-pyrimidinyl)-4-piperidinyl]oxy}-2,3-dihydro-1H-indole (102)

Compound 97 (50 mg, 0.12 mmol) was dissolved in 2 mL methylene chloride and treated with 2 mL of DIPEA followed by 2-chloro-5-phenylpyrimidine (100 mg, 0.53 mmol). The reaction was then heated at 50° C. for 48 h while stirring. The reaction was cooled to room temperature and all the solvents were removed under reduced pressure. The crude reaction was then purified via column chromatography (5→50% ethyl acetate/hexane) to give 30 mg (45%) of the title product 102 as a white solid. ¹H NMR (400 MHz, DMSO-d₆): δ 1.79-1.92 (m, 2H), 1.92-2.03 (m, 2H), 3.05 (s, 3H), 3.18 (t, J=8.0 Hz, 2H), 3.72-3.87 (m, 2H), 3.96-4.10 (m, 4H), 4.50-4.69 (m, 1H), 6.51 (d, J=8.0 Hz, 1H), 6.91 (d, J=8.0 Hz, 1H), 7.06-7.35 (m, 8H), 7.83 (d, J=9.0 Hz, 2H), 8.19 (s, 2H); LCMS (ESI): m/z 527 (M+H)⁺.

Example 45 (103)

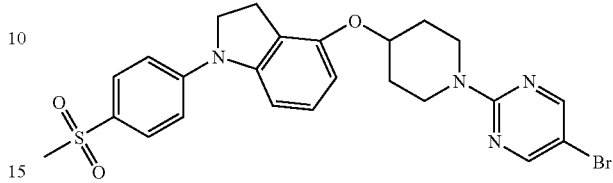

4-{[1-(5-Bromo-2-pyrimidinyl)-4-piperidinyl]oxy}-1-[4-(methylsulfonyl)phenyl]-2,3-dihydro-1H-indole (103)

Compound 97 (500 mg, 1.23 mmol) was dissolved in 10 mL CH₃CN and treated with DIPEA (655 μL, 3.69 mmol) followed by 5-bromo-2-chloropyrimidine (260 mg, 1.35 mmol). The reaction was then heated at 80° C. for 48 h while stirring. The reaction was cooled to room temperature and treated with 2 mL MeOH. A white solid formed which was removed via filtration and dried on filter plate overnight to give 627 mg (96%) of the title product 103 as a white solid. ¹H NMR (400 MHz, DMSO-d₆): δ 1.57-1.76 (m, 2H), 1.83-2.03 (m, 2H), 3.00 (t, J=8.0 Hz, 2H), 3.12 (s, 3H), 3.58-3.82 (m, 2H), 3.90-4.19 (m, 4H), 4.60-4.81 (m, 1H), 6.60 (d, J=8.0 Hz, 1H), 6.91 (d, J=8.0 Hz, 1H), 7.18 (t, J=8.0 Hz, 1H), 7.35 (d, J=9.0 Hz, 2H), 7.76 (d, J=9.0 Hz, 2H), 8.43 (s, 2H); LCMS (ESI): m/z 530 (M+H)⁺.

Example 46 (104)

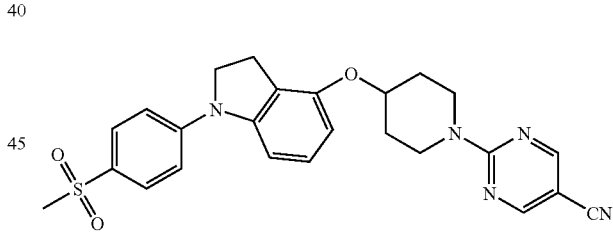

2-[4-({1-[4-(Methylsulfonyl)phenyl]-2,3-dihydro-1H-indol-4-yl}oxy)-1-piperidinyl]-5-pyrimidinecarbonitrile (104)

Compound 103 (100 mg, 0.19 mmol) was dissolved in 5 mL DMF and treated with CuCN (100 mg, 1.12 mmol). The reaction was then heated at 150° C. for 18 h while stirring. The reaction was cooled to room temperature and treated with 2 mL water. A white solid formed which was removed via filtration and dried on filter plate. The solid was dissolved in chloroform and the solids were removed via filtration. The solvent was then removed under reduced pressure to give 61 mg (68%) of the title product 104 as a white solid. ¹H NMR (400 MHz, CDCl₃): δ 1.79-1.93 (m, 2H), 1.93-2.13 (m, 2H), 3.05 (s, 3H), 3.12 (t, J=8.0 Hz, 2H), 3.73-3.88 (m, 2H), 3.96-4.10 (m, 4H), 4.56-4.70 (m, 1H), 6.54 (d, J=8.0 Hz, 1H), 6.91 (d, J=8.0 Hz, 1H), 7.10 (t, J=8.0 Hz, 1H), 7.28 (d, J=9.0 Hz, 2H), 7.84 (d, J=9.0 Hz, 2H), 8.29 (s, 2H); LCMS (ESI): m/z 476 (M+H)⁺.

Example 47 (105)

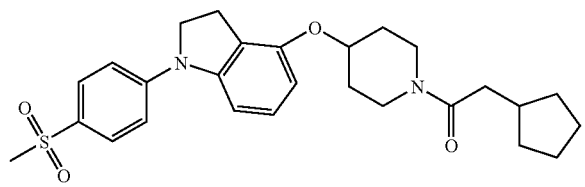

4-{[1-(Cyclopentylacetyl)-4-piperidinyl]oxy}-1-[4-(methylsulfonyl)phenyl]-2,3-dihydro-1H-indole (105)

Compound 97 (50 mg, 0.12 mmol) was dissolved in 2 mL $CH_2Cl_2$ and treated with 2 mL of DIPEA followed by cyclopentylacetyl chloride (100 mg, 0.68 mmol). The reaction was then stirred at room temperature for 18 h. All the solvents were removed under reduced pressure and the crude reaction was then purified via reverse phase chromatography (C18, 10-100% $CH_3CN/H_2O/0.05\%$ TFA) to give 12 mg (20%) of the title product 105 as a white solid. ¹H NMR (400 MHz, $CDCl_3$): δ 1.04-1.27 (m, 2H), 1.42-1.69 (m, 4H), 1.72-2.04 (m, 6H), 2.18-2.30 (m, 1H), 2.41 (d, J=7.0 Hz, 2H), 3.02 (s, 3H), 3.14 (t, J=8.0 Hz, 2H), 3.38-3.52 (m, 1H), 3.59-3.83 (m, 3H), 4.01 (t, J=8.0 Hz, 2H), 4.53-4.66 (m, 1H), 6.49 (d, J=8.0 Hz, 1H), 6.94 (d, J=8.0 Hz, 1H), 7.14 (t, J=8.0 Hz, 1H), 7.27 (d, J=9.0 Hz, 2H), 7.80 (d, J=9.0 Hz, 2H); LCMS (ESI): m/z 483 (M+H)⁺.

Example 48 (108)

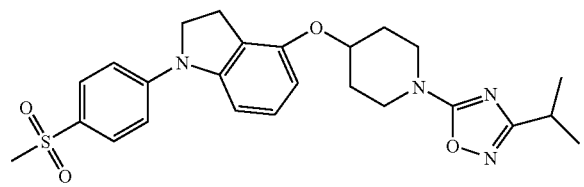

Step 1: N-Hydroxy-2-methylpropanimidamide (106)

2-Methylpropanenitrile (25 g, 0.362 mol) was combined with 100 mL hydroxylamine and the mixture was refluxed for 5 h. The solvent was then removed under reduced pressure and the residual solvent was removed azeotropically with toluene. The residue was then taken up in 50 mL methylene chloride and dried over anhydrous $MgSO_4$. The solvent was then removed in vacuo to afford 26 g of the title product 106 as clear oil which was used without purification. ¹H NMR (400 MHz, DMSO-$d_6$): δ 0.79-1.10 (m, 6H), 2.02-2.35 (m, 1H), 5.36 (s, 2H), 8.82 (s, 1H).

Step 2: 4-({1-[4-(Methylsulfonyl)phenyl]-2,3-dihydro-1H-indol-4-yl}oxy)-1-piperidine-carbonitrile (107)

$NaHCO_3$ (309 mg, 3.68 mmol) was combined with 1 mL water and cooled to 0° C. in an ice bath. Compound 97 (500 mg, 1.22 mmol) in 2.5 mL of methylene chloride was added to the above solution which was vigorously stirred. Cyanogen bromide (142 mg, 1.34 mmol) in 2.5 mL of methylene chloride was then added and the ice bath was removed. The mixture was stirred at ambient temperature for 18 h. $Na_2CO_3$ (1.5 g) was then added until pH≅7 and $MgSO_4$ (1 g) was added to remove water. The solids were removed via filtration and the solids were washed several times with methylene chloride. The solvent was then removed under reduced pressure and the material 107 was used without purification.

Step 3: 4-({1-[3-(1-Methylethyl)-1,2,4-oxadiazol-5-yl]-4-piperidinyl}oxy)-1-[4-(methylsulfonyl)phenyl]-2,3-dihydro-1H-indole (108)

Compound 107 (500 mg, 1.26 mmol) was combined with compound 106 (500 mg, 4.90 mmol) in a mixture of ethyl acetate (9 mL) and ether (1 mL) and solid $ZnCl_2$ (800 mg, 5.88 mmol) was added to the solution. The mixture was stirred for 15 min and the supernatant was decanted off. The residue was washed 2 times with 10 mL of ethyl acetate, which was decanted off after each wash. The residue was then dissolved in a mixture of 4 N HCl (5 mL) and EtOH (15 mL). The resulting solution was then refluxed for 1 h. The solvent was reduced in vacuo and 500 mg $Na_2CO_3$ was added along with 10 mL methylene chloride. The solids were removed via filtration and phases were separated. The organic phase was dried over $MgSO_4$, filtered, and concentrated to dryness to give 31 mg of the title compound 108 as a white solid. ¹H NMR (400 MHz, $CDCl_3$): δ1.10-1.43 (m, 6H), 1.89-2.18 (m, 4H), 2.80-2.98 (m, 1H), 3.04 (s, 3H), 3.12 (t, J=8.0 Hz, 2H), 3.57-3.85 (m, 4H), 4.02 (t, J=8.0 Hz, 2H), 4.51-4.72 (m, 1H), 6.45 (d, J=8.0 Hz, 1H), 6.91 (d, J=8.0 Hz, 1H), 7.10 (t, J=8.0 Hz, 1H), 7.28 (d, J=9.0 Hz, 2H), 7.86 (d, J=9.0 Hz, 2H); LCMS (ESI): m/z 483 (M+H)⁺.

Example 49 (109)

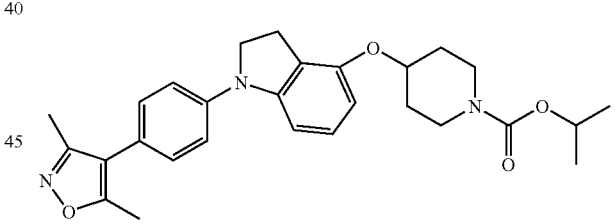

1-Methylethyl 4-({1-[4-(3,5-dimethyl-4-isoxazolyl)phenyl]-2,3-dihydro-1H-indol-4-yl}oxy)-1-piperidinecarboxylate (109)

A round-bottomed flask was charged with 68 (51 mg, 0.1 mmol), $PdCl_2(PPh_3)_2$ (7 mg, 0.01 mmol), (3,5-dimethyl-4-isoxazolyl)boronic acid (28 mg, 0.2 mmol), a 2 N aqueous solution of $Na_2CO_3$ (250 μL, 0.5 mmol), and THF (3 mL). The resultant mixture was refluxed for 3 h under $N_2$. Reaction mixture was cooled to RT, diluted with EtOAc (40 mL), and the mixture was washed with $H_2O$ (1×10 mL), brine (1×10 mL), dried over $Na_2SO_4$ and concentrated under reduced pressure to afford the crude material. The product was purified by $SiO_2$ flash column chromatography to afford 30 mg (63%) of the title product 109 as an off-white solid. ¹H NMR (400 MHz, DMSO-$d_6$): δ 7.32 (d, J=8.4 Hz, 2H), 7.27 (d, J=8.4 Hz, 2H), 7.01 (app. t, J=8.0 Hz, 1H), 6.78 (d, J=8.0 Hz, 1H), 6.49 (d, J=8.4 Hz, 1H), 4.76 (septuplet, J=7.0 Hz, 1H), 3.96 (t, J=8.4 Hz, 2H), 3.61 (br m, 2H), 3.30 (br m, 2H), 2.99 (t, J=8.4 Hz, 2H), 2.38 (s, 3H), 2.21 (s, 3H), 1.86 (br m, 2H), 1.56 (m, 2H), 1.17 (d, J=6.0 Hz, 6H); LCMS (ESI): m/z 476 (M+H)$^+$.

Example 50 (110)

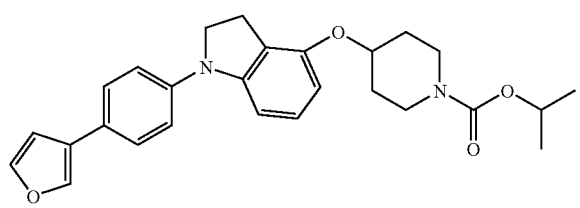

1-Methylethyl 4-({1-[4-(3-furanyl)phenyl]-2,3-dihydro-1H-indol-4-yl}oxy)-1-piperidine-carboxylate (111)

The Suzuki procedure described for 109 was employed using 68 (66 mg, 0.13 mmol), PdCl$_2$(PPh$_3$)$_2$ (9 mg, 0.013 mmol), 3-furanylboronic acid (29 mg, 0.26 mmol), a 2 N aqueous solution of Na$_2$CO$_3$ (325 μL, 0.65 mmol), and THF (3 mL). The work-up followed by purification gave 22 mg (38%) of the title product 111 as a white solid. $^1$H NMR (400 MHz, DMSO-d$_6$): δ 8.08 (s, 1H), 7.69 (t, J=1.6 Hz, 1H), 7.55 (d, J=8.4 Hz, 2H), 7.20 (d, J=8.8 Hz, 2H), 6.99 (t, J=8.0 Hz, 1H), 6.90 (d, J=1.2 Hz, 1H), 6.72 (d, J=8.0 Hz, 1H), 6.47 (d, J=8.0 Hz, 1H), 4.76 (septuplet, J=6.4 Hz, 1H), 4.56 (m, 1H), 3.93 (t, J=8.8 Hz, 2H), 3.64-3.58 (m, 2H), 3.30-3.26 (m, 2H), 2.98 (t, J=8.4 Hz, 2H), 1.90-1.84 (m, 2H), 1.60-1.52 (m, 2H), 1.17 (d, J=6.0 Hz, 6H); LCMS (ESI): m/z 447 (M+H)$^+$.

Example 51 (112)

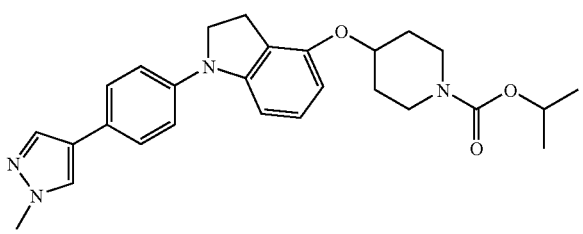

1-Methylethyl 4-({1-[4-(1-methyl-1H-pyrazol-4-yl)phenyl]-2,3-dihydro-1H-indol-4-yl}oxy)-1-piperidinecarboxylate (112)

Following the Suzuki coupling procedure described for 109, a round-bottomed flask was charged with compound 68 (51 mg, 0.1 mmol), PdCl$_2$(PPh$_3$)$_2$ (7 mg, 0.01 mmol), 1-methyl-4-(4,4,5,5-tetramethyl-1,3,2-dioxaborolan-2-yl)-1H-pyrazole (42 mg, 0.20 mmol), a 2 N aqueous solution of Na$_2$CO$_3$ (250 μL, 0.5 mmol), and THF (3 mL). The mixture was refluxed for 3 h. The work-up followed by purification gave 12 mg (25%) of the title product 112 as a off-white solid. $^1$H NMR (400 MHz, DMSO-d$_6$): δ 8.02 (s, 1H), 7.77 (s, 1H), 7.49 (d, J=8.8 Hz, 1H), 7.17 (d, J=8.8 Hz, 1H), 6.98 (app. t, J=8.0 Hz, 1H), 6.68 (d, J=8.0 Hz, 1H), 6.45 (d, J=8.4 Hz, 1H), 4.75 (septuplet, J=6.4 Hz, 1H), 4.56 (m, 1H), 3.92 (t, J=8.4 Hz, 2H), 3.83 (s, 3H), 3.62-3.56 (m, 2H), 3.29-3.25 (m, 2H), 2.97 (t, J=8.4 Hz, 2H), 1.88-1.84 (m, 2H), 1.59-1.52 (m, 2H), 1.67 (d, J=6.0 Hz, 6H); LCMS (ESI): m/z 461 (M+H)$^+$.

Example 52 (113)

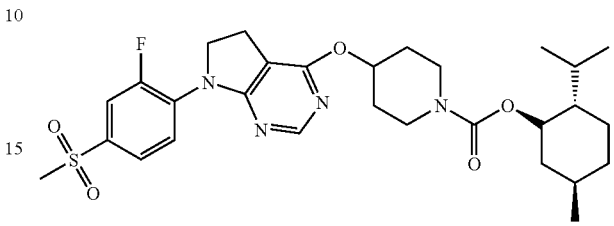

(1R,2S,5R)-5-Methyl-2-(1-methylethyl)cyclohexyl 4-({7-[2-fluoro-4-(methylsulfonyl)phenyl]-6,7-dihydro-5H-pyrrolo[2,3-d]pyrimidin-4-yl}oxy)-1-piperidinecarboxylate (113)

The two step procedure described for 67 was used. The product 126 (vide infra), obtained from compound II upon treatment with TFA in CH$_2$Cl$_2$ (125 mg, ~80% pure) was dissolved in CH$_2$Cl$_2$ (25 mL) and treated with Et$_3$N (132 μL, 1 mmol), DMAP (4 mg, 0.032 mmol), and (1R,2S,5R)-5-methyl-2-(1-methylethyl)cyclohexyl chloridocarbonate (136 μL, 0.64 mmol). The mixture was stirred at RT for 15 h. The work-up followed by purification gave 44 mg (24%) of the title product 113 as an off-white solid. $^1$H NMR (400 MHz, DMSO-d$_6$): δ 8.22 (s, 1H), 7.96 (t, J=7.6 Hz, 1H), 7.85 and 7.82 (dd, J$_1$=10.8 Hz, J$_2$=1.6 Hz, 1H), 7.75 and 7.73 (dd, J=8.4 Hz, J$_2$=2.0 Hz, 1H), 5.28 (m, 1H), 4.43 (m, 1H), 4.14 (t, J=8.4 Hz, 2H), 3.71-3.67 (m, 2H), 3.25 (s, 3H), 3.29-3.21 (m, 2H), 3.05 (t, J=8.8 Hz, 2H), 1.94-1.86 (br m, 3H), 1.86-1.81 (m, 1H), 1.63-1.51 (m, 4H), 1.44-1.40 (m, 1H), 1.41-1.30 (m, 1H), 1.07-0.91 (m, 2H), 0.86 (d, J=6.4 Hz, 6H), 0.73 (s, J=6.8 Hz, 3H); LCMS (ESI): m/z 575 (M+H)$^+$.

Example 53 (118)

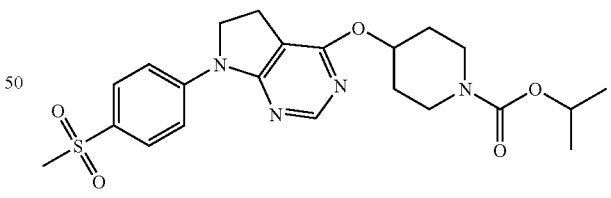

Step 1: N-(4-Bromophenyl)-6-chloro-5-(2-propen-1-yl)-4-pyrimidinamine (114)

The procedure described for 4 was used. To a mixture of NaH (3.60 g, 60% dispersion in mineral oil, washed with anhydrous toluene) and anhydrous THF (50 mL) at RT under N$_2$ was added 4-bromoaniline (5.16 g, 30 mmol) in THF (100 mL). The mixture was stirred at RT for 1 h and then compound 2 (5.67 g, 30 mmol) in THF (50 mL) was added. The resulting reaction mixture was refluxed for 4 h. Aqueous work-up followed by purification by SiO$_2$ flash column chromatography afforded 6.81 g (~85% pure) of the product 114. This material was used in the next step without further purification. ¹H NMR (400 MHz, DMSO-$d_6$): δ 8.83 (s, 1H), 8.29 (s, 1H), 7.55 (d, J=11.6 Hz, 2H), 7.49 (d, J=8.8 Hz, 2H), 5.92-5.84 (m, 1H), 5.07-5.00 (m, 2H), 3.56 (d, J=5.2 Hz, 2H); LCMS (ESI): m/z 325 (M+H)⁺.

Step 2: 2-{4-[(4-Bromophenyl)amino]-6-chloro-5-pyrimidinyl}ethanol (115)

The ozonolysis procedure described for 6 was utilized using 114 (5.80 g, 17.87 mmol), $CH_2Cl_2$ (300 mL), MeOH (50 mL), and $NaBH_4$ (2.70 g, 71.47 mmol) between −70° C. and RT. Aqueous work-up followed by purification afforded 3.120 (~90% pure) of the title product 115. ¹H NMR (400 MHz, DMSO-$d_6$): δ 9.10 (s, 1H), 8.29 (s, 1H), 7.56-7.48 (m, 4H), 5.13 (t, J=5.2 Hz, 1H), 3.65 (q, J=5.6 Hz, 2H), 2.97 (t, J=6.4 Hz, 2H); LCMS (ESI): m/z 329 (M+H)⁺.

Step 3: 7-(4-Bromophenyl)-4-chloro-6,7-dihydro-5H-pyrrolo[2,3-d]pyrimidine (116)

To a solution of 115 (2.72 g, 8.28 mmol) in $CH_2Cl_2$ (150 mL) were added, at 5° C., $Et_3N$ (6.87 mL, 49.7 mmol) followed by methanesulfonic anhydride (2.16 g, 12.42 mmol). The resultant mixture was stirred at RT for 24 h. The reaction mixture was diluted with $CH_2Cl_2$ (200 mL) and washed with $H_2O$ (2×50 mL), brine (1×25 mL), dried over $Na_2SO_4$ and concentrated to afford the crude material. The material was redissolved in $CH_2Cl_2$ (50 mL) and then treated with $Et_3N$ (10 mL). The mixture was stirred at RT for 24 h and then kept at RT for overnight. The crystals were separated and dried to give 1.76 g as a white solid. The mother liquor was concentrated to afford the crude product which was purified by $SiO_2$ column chromatography to afford an additional 450 mg of the product. A total of 2.21 g of the title product 116 was obtained as a white solid. ¹H NMR (400 MHz, DMSO-$d_6$): δ 8.38 (s, 1H), 7.65 (d, J=9.2 Hz, 2H), 7.49 (d, J=8.8 Hz, 2H), 4.12 (t, J=8.8 Hz, 2H), 3.20 (t, J=8.4 Hz, 2H); LCMS (ESI): m/z 311 (M+H)⁺.

Step 4: 1-Methylethyl 4-{[7-(4-bromophenyl)-6,7-dihydro-5H-pyrrolo[2,3-d]pyrimidin-4-yl]oxy}-1-piperidinecarboxylate (117)

Following the procedure described for 10 (Example 1, Step 10), compound 116 (932 g, 3 mmol) was allowed to react, at 65° C., with compound 9 (562 mg, 3 mmol) in presence of NaH (60% dispersion in oil, 360 mg, 9 mmol) in THF (40 mL) for 2 h. Aqueous work-up followed by $SiO_2$ flash column chromatography afforded 966 mg (70%) of the title product 117 as a white solid. ¹H NMR (400 MHz, DMSO-$d_6$): δ 8.32 (s, 1H), 7.63 (d, J=9.2 Hz, 2H), 7.47 (d, J=8.8 Hz, 2H), 5.36 (m, 1H), 4.92 (septuplet, J=6.0 Hz, 1H), 4.07 (t, J=9.2 Hz, 2H), 3.79 (br s, 2H), 3.36-3.30 (m, 2H), 3.07 (t, J=8.8 Hz, 2H), 2.02-1.97 (m, 2H), 1.77-1.68 (m, 2H), 1.25 (d, J=6.4 Hz, 6H); LCMS (ESI): m/z 463 (M+H)⁺.

Step 5: 1-Methylethyl 4-({7-[4-(methylsulfonyl)phenyl]-6,7-dihydro-5H-pyrrolo[2,3-d]pyrimidin-4-yl}oxy)-1-piperidinecarboxylate (118)

Following the representative procedure described for 3, a 10 mL glass tube was charged with compound 117 (500 mg, 1.08 mmol), sodium methanesulfinate (221 mg, 2.17 mmol), copper iodide (21 mg, 0.11 mmol), L-proline (25 mg, 0.22 mmol), NaOH (9 mg, 0.22 mmol), and DMSO (4 mL). The sealed pressure tube was stirred at 120° C. for 15 h. Aqueous work-up followed by purification afforded 315 mg (63%) of the title product 118 as an off-white solid. ¹H NMR (400 MHz, $CDCl_3$): δ 8.39 (s, 1H), 7.98-7.90 (m, 4H), 5.38 (m, 1H), 4.93 (septuplet, J=6.4 Hz, 1H), 4.15 (t, J=8.8 Hz, 2H), 3.83 (br m, 2H), 3.37-3.30 (m, 2H), 3.12 (t, J=8.8 Hz, 2H), 3.04 (s, 3H), 2.12-1.96 (m, 2H), 1.80-1.69 (m, 2H), 1.25 (d, J=6.4 Hz, 6H); LCMS (ESI): m/z 461 (M+H)⁺.

Example 54 (119)

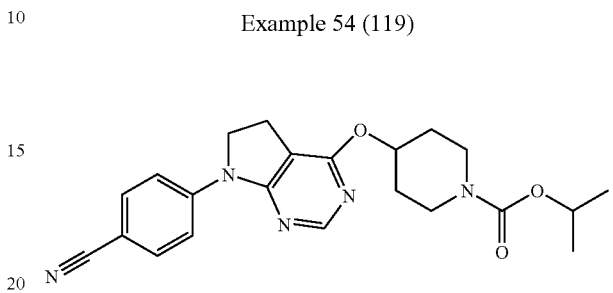

1-Methylethyl 4-{[7-(4-cyanophenyl)-6,7-dihydro-5H-pyrrolo[2,3-d]pyrimidin-4-yl]oxy}-1-piperidinecarboxylate (119)

Following the procedure described for 31 (Example 10, Step 7), a mixture of 117 (202 mg, 0.44 mmol), CuCN (99 mg, 1.1 mmol), and NMP (4 mL) was stirred at 150° C. for 36 h. Aqueous work-up followed by purification afforded 110 mg (61%) of the title product 119 as a white solid. ¹H NMR (400 MHz, DMSO-$d_6$): δ 8.38 (s, 1H), 8.0 (d, J=8.8 Hz, 2H), 7.78 (d, J=8.8 Hz, 2H), 5.28 (m, 2H), 4.75 (septuplet, J=6.4 Hz, 1H), 4.10 (t, J=9.2 Hz, 2H), 3.69-3.64 (m, 2H), 3.26-3.21 (br m, 2H), 3.02 (t, J=8.8 Hz, 2H), 1.95-1.90 (m, 2H), 1.62-1.52 (m, 2H), 1.17 (d, J=6.4 Hz, 6H); LCMS (ESI): m/z 408 (M+H)⁺.

Example 55 (120)

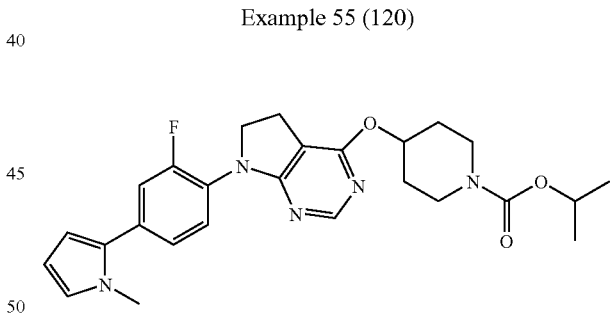

1-Methylethyl 4-({7-[2-fluoro-4-(1-methyl-1H-pyrrol-2-yl)phenyl]-6,7-dihydro-5H-pyrrolo[2,3-d]pyrimidin-4-yl}oxy)-1-piperidinecarboxylate (120)

A 5 mL glass tube was charged with 30 (100 mg, 0.2 mmol), $PdCl_2(Ph_3P)_2$ (15 mg, 0.02 mmol), 1-methyl-2-(tributylstannanyl)-1H-pyrrole (70 mg, 0.20 mmol), and THF (3 mL) under $N_2$. The tube was sealed and then the mixture was subjected to microwave conditions at 100° C. for 40 min. The reaction mixture was cooled to RT and then subjected to $SiO_2$ flash column chromatography to afford 11 mg (12%) of the title product as a white solid. ¹H NMR (400 MHz, DMSO-$d_6$): δ 8.12 (s, 1H), 7.58 (t, J=8.4 Hz, 1H), 7.37 and 7.34 (dd, $J_1$=12.4 Hz, $J_2$=2.0 Hz, 1H), 7.28 and 7.26 (dd, $J_1$=8.4 Hz, $J_2$=1.6 Hz, 1H), 6.84 (t, J=2.0 Hz, 1H), 6.23 and 6.22 (dd, $J_1$=3.6 Hz, $J_2$=2.0 Hz, 1H), 6.04 (t, J=3.2 Hz, 1H), 5.28-5.22 (m, 1H), 4.76 (septuplet, J=6.0 Hz, 1H), 4.04 (t, J=9.2 Hz, 2H), 3.67 (s, 3H), 3.71-3.65 (m, 2H), 3.23 (app. br, t, J=10 Hz, 2H), 3.04 (t, J=9.2 Hz, 2H), 1.95-1.90 (m, 2H), 1.61-1.52 (m, 2H), 1.17 (d, J=6.0 Hz, 6H); LCMS (ESI): m/z 480 (M+H)$^+$.

Example 56 (125)

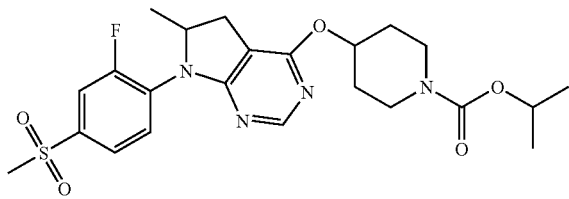

Step 1: 1,1-Dimethylethyl[6-chloro-5-(2-oxoethyl)-4-pyrimidinyl][2-fluoro-4-(methylsulfonyl)phenyl]carbamate (121)

Following the procedure described for 209 was employed (see example 117, step 1). To a solution of compound 5 (3.42 g, 10 mmol) in 3:2 acetone-$H_2O$ (250 mL) was added $K_2OsO_4$.$2H_2O$ (147 mg, 0.4 mmol). Solid $NaIO_4$ (8.56 g, 40 mmol) was added portionwise and the reaction was stirred for 4 h. The workup gave 5.0 g (~100%) of the title 121 product as an off-white solid. $^1$H NMR (400 MHz, DMSO-$d_6$): δ 9.63 (s, 1H), 8.82 (s, 1H), 7.96-7.94 (dd, $J_1$=9.6 Hz, $J_2$=2.0 Hz, 1H), 7.78-7.76 (dd, $J_1$=8.4 Hz, $J_2$=1.6 Hz, 1H), 7.59 (app. t, J=7.6 Hz, 1H), 3.93 (s, 2H), 3.30 (s, 3H), 1.38 (s, 9H).

Step 2: (±)-1,1-Dimethylethyl[6-chloro-5-(2-hydroxypropyl)-4-pyrimidinyl][2-fluoro-4-(methylsulfonyl)phenyl]carbamate (122)

To a stirred solution of aldehyde 121 (2.0 g, 4.51 mmol) in anhydrous THF (50 mL) was added a 1.4 M solution of methylmagnesium in THF (6.5 mL, 9.01 mmol) at RT under $N_2$. The resultant mixture was stirred at RT for 3 h. The reaction mixture was poured into 10% aqueous HCl (200 mL) and the mixture was extracted with EtOAc (4×75 mL). The combined organic layer was washed with brine (1×30 mL), dried over $Na_2SO_4$ and then concentrated under reduced pressure to afford the crude product, which was subjected to column chromatography to give 0.815 g (39%) of the title carbinol 122 as a white solid. $^1$H NMR (400 MHz, DMSO-$d_6$): δ 9.15 (s, 1H), 8.28 (s, 1H), 7.85 and 7.82 (dd, $J_1$=9.6 Hz, $J_2$=2.0 Hz, 1H), 7.80-7.68 (m, 2H), 5.06-4.99 (m, 1H), 3.28 (s, 3H), 3.14-3.10 (m, 1H), 3.05-3.02 (m, 1H), 1.33 (d, J=6.2 Hz, 3H), 1.25 (s, 9H); LCMS (ESI): m/z 460 (M+H)$^+$.

Step 3: (±)-1-(4-Chloro-6-{[2-fluoro-4-(methylsulfonyl)phenyl]amino}-5-pyrimidinyl)-2-propanol (123)

To a solution of carbinol 122 (800 mg, 1.74 mmol) in $CH_2Cl_2$ (20 mL) was added TFA (5 mL) at RT under $N_2$. The reaction mixture was stirred at RT for 3 h and then concentrated under reduced pressure to afford the title product 123, which was used without further purification in the next step. $^1$H NMR (400 MHz, DMSO-$d_6$): δ 9.84 (s, 1H), 8.42 (s, 1H), 8.16 (app, t, J=8.0 Hz, 1H), 7.83 and 7.80 (dd, $J_1$=10.4 Hz, $J_2$=2.0 Hz, 1H), 7.74 and 7.72 (dd, $J_1$=8.8 Hz, $J_2$=1.6 Hz, 1H), 5.87 (d, J=2.8 Hz, 1H), 4.07 (app. br. s, 1H), 3.24 (s, 3H), 2.94-2.83 (m, 2H), 1.20 (d, J=6.4 Hz, 3H); LCMS (ESI): m/z 360 (M+H)$^+$.

Step 4: (±)-4-Chloro-7-[2-fluoro-4-(methylsulfonyl)phenyl]-6-methyl-6,7-dihydro-5H-pyrrolo[2,3-d]pyrimidine (124)

Following the procedure described for the compound 7 (example 1, step 7), to a solution of compound 123 in $CH_2Cl_2$ (30 mL) was added $Et_3N$ (0.722 mL, 5.22 mmol) followed by methanesulfonic anhydride (0.606 g, 3.48 mmol) at RT for 24 h. The workup and chromatography gave 0.272 g (47%, for 2 steps) of the bicyclic compound 124 as an off-white solid. $^1$H NMR (400 MHz, DMSO-$d_6$): δ 8.23 (s, 1H), 7.94 and 7.92 (app, dd, $J_1$=10.8 Hz, $J_2$=1.2 Hz, 1H), 7.87-7.81 (m, 2H), 4.80-4.72 (m, 1H), 3.47-3.42 (dd, $J_1$=17.2 Hz, $J_2$=9.6 Hz, 1H), 3.30 (s, 3H), 2.89-2.85 (dd, $J_1$=17.2 Hz, $J_2$=7.2 Hz, 1H), 1.21 (d, J=6.0 Hz, 3H); LCMS (ESI): m/z 342 (M+H)$^+$.

Step 5: (±)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate (125)

Following the procedure described for 10, compound 9 (128 mg, 0.68 mmol) in THF (2 mL) was added to a suspension of NaH (60%, 84 mg, 2.1 mmol) in THF (2 mL). The reaction mixture was refluxed for 15 min and the compound 124 (245 mg, 2.16 mmol) in THF (2 mL) was added and the resultant mixture was refluxed for 2 h. The work-up and chromatography gave 276 mg (82%) of the title compound 125 as a white solid. $^1$H NMR (400 MHz, DMSO-$d_6$): δ 8.16 (s, 1H), 7.87 (app. br, d, J=10.4 Hz, 1H), 7.83-7.81 (app. br, d, J=7.6 Hz, 1H), 7.78-7.76 (dd, $J_1$=8.4 Hz, $J_2$=1.6 Hz, 1H), 5.30-5.22 (m, 1H), 4.78-4.66 (m, 2H), 3.68-3.64 (m, 2H), 3.32-3.28 (m, 1H), 3.28 (s, 3H), 3.28-3.22 (m, 2H), 2.70 and 2.66 (app. dd, $J_1$=16.0 Hz, $J_2$=7.2 Hz, 1H), 1.96-186 (m, 2H), 1.62-1.50 (m, 2H), 1.19 (app. d, J=5.6 Hz, 3H), 1.17 (d, J=6.0 Hz, 6H); LCMS (ESI): m/z 493 (M+H)$^+$.

Examples 57

The racemic mixture 125 (200 mg) was subjected to Chiral HPLC [column: Chiralpak OJ (analytical), Chiralpak OJ (prep.), mobile phase: 95% $CO_2$: 5% MeOH:$CHCl_3$ (90:1); 2 mL/min; pressure 140 bar, temperature 30° C., 215 nm, and 280 nm)] analysis and then separated two (R and S) enantiomers. The absolute stereochemistry was not assigned.

Enantiomer I, 57A (125A): Tr: 19.96 min, 46 mg (% ee>98%); Spectral data are essentially the same to that of example 56 (125).

Enantiomer II, 57B (125B): Tr: 21.0 min, 66 mg (% ee>98%); Spectral data are essentially the same to that of example 56 (125).

Example 58 (127)

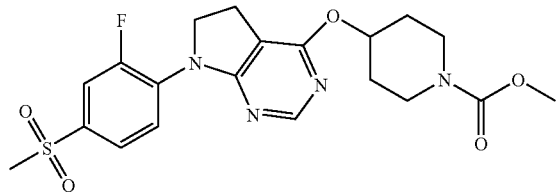

Step 1: 7-[2-Fluoro-4-(methylsulfonyl)phenyl]-4-(4-piperidinyloxy)-6,7-dihydro-5H-pyrrolo[2,3-d]pyrimidine trifluoroacetate (126)

To a solution of 11 (example 2, 1.0 g, 2.03 mmol) in $CH_2Cl_2$ (40 mL) was treated with TFA (10 mL) at RT for 2 h.

The reaction mixture was stirred at RT for 2 h and then concentrated to afford to crude product 126, which was dried and re-dissolved in 20 mL of $CH_2Cl_2$ and $Et_3N$ (1.7 mL, ~6 equiv) to use in the next steps.

Step 2: Methyl 4-({7-[2-fluoro-4-(methylsulfonyl) phenyl]-6,7-dihydro-5H-pyrrolo[2,3-d]pyrimidin-4-yl}oxy)-1-piperidinecarboxylate (127)

A solution of 126 (2.2 mL from step 1) was treated with methyl chloridocarbonate (200 μL) at RT for 18 h. The reaction mixture was diluted with $CH_2Cl_2$ (30 mL) and then washed with $H_2O$ (1×10 mL), brine (1×10 mL), dried over $Na_2SO_4$ and then concentrated under reduced pressure to afford the crude product, which was subjected for column chromatography gave 76 mg of the title product 127 as a white solid. $^1H$ NMR (400 MHz, DMSO-$d_6$): δ 8.22 (s, 1H), 7.96 (t, J=8.0 Hz, 1H), 7.85 and 7.82 (dd, $J_1$=11.2 Hz, $J_2$=2.0 Hz, 1H), 7.74 and 7.72 (dd, $J_1$=8.4 Hz, $J_2$=2.4 Hz, 1H), 5.30-5.22 (m, 1H), 4.14 (t, J=8.4 Hz, 2H), 3.58 (s, 3H), 3.70-3.64 (m, 2H), 3.28-3.24 (app. br, m, 2H), 3.25 (s, 3H), 3.05 (t, J=8.8 Hz, 2H), 1.96-1.91 (m, 2H), 1.64-1.54 (m, 2H); LCMS (ESI): m/z 451 (M+H)$^+$.

Example 59 (128)

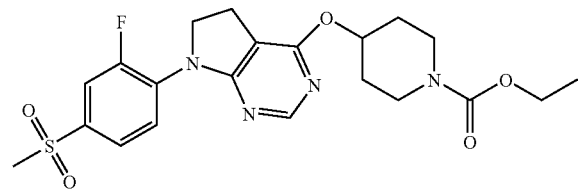

Ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate (128)

Following the general procedure described for the compound 127, a solution of 126 (2.2 mL) was treated with ethyl chloridocarbonate (100 μL) at RT for 18 h. The work up and chromatography gave 85 mg of the title product 128 as a white solid. $^1H$ NMR (400 MHz, DMSO-$d_6$): δ 8.22 (s, 1H), 7.96 (t, J=7.6 Hz, 1H), 7.84 and 7.82 (dd, $J_1$=11.2 Hz, $J_2$=2.0 Hz, 1H), 7.75 and 7.72 (dd, $J_1$=8.4 Hz, $J_2$=2.0 Hz, 1H), 5.28-5.24 (m, 1H), 4.14 (t, J=8.4 Hz, 2H), 4.02 (q, J=7.2 Hz, 2H), 3.71-3.65 (m, 2H), 3.26-3.24 (br. s, 2H), 3.25 (s, 3H), 3.05 (t, J=8.8 Hz, 2H), 1.96-1.90 (br, m, 2H), 1.62-1.54 (m, 2H), 1.17 (t, J=6.8 Hz, 3H); LCMS (ESI): m/z 465 (M+H)$^+$.

Example 60 (129)

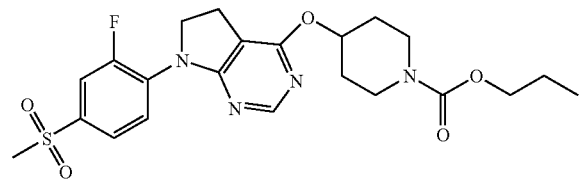

Propyl 4-({7-[2-fluoro-4-(methylsulfonyl)phenyl]-6,7-dihydro-5H-pyrrolo[2,3-d]pyrimidin-4-yl}oxy)-1-piperidinecarboxylate (129)

Following the general procedure described for the compound 127, to a solution of 126 (100 mg, 0.198 mmol, from a different batch) in $CH_2Cl_2$ (4 mL) was added $Et_3N$ (137 μL, 1 mmol) followed by propyl chloridocarbonate (100 μL) at RT and the mixture was stirred for 18 h. The work up and chromatography gave 72 mg (75%) of the title product 129 as a white solid. $^1H$ NMR (400 MHz, DMSO-$d_6$): δ 8.22 (s, 1H), 7.96 (t, J=8.0 Hz, 1H), 7.85 and 7.82 (dd, $J_1$=10.8 Hz, $J_2$=2.0 Hz, 1H), 7.75 and 7.72 (dd, $J_1$=8.4 Hz, $J_2$=2.4 Hz, 1H), 5.30-5.24 (m, 1H), 4.14 (t, J=8.4 Hz, 2H), 3.94 (t, J=6.8 Hz, 2H), 3.72-3.66 (m, 2H), 3.30-3.24 (br, m, 2H), 3.05 (t, J=8.4 Hz, 2H), 1.98-1.88 (m, 2H), 1.62-1.52 (m, 4H), 0.87 (t, J=7.2 Hz, 2H); LCMS (ESI): m/z 479 (M+H)$^+$.

Example 61 (130)

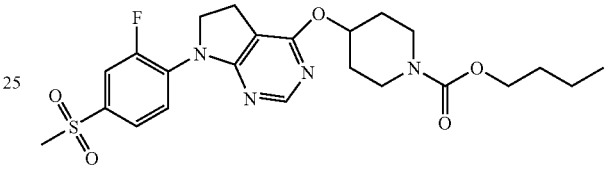

n-Butyl 4-({7-[2-fluoro-4-(methylsulfonyl)phenyl]-6,7-dihydro-5H-pyrrolo[2,3-d]pyrimidin-4-yl}oxy)-1-piperidinecarboxylate (130)

Following the general procedure described for the compound 127, to a solution of 126 (100 mg, 0.198 mmol), from a different batch) in $CH_2Cl_2$ (4 mL) was added $Et_3N$ (137 μL, 1 mmol) followed by butyl chloridocarbonate (100 μL) at RT and then stirred for 18 h. The work up and chromatography gave 76 mg (77%) of the title product 130 as a white solid. $^1H$ NMR (400 MHz, DMSO-$d_6$): δ 8.22 (s, 1H), 7.96 (t, J=8.0 Hz, 1H), 7.85 and 7.82 (dd, $J_1$=10.8 Hz, $J_2$=2.0 Hz, 1H), 7.75 and 7.73 (dd, $J_1$=8.4 Hz, $J_2$=2.4 Hz, 1H), 5.30-5.24 (m, 1H), 4.14 (t, J=8.0 Hz, 2H), 3.98 (t, J=6.4 Hz, 2H), 3.71-3.66 (m, 2H), 3.26-3.24 (br, s, 2H), 3.25 (s, 3H), 3.05 (t, J=8.8 Hz, 2H), 1.96-1.90 (m, 2H), 1.62-1.49 (m, 4H), 1.36-1.26 (m, 2H), 0.88 (t, J=7.6 Hz, 3H); LCMS (ESI): m/z 493 (M+H)$^+$.

Example 62 (131)

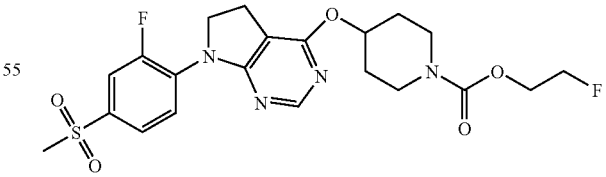

2-Fluoroethyl 4-({7-[2-fluoro-4-(methylsulfonyl) phenyl]-6,7-dihydro-5H-pyrrolo[2,3-d]pyrimidin-4-yl}oxy)-1-piperidinecarboxylate (131)

Following the general procedure described for the compound 127, to a solution of 126 (100 mg, 0.198 mmol, from a different batch) in CH$_2$Cl$_2$ (4 mL) was added Et$_3$N (137 mL, 1 mmol)) followed by 2-fluoroethyl chloridocarbonate (100 μL) at RT and then stirred for 18 h. The work up and chromatography gave 56 mg (58%) of the title product 131 as a white solid. $^1$H NMR (400 MHz, DMSO-d$_6$): δ 8.23 (s, 1H), 7.96 (t, J=8.0 Hz, 1H), 7.85 and 7.82 (dd, J$_1$=10.8 Hz, J$_2$=2.4 Hz, 1H), 7.75 and 7.73 (dd, J$_1$=8.8 Hz, J$_2$=2.0 Hz, 1H), 5.31-5.25 (m, 1H), 4.65 (app. t, J=4.0 Hz, 1H), 4.53 (app. t, J=3.6 Hz, 1H), 4.27 (app. t, J=4.0 Hz, 1H), 4.19 (app. t, J=4.0 Hz, 1H), 4.14 (t, J=8.0 Hz, 2H), 3.70 (app. m, 2H), 3.28-3.25 (br, s, 2H), 3.25 (s, 3H), 3.06 (t, J=8.8 Hz, 2H), 1.98-1.90 (m, 2H), 1.65-1.56 (m, 2H); LCMS (ESI): m/z 483 (M+H)$^+$.

Example 63 (132)

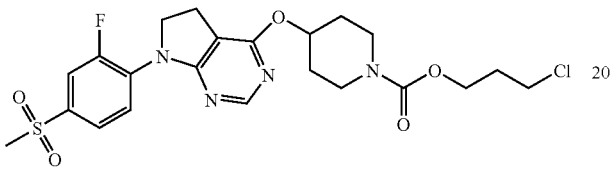

3-Chloropropyl 4-({7-[2-fluoro-4-(methylsulfonyl)phenyl]-6,7-dihydro-5H-pyrrolo[2,3-d]pyrimidin-4-yl}oxy)-1-piperidinecarboxylate (132)

Following the general procedure described for the compound 127, a solution of 2.2 mL of 126 in CH$_2$Cl$_2$ and Et$_3$N was added 3-chloropropyl chloridocarbonate (200 μL) at RT and the reaction mixture was stirred for 18 h. The work up and chromatography gave 42 mg of the title product 132 as a white solid. $^1$H NMR (400 MHz, DMSO-d$_6$): δ 8.22 (s, 1H), 7.96 (t, J=8.0 Hz, 1H), 7.86 and 7.82 (dd, J$_1$=10.8 Hz, J$_2$=2.0 Hz, 1H), 7.76 and 7.72 (dd, J$_1$=8.8 Hz, J$_2$=2.0 Hz, 1H), 5.31-5.24 (m, 1H), 4.14 (app. t, J=8.4 Hz, 2H), 4.10 (t, J=6.4 Hz, 2H), 3.70 (t, J=6.4 Hz, 2H), 3.25 (s, 3H), 3.30-3.24 (br. s, 2H), 3.05 (t, J=8.8 Hz, 2H), 2.02 (app. quintuplet, J=12.4 Hz, 2H), 1.96-1.82 (m, 2H), 1.64-1.54 (m, 2H); LCMS (ESI): m/z 513 (M+H)$^+$.

Example 64 (133)

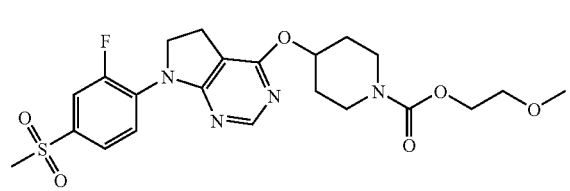

2-(Methyloxy)ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate (133)

Following the general procedure described for the compound 127, to a solution of 126 (100 mg, 0.198 mmol, from a different batch) in CH$_2$Cl$_2$ (4 mL) was added Et$_3$N (137 μL, 1 mmol) followed by 2-(methyloxy)ethyl chloridocarbonate (100 μL) at RT and the mixture was stirred for 18 h. The work up and chromatography gave 64 mg (65%) of the title product 129 as a white solid. $^1$H NMR (400 MHz, DMSO-d$_6$): δ 8.22 (s, 1H), 7.96 (t, J=7.6 Hz, 1H), 7.85 and 7.82 (dd, J$_1$=11.2 Hz, J$_2$=2.0 Hz, 1H), 7.75 and 7.72 (dd, J$_1$=8.4 Hz, J$_2$=2.0 Hz, 1H), 5.30-5.26 (m, 1H), 4.16-4.09 (m, 2H), 3.72-3.66 (m, 2H), 3.50 (t, J=4.4 Hz, 2H), 3.24 (s, 3H), 3.28-3.24 (br. s, 2H), 3.05 (t, J=8.8 Hz, 2H), 5.30-5.26 (m, 1H), 4.16-4.09 (m, 2H), 3.72-3.66 (m, 2H), 3.50 (t, J=4.4 Hz, 2H), 3.28-3.24 (br. s, 2H), 3.24 (s, 6H), 3.05 (t, J=8.8 Hz, 2H), 1.98-1.90 (m, 2H), 1.63-1.54 (m, 2H); LCMS (ESI): m/z 495 (M+H)$^+$.

Example 65 (134)

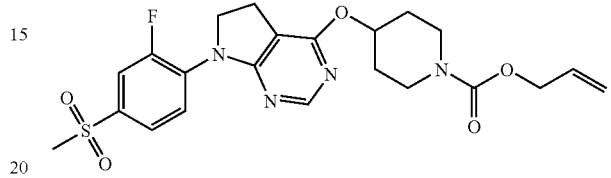

2-Propen-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate (134)

Following the general procedure described for the compound 127, to a solution of 126 (100 mg, 0.198 mmol, from a different batch) in CH$_2$Cl$_2$ (4 mL) was added Et$_3$N (137 μL, 1 mmol) followed by 2-propen-1-yl chloridocarbonate (100 μL) at RT and the mixture was stirred for 18 h. The work up and chromatography gave 56 mg (59%) of the title product 134 as a white solid. $^1$H NMR (400 MHz, DMSO-d$_6$): δ 8.22 (s, 1H), 7.96 (t, J=7.6 Hz, 1H), 7.85 and 7.82 (dd, J$_1$=10.8 Hz, J$_2$=2.4 Hz, 1H), 7.74 and 7.72 (dd, J$_1$=8.4 Hz, J$_2$=2.0 Hz, 1H), 5.96-5.87 (m, 1H), 5.30-5.24 (m, 2H), 5.18-5.16 (dd, J$_1$=10.8 Hz, J$_2$=1.2 Hz, 1H), 4.52 (d, J=5.2 Hz, 2H), 4.14 (t, J=8.4 Hz, 2H), 3.74-3.68 (m, 2H), 3.30-3.24 (br. s, 2H), 3.06 (t, J=8.8 Hz, 2H), 3.06 (t, J=8.8 Hz, 2H), 1.98-1.92 (m, 2H), 1.64-1.54 (m, 2H); LCMS (ESI): m/z 477 (M+H)$^+$.

Example 66 (135)

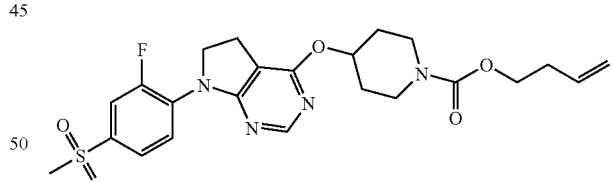

3-Buten-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate (134)

Following the general procedure described for the compound 127, a solution of 126 (2.2 mL, from step 1 of example 58) in CH$_2$Cl$_2$ was treated with Et$_3$N (1.7 mL, 6 quiv) followed by 3-buten-1-yl chloridocarbonate (200 μL) at RT for 18 h. The work up and chromatography gave 66 mg of the title product 135 as a white solid. $^1$H NMR (400 MHz, DMSO-d$_6$): δ 8.22 (s, 1H), 7.96 (t, J=8.0 Hz, 1H), 7.86 and 7.82 (dd, J$_1$=10.8 Hz, J$_2$=2.0 Hz, 1H), 7.76 and 7.74 (dd, J$_1$=8.4 Hz, J$_2$=2.0 Hz, 1H), 5.84-5.74 (m, 1H), 5.30-5.24 (m, 1H), 5.11-

5.08 (dd, $J_1$=17.2 Hz, $J_2$=2.0 Hz, 1H), 5.06 and 5.02 (app. br. d, J=10.4 Hz, 1H), 4.14 (app. t, J=8.4 Hz, 2H), 4.04 (t, J=6.8 Hz, 2H), 3.72-3.64 (m, 2H), 3.28-3.20 (br, s, 2H), 3.25 (s, 3H), 3.06 (t, J=8.8 Hz, 2H), 2.32 (app. q, J=6.8 Hz, 2H), 1.96-1.90 (m, 2H), 1.62-1.54 (m, 2H); LCMS (ESI): m/z 491 $(M+H)^+$.

Example 67 (136)

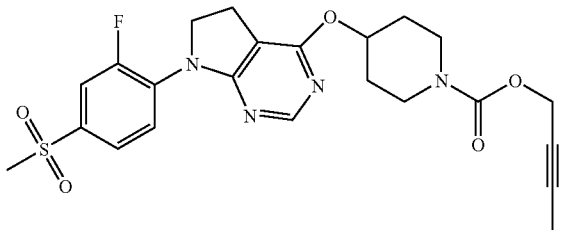

2-Butyn-1-yl 4-({7-[2-fluoro-4-(methylsulfonyl) phenyl]-6,7-dihydro-5H-pyrrolo[2,3-d]pyrimidin-4-yl}oxy)-1-piperidinecarboxylate (136)

Following the general procedure described for the compound 127, a solution of 126 (2.2 mL, from step 1 of example 58) in $CH_2Cl_2$ was treated with $Et_3N$ (1.7 mL, 6 quiv) followed by 2-butyn-1-yl chloridocarbonate (200 µL) at RT for 18 h. The work up and chromatography gave 70 mg of the title product 136 as a white solid. $^1$H NMR (400 MHz, DMSO-$d_6$): δ 8.22 (s, 1H), 7.96 (t, J=8.0 Hz, 1H), 7.84 and 7.82 (dd, $J_1$=10.8 Hz, $J_2$=2.0 Hz, 1H), 7.74 and 7.72 (dd, $J_1$=8.4 Hz, $J_2$=2.0 Hz, 1H), 5.30-5.24 (m, 1H), 4.62 (app. d, J=2.4 Hz, 2H), 4.14 (t, J=8.4 Hz, 2H), 3.70-3.64 (m, 2H), 3.28-3.24 (masked br. s, 2H), 3.25 (s, 3H), 3.06 (t, J=8.8 Hz, 2H), 1.97-1.91 (m, 2H), 1.81 (app. t, J=2.4 Hz, 3H), 1.64-1.56 (m, 2H); LCMS (ESI): m/z 489 $(M+H)^+$.

Example 68 (137)

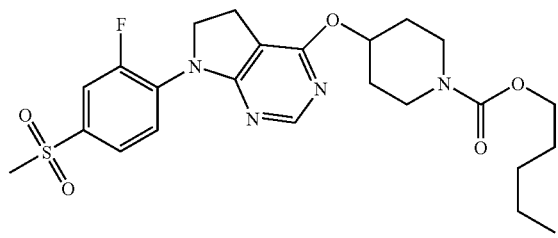

Pentyl 4-({7-[2-fluoro-4-(methylsulfonyl)phenyl]-6, 7-dihydro-5H-pyrrolo[2,3-d]pyrimidin-4-yl}oxy)-1-piperidinecarboxylate (137)

Following the general procedure described for the compound 127, to a solution of 126 (70 mg, 0.142 mmol, from different batch) in $CH_2Cl_2$ (5 mL) was added $Et_3N$ (120 µL, 0.85 mmol) followed by pentyl chloridocarbonate (100 µL) at RT and the mixture was stirred for 18 h. The work up and chromatography gave 64 mg (89%) of the title product 137 as a white solid. $^1$H NMR (400 MHz, DMSO-$d_6$): δ 8.22 (s, 1H), 7.96 (t, J=8.0 Hz, 1H), 7.84 and 7.82 (dd, $J_1$=11.2 Hz, $J_2$=2.0 Hz, 1H), 7.74 and 7.72 (dd, $J_1$=8.4 Hz, $J_2$=2.0 Hz, 1H), 5.30-5.24 (m, 1H), 4.14 (t, J=8.4 Hz, 2H), 3.98 (t, J=6.8 Hz, 2H), 3.71-3.65 (m, 2H), 3.28-3.22 (br, s, 2H), 3.25 (s, 3H), 3.05 (t, J=8.8 Hz, 2H), 1.96-1.88 (m, 2H), 1.62-1.50 (m, 4H), 1.31-1.26 (m, 4H), 0.86 (app. t, J=7.2 Hz, 3H); LCMS (ESI): m/z 507 $(M+H)^+$.

Example 69 (138)

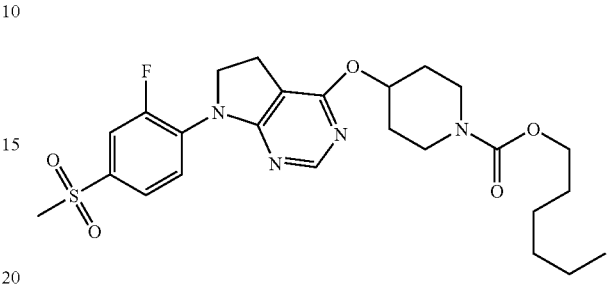

Hexyl 4-({7-[2-fluoro-4-(methylsulfonyl)phenyl]-6, 7-dihydro-5H-pyrrolo[2,3-d]pyrimidin-4-yl}oxy)-1-piperidinecarboxylate (138)

Following the general procedure described for the compound 127, to a solution of 126 (100 mg, 0.198 mmol, from a different batch) in $CH_2Cl_2$ (4 mL) was added $Et_3N$ (137 µL, 1 mmol) followed by hexyl chloridocarbonate (100 µL) at RT and the mixture was stirred for 18 h. The work up and chromatography gave 72 mg (69%) of the title product 138 as a white solid. $^1$H NMR (400 MHz, DMSO-$d_6$): δ 8.22 (s, 1H), 7.96 (t, J=8.0 Hz, 1H), 7.84 and 7.82 (dd, $J_1$=10.8 Hz, $J_2$=2.0 Hz, 1H), 7.75 and 7.72 (dd, $J_1$=8.4 Hz, $J_2$=2.0 Hz, 1H), 5.32-5.24 (m, 1H), 4.14 (t, J=8.0 Hz, 2H), 3.98 (t, J=6.4 Hz, 2H), 3.72-3.66 (m, 2H), 3.28-3.20 (masked br, s, 2H), 3.25 (s, 3H), 3.05 (t, J=6.8 Hz, 2H), 1.96-1.91 (m, 2H), 1.62-1.50 (m, 4H), 1.31-1.21 (m, 6H), 0.84 (app. t, J=6.8 Hz, 3H); LCMS (ESI): m/z 521 $(M+H)^+$.

Example 70 (140)

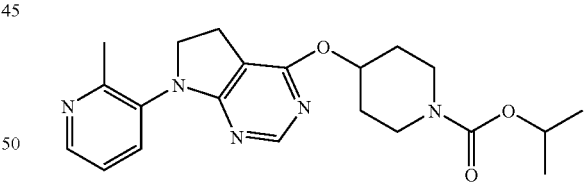

Step 1: 4-Chloro-7-(2-methyl-3-pyridinyl)-6,7-dihydro-5H-pyrrolo[2,3-d]pyrimidine (139)

A round bottom flask was charged with 2-methyl-3-pyridinamine (5.20 g, 47 mmol) and then cooled to −15° C. Trifluoroacetic acid (100 mL) was added to the above cold pyridinamine while stirring the contents for 0.5 h. $Na(OAc)_3BH$ (32.5 g, 48 mmol) was added portion-wise to the above mixture and stirred for additional 0.5 h. The aldehyde 209 (see example 117, step 1, 7.4 g, 48 mmol) in $CH_2Cl_2$ (25 mL) was added to the above mixture. The resultant mixture was allowed to warm up to the ambient temperature and stirred for 18 h. The reaction mixture was concentrated under reduced pressure and the residue was poured into sat. $NaHCO_3$ solution (250 mL) and then the mixture was extracted with CH$_2$Cl$_2$ (3×250 mL). The combined organic layer was washed with brine (1×100 mL), dried over sat. Na$_2$SO$_4$ and then concentrated under reduced pressure to afford ~11.5 g (~100%) the crude material. The required bicyclic product was not obtained, but the uncyclized N-[2-(4,6-dichloro-5-pyrimidinyl)ethyl]-2-methyl-3-pyridinamine was isolated as a major product. $^1$H NMR (400 MHz, DMSO-d$_6$): δ 8.81 (s, 1H), 7.95-7.94 (m, 1H), 7.71-7.66 (m, 2H), 6.63 (app. t, J=5.6 Hz, 1H), 3.59 (app. q, J=6.0 Hz, 2H), 3.08 (t, J=6.4 Hz, 2H), 2.40 (s, 3H), LCMS (ESI): m/z 285 (M+H)$^+$.

The round bottom flask was charged with the product (~11.0 g) obtained above. PdCl$_2$(Ph$_3$P)$_2$ (1.36 g, 2 mmol), potassium tert-butoxide (8.72 g, 77.7 mmol), K$_2$CO$_3$ (10.74 g, 77.7 mmol), and toluene (200 mL) at RT under N$_2$. The reaction mixture was refluxed for 18 h. The reaction mixture was cooled to RT and then filtered through a pad of celite. The filtrate was concentrated under reduced pressure to afford the crude product which was subjected for flash column chromatography to afford 0.850 g of the title product 139 (87% pure). $^1$H NMR (400 MHz, DMSO-d$_6$): δ 8.42 and 8.40 (dd, J$_1$=4.8 Hz, J$_2$=1.2 Hz, 1H), 8.11 (s, 1H), 7.76-7.74 (dd, J$_1$=8.0 Hz, J$_2$=1.6 Hz, 1H), 7.32 and 7.30 (dd, J$_1$=8.0 Hz, J$_2$=4.8 Hz, 1H), 4.03 (t, J=8.8 Hz, 2H), 3.20 (t, J=8.4 Hz, 2H), 2.34 (s, 3H), LCMS (ESI): m/z 247 (M+H)$^+$.

Step 2: 1-Methylethyl 4-{[7-(2-methyl-3-pyridinyl)-6,7-dihydro-5H-pyrrolo[2,3-d]pyrimidin-4-yl]oxy}-1-piperidinecarboxylate (140)

The procedure described for 10 (example 1, step 10) was employed using the compound 9 (266 mg, 1.42 mmol), NaH (170 mg, 60% dispersion in mineral oil, 4.26 mmol), compound 139 (350 mg, 1.42 mmol) in THF at reflux temperature for 2 h. Standard work-up followed by purification gave 310 mg (55%) of the title product 140 as a white solid. $^1$H NMR (400 MHz, DMSO-d$_6$): δ 8.36 and 8.35 (dd, J$_1$=4.8 Hz, J$_2$=1.2 Hz, 1H), 8.05 (s, 1H), 7.70-7.68 (dd, J$_1$=8.0 Hz, J$_2$=1.6 Hz, 1H), 7.27 and 7.25 (dd, J$_1$=8.0 Hz, J$_2$=4.8 Hz, 1H), 5.27-5.20 (m, 1H), 4.27 (septuplet, J=6.4 Hz, 1H), 3.94 (t, J=8.8 Hz, 2H), 3.71-3.66 (m, 2H), 3.21 (app. br. t, J=10.0 Hz, 2H), 3.04 (t, J=9.2 Hz, 2H), 2.35 (s, 3H), 1.95-1.89 (m, 2H), 1.60-1.50 (m, 2H), 1.17 (d, J=6.0 Hz, 6H); LCMS (ESI): m/z 398 (M+H)$^+$.

Example 71 (143)

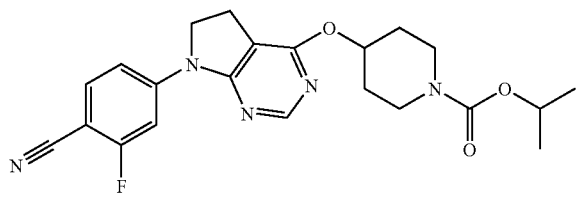

Step 1: 7-(4-Bromo-3-fluorophenyl)-4-chloro-6,7-dihydro-5H-pyrrolo[2,3-d]pyrimidine (141)

A round bottom flask was charged with 4-bromo-3-fluoroaniline (10.0 g, 52.5 mmol) and then cooled to −15° C. Trifluoroacetic acid (50 mL) was added to the above cold aniline while stirring the contents for 0.5 h. Na(OAc)$_3$BH (15.9 g, 50 mmol) was added portion wise to the above mixture and stirred for additional 0.5 h. The aldehyde 209 (see example 118, step 1, 7.85 g, 75 mmol) in CH$_2$Cl$_2$ (15 mL) was added to the above mixture. The resultant mixture was allowed to warm up to the ambient temperature and stirred for 24 h. The reaction mixture was concentrated under reduced pressure and the residue was poured into sat. NaHCO$_3$ solution (250 mL) and then the mixture was extracted with CH$_2$Cl$_2$ (3×250 mL). The combined organic layer was washed with brine (1×100 mL), dried over sat. Na$_2$SO$_4$ and then concentrated under reduced pressure to afford crude material, which was recrystallized from CH$_2$Cl$_2$ and MeOH to afford 8.65 g (53%) of the title product 141 as an off-white solid. $^1$H NMR (400 MHz, DMSO-d$_6$): δ 8.42 (s, 1H), 7.88 and 7.86 (dd, J$_1$=11.2 Hz, J$_2$=2.8 Hz, 2H), 7.51 (t, J=8.0 Hz, 1H), 7.36 and 7.34 (dd, J$_1$=9.2 Hz, J$_2$=2.4 Hz, 1H), 4.11 (t, J=8.8 Hz, 2H), 3.22 (t, J=8.4 Hz, 2H); LCMS (ESI): m/z 329 (M+H)$^+$.

Step 2: 1-Methylethyl 4-{[7-(4-bromo-3-fluorophenyl)-6,7-dihydro-5H-pyrrolo[2,3-d]pyrimidin-4-yl]oxy}-1-piperidinecarboxylate (142)

The procedure described for 10 (example 1, step 10) was employed using the compound 9 (1.79 g, 9.5 mmol), NaH (1.20 g, 60% dispersion in mineral oil, 30 mmol), compound 141 (3.30 mg, 10 mmol) in THF at reflux temperature for 2 h. Standard work-up followed by purification gave 3.46 mg (72%) of the title product 142 as a white solid. $^1$H NMR (400 MHz, CDCl$_3$): δ 8.33 (s, 1H), 7.86 and 7.82 (dd, J$_1$=12.0 Hz, J$_2$=2.4 Hz, 1H s, 1H), 7.47 (t, J=8.0 Hz, 1H), 7.35-7.32 (dd, J$_1$=8.8 Hz, J$_2$=2.8 Hz, 1H), 5.37-5.32 (m, 1H), 4.93 (septuplet, J=6.0 Hz, 1H), 4.04 (t, J=8.8 Hz, 2H), 3.82-3.76 (br, m, 2H), 3.36-3.30 (m, 2H), 3.07 (t, J=8.8 Hz, 2H), 2.02-1.95 (m, 2H), 1.77-1.69 (m, 2H), 1.25 (d, J=6.4 Hz, 6H); LCMS (ESI): m/z 481 (M+H)$^+$.

Step 3: 1-Methylethyl 4-{[7-(4-cyano-3-fluorophenyl)-6,7-dihydro-5H-pyrrolo[2,3-d]pyrimidin-4-yl]oxy}-1-piperidinecarboxylate (143)

The procedure described for 31 (example 10, step 7) was employed using the compound 142 (400 mg, 0.834 mmol), CuCN (150 mg, 1.67 mmol) in NMP at 150° C. for 18 h. Standard work-up followed by purification gave 66 mg (19%) of the title product 143 as a white solid. $^1$H NMR (400 MHz, DMSO-d$_6$): δ 8.42 (s, 1H), 8.13-8.09 (dd, J$_1$=13.6 Hz, J$_2$=1.6 Hz, 1H), 7.84 (app. t, J=8.0 Hz, 1H), 7.75-7.72 (dd, J$_1$=8.8 Hz, J$_2$=2.0 Hz, 1H), 5.32-5.25 (m, 1H), 4.75 (septuplet, J=6.4 Hz, 1H), 4.10 (t, J=8.8 Hz, 2H), 3.70-3.64 (m, 2H), 3.24 (app. J=9.6 Hz, 2H), 3.03 (t, J=8.8 Hz, 2H), 1.96-1.89 (m, 2H), 1.61-1.53 (m, 2H), 1.16 (d, J=6.0 Hz, 6H); LCMS (ESI): m/z 426 (M+H)$^+$.

Example 72 (144)

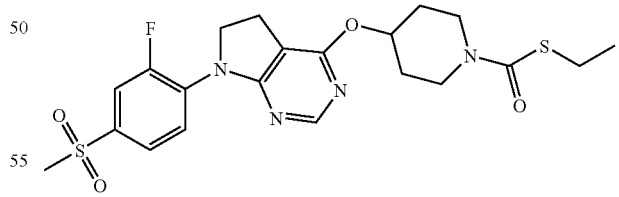

S-Ethyl 4-({7-[2-fluoro-4-(methylsulfonyl)phenyl]-6,7-dihydro-5H-pyrrolo[2,3-d]pyrimidin-4-yl}oxy)-1-piperidinecarbothioate (144)

Following the procedure described for the compound 127, compound II (example 2, 493 mg, 1 mmol) in CH$_2$Cl$_2$ (15 mL) was treated with TFA (2.5 mL) at RT for 1 h. The reaction mixture was concentrated under reduced pressure to afford the crude product 126 and the product was dried thoroughly and then re-dissolved in CH$_2$Cl$_2$ (15 min). Et$_3$N (1 mL, 7.22 mmol) followed by ethyl chlorothiolformate (208 μL, 2 mmol) was introduced slowly to the above mixture at RT under N₂. The reaction mixture was stirred at RT for 18 h. The reaction mixture was diluted with CH₂Cl₂ (50 mL), washed with H₂O (2×15 mL), brine (1×10 mL), dried over Na₂SO₄ and then concentrated under reduced pressure to afford the crude product, which was subjected for flash column chromatography to afford 416 mg (87%) of the title product 144 as a white solid. ¹H NMR (400 MHz, DMSO-d₆): δ 8.23 (s, 1H), 7.96 (t, J=8.0 Hz, 1H), 7.85 and 7.82 dd, J₁=11.2 Hz, J₂=2.0 Hz, 1H), 7.75 and 7.73 (dd, J₁=8.4 Hz, J₂=2.0 Hz, 1H), 5.36-5.29 (m, 1H), 4.14 (t, J=8.4 Hz, 2H), 3.76 (app. br. s, 2H), 3.41-3.36 (m, 2H), 3.25 (s, 3H), 3.06 (t, J=8.8 Hz, 2H), 2.81 (q, J=7.2 Hz, 2H), 1.96 (br. s, 2H), 1.62 (br. s, 2H), 1.18 (t, J=7.6 Hz, 2H); LCMS (ESI): m/z 481 (M+H)⁺.

Example 73 (145)

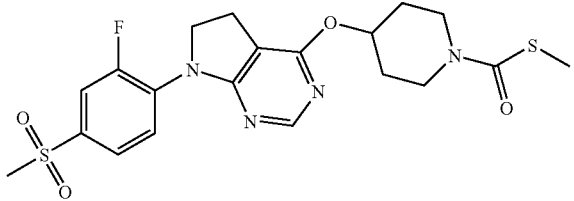

S-Methyl 4-({7-[2-fluoro-4-(methylsulfonyl)phenyl]-6,7-dihydro-5H-pyrrolo[2,3-d]pyrimidin-4-yl}oxy)-1-piperidinecarbothioate (145)

Following the procedure described for the compound 127, compound 126 (70 mg, 0.142 mmol) in CH₂Cl₂ (2 mL) was treated with TFA (0.5 mL) at RT for 2 h. The reaction mixture was concentrated under reduced pressure to afford the crude product and the product was dried thoroughly and then re-dissolved in CH₂Cl₂ (5 min). Et₃N (120 μL, 0.852 mmol) followed by methyl chlorothiolformate (37 μL, 0.43 mmol) was introduced slowly to the above mixture at RT under N₂. The work-up and chromatography gave 56 mg (85%) of the title product 145 as a white solid. ¹H NMR (400 MHz, DMSO-d₆): δ 8.22 (s, 1H), 7.96 (app. t, J=8.4 Hz, 1H), 7.86-7.82 (dd, J₁=10.8 Hz, J₂=2.0 Hz, 1H), 7.76 and 7.72 (dd, J₁=8.4 Hz, J₂=2.0 Hz, 1H), 5.36-5.28 (m, 2H), 4.14 (t, J=8.0 Hz, 2H), 3.74 (br, s, 2H), 3.42-3.34 (m, 2H), 3.25 (s, 3H), 3.06 (t, J=8.8 Hz, 2H), 2.24 (s, 3H), 1.96 (app. br. s, 2H), 1.62 (app, br, m, 2H); LCMS (ESI): m/z 467 (M+H)⁺.

Example 74 (148)

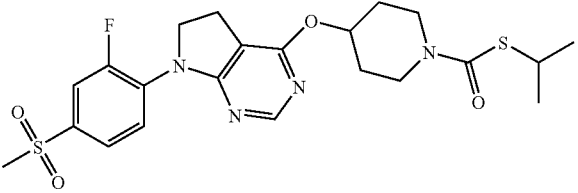

Step 1: 7-[2-Fluoro-4-(methylsulfonyl)phenyl]-4-{[1-(1H-imidazol-1-ylcarbonyl)-4-piperidinyl]oxy}-6,7-dihydro-5H-pyrrolo[2,3-d]pyrimidine (146)

Following the procedure described for 126 (example 58, step 1), the compound 11 (example 2, 20 g, 4.06 mmol) was treated with a 20% TFA in CH₂Cl₂ (50 mL) at RT for 3 h. The reaction mixture was concentrated under reduced pressure to afford to crude material. To a solution of the product, thus obtained above, in CH₂Cl₂ (150 mL) was added 1,1'-(oxomethanediyl)bis-1H-imidazole (725 mg, 4.47 mmol) at 5° C. The reaction mixture was allowed to warm to ambient temperature and allowed to stir for 24 h. The reaction mixture was diluted with CH₂Cl₂ (200 mL) and the mixture was washed with H₂O (2×40 mL). The organic layer was dried over Na₂SO₄ and then concentrated under reduced pressure to afford crude product, which was recrystallized from CH₂Cl₂ to give 1.91 g (97%) of the title product 146 as a white solid. ¹H NMR (400 MHz, DMSO-d₆): δ 8.24 (s, 1H), 8.02 (s, 1H), 7.96 (app. t, J=8.0 Hz, 1H), 7.85 and 7.83 (dd, J₁=11.2 Hz, J₂=2.4 Hz, 1H), 7.75-7.73 (dd, J₁=8.4 Hz, J₂=2.0 Hz, 1H), 7.47 (s, 1H), 7.02 (s, 1H), 5.40-5.28 (m, 1H), 4.15 (t, J=8.4 Hz, 2H), 3.71 (m, 2H), 3.48-3.42 (m, 2H), 3.25 (s, 3H), 3.07 (t, J=9.2 Hz, 2H), 2.10-2.02 (m, 2H), 1.83-1.75 (m, 2H); LCMS (ESI): m/z 487 (M+H)⁺.

Step 2: 1-{[4-({7-[2-Fluoro-4-(methylsulfonyl)phenyl]-6,7-dihydro-5H-pyrrolo[2,3-d]pyrimidin-4-yl}oxy)-1-piperidinyl]carbonyl}-3-methyl-1H-imidazol-3-ium iodide (147)

To a stirred solution of 146 (1.9 g, 3.90 mmol) in CH₃CN (30 mL) and CH₂Cl₂ (30 mL) was added methyl iodide (1.46 mL, 23.46 mmol) at RT under N₂. The reaction mixture was stirred at RT for 24 h and then concentrated under reduced pressure to afford 2.46 g (100%) of the title product 147 as an off-white solid. ¹H NMR (400 MHz, DMSO-d₆): δ 9.55 (s, 1H), 8.24 (s, 1H), 8.03 (app. t, J=3.6 Hz, 1H), 7.96 (t, J=8.0 Hz, 1H), 7.86-7.82 (m, 2H), 7.76 and 7.74 (dd, J₁=8.4 Hz, J₂=2.0 Hz, 1H), (app. t, J=8.0 Hz, 1H), 5.42 (m, 1H), 4.16 (t, J=8.4 Hz, 2H), 3.90 (s, 3H), 3.71 (br, s, 2H), 3.50 (br, s, 2H), 3.25 (s, 3H), 3.07 (t, J=9.2 Hz, 2H), 2.12-2.04 (br. m, 2H), 1.88-1.80 (m, 2H).

Step 3: S-(1-Methylethyl)4-({7-[2-fluoro-4-(methylsulfonyl)phenyl]-6,7-dihydro-5H-pyrrolo[2,3-d]pyrimidin-4-yl}oxy)-1-piperidinecarbothioate (148)

compound 147 (315 mg, 0.5 mmol) in CH₂Cl₂ (3 mL) were added Et₃N (70 μL, 0.5 mmol) and isopropylthiol (38 mg, 0.5 mmol) at RT under N₂. The reaction mixture was stirred at RT for 18 h. The work-up and column chromatography gave 156 mg (63%) of the title product 148 as a white solid. ¹H NMR (400 MHz, DMSO-d₆): δ 8.23 (s, 1H), 7.96 (app. t, J=8.0 Hz, 1H), 7.85 and 7.82 (app. br. d, J=10.8 Hz, 1H), 7.74 (app. br. d, J=6.8 Hz, 1H), 5.30-5.28 (m, 1H), 4.14 (t, J=8.4 Hz, 2H), 3.46 (m, 1H), 3.37-3.30 (app. br. m, 2H), 3.25 (s, 3H), 3.06 (t, J=8.4 Hz, 2H), 1.94 (app, br. s, 2H), 1.61 (app. br. s, 2H), 1.26 (d, J=6.4 Hz, 6H); LCMS (ESI): m/z 495 (M+H)⁺.

Example 75 (149)

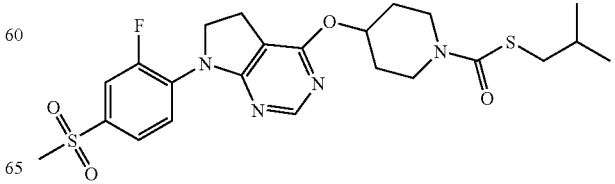

S-(2-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate (149)

Following the procedure described for the compound 148, to a solution of imidazole salt 147 (115 mg, 0.183 mmol) in CH$_2$Cl$_2$ (5 mL) were added Et$_3$N (76 μL, 0.55 mmol) and isobutylthiol (100 μL). The reaction was stirred for 15 h. The workup and chromatography gave 52 mg (56%) of the title product 149 as a white solid. $^1$H NMR (400 MHz, DMSO-d$_6$): δ 8.22 (s, 1H), 7.96 (t, J=7.2 Hz, 1H), 7.84 (br, d, J=11.2 Hz, 1H), 7.73 (br, d, J=8.4 Hz, 1H), 5.32 (app. br, s, 1H), 4.14 (t, J=8.8 Hz, 2H), 3.75 (br, s, 2H), 3.42-3.37 (m, 2H), 3.25 (s, 3H), 3.06 (t, J=8.8 Hz, 2H), 2.75 (d, J=6.8 Hz, 2H), 1.96 (app, br. s, 2H), 1.78-1.68 (m, 1H), 1.62 (app, br. s, 2H), 0.91 (d, J=5.2 Hz, 6H); LCMS (ESI): m/z 509 (M+H)$^+$.

Example 76 (150)

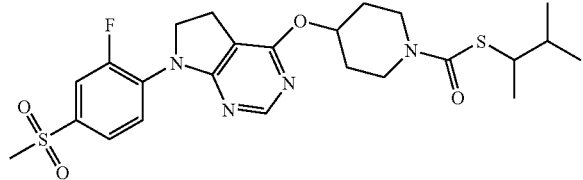

(±)-S-(1,2-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate (150)

Following the procedure described for the compound 148, to a solution of imidazole salt 147 (115 mg, 0.183 mmol) in CH$_2$Cl$_2$ (5 mL) were added Et$_3$N (76 μL, 0.55 mmol) and 3-methyl-2-butanethiol (100 μL). The reaction was stirred for 15 h. The workup and chromatography gave 65 mg (68%) of the title product 150 as a white solid. $^1$H NMR (400 MHz, DMSO-d$_6$): δ 8.22 (s, 1H), 7.96 (t, J=7.2 Hz, 1H), 7.85-7.82 (dd, J$_1$=10.8 Hz, J$_2$=2.0 Hz, 1H), 7.75 and 7.73 (dd, J$_1$=8.4 Hz, J$_2$=2.0 Hz, 1H), 5.35-5.29 (m, 1H), 4.14 (t, J=7.6 Hz, 2H), 3.73 (app. br, s, 2H), 3.44-3.35 (m, 3H), 3.25 (s, 3H), 3.06 (t, J=7.2 Hz, 2H), 1.98-1.96 (app. br, s, 2H), 1.89-1.82 (m, 2H), 1.64-1.58 (m, 2H), 1.21 (d, J=9.2 Hz, 3H), 0.90 (d, J=6.8 Hz, 6H); LCMS (ESI): m/z 523 (M+H)$^+$.

Example 77 (151)

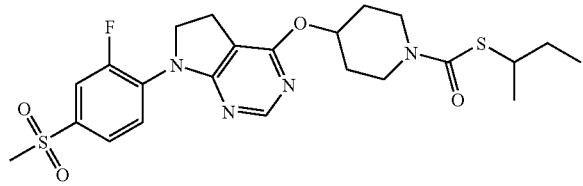

(±)-S-(1-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate (151)

Following the procedure described for the compound 148, to a solution of imidazole salt 147 (115 mg, 0.183 mmol) in CH$_2$Cl$_2$ (5 mL) were added Et$_3$N (76 μL, 0.55 mmol) and 2-butanethiol (100 μL). The reaction was stirred for 15 h. The workup and chromatography gave 58 mg (62%) of the title product 151 as a white solid. $^1$H NMR (400 MHz, DMSO-d$_6$): δ 8.22 (s, 1H), 7.96 (t, J=8.0 Hz, 1H), 7.85-7.82 (dd, J$_1$=10.8 Hz, J$_2$=2.0 Hz, 1H), 7.75 and 7.72 (dd, J$_1$=8.4 Hz, J$_2$=2.0 Hz, 1H), 5.34-5.28 (m, 1H), 4.14 (t, J=8.4 Hz, 2H), 3.40-3.30 (m, 3H), 3.25 (s, 3H), 3.06 (t, J=8.8 Hz, 2H), 1.97-1.95 (app. br. m, 2H), 1.65-1.52 (m, 4H), 1.25 (d, J=6.8 Hz, 3H), 0.90 (t, J=7.2 Hz, 3H); LCMS (ESI): m/z 509 (M+H)$^+$.

Example 78 (152)

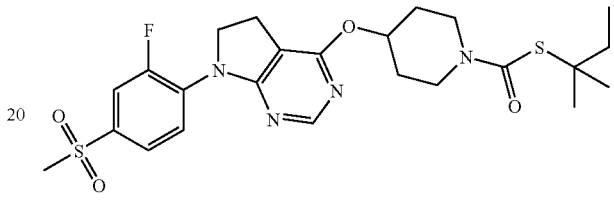

S-(1,1-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate (152)

Following the procedure described for the compound 148, to a solution of imidazole salt 147 (115 mg, 0.183 mmol) in CH$_2$Cl$_2$ (5 mL) were added Et$_3$N (76 μL, 0.55 mmol) and 2-methyl-2-butanethiol (100 μL). The reaction was stirred for 15 h. The work up and chromatography gave 56 mg (58%) of the title product 152 as a white solid. $^1$H NMR (400 MHz, DMSO-d$_6$): δ 8.22 (s, 1H), 7.96 (t, J=8.0 Hz, 1H), 7.85-7.82 (dd, J$_1$=10.8 Hz, J$_2$=2.0 Hz, 1H), 7.75 and 7.72 (dd, J$_1$=8.8 Hz, J$_2$=2.0 Hz, 1H), 5.33-5.27 (m, 1H), 4.14 (t, J=8.4 Hz, 2H), 3.71 (app. br. m, 2H), 1.76 (q, J=7.2 Hz, 2H), 1.63-1.56 (m, 2H), 1.38 (s, 6H), 0.87 (t, J=7.2 Hz, 3H); LCMS (ESI): m/z 523 (M+H)$^+$.

Example 79 (153)

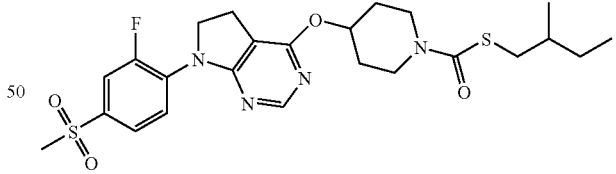

(±)-S-(2-Methyl butyl)4-({7-[2-fluoro-4-(methylsulfonyl)phenyl]-6,7-dihydro-5H-pyrrolo[2,3-d]pyrimidin-4-yl}oxy)-1-piperidinecarbothioate (153)

Following the procedure described for the compound 148, to a solution of imidazole salt 147 (115 mg, 0.183 mmol) in CH$_2$Cl$_2$ (5 mL) were added Et$_3$N (76 μL, 0.55 mmol) and 2-methyl-1-butanethiol (100 μL). The reaction was stirred for 15 h. The workup and chromatography gave 62 mg (65%) of the title product 153 as a white solid. $^1$H NMR (400 MHz, DMSO-d$_6$): δ 8.22 (s, 1H), 7.96 (t, J=8.0 Hz, 1H), 7.85-7 7.82 (dd, J$_1$=11.2 Hz, J$_2$=2.0 Hz, 1H), 7.75 and 7.72 (dd, J$_1$=8.8

Hz, J₂=2.0 Hz, 1H), 5.33-5.30 (m, 1H), 4.14 (t, J=8.4 Hz, 2H), 3.75 (app. br. s, 2H), 3.43-3.36 (m, 2H), 3.25 (s, 3H), 3.06 (t, J=8.8 Hz, 2H), 2.90 and 2.87 (dd, J₁=13.2 Hz, J₂=5.6 Hz, 1H), 1.96 (app. br, s, 2H), 1.62 (app. br. s, 2H), 1.56-1.48 (m, 1H), 1.44-1.33 (m, 1H), 1.21-1.10 (m, 1H), 0.89-0.82 (m, 6H); LCMS (ESI): m/z 523 (M+H)⁺.

Example 80 (154)

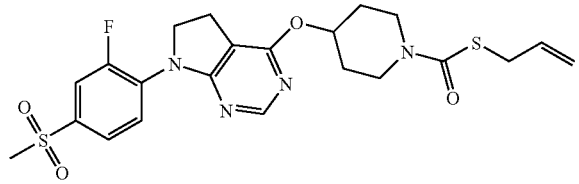

S-2-Propen-1-yl 4-({7-[2-fluoro-4-(methylsulfonyl) phenyl]-6,7-dihydro-5H-pyrrolo[2,3-d]pyrimidin-4-yl}oxy)-1-piperidinecarbothioate (154)

Following the procedure described for the compound 148, to a solution of imidazole salt 147 (115 mg, 0.183 mmol) in CH₂Cl₂ (5 mL) were added Et₃N (76 µL, 0.55 mmol) and 2-propene-1-thiol (100 µL). The reaction was stirred for 15 h. The workup and chromatography gave 32 mg (36%) of the title product 154 as a white solid. ¹H NMR (400 MHz, DMSO-d₆): δ 8.22 (s, 1H), 7.96 (t, J=8.0 Hz, 1H), 7.85-7.82 (dd, J₁=11.2 Hz, J₂=2.0 Hz, 1H), 7.75 and 7.72 (dd, J₁=8.8 Hz, J₂=2.0 Hz, 1H), 5.86-5.75 (m, 1H), 5.35-5.30 (m, 1H), 5.23 and 5.19 (dd, J₁=16.8 Hz, J₂=1.6 Hz, 1H), 5.05 (app. br. d, J=10.0 Hz, 1H), 4.14 (t, J=8.4 Hz, 2H), 3.72 (app. br. s, 2H), 3.52 (app. d, J=6.8 Hz, 2H), 3.42-3.36 (m, 2H), 3.25 (s, 3H), 3.06 (t, J=8.8 Hz, 2H), 2.02-1.92 (br. m, 2H), 1.68-1.56 (br. m, 2H); LCMS (ESI): m/z 493 (M+H)⁺.

Example 81 (155)

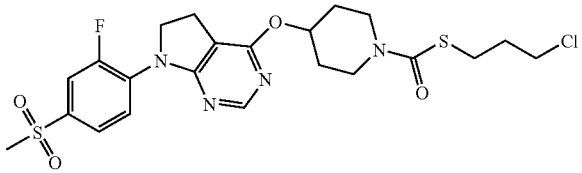

S-(3-Chloropropyl)4-({7-[2-fluoro-4-(methylsulfonyl)phenyl]-6,7-dihydro-5H-pyrrolo[2,3-d]pyrimidin-4-yl}oxy)-1-piperidinecarbothioate (155)

Following the procedure described for the compound 148, to a solution of imidazole salt 147 (115 mg, 0.183 mmol) in CH₂Cl₂ (5 mL) were added Et₃N (76 µL, 0.55 mmol) and 3-chloro-1-propanethiol (100 µL). The reaction was stirred for 15 h. The workup and chromatography gave 71 mg (73%) of the title product 155 as a white solid. ¹H NMR (400 MHz, DMSO-d₆): δ 8.22 (s, 1H), 7.96 (t, J=8.0 Hz, 1H), 7.85-7.82 (dd, J₁=11.2 Hz, J₂=2.0 Hz, 1H), 7.75 and 7.72 (dd, J₁=8.8 Hz, J₂=2.0 Hz, 1H), 5.35-5.30 (m, 1H), 4.14 (t, J=8.4 Hz, 2H), 3.65 (br, s, 2H), 3.67 (t, J=6.4 Hz, 2H), 3.40-3.36 (m, 2H), 3.25 (s, 3H), 3.06 (t, J=9.2 Hz, 2H), 2.99 (t, J=7.2 Hz, 2H), 2.00-1.94 (m, 4H), 1.68-1.58 (m, 2H); LCMS (ESI): m/z 530 (M+H)⁺.

Example 82 (156)

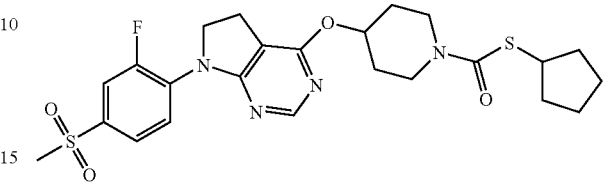

S-Cyclopentyl 4-({7-[2-fluoro-4-(methylsulfonyl) phenyl]-6,7-dihydro-5H-pyrrolo[2,3-d]pyrimidin-4-yl}oxy)-1-piperidinecarbothioate (156)

Following the procedure described for the compound 148, to a solution of imidazole salt 147 (115 mg, 0.183 mmol) in CH₂Cl₂ (5 mL) were added Et₃N (76 µL, 0.55 mmol) and cyclopentanethiol (100 µL). The reaction was stirred for 15 h. The work up and chromatography gave 74 mg (78%) of the title product 156 as a white solid. ¹H NMR (400 MHz, DMSO-d₆): δ 8.22 (s, 1H), 7.96 (t, J=8.0 Hz, 1H), 7.85-7.82 (dd, J₁=11.2 Hz, J₂=2.0 Hz, 1H), 7.75 and 7.72 (dd, J₁=8.8 Hz, J₂=2.0 Hz, 1H), 5.34-5.28 (m, 1H), 4.14 (t, J=8.4 Hz, 2H), 3.70 (br. s, 2H), 3.56 (m, 1H), 3.38-3.31 (m, 3H), 3.25 (s, 3H), 3.06 (t, J=8.4 Hz, 2H), 2.06-1.90 (m, 4H), 1.67-1.44 (m, 8H); LCMS (ESI): m/z 521 (M+H)⁺.

Example 83 (157)

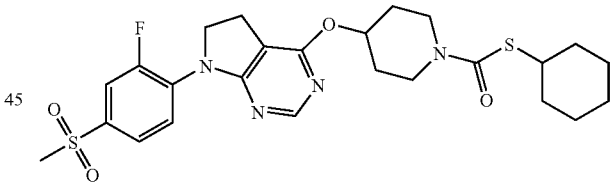

S-Cyclohexyl 4-({7-[2-fluoro-4-(methylsulfonyl) phenyl]-6,7-dihydro-5H-pyrrolo[2,3-d]pyrimidin-4-yl}oxy)-1-piperidinecarbothioate (157)

Following the procedure described for the compound 148, to a solution of imidazole salt 147 (115 mg, 0.183 mmol) in CH₂Cl₂ (5 mL) were added Et₃N (76 µL, 0.55 mmol) and cyclohexanethiol (100 µL). The reaction was stirred for 15 h. The workup and chromatography gave 69 mg (70%) of the title product 157 as a white solid. ¹H NMR (400 MHz, DMSO-d₆): δ 8.22 (s, 1H), 7.95 (t, J=8.0 Hz, 1H), 7.85-7.82 (dd, J₁=11.2 Hz, J₂=2.0 Hz, 1H), 7.75 and 7.72 (dd, J₁=8.8 Hz, J₂=2.0 Hz, 1H), 5.35-5.28 (m, 1H), 4.14 (t, J=8.4 Hz, 2H), 3.70 (br, s, 2H), 3.39-3.31 (m, 4H), 3.25 (s, 3H), 3.06 (t, J=8.8 Hz, 2H), 1.97-1.87 (m, 4H), 1.64-1.58 (m, 4H), 1.41-1.29 (m, 4H), 1.26-1.21 (m, 1H); LCMS (ESI): m/z 535 (M+H)⁺.

115

Example 84 (158)

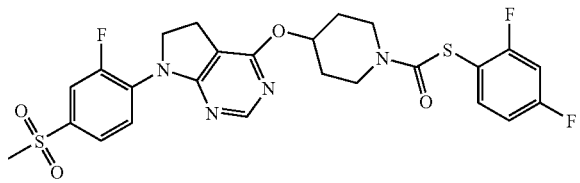

S-(2,4-Difluorophenyl)4-({7-[2-fluoro-4-(methylsulfonyl)phenyl]-6,7-dihydro-5H-pyrrolo[2,3-d]pyrimidin-4-yl}oxy)-1-piperidinecarbothioate (158)

Following the procedure described for the compound 148, to a solution of imidazole salt 147 (115 mg, 0.183 mmol) in CH$_2$Cl$_2$ (5 mL) were added Et$_3$N (76 µL, 0.55 mmol) and 2,4-difluorobenzenethiol (100 µL). The reaction was stirred for 15 h. The workup and chromatography gave 76 mg (73%) of the title product 158 as a white solid. $^1$H NMR (400 MHz, DMSO-d$_6$): δ 8.24 (s, 1H), 7.96 (t, J=8.0 Hz, 1H), 7.85-7.82 (dd, J$_1$=10.8 Hz, J$_2$=2.0 Hz, 1H), 7.75 and 7.72 (dd, J$_1$=8.8 Hz, J$_2$=2.0 Hz, 1H), 7.62-7.56 (m, 1H), 7.44-7.38 (m, 1H), 7.18-7.13 (m, 1H), 5.39-5.33 (m, 1H), 4.15 (t, J=8.4 Hz, 2H), 3.78-3.74 (m, 2H), 3.47 (br. s, 2H), 3.25 (s, 3H), 3.08 (t, J=8.8 Hz, 2H), 2.02 (br. s, 2H), 1.70 (br. s, 2H); LCMS (ESI): m/z 565 (M+H)$^+$.

Example 85 (161)

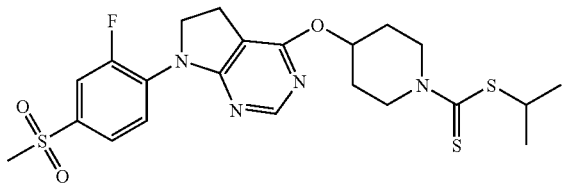

Step 1: 7-[2-Fluoro-4-(methylsulfonyl)phenyl]-4-{[1-(1H-imidazol-1-ylcarbonothioyl)-4-piperidinyl]oxy}-6,7-dihydro-5H-pyrrolo[2,3-d]pyrimidine (159)

Following the procedure described for 126 (example 58, step 1), the compound 11 (example 2, 1.14 g, 2.31 mmol) was treated with a 20% TFA in CH$_2$Cl$_2$ (25 mL) at RT for 2 h. The reaction mixture was concentrated under reduced pressure to afford to crude material. To a solution of the product, thus obtained above, in CH$_2$Cl$_2$ (100 mL) was added 1,1'-(thioxomethanediyl)bis-1H-imidazole (453 mg, 2.54 mmol) at 5° C. The reaction mixture was allowed to warm to ambient temperature and allowed to stir for 24 h. The work up described for 146 was employed to isolate 1.12 g (95%) of the title product 159 (95%) as a white solid. $^1$H NMR (400 MHz, DMSO-d$_6$): δ 8.24 (s, 1H), 8.03 (s, 1H), 7.96 (t, J=8.0 Hz, 1H), 7.86 and 7.83 (dd, J$_1$=10.8 Hz, J$_2$=2.0 Hz, 1H), 7.76 and 7.73 (dd, J$_1$=8.4 Hz, J$_2$=2.4 Hz, 1H), 7.51 (s, 1H), 7.02 (s, 1H), 5.47-5.41 (m, 1H), 4.16 (t, J=8.4 Hz, 2H), 3.25 (s, 3H), 3.07 (t, J=8.8 Hz, 2H), 2.12 (app. br. s, 2H), 1.89 (app. br. s, 2H); LCMS (ESI): m/z 503 (M+H)$^+$.

116

Step 2: 1-{[4-({7-[2-Fluoro-4-(methylsulfonyl)phenyl]-6,7-dihydro-5H-pyrrolo[2,3-d]pyrimidin-4-yl}oxy)-1-piperidinyl]carbonothioyl}-3-methyl-1H-imidazol-3-ium iodide (160)

The procedure described for 147 was employed using compound 159 (1.0 g, 2 mmol), MeI (750 µL, 12 mmol), CH$_2$Cl$_2$ (20 mL), and CH$_3$CN (20 mL) at RT. The reaction mixture was concentrated under reduced pressure to afford 1.30 g (~100%) of the title salt 160 as a yellow solid. $^1$H NMR (400 MHz, DMSO-d$_6$): δ 9.62 (s, 1H), 8.24 (s, 1H), 8.10 (m, 1H), 7.96 (t, J=7.6 Hz, 1H), 7.86 and 7.84 (m, 2H), 7.76 and 7.74 (dd, J$_1$=8.8 Hz, J$_2$=4.0 Hz, 1H), 5.50-5.46 (m, 1H), 4.32 (br, s, 1H), 4.19-4.10 (br, s, 4H), 3.89 (s, 3H), 3.76 (br, s, 1H), 3.64 (br, s, 1H), 3.25 (s, 3H), 3.08 (t, J=8.4 Hz, 2H), 2.22 and 2.10 (br, s, 2H), 1.96-1.90 (br. s, 1H), (app. br. s, 2H), 1.89 (app. br. s, 2H).

Step 3: 1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarbodithioate (161)

The procedure described for 148 (example 74, step 3) was employed using compound 160 (323 g, 0.5 mmol), Et$_3$N (70 µL, 0.5 mmol), 2-propanethiol (38 mg, 0.5 mmol), and CH$_2$Cl$_2$ (3 mL). The work up followed by purification afforded 132 mg (52%) of the title product 161 as an off-white solid. $^1$H NMR (400 MHz, DMSO-d$_6$): δ 8.24 (s, 1H), 7.96 (t, J=8.0 Hz, 1H), 7.85 and 7.82 (dd, J$_1$=11.2 Hz, J$_2$=2.0 Hz, 1H), 7.76 and 7.73 (dd, J$_1$=8.8 Hz, J$_2$=2.0 Hz, 1H), 7.51 (s, 1H), 7.02 (s, 1H), 5.44-5.39 (m, 1H), 4.47 (app. br, s, 1H), 4.21 (app. br. s, 1H), 4.15 (t, J=8.8 Hz, 2H), 4.14-4.06 (app. br. m, 2H), 3.92-3.84 (m, 1H), 3.25 (s, 3H), 3.07 (t, J=8.4 Hz, 2H), 2.06-2.00 (m, 2H), 1.74-1.68 (m, 2H), 1.35 (d, J=6.8 Hz, 6H); LCMS (ESI): m/z 511 (M+H)$^+$.

Example 86 (162)

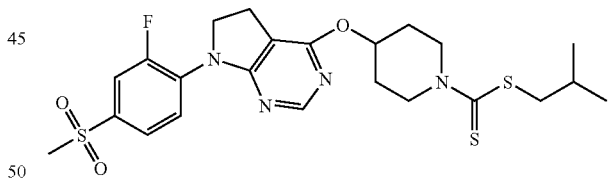

2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarbodithioate (162)

The procedure described for 148 (example 74, step 3) was employed using compound 160 (120 g, 0.19 mmol), Et$_3$N (76 µL, 0.56 mmol), 2-methyl-1-propanethiol (34 mg, 0.37 mL), and CH$_2$Cl$_2$ (5 mL). The work up followed by purification afforded 58 mg (60%) of the title product 162 as an off-white solid. $^1$H NMR (400 MHz, DMSO-d$_6$): δ 8.24 (s, 1H), 7.96 (t, J=8.0 Hz, 1H), 7.85 and 7.82 (dd, J$_1$=10.8 Hz, J$_2$=2.0 Hz, 1H), 7.75 and 7.73 (dd, J$_1$=8.4 Hz, J$_2$=2.0 Hz, 1H), 5.45-5.40 (m, 1H), 4.49 (br. s, 1H), 4.22 (br. s, 1H), 4.14 (app. br. s, 1H), 4.15 (t, J=8.0 Hz, 2H), 3.95 (br, s, 1H), 3.25 (s, 3H), 3.15 (d, J=7.2 Hz, 2H), 3.08 (t, J=9.2 Hz, 2H), 2.04 (br, s, 2H), 1.98-1.84 (m, 1H), 1.75 (m, 2H), 0.95 (d, J=6.8 Hz, 6H); LCMS (ESI): m/z 525 (M+H)⁺.

Example 87 (163)

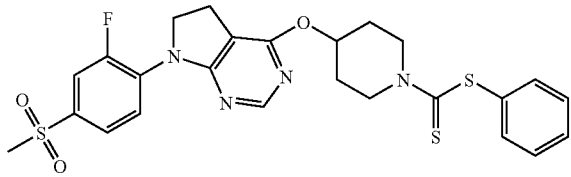

Phenyl 4-({7-[2-fluoro-4-(methylsulfonyl)phenyl]-6,7-dihydro-5H-pyrrolo[2,3-d]pyrimidin-4-yl}oxy)-1-piperidinecarbodithioate (163)

To a stirred solution of 11 (example 2, 175 mg, 0.355 mmol) was treated with 20% TFA in CH₂Cl₂ (5 mL) at RT for 2 h. The reaction mixture concentrated under reduced pressure to afford the crude product 126, which was dried and then dissolved in CH₂Cl₂. Et₃N (280 μL, 2.01 mmol) and phenyl chloridodithiocarbonate (167 mg, 0.89 mmol) were added sequentially and the reaction mixture was stirred at RT for 15 h. The work up followed by purification gave 106 mg (55%) of the title product 163 as a white solid. ¹H NMR (400 MHz, DMSO-d₆): δ 8.25 (s, 1H), 7.96 (t, J=8.0 Hz, 1H), 7.86 and 7.84 (dd, J₁=11.2 Hz, J₂=2.0 Hz, 1H), 7.76 and 7.74 (dd, J₁=8.4 Hz, J₂=1.6 Hz, 1H), 7.48-7.40 (m, 5H), 5.48-5.42 (m, 1H), 4.46 (app. br. s, 1H), 4.22 (br. s, 2H), 4.16 (t, J=8.4 Hz, 2H), 4.06 (br. s, 2H), 3.26 (s, 3H), 3.09 (t, J=8.8 Hz, 2H), 2.20-2.06 (br. s, 2H), 1.92-1.72 (br. s, 2H); LCMS (ESI): m/z 525 (M+H)⁺.

Example 88 (164)

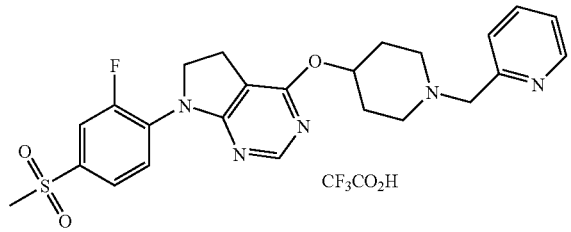

Step 1: 7-[2-Fluoro-4-(methylsulfonyl)phenyl]-4-(4-piperidinyloxy)-6,7-dihydro-5H-pyrrolo[2,3-d]pyrimidine trifluoroacetate (126)

1,1-Dimethylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate (11) (550 mg, 1.12 mmol) was dissolved in CH₂Cl₂ (15 mL) and of trifluoroacetic acid (2 mL). The resulting solution was stirred at room temperature for 1 h. All solvents were then removed under reduced pressure to give 560 mg of the desired compound 126 as a clear oil that was used without additional purification. ¹H NMR (400 MHz, DMSO-d₆): δ 8.67-8.34 (m, 2H), 8.21 (s, 1H), 7.95 (app. t, J=8.5 Hz, 1H), 7.85 (dd, J₁=10.9, J₂=2.2 Hz, 1H), 7.79 (dd, J₁=8.5, J₂=2.2 Hz, 1H), 5.41-5.30 (m, 1H), 4.18 (t, J=8.5 Hz, 2H), 3.38-3.33 (m, 5H), 3.19-3.0 (m, 4H), 2.19-2.06 (m, 2H) 1.93-1.76 (m, 2H); LCMS (ESI): m/z 393 (M+H)⁺.

Step 2: 7-[2-Fluoro-4-(methylsulfonyl)phenyl]-4-{[1-(2-pyridinylmethyl)-4-piperidinyl]oxy}-6,7-dihydro-5H-pyrrolo[2,3-d]pyrimidine trifluoroacetate (164)

Compound 126 (50 mg, 0.100 mmol) was combined with triethylamine (50 μL, 0.535 mmol) into 10 mL of methylene chloride. The mixture was stirred at room temperature for 15 minutes. 2-Pyridyl benzaldehyde (50 mg, 0.467 mmol) was then added to the solution followed by macroporous cyanoborohydride resin (100 mg, 47.6 mmol). The resulting mixture was stirred at room temperature for 18 h. The crude reaction was then filtered and concentrated to dryness, and purified via reverse phase chromatography using a gradient of 5-95% acetonitrile in water (0.1% trifluoroacetic acid additive) to give 21 mg (36%) of the desired compound 164 as a trifluoroacetate salt. ¹H NMR (400 MHz, CDCl₃): δ 8.71-8.53 (m, 1H), 8.23 (s, 1H), 8.10 (app. t, J=8.5 Hz, 1H), 7.95-7.87 (m, 2H), 7.57 (d, J=8.5 Hz, 2H), 7.53-7.35 (m, 2H), 5.52-5.36 (m, 1H), 4.48 (s, 2H), 4.22 (t, J=8.5 Hz 2H), 3.56-3.30 (m, 4H), 3.17 (t, J=8.5 Hz 2H), 3.05 (s, 3H), 2.41-2.29 (m, 2H), 2.29-2.18 (m, 2H); LCMS (ESI): m/z 568 (M+H)⁺.

Example 89 (165)

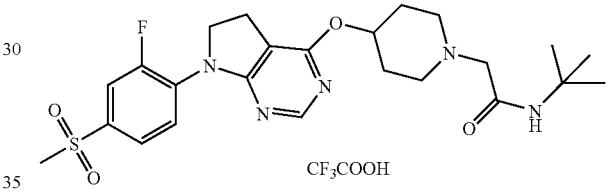

N-(1,1-Dimethylethyl)-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate (165)

The title compound was prepared in a manner similar to that described for example 88 (step 2) using compound 126 (50 mg, 0.098 mmol), macroporous carbonate resin (100 mg, 36.2 mmol), a catalytic amount of sodium iodide, and 2-chloro-N-(1-tert-butyl)acetamide. (50 mg, 0.336 mmol) to give 5 mg (8%) of trifluoroacetate salt after purification. ¹H NMR (400 MHz, CDCl₃): δ 8.26 (s, 1H), 7.96 (app. t, J=8.5 Hz, 1H), 7.84-7.66 (m, 2H), 5.61-5.37 (m, 1H), 4.29 (t, J=8.5 Hz, 2H), 3.74 (s, 2H), 3.61-3.33 (m, 4H), 3.19 (t, J=8.5 Hz, 2H), 3.00 (s, 3H), 2.55-2.12 (m, 4H), 1.85 (s, 9H); LCMS (ESI): m/z 505 (M+H)⁺.

Example 90 (166)

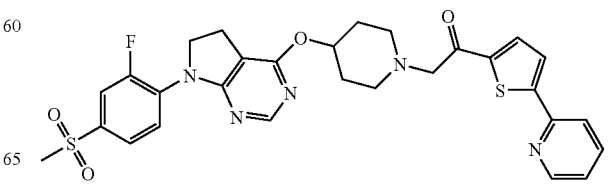

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-[5-(2-pyridinyl)-2-thienyl]ethanone trifluoroacetate (166)

The title compound was prepared in a manner similar to that described for example 88 (step 2) using compound 126 (50 mg, 0.098 mmol), macroporous carbonate (100 mg, 36.2 mmol), a catalytic amount of sodium iodide, and 2-bromo-1-[5-(2-pyridinyl)-2-thienyl]ethanone (50 mg, 0.177 mmol) to give 9 mg (13%) of trifluoroacetate salt of the title product 166 after purification. $^1$H NMR (400 MHz, CDCl$_3$): δ 8.68-8.58 (m, 2H), 8.27 (s, 1H), 8.05 (app. t, J=8.5 Hz, 1H), 7.92 (d, J=4.2 Hz, 1H), 7.82-7.65 (m, 3H), 7.60 (d, J=4.2 Hz, 1H), 5.35-5.11 (m, 1H), 4.26 (t, J=8.5 Hz, 2H), 3.73 (s, 2H), 3.61-3.33 (m, 2H), 3.19 (t, J=8.5 Hz, 2H), 3.01 (s, 3H), 2.96-2.81 (m, 2H), 2.67-2.44 (m, 2H), 2.19-2.06 (m, 2H), 2.04-1.85 (m, 2H); LCMS (ESI): m/z 594 (M+H)$^+$.

Example 91 (167)

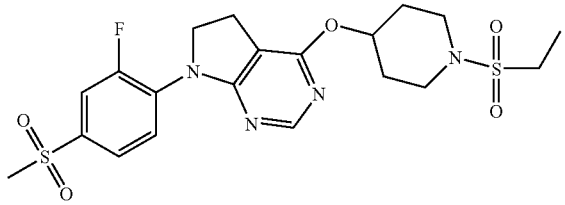

4-{[1-(Ethylsulfonyl)-4-piperidinyl]oxy}-7-[2-fluoro-4-(methylsulfonyl)phenyl]-6,7-dihydro-5H-pyrrolo[2,3-d]pyrimidine (167)

Compound 126 (70 mg, 0.138 mmol) was combined with diisopropylethylamine (1 mL, 7.72 mmol) into 5 mL of methylene chloride. The mixture was stirred at room temperature for 30 minutes. Ethanesulfonyl chloride (50 mg, 0.467 mmol) was then added to the solution. The resulting mixture was stirred at room temperature for 18 hours. The crude reaction was then concentrated to dryness, and purified via reverse phase chromatography using a gradient of 5-90% acetonitrile (contains 0.5% TFA) in water to give 46 mg (70%) of the desired compound 167 as a tan solid. $^1$H NMR (400 MHz, CDCl$_3$): δ 8.27 (s, 1H), 7.86 (app. t, J=8.5 Hz, 1H), 7.78-7.68 (m, 2H), 5.42-5.25 (m, 1H), 4.26 (t, J=8.5 Hz 2H), 3.69-3.52 (m, 2H), 3.35-3.23 (m, 2H), 3.19 (t, J=8.5 Hz, 2H), 3.06 (s, 3H), 2.99 (q, J=7.8 Hz, 2H), 2.20-2.05 (m, 2H), 1.98-1.81 (m, 2H), 1.38 (t, J=8.5 Hz 3H); LCMS (ESI): m/z 485 (M+H)$^+$.

Example 92 (168)

7-[2-Fluoro-4-(methylsulfonyl)phenyl]-4-({1-[(1-methylethyl)sulfonyl]-4-piperidinyl}oxy)-6,7-dihydro-5H-pyrrolo[2,3-d]pyrimidine (168)

The title compound was prepared in a manner similar to that described for example 91 using compound 126 (70 mg, 0.138 mmol), diisopropylethylamine (1 mL, 7.72 mmol), and 2-propanesulfonyl chloride (70 mg, 0.492 mmol) to give 37 mg (54%) of the title product 168 after purification. $^1$H NMR (400 MHz, CDCl$_3$): δ 8.31 (s, 1H), 7.91 (app. t, J=8.5 Hz, 1H), 7.87-7.60 (m, 2H), 5.49-5.20 (m, 1H), 4.31 (t, J=8.5 Hz, 2H), 3.80-3.52 (m, 2H), 3.42-3.26 (m, 2H), 3.24-3.12 (m, 4H), 2.23-1.99 (m, 2H), 1.98-1.81 (m, 2H), 1.97-1.75 (m, 2H), 1.32 (d, J=6.8 Hz, 6H); LCMS (ESI): m/z 499 (M+H)$^+$.

Example 93 (169)

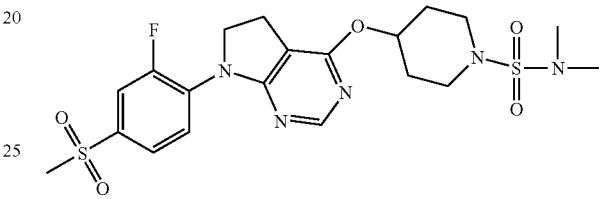

4-({7-[2-Fluoro-4-(methylsulfonyl)phenyl]-6,7-dihydro-5H-pyrrolo[2,3-d]pyrimidin-4-yl}oxy)-N,N-dimethyl-1-piperidinesulfonamide (169)

The title compound was prepared in a manner similar to that described for example 91 using compound 126 (70 mg, 0.138 mmol), diisopropylethylamine (1 mL, 7.72 mmol), and dimethylsulfamoyl chloride (70 mg, 0.489 mmol) to give 10 mg (14%) of the title product 169 after purification. $^1$H NMR (400 MHz, CDCl$_3$): δ 8.28 (s, 1H), 8.00 (app. t, J=8.5 Hz, 1H), 7.76-7.67 (m, 2H), 5.38-5.29 (m, 1H), 4.19 (t, J=8.5 Hz, 2H), 3.57-3.48 (m, 2H), 3.29-3.20 (m, 2H), 3.13 (t, J=8.5 Hz, 2H), 3.04 (s, 3H), 2.84 (s, 6H), 2.13-2.02 (m, 2H), 1.96-1.85 (m, 2H); LCMS (ESI): m/z 500 (M+H)$^+$.

Example 94 (170)

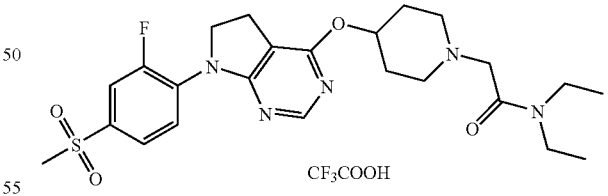

N,N-Diethyl-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate (170)

The title compound was prepared in a manner similar to that described for example 88 (step 2) using compound 126 (75 mg, 0.148 mmol), diisopropylethylamine (92 µL, 0.518 mmol), a catalytic amount of sodium iodide, and 2-chloro-N,N-diethylacetamide (24 mg, 0.163 mmol) to give 23 mg (37%) of the product 170 as a trifluoroacetate salt after purification. ¹H NMR (400 MHz, CDCl₃): δ 8.28 (s, 1H), 7.96 (app. t, J=8.5 Hz, 1H), 7.76-7.73 (m, 2H), 5.58-5.39 (m, 1H), 4.22 (t, J=8.5 Hz, 2H), 4.08 (s, 2H), 3.74-3.58 (m, 2H), 3.56-3.43 (m, 2H), 3.41-3.16 (m, 6H), 3.06 (s, 3H), 2.43-2.30 (m, 2H), 2.29-2.17 (m, 2H), 1.18-1.12 (m, 6H); LCMS (ESI): m/z 506 (M+H)⁺.

Example 95 (171)

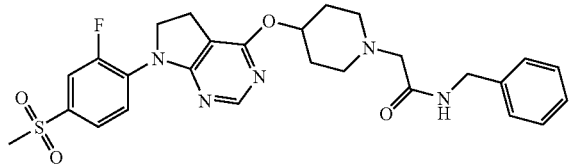

2-[4-({7-[2-Fluoro-4-(methylsulfonyl)phenyl]-6,7-dihydro-5H-pyrrolo[2,3-d]pyrimidin-4-yl}oxy)-1-piperidinyl]-N-(phenyl methyl)acetamide (171)

The title compound was prepared in a manner similar to that described for example 88 (step 2) using compound 126 (75 mg, 0.148 mmol), diisopropylethylamine (92 μL, 0.518 mmol), a catalytic amount of sodium iodide, and 2-chloro-N-(phenylmethyl)acetamide (27 mg, 0.148 mmol) to give 18 mg (28%) of the product 171 after purification. ¹H NMR (400 MHz, CD₃OD): δ 8.15 (s, 1H), 7.97 (app. t, J=8.5 Hz, 1H), 7.80-7.75 (m, 2H), 7.33-7.22 (m, 5H), 5.21-5.17 (m, 1H), 4.42 (s, 2H), 4.17 (t, J=8.5 Hz, 2H), 3.30 (s, 2H), 3.15-3.09 (m, 5H), 2.80-2.74 (m, 2H), 2.71-2.60 (m, 2H), 2.10-2.02 (m, 2H), 1.89-1.80 (m, 2H); LCMS (ESI): m/z 540 (M+H)⁺.

Example 96 (172)

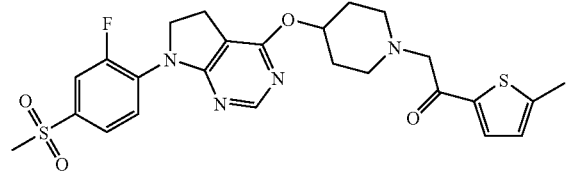

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-methyl-2-thienyl)ethanone (172)

The title compound was prepared in a manner similar to that described for example 88 (step 2) using compound 126 (100 mg, 0.197 mmol), diisopropylethylamine (70 μL, 0.395 mmol), and 2-chloro-1-(5-methyl-2-thienyl)ethanone (34 mg, 0.197 mmol) to give 21 mg (17%) of the product 172 after purification. ¹H NMR (400 MHz, CDCl₃): δ 8.26 (s, 1H), 8.02 (app. t, J=8.5 Hz, 1H), 7.76-7.68 (m, 3H), 6.79 (d, J=3.4 Hz, 1H), 5.22-5.10 (m, 1H), 4.19 (t, J=8.5 Hz, 2H), 3.63 (s, 2H), 3.14-2.87 (m, 5H), 2.86-2.80 (m, 2H), 2.71-2.60 (m, 5H), 2.16-2.01 (m, 2H), 1.93-1.80 (m, 2H); LCMS (ESI): m/z 531 (M+H)⁺.

Example 97 (173)

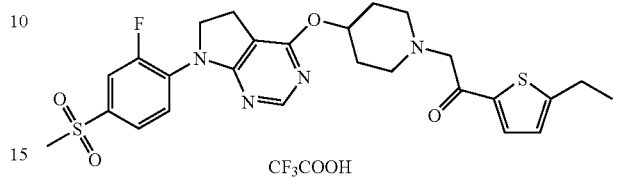

1-(5-Ethyl-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate (173)

The title compound was prepared in a manner similar to that described in example 88 (step 2) using compound 126 (100 mg, 0.197 mmol), diisopropylethylamine (70 uL, 0.395 mmol), and 2-chloro-1-(5-ethyl-2-thienyl)ethanone (37 mg, 0.197 mmol) in 5 mL acetonitrile to give 13 mg (10%) of the product 173 as a trifluoroacetate salt after purification. ¹H NMR (400 MHz, CDCl₃): δ 8.26 (s, 1H), 7.99 (app. t, J=8.5 Hz, 1H), 7.75-7.68 (m, 2H), 7.63 (d, J=3.6 Hz, 1H), 6.90 (d, J=3.6 Hz, 1H), 5.51-5.45 (m, 1H), 4.57 (s, 2H), 4.26 (t, J=8.5 Hz, 2H), 3.82-3.69 (m, 2H), 3.58-3.42 (m, 2H), 3.28-3.09 (m, 2H), 3.06 (s, 3H), 2.91 (q, J=7.6 Hz, 2H), 2.46-2.38 (m, 2H), 2.30-2.18 (m, 2H), 1.34 (t, J=7.3 Hz, 3H); LCMS (ESI): m/z 545 (M+H)⁺.

Example 98 (174)

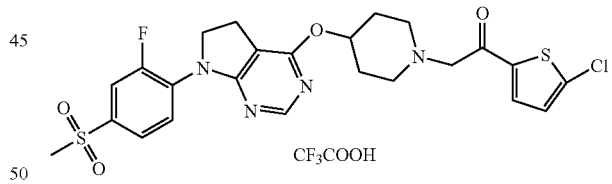

1-(5-Chloro-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate (175)

The title compound was prepared in a manner similar to that described for example 88 (step 2) using compound 126 (100 mg, 0.197 mmol), diisopropylethylamine (70 μL, 0.395 mmol), and 2-bromo-1-(5-chloro-2-thienyl)ethanone (47 mg, 0.197 mmol) in 5 mL acetonitrile to give 2 mg (1%) of the product 174 as a trifluoroacetate salt after purification. ¹H NMR (400 MHz, CDCl₃): δ 8.27 (s, 1H), 8.00 (app. t, J=8.5 Hz, 1H), 7.98-7.71 (m, 2H), 7.60 (d, J=3.4 Hz, 1H), 6.79 (d, J=3.4 Hz, 1H), 5.53-5.40 (m, 1H), 4.59 (s, 2H), 4.24 (t, J=8.5

Hz, 2H), 3.89-3.71 (m, 2H), 3.58-3.41 (m, 2H), 3.28-3.19 (m, 2H), 3.06 (s, 3H), 2.43-2.21 (m, 4H); LCMS (ESI): m/z 552 (M+H)⁺.

Example 99 (175)

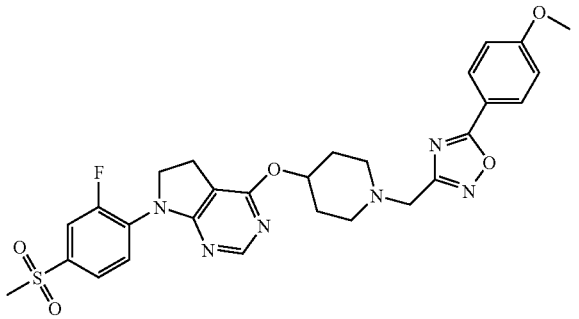

7-[2-Fluoro-4-(methylsulfonyl)phenyl]-4-{[1-({5-[4-(methyloxy)phenyl]-1,2,4-oxadiazol-3-yl}methyl)-4-piperidinyl]oxy}-6,7-dihydro-5H-pyrrolo[2,3-d]pyrimidine (175)

The title compound was prepared in a manner similar to that described for example 88 (step 2) using compound 126 (100 mg, 0.197 mmol), diisopropylethylamine (70 uL, 0.395 mmol), and 3-(chloromethyl)-5-[4-(methyloxy)phenyl]-1,2,4-oxadiazole (44 mg, 0.20 mmol) in 5 mL acetonitrile to give 38 mg (28%) of the title compound 175 after purification via flash column chromatography using 0-1.5% methanol in methylene chloride. ¹H NMR (400 MHz, CDCl₃): δ 8.26 (s, 1H), 8.17-7.96 (m, 3H), 7.78-7.60 (m, 2H), 7.00 (d, J=9.0 Hz, 2H), 5.27-5.02 (m, 1H), 4.19 (t, J=8.5 Hz, 2H), 3.87 (s, 3H), 3.76 (s, 2H), 3.16-2.98 (m, 5H), 2.97-2.80 (m, 2H), 2.63-2.46 (m, 2H), 2.14-2.00 (m, 2H), 1.97-1.82 (m, 2H); LCMS (ESI): m/z 580 (M+H)⁺.

Example 100 (176)

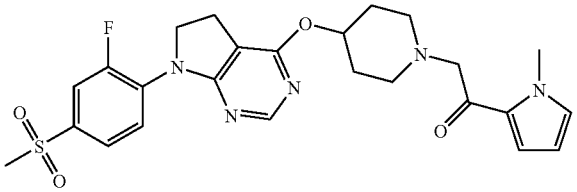

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(1-methyl-1H-pyrrol-2-yl)ethanone (176)

The title compound was prepared in a manner similar to that described in example 88 (step 2) using compound 126 (100 mg, 0.197 mmol), diisopropylethylamine (87 μL, 0.492 mmol), and 2-chloro-1-(1-methyl-1H-pyrrol-2-yl)ethanone (31 mg, 0.197 mmol) in mL acetonitrile to give 62 mg (61%) of the title compound 176 after purification via flash column chromatography using 1% methanol in methylene chloride. ¹H NMR (400 MHz, CDCl₃): δ 8.26 (s, 1H), 8.05 (app. t, J=8.5 Hz, 1H), 7.77-7.62 (m, 2H), 7.05 (dd, J=1.3 Hz; J=4.0 Hz, 1H), 6.80 (m, 1H), 6.11 (dd, J=2.4 Hz; J=4.0 Hz, 1H), 5.27-5.12 (m, 1H), 4.19 (t, J=8.5 Hz, 2H), 3.94 (s, 3H), 3.64 (s, 2H), 3.16-2.98 (m, 5H), 2.94-2.78 (m, 2H), 2.56-2.41 (m, 2H), 2.15-2.03 (m, 2H), 2.01-1.79 (m, 2H); LCMS (ESI): m/z 514 (M+H)⁺.

Example 101 (177)

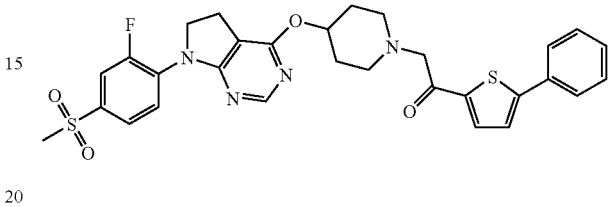

2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-phenyl-2-thienyl)ethanone (177)

The title compound was prepared in a manner similar to that described for example 88 using compound 126 (100 mg, 0.197 mmol), diisopropylethylamine (87 μL, 0.492 mmol), and 2-chloro-1-(5-phenyl-2-thienyl)ethanone (55 mg, 0.197 mmol) in 5 mL acetonitrile to give 62 mg (61%) of the title compound 177 after purification via flash column chromatography using 0-1.5% methanol in methylene chloride. ¹H NMR (400 MHz, CDCl₃): δ 8.27 (s, 1H), 8.06 (app. t, J=8.5 Hz, 1H), 7.92 (d, J=4.2 Hz, 1H), 7.74-7.62 (m, 3H), 7.49-7.28 (m, 5H), 5.30-5.15 (m, 1H), 4.20 (t, J=8.5 Hz, 2H), 3.70 (s, 2H), 3.15 (t, J=8.5 Hz, 2H), 3.04 (s, 3H), 3.00-2.88 (m, 2H), 2.67-2.51 (m, 2H), 2.20-2.06 (m, 2H), 2.02-1.90 (m, 2H); LCMS (ESI): m/z 593 (M+H)⁺.

Example 102 (178)

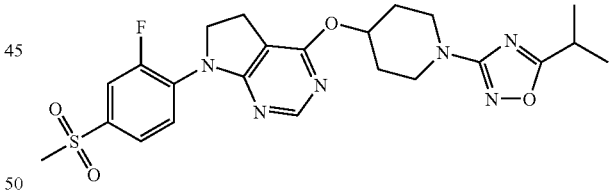

Step 1: 4-({7-[2-Fluoro-4-(methylsulfonyl)phenyl]-6,7-dihydro-5H-pyrrolo[2,3-d]pyrimidin-4-yl}oxy)-N-hydroxy-1-piperidinecarboximidamide (178)

Compound 126 (obtained from a different batch, 500 mg, 0.99 mmol) was combined with cyanogen bromide (560 μL, 1.68 mmol), and diisopropylethyl amine (526 μL, 2.96 mmol) in 10 mL of dichloromethane at 0° C. The reaction was allowed to warm to room temperature while stirring for 18 h. The crude reaction mixture was then purified via flash column chromatography with 1% methanol in dichloromethane to give 142 mg (34%) of 4-({7-[2-fluoro-4-(methylsulfonyl)phenyl]-6,7-dihydro-5H-pyrrolo[2,3-d]pyrimidin-4-yl}oxy)-1-piperidinecarbonitrile (178A) as a white solid. ¹H NMR (400 MHz, CDCl₃): δ 8.27 (s, 1H), 8.03 (app. t, J=8.5

Hz, 1H), 7.76-7.62 (m, 2H), 5.39-5.25 (m, 1H), 4.22 (t, J=8.5 Hz, 2H), 3.57-3.43 (m, 2H), 3.29-3.19 (m, 2H), 3.13 (t, J=8.4 Hz, 2H), 3.05 (s, 3H), 2.16-2.03 (m, 2H), 1.98-1.83 (m, 2H); LCMS (ESI): m/z 418 (M+H)+. The compound 178A (130 mg, 0.310 mmol) was combined with hydroxylamine hydrochloride (64 mg, 0.930 mmol), and sodium carbonate (131 mg, 1.24 mmol) in 20 mL of ethanol and heated to reflux for 2 h. The solids were removed via filtration and the material 178 was used without purification (143 mg); LCMS (ESI): m/z 451 (M+H)+.

Step 2: 7-[2-Fluoro-4-(methylsulfonyl)phenyl]-4-({1-[5-(1-methylethyl)-1,2,4-oxadiazol-3-yl]-4-piperidinyl}oxy)-6,7-dihydro-5H-pyrrolo[2,3-d]pyrimidine (179)

2-Methylpropanoic acid (19 µL, 0.310 mmol) was combined with HATU [O-(7-azabenzotriazol-1-yl)-1,1,3,3-tetramethyluronium hexafluorophosphate, 129 mg, 0.340 mmol] and diisopropylethylamine (129 mg, 0.340 mmol) into N,N-dimethyl formamide (10 mL) and the solution was stirred at room temperature for 15 minutes. Compound 178 (140 mg, 0.310 mmol) was then added and the mixture was stirred at room temperature for 30 minutes. The reaction was then heated to 100° C. for 1 hour. The reaction was then diluted with water and extracted three times with diethylether. The combined organic extracts were washed three times with water and the organic layer was dried over anhydrous magnesium sulfate, filtered and concentrated to dryness under reduced pressure. The crude reaction was then purified on via reverse phase chromatography using a gradient of 50-100% acetonitrile in water (0.1% trifluoroacetic acid additive) to give 15 mg (9%) of the title compound 179 as a tan solid. ¹H NMR (400 MHz, CDCl₃): δ 8.28 (s, 1H), 7.98 (app. t, J=8.5 Hz, 1H), 7.82-7.67 (m, 2H), 5.45-5.34 (m, 1H), 4.21 (t, J=8.5 Hz, 2H), 3.87-3.68 (m, 2H), 3.46-3.27 (m, 2H), 3.20-2.97 (m, 5H), 2.15-2.02 (m, 2H), 1.94-1.79 (m, 2H) 1.2 (d, J=7.1 Hz, 6H); LCMS (ESI): m/z 503 (M+H)+.

Example 103 (182)

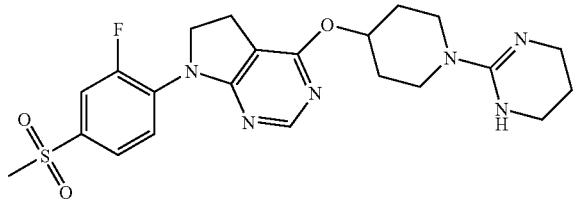

Step 1: 1-(2-Pyrimidinyl)-4-piperidinol (180)

4-Hydroxypiperidine (1.5 g, 14.7 mmol) was combined with 2-chloropyrimidine (1.5 g, 13.4 mmol) and diisopropylethylamine (6 mL, 33.5 mmol) into 50 mL acetonitrile. The mixture was heated at 80° C. for 18 hours. The reaction mixture was then concentrated to dryness and the crude residue was then purified on via flash column chromatography using a gradient of 0-60% ethylacetate/hexane to give 2.1 g (81%) of the desired compound 180 as a white solid. ¹H NMR (400 MHz, CDCl₃): δ 8.28 (d, J=4.6 Hz 2H), 6.49 (t, J=4.8 Hz, 1H), 4.49-4.33 (m, 2H), 4.01-3.88 (m, 1H), 3.37-3.21 (m, 2H), 2.02-1.90 (m, 2H), 1.60-1.45 (m, 2H); LCMS (ESI): m/z 180 (M+H)+.

Step 2: 1-(1,4,5,6-Tetrahydro-2-pyrimidinyl)-4-piperidinol (181)

Compound 180 (300 mg, 1.67 mmol) was combined with 10% palladium on carbon (Degussa type) (100 mg, cat.) and concentrated hydrochloric acid (500 µL) into 10 mL of acetic acid. The mixture was subjected to hydrogenation for 18 h at room temperature. The reaction mixture was then filtered and the solvent was removed under reduced pressure to give 304 mg (84%) of the desired compound 181. ¹H NMR (400 MHz, DMSO-d₆): δ 8.25 (m, 2H), 4.03-3.41 (m, 3H), 2.95-2.86 (m, 4H), 2.09-1.55 (m, 6H), 1.55-1.18 (m, 2H).

Step 3: 7-[2-Fluoro-4-(methylsulfonyl)phenyl]-4-{[1-(1,4,5,6-tetrahydro-2-pyrimidinyl)-4-piperidinyl]oxy}-6,7-dihydro-5H-pyrrolo[2,3-d]pyrimidine (182)

Compound 181 (300 mg, 1.38 mmol) was dissolved in 5 mL anhydrous DMF and treated with sodium hydride (294 mg, 7.3 mmol). The mixture was stirred at room temperature for 15 minutes. 4-Chloro-7-[2-fluoro-4-(methylsulfonyl)phenyl]-6,7-dihydro-5H-pyrrolo[2,3-d]pyrimidine 8 in 5 mL DMF was then added dropwise to the stirring solution. The mixture was then stirred at room temperature for 18 h. The reaction was then quenched with water. The crude reaction was then concentrated to dryness under reduced pressure and the crude residue was then purified via reverse phase chromatography using a gradient of 5-95% acetonitrile in water (0.5% trifluoroacetic acid additive) on C18 to give 56 mg (6%) of the title compound 182 as a white solid. ¹H NMR (400 MHz, CD₃OD): δ 8.46 (s, 1H), 8.17 (s, 1H), 7.95 (app. t, J=8.5 Hz, 1H), 7.88-7.66 (m, 2H), 5.54-5.37 (m, 1H), 4.20 (t, J=8.5 Hz, 2H), 3.75-3.57 (m, 2H), 3.49-3.33 (m, 6H), 3.19-3.07 (m, 5H), 2.21-2.06 (m, 2H), 2.01-1.76 (m, 4H); LCMS (ESI): m/z 475 (M+H)+.

Example 104 (184)

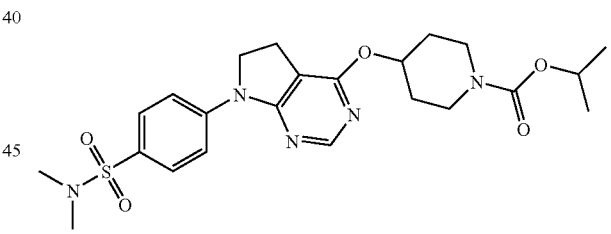

Step 1: 4-(4-Chloro-5,6-dihydro-7H-pyrrolo[2,3-d]pyrimidin-7-yl)-N,N-dimethylbenzenesulfonamide (183)

Following the procedure described for 141 (example 71, step 1), a round bottom flask was charged with N1,N1-dimethylsulfanilamide (0.19 g, 0.95 mmol) and cooled to −15° C. Trifluoroacetic acid (0.9 mL, 11.7 mmol) was added and the solution was stirred for 10 minutes at −15° C. Na(OAc)₃BH (0.32 g, 1.51 mmol) was added to the reaction mixture and stirred for 10 minutes. A solution of aldehyde 209 (0.2 g, 1.05 mmol) in CH₂Cl₂ (1.2 mL) was added dropwise and the reaction mixture was stirred at −15° C. for 30 minutes, then stirred at RT for 15 h. Mixture was concentrated under reduced pressure, diluted with 10% NaHCO₃, extracted with CH₂Cl₂ (3×10 mL), dried over MgSO₄, filtered, and concentrated under reduced pressure to afford the crude material, which was purified by SiO₂ flash column chromatography to give 0.17 g (47%) of the title compound 183 as a white solid. ¹H NMR (400 MHz, CDCl₃): δ 8.51 (s, 1H), 8.00 (d, J=9.28 Hz, 2H), 7.83 (d, J=9.10 Hz, 2H), 4.11-4.36 (m, 2H), 3.19-3.37 (m, 2H), 2.73 (s, 1H); LCMS (APCI): m/z 339 (M+H)⁺.

Step 2: 1-Methylethyl 4-[(7-{4-[(dimethylamino)sulfonyl]phenyl}-6,7-dihydro-5H-pyrrolo[2,3-d]pyrimidin-4-yl)oxy]-1-piperidinecarboxylate (184)

Following the general procedure described for example 1 (step 10), a solution of 9 (0.15 g, 0.8 mmol) and THF (1.5 mL) was added to a round bottom flask containing NaH (0.027 g, 95%, 1.12 mmol) and the resulting solution was heated to 50° C. and stirred for 35 minutes. A solution of 183 (0.109 g, 0.32 mmol) and THF (1.5 mL) was added and resulting mixture was refluxed for 16 h. The reaction mixture was cooled to RT, poured into H₂O (10 mL) and then extracted with ethyl acetate. The combined organic layer was dried over MgSO₄, filtered, and concentrated under reduced pressure. The crude product was purified by recrystallization from methanol to give 0.026 g (17%) of the title product 184 as a white solid. ¹H NMR (400 MHz, CDCl₃): δ 8.38 (s, 1H), 7.96 (d, J=9.0 Hz, 2H), 7.77 (d, J=8.8 Hz, 2H), 5.30-5.42 (m, 1H), 4.86-4.99 (m, 1H), 4.14 (t, J=8.8 Hz, 2H), 3.75-3.91 (m, 2H), 3.27-3.41 (m, 2H), 3.12 (t, J=8.8 Hz, 2H), 2.70 (s, 6H), 1.92-2.09 (m, 2H), 1.66-1.83 (m, 2H), 1.26 (d, J=6.24 Hz, 6H); LCMS (ESI): m/z 491 (M+H)⁺.

Example 105 (186)

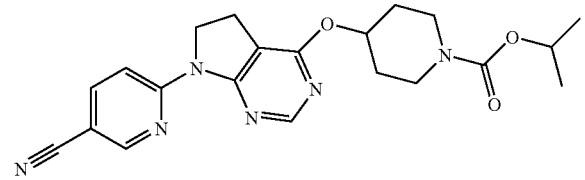

Step 1: 6-(4-Chloro-5,6-dihydro-7H-pyrrolo[2,3-d]pyrimidin-7-yl)-3-pyridinecarbonitrile (185)

A round bottom flask was charged with 2-amino-5-cyanopyridine (0.26 g, 2.18 mmol) and cooled to −15° C. Acetic acid (1.52 mL, 26.8 mmol) was added and the solution was stirred for 10 minutes at −15° C. Na(OAc)₃BH (0.742 g, 3.5 mmol) was added to the reaction mixture and stirred for 5 minutes. A solution of the aldehyde 209 (0.5 g, 2.62 mmol) in CH₂Cl₂ (1.6 mL) was added dropwise and the reaction mixture was stirred at 15° C. for 30 minutes, then stirred at RT for 15 h. Mixture was diluted with H₂O, extracted with CH₂Cl₂, dried over MgSO₄, filtered, and concentrated under reduced pressure to afford the crude material, which was purified by SiO₂ flash column chromatography to give 0.16 g of the title compound 185 and 6-{[2-(4,6-dichloro-5-pyrimidinyl)ethyl]amino}-3-pyridinecarbonitrile as an inseparable mixture. ¹H NMR (400 MHz, CD₃OD): δ 8.66 (s, 1H), 8.19-8.27 (m, 1H), 7.52-7.61 (m, 1H), 6.42-6.52 (m, 1H), 3.83 (t, J=6.87 Hz, 3H), 3.19 (t, J=6.87 Hz, 3H); LCMS (APCI): m/z 258 (M+H)⁺.

Step 2: 1-Methylethyl 4-{[7-(5-cyano-2-pyridinyl)-6,7-dihydro-5H-pyrrolo[2,3-d]pyrimidin-4-yl]oxy}-1-piperidinecarboxylate (186)

To a stirred solution of 9 (0.252 g, 1.35 mmol) and THF (2 mL) was added NaH (0.045 g, 95%, 1.89 mmol) and heated to 50° C. for 30 minutes. A solution of 185 (0.139 g, 0.54 mmol) in THF (3 mL) was added dropwise and the resulting mixture was refluxed for 16 h. The reaction mixture was cooled to RT, poured into H₂O and then extracted with ethyl acetate. The combined organic layer was dried over MgSO₄, filtered, and concentrated under reduced pressure. The crude product was purified by recrystallization from methanol to give 0.012 g (5%) of the title product 186 as a white solid. ¹H NMR (400 MHz, CDCl₃): δ 8.85-8.90 (m, 1H), 8.57-8.61 (m, 1H), 8.42 (s, 1H), 7.82-7.87 (m, 1H), 5.33-5.42 (m, 1H), 4.90-4.99 (m, 1H), 4.35 (t, J=8.61 Hz, 2H), 3.74-3.89 (m, 2H), 3.29-3.42 (m, 2H), 3.07 (t, J=8.06 Hz, 2H), 1.94-2.08 (m, 2H), 1.70-1.83 (m, 2H), 1.27 (d, J=6.23 Hz, 6H); LCMS (ESI): m/z 409 (M+H)⁺.

Example 106 (188)

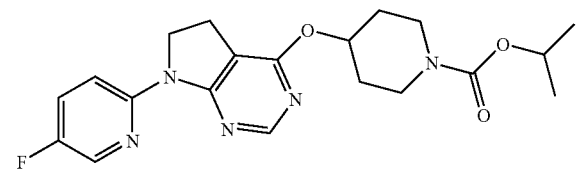

Step 1: N-[2-(4,6-Dichloro-5-pyrimidinyl)ethyl]-5-fluoro-2-pyridinamine (187)

A round bottom flask was charged with 2-amino-5-fluoropyridine (0.323 g, 2.88 mmol) and cooled to −15° C. Trifluoroacetic acid (2.5 mL, 32.2 mmol) was added and the solution was stirred for 10 minutes at −15° C. Na(OAc)₃BH (0.89 g, 4.2 mmol) was added to the reaction mixture and stirred for 10 minutes. A solution of 209 (0.5 g, 2.62 mmol) in CH₂Cl₂ (2.0 mL) was added dropwise and the reaction mixture was stirred at −15° C. for 30 minutes, then stirred at RT for 15 h. Mixture was concentrated under reduced pressure, diluted with 10% NaHCO₃, extracted with CH₂Cl₂ (3×10 mL), dried over MgSO₄, filtered, and concentrated under reduced pressure to afford the crude material, which was purified by SiO₂ flash column chromatography to give 0.17 g of the title compound 187 and 4-chloro-7-(5-fluoro-2-pyridinyl)-6,7-dihydro-5H-pyrrolo[2,3-d]pyrimidine as an inseparable mixture. ¹H NMR (400 MHz, CDCl₃): δ 8.62 (s, 1H), 7.92 (d, J=2.68 Hz, 1H), 7.14-7.23 (m, 1H), 6.37 (dd, J₁=9.10 Hz, J₂=3.39 Hz, 1H), 4.60 (br. s, 1H), 6.67 (q, J=6.54 Hz, 2H), 3.24 (t, J=6.87 Hz, 2H); LCMS (APCI): m/z 287 (M+H)⁺.

Step 2: 1-Methylethyl 4-{[7-(5-fluoro-2-pyridinyl)-6,7-dihydro-5H-pyrrolo[2,3-d]pyrimidin-4-yl]oxy}-1-piperidinecarboxylate (188)

The procedure described for 10 was employed using 9 (0.166 g, 0.88 mmol), NaH (0.037 g, 1.54 mmol), and compound 187 (0.11 g, 0.44 mmol). Aqueous work-up followed by recrystallization from methanol gave 0.027 g (15%) of the title compound 188 as a white solid. ¹H NMR (400 MHz, CDCl₃): δ 8.66 (dd, J₁=9.34 Hz, J₂=4.03 Hz, 1H), 8.35 (s, 1H), 8.17 (d, J=3.11 Hz, 1H), 7.40-7.47 (m, 1H), 5.30-5.41 (m, 1H), 4.89-5.00 (m, 1H), 4.30 (t, J=8.61 Hz, 2H), 3.73-3.89 (m, 2H), 3.30-3.42 (m, 2H), 3.04 (t, J=8.61 Hz, 2H), 1.93-2.07 (m, 2H), 1.67-1.84 (m, 2H), 1.26 (d, J=6.23 Hz, 6H); LCMS (ESI): m/z 402 (M+H)+.

Example 107 (189)

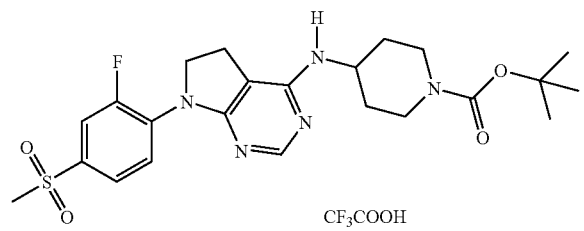

CF₃COOH 1,1-Dimethylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate (189)

To a solution of 8 (50 mg, 0.153 mmol) in DMF (1.5 mL) was added 1,1-dimethylethyl 4-amino-1-piperidinecarboxylate (62 mg, 0.306 mmol) and K₂CO₃ (42 mg, 0.306 mmol). The reaction mixture was sealed and heated in a microwave for 15 min at 150° C. After an LCMS trace showed mostly 8, the reaction mixture was heated in a microwave an additional 20 min at 200° C. Another LCMS trace still showed the presence of 8, so the reaction mixture was heated again in a microwave for 20 min at 175° C. The reaction mixture was then diluted with water (2 mL) and extracted with EtOAc (3×5 mL). The combined organic layer was dried over MgSO₄, filtered, and concentrated under reduced pressure. The crude product was purified twice by preparative HPLC (water/acetonitrile eluent) to give 4 mg (4%) of the title product 189 as a light tan solid. LCMS (ESI): m/z 492 (M+H)+.

Example 108 (191)

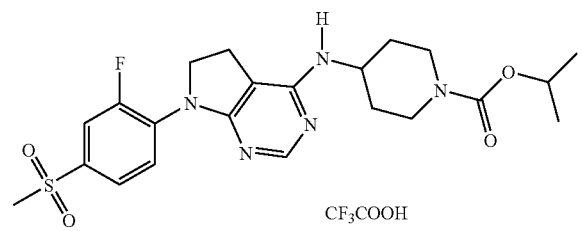

CF₃COOH

Step 1: 1-Methylethyl 4-({[(1,1-dimethylethyl)oxy]carbonyl}amino)-1-piperidinecarboxylate (190)

To a stirred solution of 1,1-dimethylethyl 4-piperidinylcarbamate (512 mg, 2.56 mmol) and Et₃N (0.714 mL, 5.12 mmol) in CH₂Cl₂ (25 mL) was added isopropylchloroformate (1.0 M in toluene, 2.8 mL, 2.81 mmol) dropwise via an addition funnel at RT. The reaction mixture was stirred at RT for 17 hours, then washed with water (1×15 mL), dried over MgSO₄, filtered, and concentrated under reduced pressure to give 585 mg (80%) of the title product 190 as a colorless oil. ¹H NMR (400 MHz, CDCl₃): δ 4.85 (septuplet, J=6.4 Hz, 1H), 4.63-4.48 (m, 1H), 4.13-3.89 (m, 2H), 3.55 (br s, 1H), 2.82 (t, J=11.7 Hz, 2H), 1.88-1.85 (m, 2H), 1.39 (s, 9H), 1.29-1.22 (m, 2H), 1.19 (d, J=6.1 Hz, 6H).

Step 2: 1-Methylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate (191)

To a solution of 8 (50 mg, 0.153 mmol) in DMF (1.5 mL) was added 190 (87 mg, 0.305 mmol) and K₂CO₃ (42 mg, 0.305 mmol). The reaction mixture was sealed and heated in a microwave for 20 min at 200° C. After an LCMS trace showed mostly 8, the reaction mixture was heated in a microwave an additional 60 min at 220° C. The reaction mixture was then diluted with water (2 mL) and extracted with EtOAc (3×5 mL). The combined organic layer was dried over MgSO₄, filtered, and concentrated under reduced pressure. The crude product was purified by preparative HPLC (water/acetonitrile eluent) to give 11 mg (12%) of the title product 191 as a yellow solid. ¹H NMR (400 MHz, CDCl₃): δ 8.09 (s, 1H), 7.81-7.77 (m, 2H), 7.72-7.69 (m, 1H), 4.91 (septuplet, J=6.4 Hz, 1H), 4.29 (t, J=9.0 Hz, 2H), 4.23-4.12 (m, 2H), 3.79-3.68 (m, 1H), 3.43-3.38 (m, 2H), 3.09 (s, 3H), 2.96-2.86 (m, 2H), 1.97-1.93 (m, 2H), 1.77-1.67 (m, 2H), 1.25 (d, J=6.4 Hz, 6H); LCMS (ESI): m/z 478 (M+H)+.

Example 109 (193)

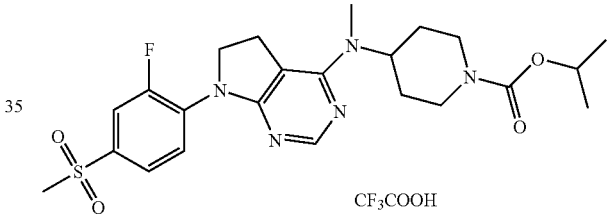

CF₃COOH

Step 1: 1-Methylethyl 4-[{[(1,1-dimethylethyl)oxy]carbonyl}(methyl)amino]-1-piperidinecarboxylate (192)

To a stirred solution of 1,1-dimethylethyl methyl(4-piperidinyl)carbamate (500 mg, 2.33 mmol) and Et₃N (0.65 mL, 4.66 mmol) in CH₂Cl₂ (23 mL) was added isopropylchloroformate (1.0 M in toluene, 2.6 mL, 2.57 mmol) dropwise via an addition funnel at RT. The reaction mixture was stirred at RT for 17 hours, then washed with water (1×15 mL), dried over MgSO₄, filtered, and concentrated under reduced pressure to give 608 mg (87%) of the title product 192 as a colorless oil. ¹H NMR (400 MHz, CDCl₃): δ 4.88 (septuplet, J=6.4 Hz, 1H), 4.28-4.16 (m, 3H), 2.77-2.71 (m, 2H), 2.68 (s, 3H), 1.62-1.57 (m, 2H), 1.55-1.50 (m, 2H), 1.44 (s, 9H), 1.21 (d, J=6.4 Hz, 6H).

Step 2: 1-Methylethyl 4-[{7-[2-fluoro-4-(methylsulfonyl)phenyl]-6,7-dihydro-5H-pyrrolo[2,3-d]pyrimidin-4-yl}(methyl)amino]-1-piperidinecarboxylate trifluoroacetate (193)

To a solution of 8 (50 mg, 0.153 mmol) in DMF (1.5 mL) was added 192 (92 mg, 0.305 mmol) and K₂CO₃ (42 mg, 0.305 mmol). The reaction mixture was sealed and heated in a microwave for 1 h at 220° C. The reaction mixture was then diluted with water (2 mL) and extracted with EtOAc (3×5 mL). The combined organic layer was dried over MgSO$_4$, filtered, and concentrated under reduced pressure. The crude product was purified by preparative HPLC (water/acetonitrile eluent) to give 8 mg (9%) of the title product 193 as a yellow solid. LCMS (ESI): m/z 492 (M+H)$^+$.

Example 110 (195)

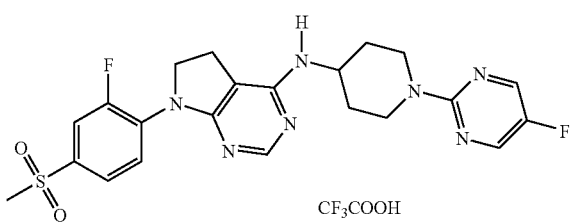

Step 1: 1,1-Dimethylethyl[1-(2-fluoro-5-pyrimidinyl)-4-piperidinyl]carbamate (194)

To a stirred solution of 1,1-dimethylethyl 4-piperidinylcarbamate (500 mg, 2.50 mmol) and diisopropylethylamine (0.871 mL, 5.0 mmol) in acetonitrile (25 mL) was added 2-chloro-5-fluoropyrimidine (0.34 mL, 2.75 mmol) via syringe at RT. The reaction mixture was heated to reflux for 19 hours, then cooled to RT and concentrated under reduced pressure. The crude oil was purified by SiO$_2$ flash chromatography (20% to 50% EtOAc in hexanes) to give 495 mg (67%) of the title product 194 as a viscous oil. $^1$H NMR (400 MHz, CDCl$_3$): δ 8.17 (s, 2H), 4.56-4.52 (m, 2H), 4.47-4.41 (m, 1H), 3.70 (br s, 1H), 3.07-3.00 (m, 2H), 2.02-1.98 (m, 2H), 1.44 (s, 9H), 1.39-1.28 (m, 2H).

Step 2: 7-[2-Fluoro-4-(methylsulfonyl)phenyl]-N-[1-(2-fluoro-5-pyrimidinyl)-4-piperidinyl]-6,7-dihydro-5H-pyrrolo[2,3-d]pyrimidin-4-amine trifluoroacetate (195)

To a solution of 8 (57 mg, 0.174 mmol) in DMF (1.7 mL) was added 194 (103 mg, 0.348 mmol) and K$_2$CO$_3$ (48 mg, 0.348 mmol). The reaction mixture was sealed and heated in a microwave for 1 h at 220° C. After an LCMS trace showed an appreciable amount of 8, the reaction mixture was heated in a microwave an additional 60 min at 220° C. The reaction mixture was then diluted with water (2 mL) and extracted with EtOAc (3×5 mL). The combined organic layer was dried over MgSO$_4$, filtered, and concentrated under reduced pressure. The crude product was purified by preparative HPLC (water/acetonitrile eluent) to give 3 mg (3%) of the title product 195 as a yellow solid. LCMS (ESI): m/z 488 (M+H)$^+$.

Example 111 (198)

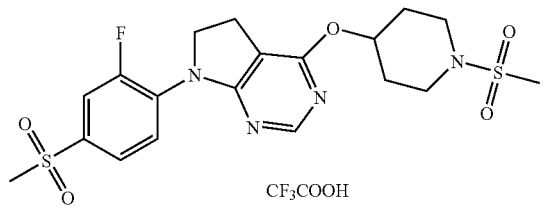

Step 1: 1,1-Dimethylethyl 4-(acetyloxy)-1-piperidinecarboxylate (196)

To a stirred solution of 1,1-dimethylethyl 4-hydroxy-1-piperidinecarboxylate (4.0 g, 19.9 mmol) in CH$_2$Cl$_2$ (50 mL) was added sequentially Et$_3$N (8.3 mL, 59.6 mmol) and acetic anhydride (5.6 mL, 59.6 mmol) via syringes at RT. The reaction mixture was stirred at RT for 5 h. The reaction mixture was then washed with water (1×25 mL), dried over MgSO$_4$, filtered, and concentrated under reduced pressure. The crude oil was dried under high vacuum overnight to give 5.83 g (120%; some acetic anhydride is present in the sample) of the title product 196 as a light brown oil which was used without further purification. $^1$H NMR (400 MHz, CDCl$_3$): δ 4.88 (septuplet, J=3.9 Hz, 1H), 3.74-3.67 (m, 2H), 3.20-3.14 (m, 2H), 2.04 (s, 3H), 1.86-1.79 (m, 2H), 1.61-1.52 (m, 2H), 1.44 (s, 9H).

Step 2: 1-(Methylsulfonyl)-4-piperidinol (197)

To a stirred solution of 196 (5.83 g from previous reaction) in CH$_2$Cl$_2$ (100 mL) was added TFA (18.5 mL, 239.6 mmol) via syringe at RT. The reaction mixture was stirred at RT for 3 h at which point it was concentrated under reduced pressure and dried under high vacuum to remove as much excess TFA as possible. The crude yellow oil was then dissolved in CH$_2$Cl$_2$ (150 mL) with stirring. To this solution was added Et$_3$N (54 mL, 389 mmol) via syringe at RT and then the reaction mixture was cooled to 0° C. Methanesulfonyl chloride (9.0 mL, 116.4 mmol) was added dropwise via addition funnel at 0° C. The reaction mixture was then allowed to warm to RT and stirred 15 h. The reaction mixture was washed with water (1×50 mL), dried over MgSO$_4$, filtered, concentrated under reduced pressure, and dried under high vacuum for 1 h to remove excess Et$_3$N. The crude oil was then dissolved in dioxane (100 mL) with stirring. To this solution was added NaOH (2.5 M in water, 100 mL) and the reaction mixture was stirred at RT for 5 h during which time it turned to a brownish color. The reaction mixture was acidified with conc. HCl to pH~7 and then extracted with EtOAc (3×100 mL). The combined organic layer was dried over MgSO$_4$, filtered, and concentrated under reduced pressure to give 1.99 g (56% from starting material in step 1) of the title product 197 as a light brown solid. $^1$H NMR (400 MHz, CDCl$_3$): δ 3.93 (septuplet, J=3.7 Hz, 1H), 3.70 (s, 1H), 3.49-3.43 (m, 2H), 3.15-3.09 (m, 2H), 2.78 (s, 3H), 1.99-1.93 (m, 2H), 1.74-1.66 (m, 2H).

Step 3: 7-[2-Fluoro-4-(methylsulfonyl)phenyl]-4-{[1-(methylsulfonyl)-4-piperidinyl]oxy}-6,7-dihydro-5H-pyrrolo[2,3-d]pyrimidine trifluoroacetate (198)

To a stirred solution of 8 (50 mg, 0.153 mmol) and 197 (41 mg, 0.229 mmol) in THF (2.0 mL) was added NaH (60% dispersion in mineral oil, 25 mg, 0.612 mmol) in one portion at RT. The reaction mixture was heated to reflux for 18 h, cooled to RT, and quenched with water (2 mL). The mixture was extracted with EtOAc (3×5 mL), dried over MgSO$_4$, filtered, and concentrated under reduced pressure. The crude oil was purified via preparative HPLC (water/acetonitrile eluent) to give 15 mg (17%) of the title product 198 as a white solid. $^1$H NMR (400 MHz, CDCl$_3$): δ 8.32 (s, 1H), 7.83-7.74 (m, 3H), 5.35 (septuplet, J=3.9 Hz, 1H), 4.23 (t, J=9.3 Hz, 2H), 3.59-3.54 (m, 2H), 3.24-3.18 (m, 4H), 3.07 (s, 3H), 2.83 (s, 3H), 2.19-2.11 (m, 2H), 2.00-1.91 (m, 2H); LCMS (ESI): m/z 471 (M+H)$^+$.

Example 112 (202)

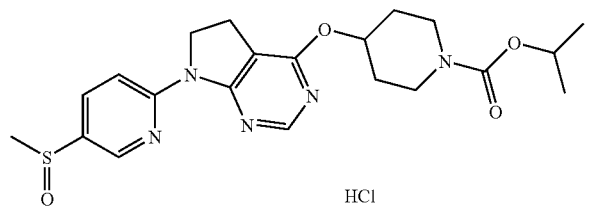

Step 1: 5-(Methylthio)-2-pyridinamine (199)

To a stirred solution of 2-amino-5-iodopyridine (11.6 g, 52.6 mmol) in MeOH (250 mL) was added sodium thiomethoxide (5.16 g, 73.6 mmol) and copper powder (1.07 g, 16.8 mmol) at RT. The reaction mixture was heated in a sealed tube at 120° C. for 68 h. The reaction mixture was then cooled to RT and filtered through a pad of Celite. The Celite was rinsed with MeOH and the combined organics were concentrated under reduced pressure and redissolved in EtOAc. The organic layer was washed with water (1×50 mL) and the aqueous layer was extracted with EtOAc (2×100 mL). The combined organic layer was dried over MgSO$_4$, filtered, and concentrated under reduced pressure to give 6.23 g (84%) of the title product 199 as an off-white solid. $^1$H NMR (400 MHz, CDCl$_3$): δ 8.09 (s, 1H), 7.51-7.48 (m, 1H), 6.48-6.45 (m, 1H), 4.35 (br s, 2H), 2.38 (s, 3H).

Step 2: 4-Chloro-7-[5-(methylthio)-2-pyridinyl]-6,7-dihydro-5H-pyrrolo[2,3-d]pyrimidine (200)

To a stirred solution of (4,6-dichloro-5-pyrimidinyl)acetaldehyde 209 (see example 116, step 1, 3.41 g, 17.8 mmol) in MeOH (180 mL) was added 199 (3.0 g, 21.4 mmol) at RT. The reaction mixture was cooled to −15° C. with an ice/methanol bath and glacial acetic acid (3.1 mL, 53.4 mmol) and NaBH$_3$CN (3.35 g, 53.4 mmol) were added. The reaction mixture was stirred at −15° C. for 15 min then allowed to warm to RT and stir for 19 h. The reaction mixture was then diluted with water (50 mL) and extracted with CH$_2$Cl$_2$ (3×100 mL). The combined organic layer was dried over MgSO$_4$, filtered, and concentrated under reduced pressure to a yellow oil. The crude oil was dissolved in THF (500 mL) with stirring and then t-BuOK (5.99 g, 53.4 mmol) was added in one portion at RT. The reaction mixture changed immediately to a brown color and was stirred at RT for 22 h. The reaction mixture was quenched with water (50 mL), concentrated under reduced pressure, and then redissolved in EtOAc (200 mL). The organic layer was washed with water (1×50 mL) and the aqueous layer was extracted with EtOAc (2×100 mL). The combined organic layer was dried over MgSO$_4$, filtered, and concentrated under reduced pressure to a brown oil. The crude oil was purified using SiO$_2$ flash chromatography (20% to 40% EtOAc in hexanes; monitored at 319 nm) to give 550 mg (11%) of the title product 200 as a colorless oil. $^1$H NMR (400 MHz, CDCl$_3$): δ 8.57 (d, J=9.0 Hz, 1H), 8.43 (s, 1H), 8.29 (d, J=2.4 Hz, 1H), 7.68 and 7.66 (dd, J$_1$=8.8 Hz, J$_2$=2.4 Hz, 1H), 4.37-4.33 (m, 2H), 3.16 (t, J=8.8 Hz, 2H), 2.47 (s, 3H).

Step 3: 1-Methylethyl 4-({7-[5-(methylthio)-2-pyridinyl]-6,7-dihydro-5H-pyrrolo[2,3-d]pyrimidin-4-yl}oxy)-1-piperidinecarboxylate (201)

To a stirred solution of 200 (652 mg, 2.35 mmol) and 1-methylethyl 4-hydroxy-1-piperidinecarboxylate 9 (526 mg, 2.81 mmol) in THF (24 mL) was added NaH (60% dispersion in mineral oil, 282 mg, 7.05 mmol) in one portion at RT. The reaction mixture was heated to reflux for 18 h, cooled to RT, and quenched with water (20 mL). The mixture was extracted with EtOAc (3×50 mL), dried over MgSO$_4$, filtered, and concentrated under reduced pressure. The crude oil was purified using SiO$_2$ flash chromatography (40% EtOAc in hexanes) to give 373 mg (37%) of the title product 201 as a colorless oil. $^1$H NMR (400 MHz, CDCl$_3$): δ 8.73-8.66 (m, 1H), 8.42-8.39 (m, 1H), 8.30 (d, J=2.4 Hz, 1H), 8.77-8.70 (m, 1H), 5.39-5.32 (m, 1H), 4.92 (septuplet, J=6.1 Hz, 1H), 4.46-4.36 (m, 2H), 3.85-3.76 (m, 2H), 3.36-3.30 (m, 2H), 3.12-3.05 (m, 2H), 2.48 (s, 3H), 2.03-1.95 (m, 2H), 1.79-1.70 (m, 2H), 1.25 (d, J=6.4 Hz, 6H); LCMS (ESI): m/z 430 (M+H)$^+$.

Step 4: (±)-1-Methylethyl 4-({7-[5-(methylsulfinyl)-2-pyridinyl]-6,7-dihydro-5H-pyrrolo[2,3-d]pyrimidin-4-yl}oxy)-1-piperidinecarboxylate hydrochloride (202)

To a stirred solution of 201 (180 mg, 0.419 mmol) in hexafluoroisopropanol (4.0 mL) at 0° C. was added H$_2$O$_2$ (30% wt aqueous solution, 95 mg, 0.839 mmol) via syringe. The reaction mixture was allowed to warm to RT and stirred for 30 min. The reaction mixture was diluted with water (5 mL) and extracted with CH$_2$Cl$_2$ (3×20 mL). The combined organic layer was dried over MgSO$_4$, filtered, and concentrated under reduced pressure. The resulting colorless oil was dissolved in a 1:1 mixture of acetone:Et$_2$O (15 mL) using a heat gun with stirring. To this solution was added HCl (1.0 M in Et$_2$O, 1.5 mL) and a white solid precipitated immediately. The solvent was removed under reduced pressure and the material was triturated with Et$_2$O, filtered, and dried under high vacuum to give 169 mg (84%) of the title product 202 as a white solid. $^1$H NMR (400 MHz, CDCl$_3$): δ 8.67-8.63 (m, 1H), 8.60 (s, 1H), 8.52 (s, 1H), 8.09-8.05 (m, 1H), 5.42-5.36 (m, 1H), 4.91 (septuplet, J=6.1 Hz, 1H), 4.41-4.37 (m, 2H), 3.86-3.77 (m, 2H), 3.35-3.29 (m, 2H), 3.13-3.09 (m, 2H), 2.78 (s, 3H), 2.04-1.96 (m, 2H), 1.78-1.70 (m, 2H), 1.24 (d, J=6.1 Hz, 6H); LCMS (ESI): m/z 446 (M+H)$^+$.

Example 113 (203)

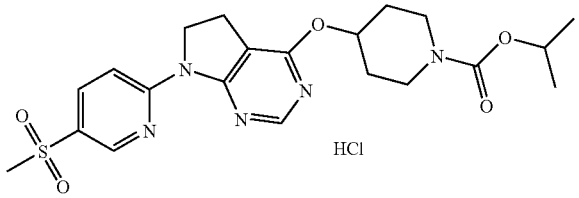

1-Methylethyl 4-({7-[5-(methylsulfonyl)-2-pyridinyl]-6,7-dihydro-5H-pyrrolo[2,3-d]pyrimidin-4-yl}oxy)-1-piperidinecarboxylate hydrochloride (203)

To a stirred solution of 201 (186 mg, 0.433 mmol) in MeOH (4 mL) and acetone (3 mL) was added a solution of Oxone (798 mg, 1.3 mmol) in water (4 mL) via pipet at RT. A white solid precipitated immediately and the reaction mixture was stirred at RT for 1 h. The reaction mixture was quenched with a sat. aqueous solution of $Na_2SO_3$ and extracted with $CH_2Cl_2$ (3×10 mL). The combined organic layer was dried over $MgSO_4$, filtered, and concentrated under reduced pressure. The resulting solid was dissolved in a mixture of $Et_2O$ (8 mL) and acetone (3 mL) using a heat gun with stirring. To this solution was added HCl (1.0 M in $Et_2O$, 0.88 mL) and a white solid precipitated immediately. The material was filtered, washed with $Et_2O$, and dried under high vacuum to give 190 mg (81%) of the title product 203 as a white solid. $^1$H NMR (400 MHz, $CDCl_3$): δ 9.01 (d, J=2.4 Hz, 1H), 8.83 (s, 1H), 8.19 and 8.16 (dd, $J_1$=8.8 Hz, $J_2$=2.2 Hz, 1H), 7.70 (d, J=8.8 Hz, 1H), 5.56 (septuplet, J=4.2 Hz, 1H), 4.93 (app. quintuplet, J=6.4 Hz, 1H), 4.57 (t, J=8.8 Hz, 2H), 3.89-3.83 (m, 2H), 3.38-3.29 (m, 4H), 3.05 (s, 3H), 2.10-2.04 (m, 2H), 1.84-1.76 (m, 2H), 1.26 (d, J=6.4 Hz, 6H); LCMS (ESI): m/z 462 $(M+H)^+$.

Example 114 (206)

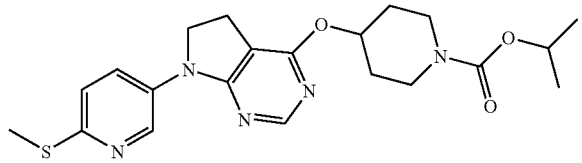

Step 1: 6-(Methylthio)-3-pyridinamine (204)

To a stirred solution of 5-amino-2-bromopyridine (9.97 g, 57.63 mmol) in MeOH (250 mL) was added sodium thiomethoxide (5.65 g, 80.68 mmol) and copper powder (1.17 g, 18.44 mmol) at RT. The reaction mixture was heated in a sealed tube at 120° C. for 64 h. The reaction mixture was then cooled to RT and filtered through a pad of Celite. The Celite® was rinsed with MeOH and the combined organics were concentrated under reduced pressure and redissolved in EtOAc. The organic layer was washed with water (1×50 mL) and the aqueous layer was extracted with EtOAc (2×100 mL). The combined organic layer was dried over $MgSO_4$, filtered, and concentrated under reduced pressure. The resulting crude oil was purified using $SiO_2$ flash chromatography (40% to 70% EtOAc in hexanes) to give 2.08 g (26%) of the title product 204 as a brown solid. $^1$H NMR (400 MHz, $CDCl_3$): δ 8.00 (d, J=2.9 Hz, 1H), 7.06-7.00 (m, 1H), 6.92-6.89 (m, 1H), 3.50 (br s, 2H), 2.51 (s, 3H).

Step 2: 4-Chloro-7-[6-(methylthio)-3-pyridinyl]-6,7-dihydro-5H-pyrrolo[2,3-d]pyrimidine (205)

To a stirred solution of (4,6-dichloro-5-pyrimidinyl)acetaldehyde 209 (2.36 g, 12.36 mmol) in MeOH (120 mL) was added 204 (2.08 g, 14.8 mmol) at RT. The reaction mixture was cooled to −15° C. with an ice/methanol bath and glacial acetic acid (2.12 mL, 37.08 mmol) and $NaBH_3CN$ (2.33 g, 37.08 mmol) were added. The reaction mixture was stirred at −15° C. for 15 min then allowed to warm to RT and stir for 18 h. The reaction mixture was then diluted with water (50 mL) and extracted with $CH_2Cl_2$ (3×100 mL). The combined organic layer was dried over $MgSO_4$, filtered, and concentrated under reduced pressure to a yellow oil. The crude oil was dissolved in THF (350 mL) with stirring and then t-BuOK (4.16 g, 37.08 mmol) was added in one portion at RT. The reaction mixture changed immediately to a brown color and was stirred at RT for 17 h. The reaction mixture was quenched with water (50 mL), concentrated under reduced pressure, and then redissolved in EtOAc (200 mL). The organic layer was washed with water (1×50 mL) and the aqueous layer was extracted with EtOAc (2×100 mL). The combined organic layer was dried over $MgSO_4$, filtered, and concentrated under reduced pressure to a brown oil. The crude oil was purified using $SiO_2$ flash chromatography (20% to 40% EtOAc in hexanes; monitored at 319 nm) to give 1.31 g (38%) of the title product 205 as a colorless oil. $^1$H NMR (400 MHz, $CDCl_3$): δ 8.63 and 8.62 (dd, $J_1$=2.9 Hz, $J_2$=0.7 Hz, 1H), 8.36-8.35 (m, 1H), 8.28-8.24 (m, 1H), 7.21-7.19 (m, 1H), 4.15-4.11 (m, 2H), 3.25-3.20 (m, 2H), 2.56 (s, 3H).

Step 3: 1-Methylethyl 4-({7-[6-(methylthio)-3-pyridinyl]-6,7-dihydro-5H-pyrrolo[2,3-d]pyrimidin-4-yl}oxy)-1-piperidinecarboxylate (206)

To a stirred solution of 205 (1.31 g, 4.71 mmol) and 1-methylethyl 4-hydroxy-1-piperidinecarboxylate 9 (1.06 g, 5.65 mmol) in THF (47 mL) was added NaH (60% dispersion in mineral oil, 565 mg, 14.13 mmol) in one portion at RT. The reaction mixture was heated to reflux for 18 h, cooled to RT, and quenched with water (10 mL). The mixture was extracted with EtOAc (3×75 mL), dried over $MgSO_4$, filtered, and concentrated under reduced pressure. The crude oil was purified using $SiO_2$ flash chromatography (40% EtOAc in hexanes) to give 500 mg (25%) of the title product 206 as a colorless oil. $^1$H NMR (400 MHz, $CDCl_3$): δ 8.58 (d, J=2.7 Hz, 1H), 8.41-8.37 (m, 1H), 8.27 (s, 1H), 7.21 (d, J=8.8 Hz, 1H), 5.32 (septuplet, J=3.9 Hz, 1H), 4.91 (app. quintuplet, J=6.1 Hz, 1H), 4.05 (t, J=8.8 Hz, 2H), 3.82-3.75 (m, 2H), 3.35-3.28 (m, 2H), 3.08 (t, J=8.8 Hz, 2H), 2.59 (s, 3H), 2.00-1.93 (m, 2H), 1.75-1.67 (m, 2H), 1.24 (d, J=6.8 Hz, 6H); LCMS (ESI): m/z 430 $(M+H)^+$.

Example 115 (207)

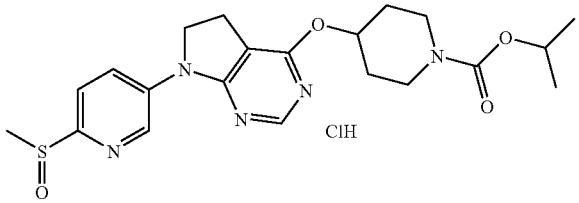

(±)-1-Methylethyl 4-({7-[6-(methylsulfinyl)-3-pyridinyl]-6,7-dihydro-5H-pyrrolo[2,3-d]pyrimidin-4-yl}oxy)-1-piperidinecarboxylate hydrochloride (207)

To a stirred solution of 206 (198 mg, 0.460 mmol) in hexafluoroisopropanol (4.0 mL) at 0° C. was added $H_2O_2$ (30% wt aqueous solution, 104 mg, 0.920 mmol) via syringe. The reaction mixture was allowed to warm to RT and stirred for 30 min. The reaction mixture was diluted with water (5 mL) and extracted with $CH_2Cl_2$ (3×20 mL). The combined organic layer was dried over $MgSO_4$, filtered, and concentrated under reduced pressure. The resulting colorless oil was dissolved in a 1:1 mixture of acetone:$Et_2O$ (15 mL) using a heat gun with stirring. To this solution was added HCl (1.0 M in Et$_2$O, 1.7 mL) and a white solid precipitated immediately. The solvent was removed under reduced pressure and the material was triturated with Et$_2$O, filtered, and dried under high vacuum to give 151 mg (68%) of the title product 207 as a light yellow solid. $^1$H NMR (400 MHz, CDCl$_3$): δ 9.12 (d, J=1.5 Hz, 1H), 8.55 (s, 1H), 8.46 and 8.43 (dd, J$_1$=9.0 Hz, J$_2$=2.2 Hz, 1H), 8.15 (d, J=8.6 Hz, 1H), 5.64 (septuplet, J=4.1 Hz, 1H), 4.91 (app. quintuplet, J=6.4 Hz, 1H), 4.33 (t, J=8.6 Hz, 2H), 3.93-3.87 (m, 2H), 3.36-3.24 (m, 4H), 2.96 (s, 3H), 2.14-2.08 (m, 2H), 1.78-1.69 (m, 2H), 1.23 (d, J=6.1 Hz, 6H); LCMS (ESI): m/z 446 (M+H)$^+$.

Example 116 (208)

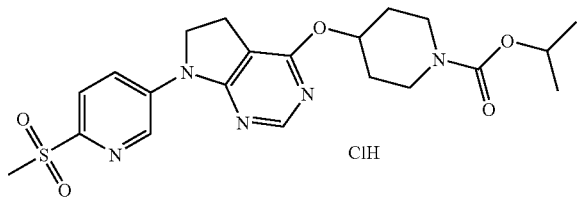

1-Methylethyl 4-({7-[6-(methylsulfonyl)-3-pyridinyl]-6,7-dihydro-5H-pyrrolo[2,3-d]pyrimidin-4-yl}oxy)-1-piperidinecarboxylate hydrochloride (208)

To a stirred solution of 206 (302 mg, 0.70 mmol) in MeOH (5 mL) and acetone (5 mL) was added a solution of Oxone (1.30 g, 2.11 mmol) in water (5 mL) via pipet at RT. A white solid precipitated immediately and the reaction mixture was stirred at RT for 1 h. The reaction mixture was quenched with a sat. aqueous solution of Na$_2$SO$_3$ and extracted with CH$_2$Cl$_2$ (3×10 mL). The combined organic layer was dried over MgSO$_4$, filtered, and concentrated under reduced pressure. The resulting solid was dissolved in a mixture of Et$_2$O (10 mL) and acetone (5 mL) using a heat gun with stirring. To this solution was added HCl (1.0 M in Et$_2$O, 1.2 mL) and a white solid precipitated immediately. The material was filtered, washed with Et$_2$O, and dried under high vacuum to give 260 mg (75%) of the title product 208 as a white solid. $^1$H NMR (400 MHz, CDCl$_3$): δ 9.02 (d, J=2.4 Hz, 1H), 8.58 and 8.56 (dd, J$_1$=8.8 Hz, J$_2$=2.7 Hz, 1H), 8.37 (s, 1H), 8.04 (d, J=8.8 Hz, 1H), 5.36 (septuplet, J=3.9 Hz, 1H), 4.91 (app. quintuplet, J=6.4 Hz, 1H), 4.14 (t, J=8.8 Hz, 2H), 3.84-3.76 (m, 2H), 3.35-3.28 (m, 2H), 3.18 (s, 3H), 3.15 (t, J=8.8 Hz, 2H), 2.02-1.95 (m, 2H), 1.77-1.68 (m, 2H), 1.24 (d, J=6.4 Hz, 6H); LCMS (ESI): m/z 462 (M+H)$^+$.

Example 117 (112)

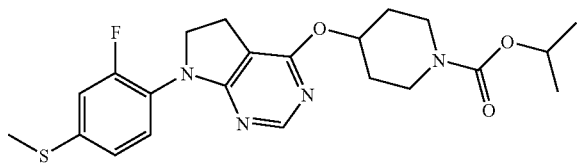

Step 1: (4,6-Dichloro-5-pyrimidinyl)-acetaldehyde (209)

To a stirred solution of 4,6-dichloro-5-(2-propen-1-yl)pyrimidine (2, 274 g, 1.45 mol) in 1:1 acetone-H$_2$O (7.6 L) was added K$_2$OsO$_4$·2H$_2$O (18 g, 0.0493 mol). Solid NaIO$_4$ (1.24 kg, 5.8 mol) was added portionwise during 1 h; the reaction temperature did not exceed 40° C. The resulting suspension was stirred for 1 h as the reaction cooled to RT. The mixture was filtered and the filtrate was concentrated to remove the acetone. The aqueous layer was extracted with CH$_2$Cl$_2$ (5×1 L). The combined extracts were washed with 10% Na$_2$S$_2$O$_3$ solution (2×3.5 L), with brine, dried over anhydrous Na$_2$SO$_4$, filtered, and concentrated to give 204 g (74%) of the product 209 as a shiny amber solid. $^1$H NMR (400 MHz, DMSO-d$_6$): δ 9.72 (s, 1H), 8.86 (s, 1H), 4.21 (s, 2H).

Step 2: [2-Fluoro-4-(methylthio)phenyl]amine (210)

To a mixture of Nickel (II) bromide (9.12 g, 42 mmol), 2,2'-dipyridyl (6.56 g, 42 mmol), zinc dust (55 g, 844 mmol), and anhydrous DMF (300 mL) were added 2-fluoro-4-iodoaniline (100 g, 0.422 g, mmol) and dimethyldisulfide (96 mL, 1.06 mol) under N$_2$. The resultant mixture was stirred at 75° C. for 1.5 h. The reaction mixture was concentrated under reduced pressure to afford the crude residue, which was dissolved in Et$_2$O (500 mL) and filtered through a pad of Celite (washings were done with Et$_2$O). The filtrate was concentrated under reduced pressure to afford the crude material. The crude material was subjected to flash column chromatography to afford 48.70 g (73%) of the title product 210 as a brown liquid. $^1$H NMR (400 MHz, DMSO-d$_6$): δ 7.02 and 6.98 (dd, J$_1$=11.2 Hz, J$_2$=2.0 Hz, 1H), 6.94 and 6.92 (dd, J$_1$=8.4 Hz, J$_2$=4.0 Hz, 1H), 6.70 (t, J=8.8 Hz, 1H), 3.69 (br, s, 2H), 2.40 (s, 3H), 9.72 (s, 1H), 8.86 (s, 1H), 4.21 (s, 2H); LCMS (ESI): m/z 158 (M+H)$^+$.

Step 3: 4-Fluoro-7-[2-fluoro-4-(methylthio)phenyl]-6,7-dihydro-5H-pyrrolo[2,3-d]pyrimidine (211)

A round bottom flask was charged with aniline 210 (7.86 g, 50 mmol) and then cooled to −15° C. Trifluoroacetic acid (50 mL) was added to the above cold aniline 210 while stirring the contents for 0.5 h. Na(OAc)$_3$BH was added portion wise to the above mixture and stirred for additional 0.5 h. The aldehyde 209 (9.17 g 48 mmol) in CH$_2$Cl$_2$ (20 mL) was added to the above mixture. The resultant mixture was allowed to warm up to the ambient temperature and stirred for 15 h. The reaction mixture was concentrated under reduced pressure and the residue was poured into sat. NaHCO$_3$ solution (300 mL) and then the mixture was extracted with CH$_2$Cl$_2$ (4×250 mL). The combined organic layer was washed with brine (1×100 mL), dried over sat. Na$_2$SO$_4$ and then concentrated under reduced pressure to afford the crude material. The crude material was recrystallized from CH$_2$Cl$_2$ and MeOH to afford 6.26 g (44%) of the title product 211 as an off-white solid. $^1$H NMR (400 MHz, DMSO-d$_6$): δ 8.16 (s, 1H), 7.48 (t, J=8.0 Hz, 1H), 7.26 and 7.22 (dd, J$_1$=11.6 Hz, J$_2$=2.0 Hz, 1H), 7.14 and 7.11 (dd, J$_1$=8.0 Hz, J$_2$=2.4 Hz, 1H), 4.05 (t, J=8.8 Hz, 1H), 3.18 (t, J=8.4 Hz, 2H), 2.49 (s, 3H); LCMS (ESI): m/z 296 (M+H)$^+$.

Step 4: 1-Methylethyl 4-({7-[2-fluoro-4-(methylthio)phenyl]-6,7-dihydro-5H-pyrrolo[2,3-d]pyrimidin-4-yl}oxy)-1-piperidinecarboxylate (212)

Following the procedure described for 10 (example 1, step 10), the reagent 9 (3.07 g, 16.4 mmol), NaH (2.08 g, 52 mmol), and the compound 211 (5.11 g, 17.3 mmol) were refluxed for 2.5 h. The regular work-up and chromatography afforded 5.72 g (78%) of the title product 212 as an off-white solid. $^1$H NMR (400 MHz, DMSO-d$_6$): δ 8.10 (s, 1H), 7.46 (t, J=8.4 Hz, 1H), 7.22 and 7.19 (dd, J$_1$=12.0 Hz, J$_2$=2.0 Hz, 1H), 7.10 and 7.08 (dd, J$_1$=8.0 Hz, J$_2$=2.0 Hz, 1H), 5.26-5.20 (m, 1H), 4.75 (septuplet, J=6.4 Hz, 1H), 3.96 (t, J=8.8 Hz, 2H), 3.70-3.64 (m, 2H), 3.22 (app. t, J=9.6 Hz, 2H), 3.01 (t, J=8.8 Hz, 2H), 1.94-1.88 (m, 2H), 1.59-1.50 (m, 2H), 1.17 (d, J=6.4 Hz, 6H); LCMS (ESI): m/z 447 (M+H)$^+$.

Example 118 (213)

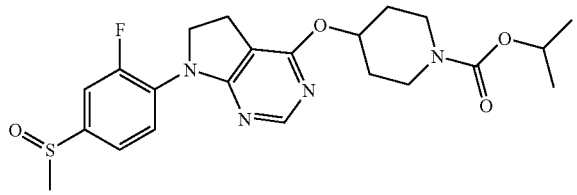

(±)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate (213)

Following the oxidation procedure described for 85 (example 32, step 3), the sulfide 212 (1.8 g, 4.03 mmol) was treated with a 35% wt $H_2O_2$ (800 μL, 8.06 mmol) in HFIP (20 mL) at RT to afford 1.85 g (~100%) of the desired sulfoxide 213 as a white solid after work up. $^1$H NMR (400 MHz, DMSO-$d_6$): δ 8.16 (s, 1H), 7.82 (app. t, J=8.0 Hz, 1H), 7.64 and 7.60 (dd, $J_1$=10.8 Hz, $J_2$=2.0 Hz, 1H), 7.52 and 7.50 (dd, $J_1$=8.4 Hz, $J_2$=2.0 Hz, 1H), 5.28-5.22 (m, 1H), 4.76 (septuplet, J=6.4 Hz, 1H), 4.08 (t, J=8.4 Hz, 2H), 3.70-3.64 (m, 2H), 3.22 (app. br. t, J=9.6 Hz, 2H), 3.04 (t, J=8.8 Hz, 2H), 2.77 (s, 3H), 1.94-1.90 (m, 2H), 1.60-1.52 (m, 2H), 1.17 (d, J=6.0 Hz, 6H); LCMS (ESI): m/z 463 (M+H)$^+$.

Example 119

The racemic sulfoxide 213 (2.60 g) was subjected for Chiral HPLC [column: Chiralpak AS-H, mobile phase: 80% $CO_2$: 20% MeOH (2 mL/min), pressure 140 bar, temperature 40° C., 240 nm)] analysis and then separated two (R and S) enantiomers. The absolute stereochemistry was determined based on VCD spectroscopy.
Enantiomer I, 119A (213A)

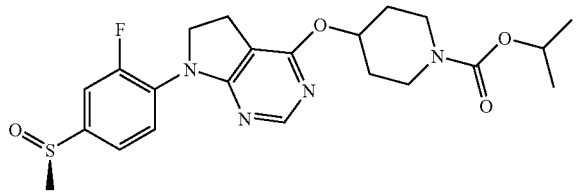

(R)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate (213A)

Tr: 8.30 min, 1.150 g (% ee>98%); Spectral data are essentially the same to that of example 118 (213).
Enantiomer II, 119B (213B)

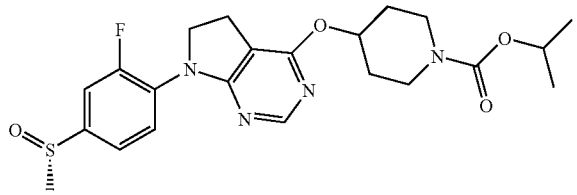

(S)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate (213B)

Tr: 10.4 min, 1.0 g (% ee, >98%), Spectral data are essentially the same to that of example 118 (213).

Example 120 (218)

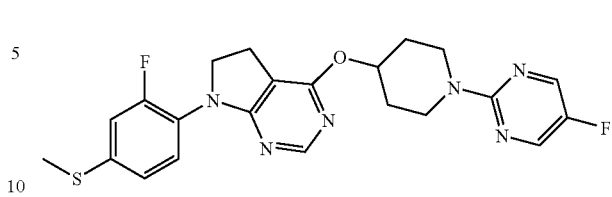

7-[2-Fluoro-4-(methylthio)phenyl]-4-{[1-(5-fluoro-2-pyrimidinyl)-4-piperidinyl]oxy}-6,7-dihydro-5H-pyrrolo[2,3-d]pyrimidine (214)

Following the procedure described for 10 (example 1, step 10), the reagent 23 (0.641 g, 3.25 mmol), NaH (0.39 g, 9.8 mmol), and the compound 211 (0.96 g, 3.25 mmol) were refluxed for 5 h. The regular work-up and chromatography afforded 1.145 g (77%) of the title product 214 as a white solid. $^1$H NMR (400 MHz, DMSO-$d_6$): δ 8.43 (s, 2H), 8.11 (s, 1H), 7.47 (t, J=8.4 Hz, 1H), 7.22 and 7.20 (dd, $J_1$=12.0 Hz, $J_2$=2.0 Hz, 1H), 7.10 and 7.08 (dd, $J_1$=8.4 Hz, $J_2$=2.0 Hz, 1H), 5.36-5.20 (m, 1H), 4.16-4.10 (m, 2H), 3.96 (t, J=8.8 Hz, 2H), 3.53-3.47 (m, 2H), 3.0 (t, J=8.8 Hz, 2H), 2.48 (s, 3H), 2.01-1.96 (m, 2H), 1.66-1.58 (m, 2H); LCMS (ESI): m/z 457 (M+H)$^+$.

Example 121 (215)

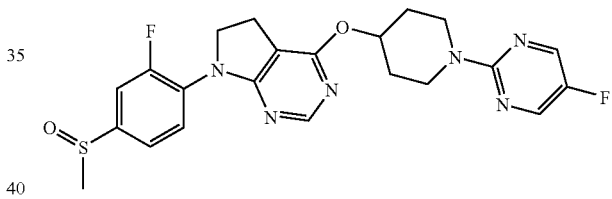

(±)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine (215)

Following the oxidation procedure described for 85 (example 32, step 3), the sulfide 214 (1.07 g, 2.34 mmol) was treated with a 35% wt $H_2O_2$ (460 μL, 4.7 mmol) in HFIP (15 mL) at RT to afford 1.10 g (99%) of the desired sulfoxide 215 as a white solid after recrystallization from EtOAc/n-hexanes. $^1$H NMR (400 MHz, DMSO-$d_6$): δ 8.44 (s, 2H), 8.18 (s, 1H), 7.82 (t, J=8.0 Hz, 1H), 7.62 (app. br. d, J=10.8 Hz, 1H), 7.52 (app. br. d, J=8.4 Hz, 1H), 5.36-5.30 (m, 1H), 4.16 4.10 (m, 2H), 4.08 (t, J=8.8 Hz, 2H), 3.51 (app. t, J=9.6 Hz, 2H), 3.04 (t, J=8.8 Hz, 2H), 2.78 (s, 3H), 2.04-1.96 (m, 2H), 1.68-1.58 (m, 2H); LCMS (ESI): m/z 473 (M+H)$^+$.

Example 122

The racemic sulfoxide 215 (545 mg) was subjected for Chiral HPLC [column: Chiralpak AS-H (analytical), Chiralpak AS-H (prep.), mobile phase: 75% $CO_2$: 25% MeOH (2 mL/min), pressure 140 bar, temperature 40° C., 230 nm)] analysis and then separated two (R and S) enantiomers. The absolute stereochemistry was determined based on VCD spectroscopy.

Enantiomer I, 122A (215A)

(R)-7-[2-fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine (215A)

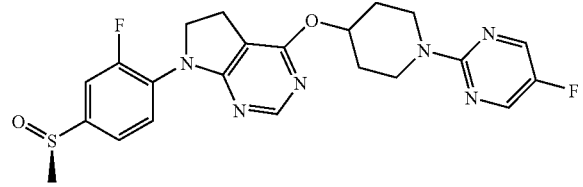

Tr: 12.4 min, 172 mg (% ee>99%), Spectral data are essentially the same to that of example 121 (125A).

Enantiomer II, 122B (215B)

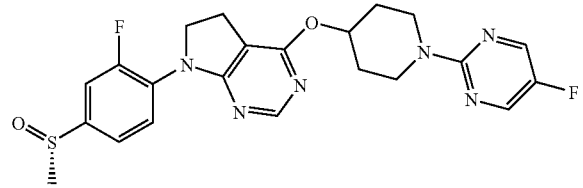

(S)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine (215B)

Tr: 17.4 min, 181 mg (% ee>97%), Spectral data are essentially the same to that of example 121 (215).

Example 123 (216)

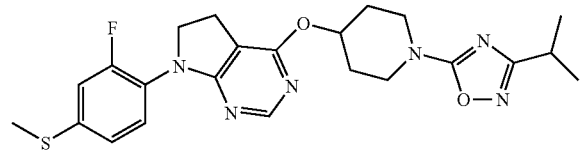

7-[2-Fluoro-4-(methylthio)phenyl]-4-({1-[3-(1-methylethyl)-1,2,4-oxadiazol-5-yl]-4-piperidinyl}oxy)-6,7-dihydro-5H-pyrrolo[2,3-d]pyrimidine (216)

Following the procedure described for 10 (example 1, step 10), the reagent 49 (0.678 g, 3.21 mmol), NaH (0.406 g, 3.21 mmol), and the compound 211 (1.0 g, 3.38 mmol) were refluxed for 2.5 h. The regular work-up and chromatography afforded 1.140 g (76%) of the title product 216 as a white solid. $^1$H NMR (400 MHz, DMSO-$d_6$): δ 8.11 (s, 1H), 7.47 (t, J=8.4 Hz, 1H), 7.22 and 7.20 (dd, $J_1$=12.0 Hz, $J_2$=2.0 Hz, 1H), 7.10 and 7.08 (dd, $J_1$=8.4 Hz, $J_2$=2.0 Hz, 1H), 5.32-5.28 (m, 1H), 3.98 (t, J=8.8 Hz, 2H), 3.79-3.73 (m, 2H), 3.52-3.45 (m, 2H), 3.03 (t, J=8.8 Hz, 2H), 2.80 (septuplet, J=6.8 Hz, 1H), 2.48 (s, 3H), 2.05-2.00 (m, 2H), 1.76-1.68 (m, 2H), 1.17 (d, J=6.8 Hz, 6H); LCMS (ESI): m/z 471 (M+H)$^+$.

Example 124 (217)

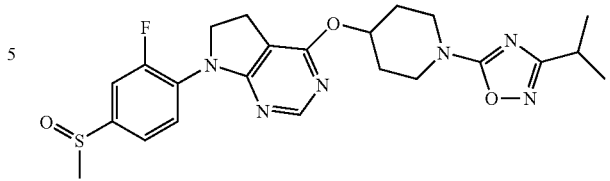

(±)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine (217)

Following the oxidation procedure described for 85 (example 32, step 3), the sulfide 216 (600 mg, 1.28 mmol) was treated with a 35% wt $H_2O_2$ (300 μL, 3.1 mmol) in HFIP (5 mL) at RT. The work-up and chromatography gave 0.620 g (~100%) of the desired sulfoxide 217 as a white solid after work up. $^1$H NMR (400 MHz, DMSO-$d_6$): δ 8.18 (s, 1H), 7.82 (t, J=8.0 Hz, 1H), 7.64 and 7.61 (dd, $J_1$=10.8 Hz, $J_2$=1.6 Hz, 1H), 7.54 and 7.51 (dd, $J_1$=8.4 Hz, $J_2$=1.6 Hz, 1H), 5.34-5.28 (m, 1H), 4.08 (t, J=8.4 Hz, 2H), 3.80-3.74 (m, 2H), 3.52-3.46 (m, 2H), 3.06 (t, J=8.8 Hz, 2H), 2.08-2.0 (m, 2H), 1.78-1.70 (m, 2H), 1.17 (d, J=7.2 Hz, 6H); LCMS (ESI): m/z 487 (M+H)$^+$.

Example 125

The racemic sulfoxide 217 (560 mg) was subjected for Chiral HPLC [column: Chiralpak AS-H (analytical), Chiralpak AS-H (prep.), mobile phase: 78% $CO_2$: 22% MeOH (2 mL/min), pressure 140 bar, temperature 40° C., 240 nm)] analysis and then separated two (R and S) enantiomers. The absolute stereochemistry was determined based on VCD spectroscopy.

Enantiomer I, 125A (217A)

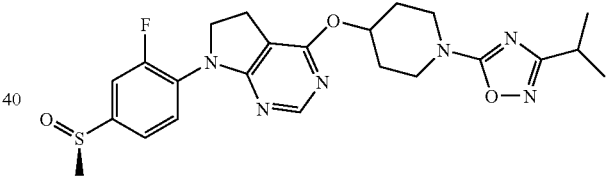

(R)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine (217A)

Tr: 8.6 min, 186 mg (% ee>98%); Spectral data are essentially the same to that of example 124 (217).

Enantiomer II, 125B (217B)

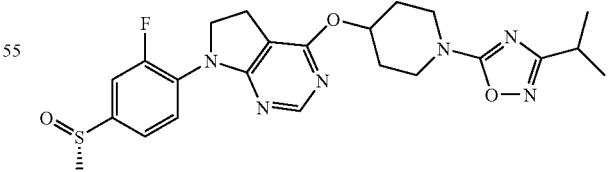

(S)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine (217B)

Tr: 10.92, 201 mg (% ee>98%); Spectral data are essentially the same to that of example 124 (217).

Example 126 (218)

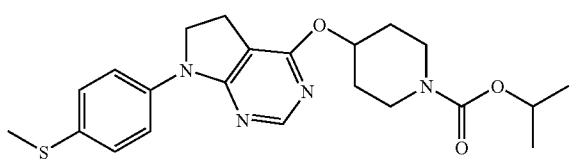

Step 1: 7-(4-Bromophenyl)-4-chloro-6,7-dihydro-5H-pyrrolo[2,3-d]pyrimidine (116)

Following the general reductive amination procedure described for 211 (example 117, step 3), a round bottom flask was charged with 4-bromoaniline (9.03 g, 52.5 mmol) in TFA (50 mL), Na(OAc)$_3$BH (15.03 g, mmol), aldehyde 209 (7.85 g, 50 mmol) in CH$_2$Cl$_2$ (20 mL) at −15° C. The resultant mixture was stirred for 15 h at RT. The work-up and recrystallization from CH$_2$Cl$_2$ and MeOH gave 7.86 g (51%) of the title product 116 as an off-white solid. $^1$H NMR (400 MHz, CDCl$_3$): δ 8.38 (s, 1H), 7.66 (app, dd, J$_1$=6.8 Hz, J$_2$=2.0 Hz, 2H), 7.49 (app. dd, J$_1$=6.8 Hz, J$_2$=2.0 Hz, 2H), 4.12 (t, J=8.80 Hz, 2H), 3.21 (t, J=8.4 Hz, 2H); LCMS (ESI): m/z 311 (M+H)$^+$.

Step 2: 1-Methylethyl 4-{[7-(4-bromophenyl)-6,7-dihydro-5H-pyrrolo[2,3-d]pyrimidin-4-yl]oxy}-1-piperidinecarboxylate (117)

Following the procedure described for 10 (example 1, step 10), the reagent 9 (1.51 g, 8.05 mmol), NaH (0.966 g, 24.2 mmol), and the compound 116 (2.50 g, 8.05 mmol) were refluxed for 2 h. The regular work-up and chromatography afforded 3.15 g (85%) of the title product 117 as a white solid $^1$H NMR (400 MHz, CDCl$_3$): δ 8.30 (s, 1H), 7.65 and 7.63 (app, dd, J$_1$=8.8 Hz, J$_2$=2.0 Hz, 2H), 7.46 and 7.44 (app. dd, J$_1$=9.2 Hz, J$_2$=2.0 Hz, 2H), 5.36-5.28 (m, 1H), 4.92 (septuplet, J=6.4 Hz, 1H), 4.04 (t, J=8.8 Hz, 2H), 3.82-3.78 (br, m, 2H), 3.36-3.30 (m, 2H), 3.06 (t, J=9.2 Hz, 2H), 2.02-1.94 (m, 2H), 1.76-1.68 (m, 2H), 1.24 (d, J=6.4 Hz, 6H); LCMS (ESI): m/z 463 (M+H)$^+$.

Step 3: 1-Methylethyl 4-({7-[4-(methylthio)phenyl]-6,7-dihydro-5H-pyrrolo[2,3-d]pyrimidin-4-yl}oxy)-1-piperidinecarboxylate (218)

Following the procedure described for 210 (example 117, step 2) to a mixture of nickel (II) bromide (76 mg, 0.35 mmol), 2,2'-dipyridyl (55 mg, 0.35 mmol), zinc dust (284 mg, 4.4 mmol), and anhydrous DMF (20 mL) were added compound 117 (1.6 g, 3.47 mmol) and dimethyldisulfide (1.6 mL, 26.1 mmol) under N$_2$. The resultant mixture was stirred at 75° C. for 12 h. The reaction was not complete, but the productive was seen (TLC). At that point of time additional nickel (II) bromide (152 mg), dipyridyl (110 mg), zn (568 mg), and dimethyldisulfide (1.6 mL) were introduced. The reaction mixture was stirred at 120° C. for 12 h. The work up and chromatography gave 280 mg of the titled sulfide 218 as a white solid. Around 800 mg of starting material was also recovered from this reaction. $^1$H NMR (400 MHz, CDCl$_3$): δ 8.30 (s, 1H), 7.65 and 7.63 (app, dd, J$_1$=7.6 Hz, J$_2$=2.0 Hz, 2H), 7.42 and 7.30 (app. dd, J$_1$=8.0 Hz, J$_2$=2.0 Hz, 2H), 5.34-5.30 (m, 1H), 5.0-4.88 (m, 1H), 4.07 (t, J=8.8 Hz, 2H), 3.78 (app, br, s, 2H), 3.36-3.30 (m, 2H), 3.05 (t, J=8.8 Hz, 2H), 1.98 (app. br. s, 2H), 1.78-1.66 (br, m, 2H), 1.24 (d, J=6.0 Hz, 6H), LCMS (ESI): m/z 429 (M+H)$^+$.

Example 127 (219)

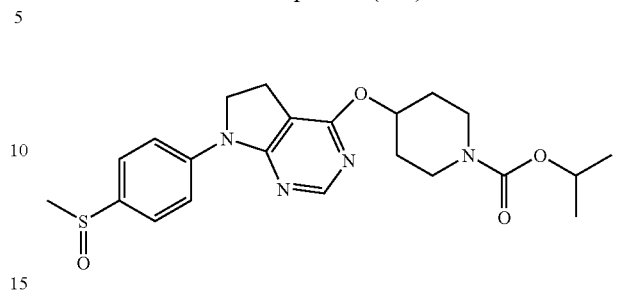

(±)-1-Methylethyl 4-({7-[4-(methylsulfinyl)phenyl]-6,7-dihydro-5H-pyrrolo[2,3-d]pyrimidin-4-yl}oxy)-1-piperidinecarboxylate (219)

Following the oxidation procedure described for 85 (example 32, step 3), the sulfide 218 (260 mg, 0.61 mmol), was treated with a 35% wt H$_2$O$_2$ (120 μL, 1.24 mmol), in HFIP (10 mL) at RT for 0.5 h. The work-up and chromatography followed by recrystallization gave 265 mg (98%) of the desired sulfoxide 219 as a white solid. $^1$H NMR (400 MHz, DMSO-d$_6$): δ 8.34 (s, 1H), 8.0 (app, d, J=8.8 Hz, 2H), 7.65 (app. d, J=8.8 Hz, 2H), 5.30-5.24 (m, 1H), 4.76 (septuplet, J=6.4 Hz, 1H), 4.10 (t, J=9.2 Hz, 2H), 3.70 (m, 2H), 3.23 (app. br. t, J=9.6 Hz, 2H), 3.02 (t, J=8.8 Hz, 2H), 2.70 (s, 3H), 1.96-1.90 (m, 2H), 1.62-1.50 (m, 2H), 1.17 (d, J=6.4 Hz, 6H); LCMS (ESI): m/z 445 (M+H)$^+$.

Example 128

The racemic sulfoxide 127 (150 mg) was subjected for Chiral HPLC [column: R, R Whelk O-1 column mobile phase: 70% CO$_2$: 30% MeOH (2 mL/min), pressure 140 bar, temperature 40° C., 240 nm)] analysis and then separated two (R and S) enantiomers. The absolute stereochemistry was not assigned.

Enantiomer I, 128A: Tr: 22.9 min. Spectral data are essentially the same to that of example 127 (219).

Enantiomer II, 128B: Tr 33.4 min, Spectral data are essentially same to that of example 127 (219).

Example 129 (224)

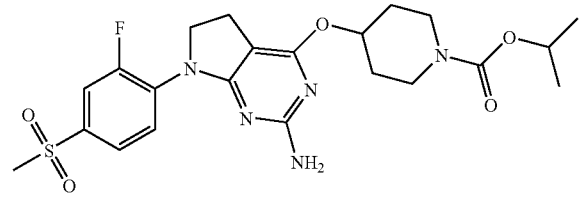

Step 1: Methyl 1-[2-fluoro-4-(methylsulfonyl)phenyl]-2-oxo-3-pyrrolidinecarboxylate (220)

A mixture of 2-fluoro-4-(methylsulfonyl)aniline (3.3 g, 17.3 mmol), 6,6-dimethyl-5,6-dioxaspiro[2.5]octane (9.7 g, 57 mmol) and CH$_3$CN (10 mL) was heated at 60° C. for 3 h under N$_2$. Solvent was evaporated and the residue was heated to 70° C. for 5 h. Methanol (15 mL) and concentrated H$_2$SO$_4$ (0.2 mL) were added and the mixture was heated to reflux for 2 h. The mixture was concentrated and the residue was purified by SiO$_2$ flash column chromatography to give 2.3 g (43%) of the title compound 220 as an off-white solid. $^1$H NMR (400 MHz, DMSO-d$_6$): δ7.89 (br d, J=10.0 Hz, 1H), 7.81-7.73 (m, 2H), 3.85 (br t, J=7.2 Hz, 2H), 3.75 (t, J=8.7 Hz, 1H), 3.68 (s, 3H), 3.30-3.25 (br s, 3H), 2.45-2.35 (m, 2H); LCMS (ESI): m/z 316 (M+H)$^+$.

Step 2: Methyl 1-[2-fluoro-4-(methylsulfonyl)phenyl]-2-thioxo-3-pyrrolidinecarboxylate (221)

A mixture of methyl 1-[2-fluoro-4-(methylsulfonyl)phenyl]-2-oxo-3-pyrrolidinecarboxylate (220) (2.3 g, 7.2 mmol) and P$_4$S$_{10}$ (3.9 g, 8.7 mmol) and THF (100 mL) was heated to 70° C. for 12 h under N$_2$. The mixture was filtered twice washing with EtOAc. The filtrate was concentrated and the residue was purified by Si$_2$O flash column chromatography to afford 1.2 g (50%) of the title product 221 as a pale yellow solid. $^1$H NMR (400 MHz, DMSO-d$_6$): δ7.98 (br d, J=9.3 Hz, 1H), 7.89 (br d, J=8.3 Hz, 1H), 7.81 (dd, J=7.5 Hz, 1H), 4.12-4.08 (m, 3H), 3.70 (s, 3H), 3.30 (s, 3H), 2.60-2.50 (m, 2H); LCMS (ESI): m/z 332 (M+H)$^+$.

Step 3: 2-Amino-7-[2-fluoro-4-(methylsulfonyl)phenyl]-1,5,6,7-tetrahydro-4H-pyrrolo[2,3-d]pyrimidin-4-one (222)

To a solution of guanidine hydrochloride (0.3 g, 3.2 mmol) in anhydrous MeOH (3 mL) was added freshly prepared 1 M NaOMe/MeOH (3.2 mL, 3.2 mmol) and the mixture was stirred for 30 min at ambient temperature under N$_2$. The mixture was filtered and the filtrate added to methyl 1-[2-fluoro-4-(methylsulfonyl)phenyl]-2-thioxo-3-pyrrolidinecarboxylate (222) (0.22 g, 0.64 mmol). The yellow mixture was stirred for 5 min then concentrated and heated stepwise from 60 to 90° C. with a slight vacuum for 1 h. The mixture was allowed to cool to ambient temperature and H$_2$O was added. The pH was adjusted to 6 with 1 M HCl/H$_2$O and the mixture was stirred at ambient temperature for 18 h. The solid was filtered and dried in vacuum for 2 h to provide 0.12 g of crude 3 as an yellow solid. LCMS (ESI): m/z 325 (M+H)$^+$.

Step 4: 4-Chloro-7-[2-fluoro-4-(methylsulfonyl)phenyl]-6,7-dihydro-5H-pyrrolo[2,3-d]pyrimidin-2-amine (223)

To a suspension of crude 2-amino-7-[2-fluoro-4-(methylsulfonyl)phenyl]-1,5,6,7-tetrahydro-4H-pyrrolo[2,3-d]pyrimidin-4-one (222) (0.12 g, 0.36 mmol) in POCl$_3$ (1.2 mL) was added carefully iPr$_2$NEt (0.13 mL, 0.1 g, 0.72 mmol) and the mixture was slowly heated to 70° C. After 1 h, the mixture was concentrated and the residue was partitioned between EtOAc/CH$_2$Cl$_2$ and saturated NaHCO$_3$/H$_2$O. The organic phase was filtered, dried over Na$_2$SO$_4$, and concentrated to give 51 mg of crude 223 as a dark green solid. LCMS (ESI): m/z 343 (M+H)$^+$.

Step 5: 1-Methylethyl 4-({2-amino-7-[2-fluoro-4-(methylsulfonyl)phenyl]-6,7-dihydro-5H-pyrrolo[2,3-d]pyrimidin-4-yl}oxy)-1-piperidinecarboxylate (224)

To a suspension of 60% NaH/mineral oil (70 mg, 1.8 mmol) in THF (3 mL) was added 1-methylethyl 4-hydroxy-1-piperidinecarboxylate (0.16 g, 0.87 mmol) and the mixture was heated to 50° C. for 30 min under N$_2$ then cooled to 0° C. This mixture was added to a solution of crude 4-chloro-7-[2-fluoro-4-(methylsulfonyl)phenyl]-6,7-dihydro-5H-pyrrolo[2,3-d]pyrimidin-2-amine (223) (51 mg, 0.15 mmol) in THF (1 mL). The mixture was heated to 60° C. for 4 h then partitioned between saturated NH$_4$Cl/H$_2$O and EtOAc.

The organic phase was dried over Na$_2$SO$_4$, concentrated, and purified by Si$_2$O flash column chromatography using EtOAc:hexanes (0:100 to 70:30) as eluent to afford 5 mg (7%) of the title product 224 as an off-white solid. $^1$H NMR (400 MHz, CDCl$_3$): δ 8.10-8.00 (br s, 1H), 7.7-7.65 (m, 2H), 5.30 (br s, 1H), 4.90 (heptuplet, J=6.0 Hz, 1H), 4.85-4.60 (m, 2H), 4.15 (br t, J=7.7 Hz, 2H), 3.85-3.70 (m, 2H), 3.40-3.30 (m, 2H), 3.05 (s, 3H), 2.95 (t, J=8.5 Hz, 2H), 2.00-1.95 (m, 2H), 1.85-1.80 (m, 2H), 1.24 (d, J=6.0 Hz, 6H); LCMS (ESI): m/z 494 (M+H)$^+$.

Example 130 (225)

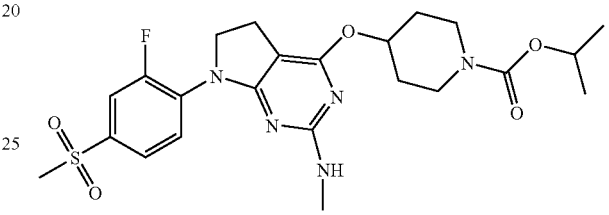

Step 1: 7-[2-Fluoro-4-(methylsulfonyl)phenyl]-2-(methylamino)-1,5,6,7-tetrahydro-4H-pyrrolo[2,3-d]pyrimidin-4-one (225)

To a solution of N-methylguanidine hydrochloride (0.35 g, 3.2 mmol) in anhydrous MeOH (3 mL) was added freshly prepared 1 M NaOMe/MeOH (3.2 mL, 3.2 mmol) and the mixture was stirred for 30 min at ambient temperature under N$_2$. The mixture was filtered and the filtrate added to methyl 1-[2-fluoro-4-(methylsulfonyl)phenyl]-2-thioxo-3-pyrrolidinecarboxylate (221) (0.22 g, 0.64 mmol). The yellow mixture was stirred for 5 min then concentrated and heated stepwise from 60 to 90° C. with a slight vacuum for 1 h. The mixture was allowed to cool to ambient temperature and H$_2$O was added. The pH was adjusted to 6 with 1 M HCl/H$_2$O and the mixture was stirred at ambient temperature for 18 h. The aqueous phase was decanted and the sticky solid was co-evaporated with CH$_3$CN to provide 0.12 g of crude 225 as an orange solid. LCMS (ESI): m/z 339 (M+H)$^+$.

Step 2: 4-Chloro-7-[2-fluoro-4-(methylsulfonyl)phenyl]-N-methyl-6,7-dihydro-5H-pyrrolo[2,3-d]pyrimidin-2-amine (226)

To a suspension of crude 7-[2-fluoro-4-(methylsulfonyl)phenyl]-2-(methylamino)-1,5,6,7-tetrahydro-4H-pyrrolo[2,3-d]pyrimidin-4-one (225) (0.12 g, 0.36 mmol) in POCl$_3$ (1.2 mL) was added carefully iPr$_2$NEt (0.13 mL, 0.1 g, 0.72 mmol) and the mixture was slowly heated to 70° C. After 1 h, the mixture was concentrated and the residue was partitioned between EtOAc/CH$_2$Cl$_2$ and saturated NaHCO$_3$/H$_2$O. The organic phase was filtered, dried over Na$_2$SO$_4$, and concentrated. The dark green residue was triturated with EtOAc and filtered. The filtrate was concentrated to give 16 mg of 226 as an off-white solid. $^1$H NMR (400 MHz, DMSO-d$_6$): δ 8.00-7.90 (br m, 1H), 7.84 (br d, J=7.8 Hz, 1H), 7.74 (dd, J$_1$=8.5, J$_2$=1.7 Hz, 1H), 7.20-7.10 (br m, 1H), 4.20-4.00 (br m, 2H), 3.26 (s, 3H), 3.00 (t, J=8.3 Hz, 2H), 2.66 (d, J=4.6 Hz, 3H); LCMS (ESI): m/z 357 (M+H)$^+$.

Step 3: 1-Methylethyl 4-{[7-[2-fluoro-4-(methylsulfonyl)phenyl]-2-(methylamino)-6,7-dihydro-5H-pyrrolo[2,3-d]pyrimidin-4-yl]oxy}-1-piperidinecarboxylate (227)

To a suspension of 60% NaH/mineral oil (8.4 mg, 0.21 mmol) in THF (1.5 mL) was added 1-methylethyl 4-hydroxy-1-piperidinecarboxylate (20 mg, 0.11 mmol) and the mixture was heated to 50° C. for 30 min under $N_2$ then cooled to 0° C. This mixture was added to a solution of 4-chloro-7-[2-fluoro-4-(methylsulfonyl)phenyl]-N-methyl-6,7-dihydro-5H-pyrrolo[2,3-d]pyrimidin-2-amine (226) (15 mg, 0.04 mmol) in THF (1 mL). The mixture was heated to 60° C. for 4 h then partitioned between saturated $NH_4Cl/H_2O$ and EtOAc. The organic phase was dried over $Na_2SO_4$, concentrated, and purified by preparative HPLC (C18 column, $CH_3CN:H_2O$ gradient) followed by $Si_2O$ flash column chromatography using EtOAc:hexanes (0:100 to 70:30) as eluent to afford 5 mg (23%) of the title product 227 as an off-white solid foam. $^1H$ NMR (400 MHz, $CDCl_3$): δ 8.15-8.05 (br s, 1H), 7.7-7.65 (m, 2H), 5.30 (br s, 1H), 4.90 (heptuplet, J=6.0 Hz, 1H), 4.85-4.60 (m, 1H), 4.15 (br t, J=7.3 Hz, 2H), 3.85-3.70 (m, 2H), 3.40-3.30 (m, 2H), 3.05 (s, 3H), 2.95 (t, J=8.5 Hz, 2H), 2.92 (d, J=4.9 Hz, 3H), 2.00-1.95 (m, 2H), 1.85-1.80 (m, 2H), 1.24 (d, J=6.0 Hz, 6H); LCMS (ESI): m/z 508 (M+H)$^+$.

Example 131 (228)

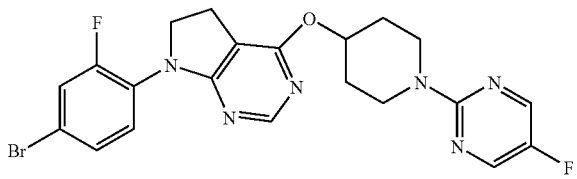

7-(4-Bromo-2-fluorophenyl)-4-{[1-(5-fluoro-2-pyrimidinyl)-4-piperidinyl]oxy}-6,7-dihydro-5H-pyrrolo[2,3-d]pyrimidine (228)

Following the procedure described for 10 (example 1, step 10), the reagent 23 (1.25 g, 6.34 mmol), NaH (0.950 g, 23.73 mmol), and the compound 29 (prepared via reductive amination using the aldehyde 209 and 4-bromo-2-fluoroaniline following the procedure described for 211, 2.60 g, 7.91 mmol) were refluxed for 4 h. The regular work-up and chromatography afforded 2.90 g (94%) of the title product 228 as a white solid. $^1H$ NMR (400 MHz, DMSO-$d_6$): δ 8.23 (s, 1H), 8.20 (s, 2H), 7.50 (t, J=8.4 Hz, 1H), 7.33-7.28 (m, 2H), 5.44-5.36 (m, 1H), 4.22-4.16 (m, 2H), 4.05 (t, J=8.8 Hz, 2H), 3.63-3.56 (m, 2H), 3.09 (t, J=8.8 Hz, 2H), 2.09-2.03 (m, 2H), 1.83-1.74 (m, 2H), LCMS (ESI): m/z 490 (M+H)$^+$.

Prophetic Examples

The following examples may be prepared by methods analogous to those herein described:

Example 132

3-Fluoro-4-(4-{[1-(5-fluoro-2-pyrimidinyl)-4-piperidinyl]oxy}-5,6-dihydro-7H-pyrrolo[2,3-d]pyrimidin-7-yl)benzonitrile

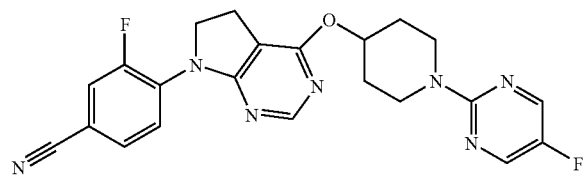

Example 133

3-Fluoro-4-[4-({1-[3-(1-methylethyl)-1,2,4-oxadiazol-5-yl]-4-piperidinyl}oxy)-5,6-dihydro-7H-pyrrolo[2,3-d]pyrimidin-7-yl]benzonitrile

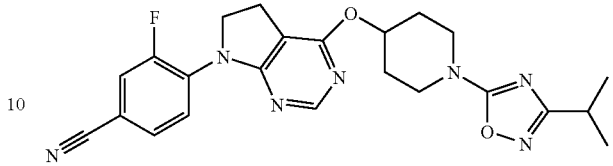

Example 134

4-[4-({1-[3-(1-Methylethyl)-1,2,4-oxadiazol-5-yl]-4-piperidinyl}oxy)-5,6-dihydro-7H-pyrrolo[2,3-d]pyrimidin-7-yl]benzonitrile

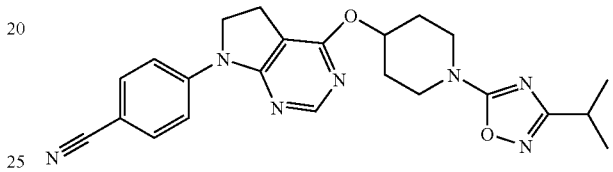

Example 135

4-(4-{[1-(5-Fluoro-2-pyrimidinyl)-4-piperidinyl]oxy}-5,6-dihydro-7H-pyrrolo[2,3-d]pyrimidin-7-yl)benzonitrile

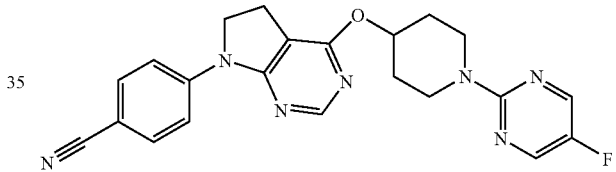

Example 136

4-{[1-(5-Fluoro-2-pyrimidinyl)-4-piperidinyl]oxy}-7-[4-(methylsulfonyl)phenyl]-6,7-dihydro-5H-pyrrolo[2,3-d]pyrimidine

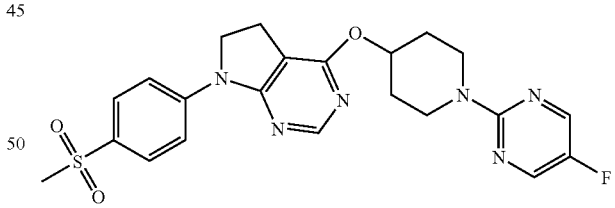

Example 137

4-({1-[3-(1-Methylethyl)-1,2,4-oxadiazol-5-yl]-4-piperidinyl}oxy)-7-[4-(methylsulfonyl)phenyl]-6,7-dihydro-5H-pyrrolo[2,3-d]pyrimidine

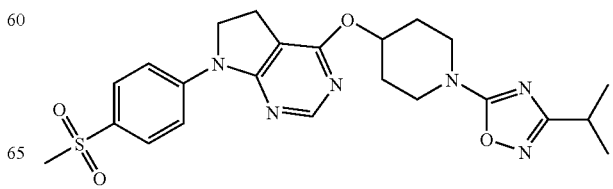

Example 138

4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine

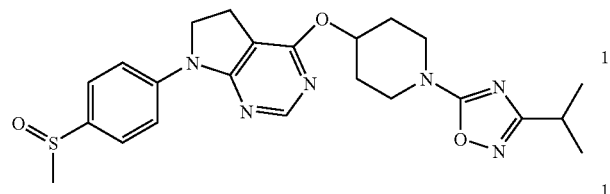

Example 139

Example 139A (R)-4-({1-[3-(1-methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine

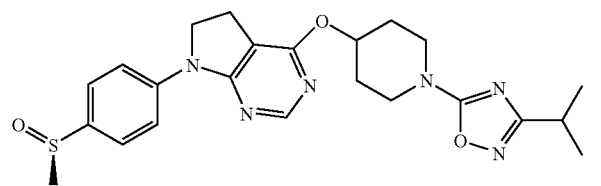

Example 139B (S)-4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine

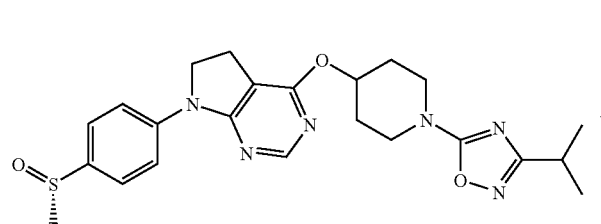

Example 140

4-{[1-(5-fluoro-2-pyrimidinyl)-4-piperidinyl]oxy}-7-[4-(methylsulfinyl)phenyl]-6,7-dihydro-5H-pyrrolo[2,3-d]pyrimidine

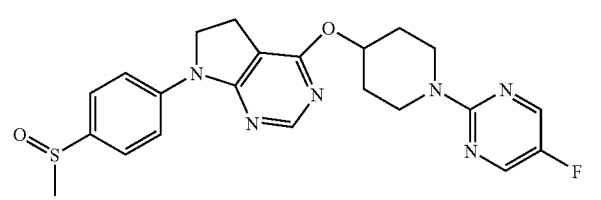

Example 141

Example 141A (R)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine

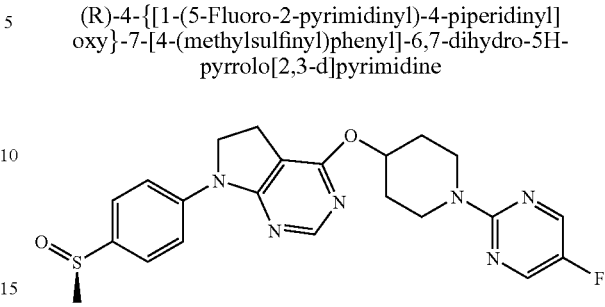

Example 141B (S)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine

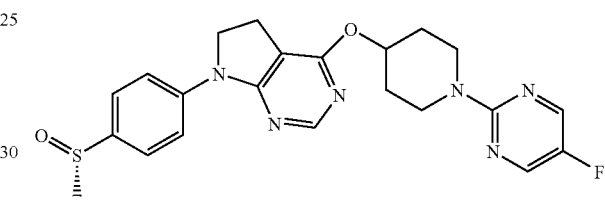

Example 142

S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate

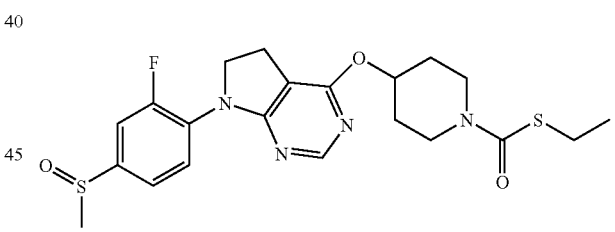

Example 143

Example 143A (R)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate

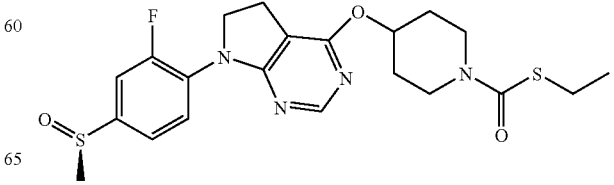

Example 143B (S)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate

Example 147

1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate

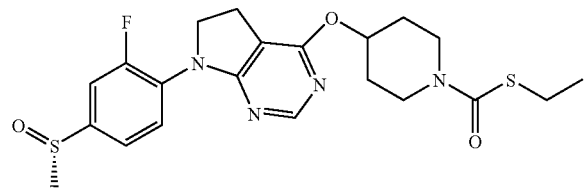

Example 144

1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate

Example 148

(R)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate

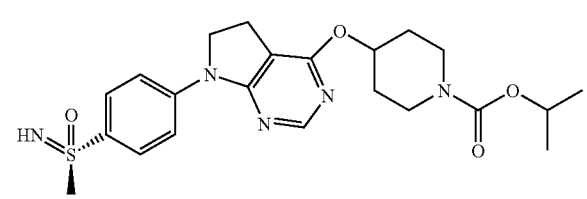

Example 145

(R)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate

Example 149

(S)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate

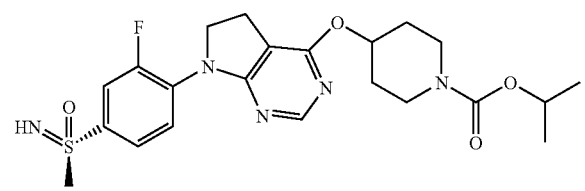

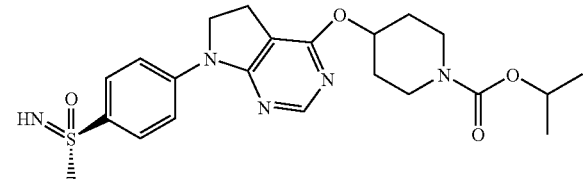

Example 146

(S)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate

Example 150

(R)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate

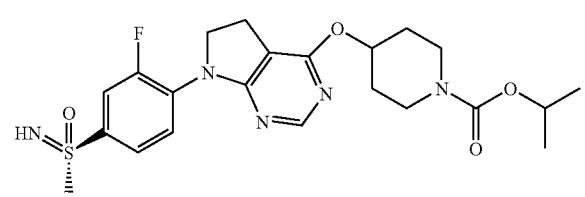

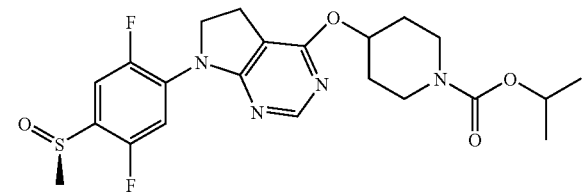

Example 151

(S)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate

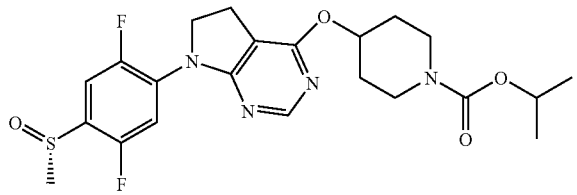

Biological Experimentals and Data

GPR119Agonist Activity

Compounds of the current invention are believed useful in the treatment and/or prophylaxis of conditions and diseases mediated through GPR119. Activity mediated through GPR119 was determined using cells transfected with the human GPR119 receptor.

Materials

Black, 384-well, tissue culture-treated plates (#781091) were obtained from Greiner, (Germany), Steady-Glotm Luciferase Assay System Kit (# E2550) was from Promega (Madison, Wis.), plate seals (#097-05-00006) were from Beckman/Sagian (Fullerton, Calif.). DMEM/F12 medium (#11039-021), fetal bovine serum (#16140-071), L-glutamine (#25030-081), 0.05% trypsin (#25300-054), G418 (#10131-035) and dPBS (#4190-144) were obtained from Gibco BRL (Gaithersburg, Md.). Chinese hamster ovary cells stably expressing 6×CRE-luc+ (CHO6CRE) were generated in-house.

Methods

CHO6CRE cells were transfected by electroporation with the human GPR119 receptor. A stable clone was selected using G418 for functional agonist assays. GPR119-CHO6CRE cells were propagated in complete medium (DMEM/F12, 5% FBS, 2 mM I-glutamine) in T225 flasks. Twenty-four hours prior to assay, cells were harvested with 5 ml of 0.05% trypsin, washed with complete medium and plated at a concentration of 15,000 cells/well in complete medium in black 384-well plates. The next day, the medium was removed from the cells and replaced with 20 µl/well of serum-free DMEM/F12, 1% DMSO using Matrix Well-mate. Immediately following this addition, agonists (20 µL, 1% DMSO) as 11-point concentration curves were pipetted into the medium using a Packard Minitrak and plates were incubated for five hours at 37° C. in a cell culture incubator. Following the incubation, 15 µl of a 1:1 mixture of Steady-Glo™ and dPBS/1 mM $CaCl_2$/1 mM $MgCl_2$ was added to the plates using the Well-mate. Plates were sealed and luciferase activity was quantitated on a TopCount™ microplate scintillation counter (Packard) using 3 seconds/well count time. Agonist activity was quantified by non-linear regression analysis using a curve-fitting program based in Microsoft EXCEL.

The compounds of the present invention are believed to provide a $pIC_{50}$ of 5 or greater.

Although $pIC_{50}$ values were generated for certain of the present compounds, these values should be considered exemplary. Those skilled in the art will appreciate the variability in performing and recording data using the biological activity assays that are herein described. As used herein, the focus on $pIC_{50}$ values of 5 or greater is a subjective choice and is not indicative that compounds having less activity are inactive or inoperable.

GPR119 Agonists as GLP-1 and GIP Secretagogues

The Effect of a GPR119 Agonist on Circulating GLP-1 and GIP Assessed In Vivo in Mice.

Ten weeks old C57BL/6 male mice (Taconic Farms, USA) were fasted overnight then randomly distributed into 6 treatment groups (n=10 mice per treatment group) receiving either vehicle (0.5% HPMC/0.1% Tween80), or a GPR119 agonist (Example 1) at five different doses (1, 3, 10, 30 or 60 mg/kg) by oral gavage. All animals were dosed with a volume of 10 mL/kg of their designated treatment. Sixty minutes after the oral gavage the mice were anesthetized using isofluorane for collection of blood samples by cardiac puncture. All mice were euthanized by cervical dislocation immediately following the cardiac puncture. Blood samples were placed in chilled $K_2$-EDTA coated capiject tubes (Cat. #T-MQK, Terumo Medical Corp, Elkton Md.), supplemented with a DPP4 inhibitor and Aprotenin (Trasylol; Bayer Pharmaceuticals, West Haven, Conn.) yielding a final concentration of 30 µL and 250 KIU/mL respectively. The tubes were immediately centrifuged at 4° C., the plasma collected and stored at −80° C. for subsequent hormone measurements. Total GLP-1 levels were determined using a MULTI-ARRAY® electrochemoluminescence assay from Meso Scale Discovery (Cat #K110-FAC-2; Gaithersburg, Md.). Total GIP levels were determined using an ELISA assay (Cat# EZRMGIP-55K, Linco Diagnostic Services, St Charles, Mo.).

Figure 2:
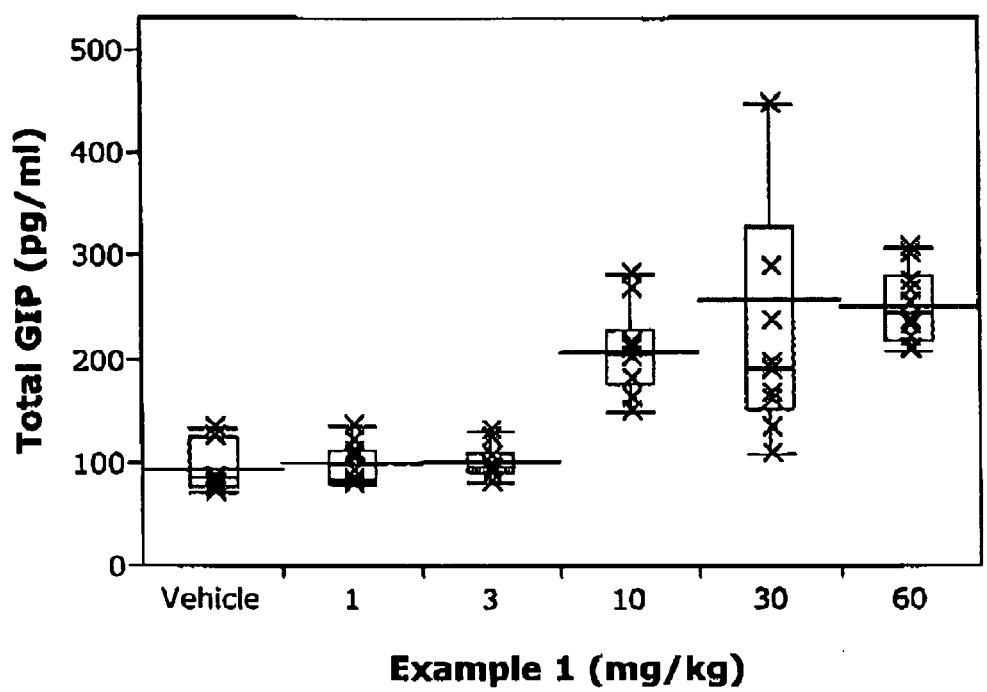

Data is represented as box plots summarizing the distribution of individual data point for each treatment group. The upper and lower end of the box corresponds to the $75^{th}$ and $25^{th}$ percentile respectively, with whiskers extending to points within the 1.5*interquartile range. Horizontal lines represents mean data. FIG. 1 and FIG. 2 show total GLP-1 and total GIP respectively measured in circulation following administration of vehicle or a GPR119 agonist (Example 1) at doses as indicated.

These results illustrate that administration of Example 1, a GPR119 agonist, produces a dose dependent increase in circulating total GLP-1 and total GIP levels in mice.

The Effect of a GPR119 Agonist on Circulating GLP-1 and GIP Evaluated In Vivo in Wild-Type and GPR119 Knock-Out Mice.

17 weeks old male transgenic wild-type (WT) and GPR119 knock-out (KO) mice (Charles River Laboratories, USA) were fasted overnight then randomly distributed into two treatment groups for each genotype with n=8 and n=10 animals per treatment group for KO and WT mice respectively. Animals received either vehicle (0.5% HPMC/0.1% Tween80) or a GPR119 agonist (Example 1) at a dose of 30 mg/kg (10 mL/kg), administered by oral gavage. Sixty minutes after the oral gavage the mice were anesthetized using isofluorane and a blood sample was collected by cardiac puncture, before sacrificing the animal by cervical dislocation. Blood samples were treated as described above for determination of incretin hormone levels. Plasma glucose levels were measured using an Olympus AU640 analyzer (Olympus America Inc, Melville, N.Y.), and insulin levels an electrochemoluminescence assay (Bioveris, Gaithersburg Md.).

Figure 3:
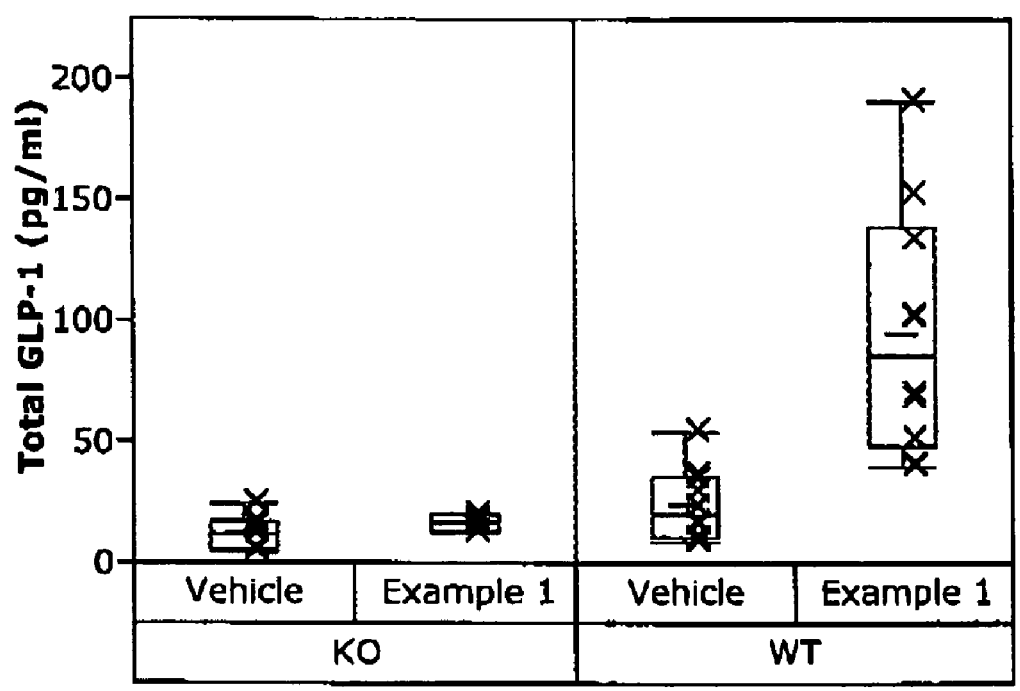
Figure 4:
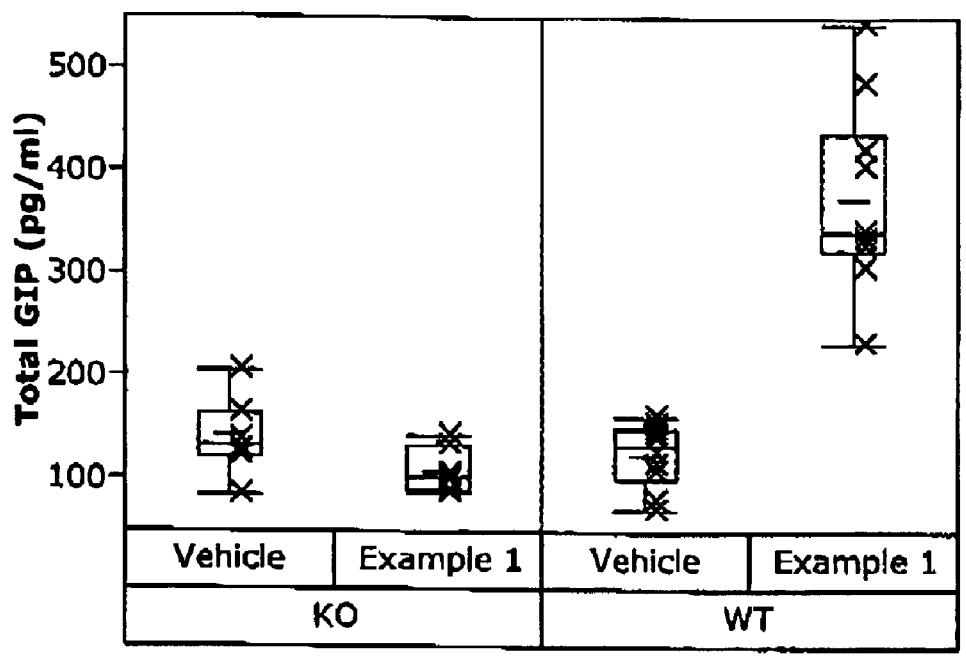
Figure 5:
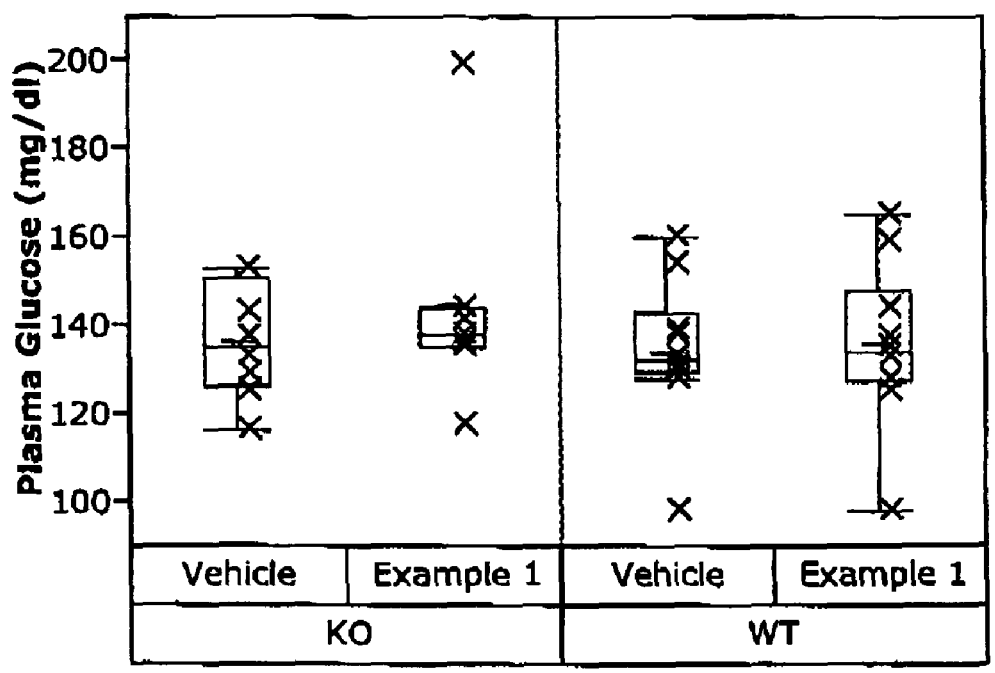
Figure 6:
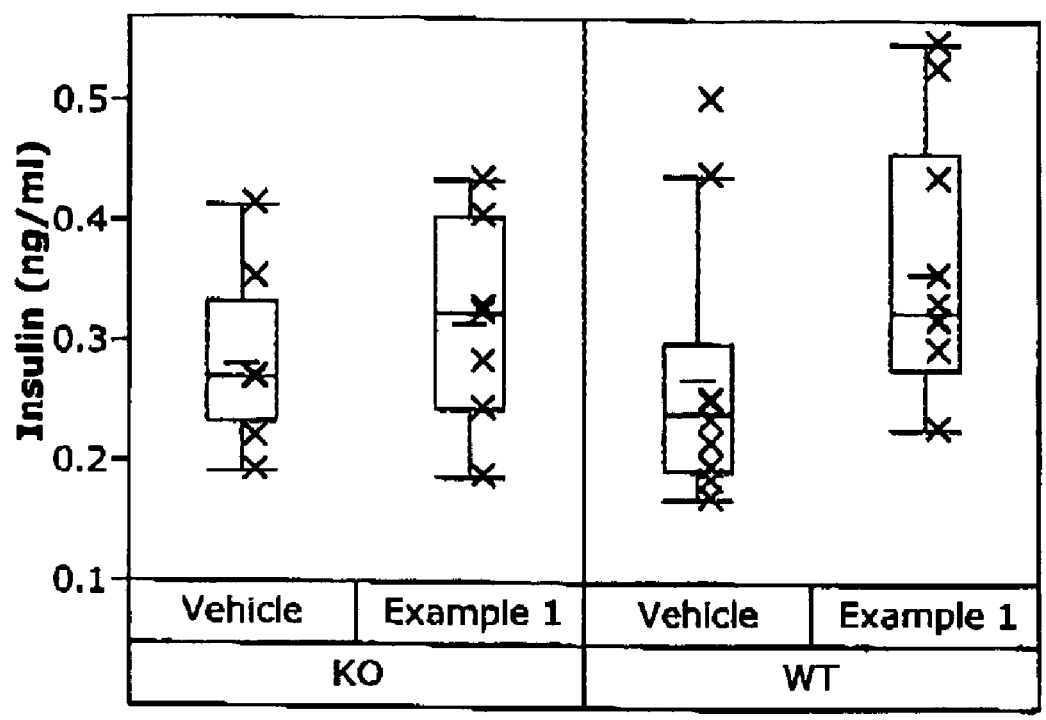

Data is represented as box plots summarizing the distribution of data for each treatment group, as described above. Horizontal lines represent the mean data. FIG. 3 and FIG. 4 show total GLP-1 and GIP levels measured in circulation following administration of vehicle or 30 mg/kg GPR119 agonist (Example 1) in WT and KO mice. Corresponding glucose and insulin levels are shown in FIG. 5 and FIG. 6.

These results illustrate that the increase in incretin hormone levels produced by Example 1, a GPR119 agonist, is dependent on the GPR119 receptor as the compound was without effect in GPR119 knock out mice. Furthermore, fasting glucose and insulin levels were not affected.

The Effect of a GPR119 Agonist on Circulating GLP-1 and GIP Evaluated In Vivo in Rats Male Sprague-Dawley rats (Charles River Laboratories, USA) had a catheter surgically implanted into the jugular and allowed to recover for one week following the surgery. On the day before the experiment, food was removed in the afternoon and the following morning animals were randomly assigned to two treatment groups, vehicle (n=7) or a GPR119 agonist (Example 1; n=8). Blood samples were collected prior to, and 90 minutes following oral administration of either vehicle (0.5% HPMC/0.1% Tween80) or 10 mg/kg of Example 1. Blood samples were treated as described above and analyzed for incretin hormones, plasma glucose and insulin. The rats were sacrificed at the end of the study by an overdose of Nembutal® pentobarbital.

Figure 7:
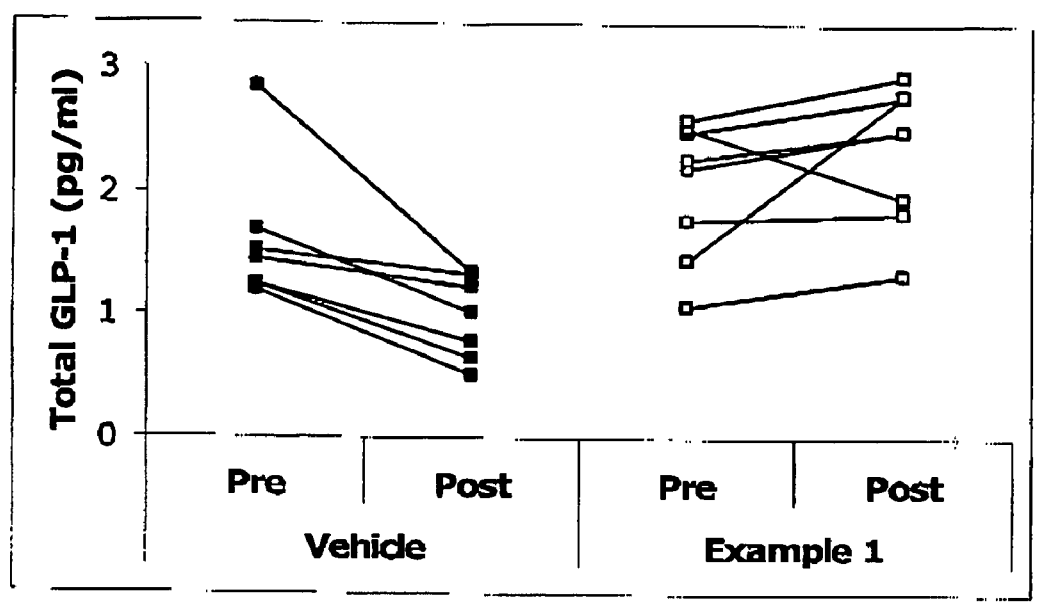
Figure 8:
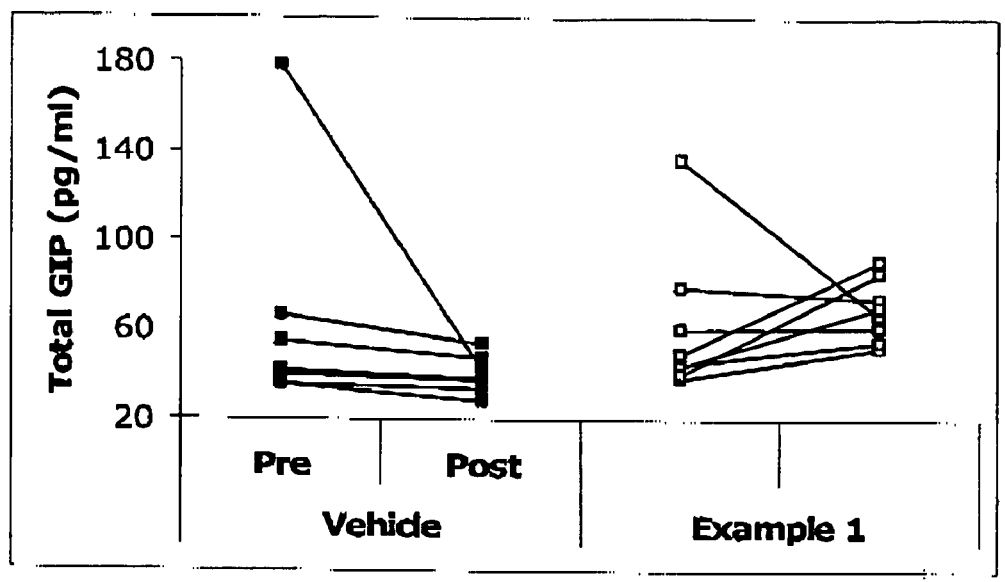
Figure 9:
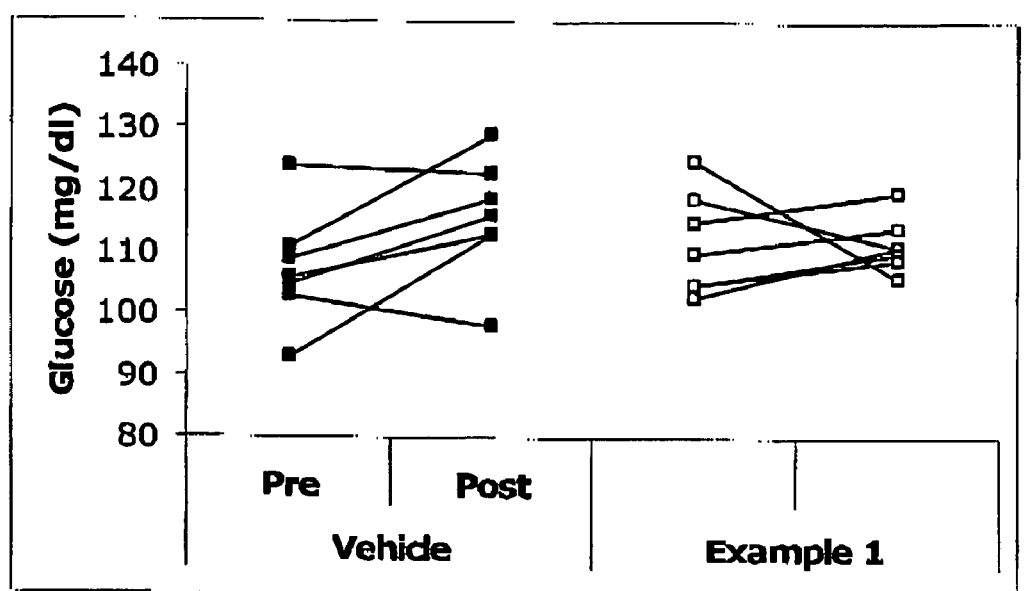
Figure 10:
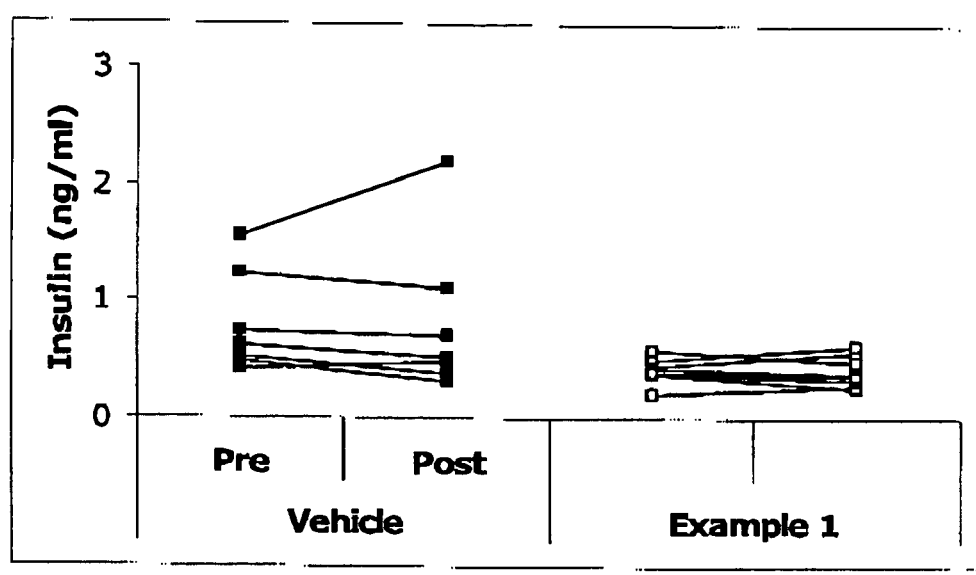

Data is represented as line graphs of the measurements prior to gavage (Pre) and 90 min following administration of vehicle or GPR119 agonist (Post) analyzed for total GLP-1 (FIG. 7), total GIP (FIG. 8), plasma glucose (FIG. 9) and insulin (FIG. 10) for individual animals.

These results demonstrates that the circulating levels of total GLP-1 and total GIP increases in rats treated with a GPR119 agonist whereas the hormone levels decrease with time in vehicle treated animal. As in mice, fasting glucose and insulin are not significantly affected by the GPR119 agonist compared to vehicle, or the baseline measurements within the treatment group.

GPR119 agonists as modulator of glucose stimulated insulin secretion.

The Effect of a GPR119 Agonist on Glucose Stimulated Insulin Secretion In Vivo in Rats Assessed by the Hyperglycemic Clamp.

Male Wistar rats (Taconic farms, USA), weighing 300-350 gram, had catheters surgically implanted into the jugular and femoral veins and allowed to recover for one week following the surgery. On the day before the experiment, food was removed in the afternoon for an overnight fast. The following morning animals were randomly assigned to three treatment groups, vehicle (n=19) and either 1 mg/kg (n=8) or 10 mg/kg (n=8) of a GPR119 agonist (Example 1), and baseline blood samples were collected from the jugular vein. Animals were then administered either vehicle or Example 1 by oral gavage. A second blood sample was collected approximately 90 minutes after the oral gavage immediately prior to starting the hyperglycemic clamp. The clamp was initiated by infusing an empirically determined glucose bolus over 15-30 seconds into the femoral vein, followed by a variable rate glucose infusion adjusted to achieve a stable plasma glucose level of 190-210 mg/dl. After infusion of the glucose bolus, blood samples were collected every 5 minutes for glucose measurements. Samples for C-peptide level were collected a 2, 5, 10, 15, 20, 25, 30, 46, 60, 90 and 120 minutes during the hyperglycemic clamp. C-peptide was measured as a surrogate for insulin as it is co-secreted with insulin in equimolar amount with lower hepatic clearance, thus a better reflection of insulin secretion from the pancreatic β-cells. All blood samples were placed in individual tubes containing a gel clot activator (Cat # T-MG, Terumo Medial Corporation, Elkton, Md.) and allowed to clot in room temperature for 20 min before centrifugation and collection of serum. Glucose levels were measured using an Olympus AU640 analyzer (Olympus America Inc, Melville, N.Y.), and C-peptide levels by an RIA (Linco Diagnostic services, St Charles, Mo.). The rats were sacrificed at the end of the study by an overdose of Nembutal.

Figure 11:
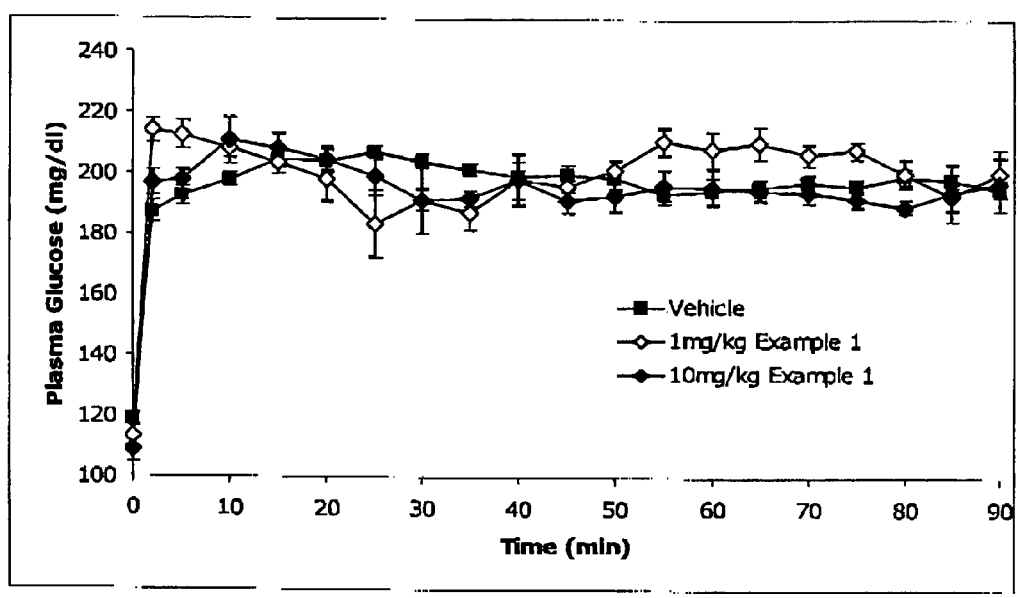
Figure 12:
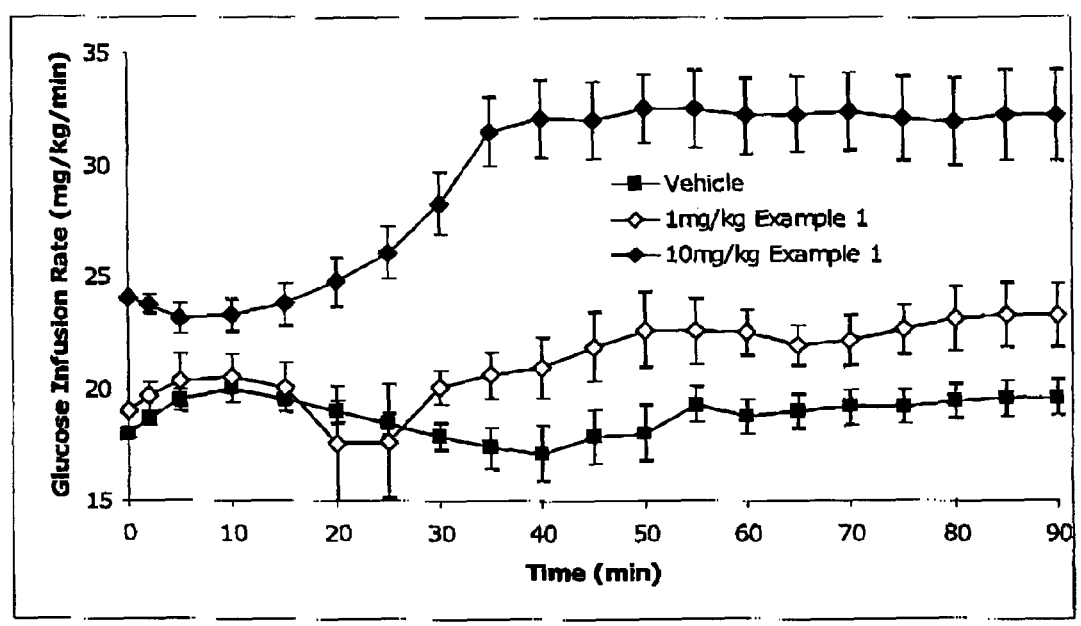
Figure 13:
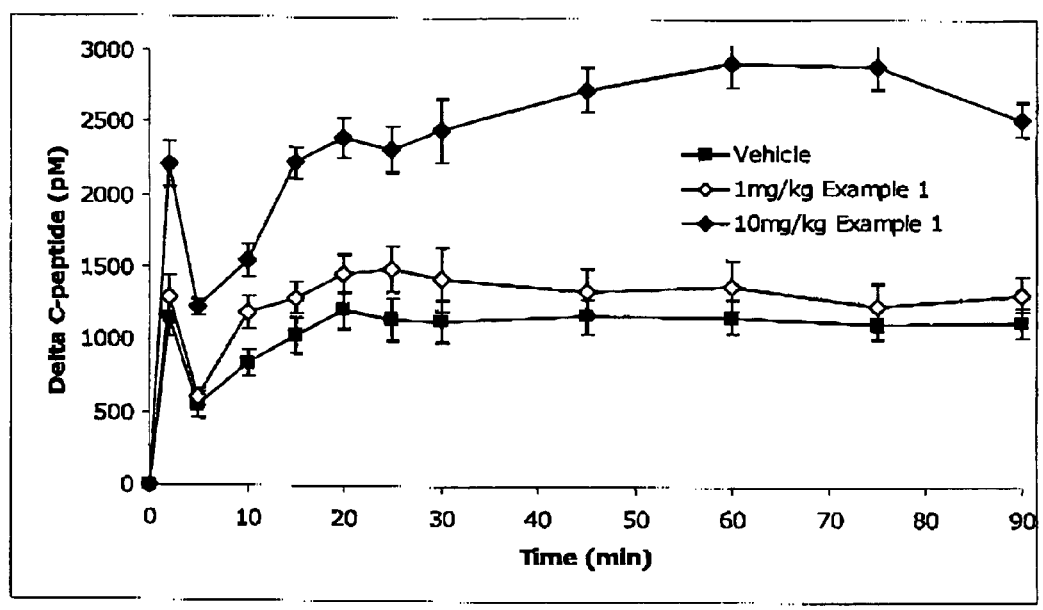

FIG. 11 shows the plasma glucose levels±SEM achieved during the hyperglycemic clamp. There was no difference in plasma glucose levels between treatment groups. The glucose infusion rates (GIR) required to sustain the hyperglycemic clamp is shown in FIG. 12. Animals treated with 10 mg/kg Example 1 required more exogenous glucose to maintain the clamp compared to 1 mg/kg Example 1 or vehicle. The characteristic biphasic insulin secretion response (measured as an increase in C-peptide levels) elicited by the rapid increase in plasma glucose levels is shown in FIG. 13, with the first phase occurring within the first 5 minutes and the second phase from 15 minutes and beyond. At 10 mg/kg, Example 1 significantly increased C-peptide levels compared to either vehicle or 1 mg/kg of Example 1 throughout the duration of the hyperglycemic clamp.

These data illustrate that GPR119 agonists, as demonstrated with Example 1 augments both the first (0-5 min) and the second phase (15-90 min) glucose stimulated insulin secretory response during the hyperglycemic clamp in rat.

Effect of a GPR119 Agonist on Glucose Stimulated Insulin Secretion and Glucose Disposal In Vivo in Rats Assessed by the Intravenous Glucose Tolerance Test.

Male Sprague-Dawley rats (Charles River Laboratories, USA) had catheters surgically implanted into the jugular vein and allowed to recover for one week. On the day of the experiment, food was removed in the morning and animals were randomly assigned to two treatment groups, vehicle (n=8) or GPR119 agonist (Example 1; n=9). In the afternoon, baseline blood samples were collected prior to, and 90 minutes following oral administration of either vehicle (0.5% HPMC/0.1% Tween80) or 10 mg/kg Example 1. The intravenous glucose tolerance test was initiated immediately after the 90 minute blood sample by intravenous infusion of 0.5 g/kg dextrose over 15-30 seconds into the jugular vein, Blood samples were collected from the jugular vein at 2, 5, 10, 15, and 30 min and treated as described for the hyperglycemic clamp. Serum was collected for analysis of glucose levels using an Olympus AU640 clinical chemistry analyzer (Olympus America Inc, Melville, N.Y.) and insulin levels by an electrochemoluminescence assay (Bioveris, Gaithersburg Md.). The rats were sacrificed at the end of the study by an overdose of Nembutal.

Figure 14:
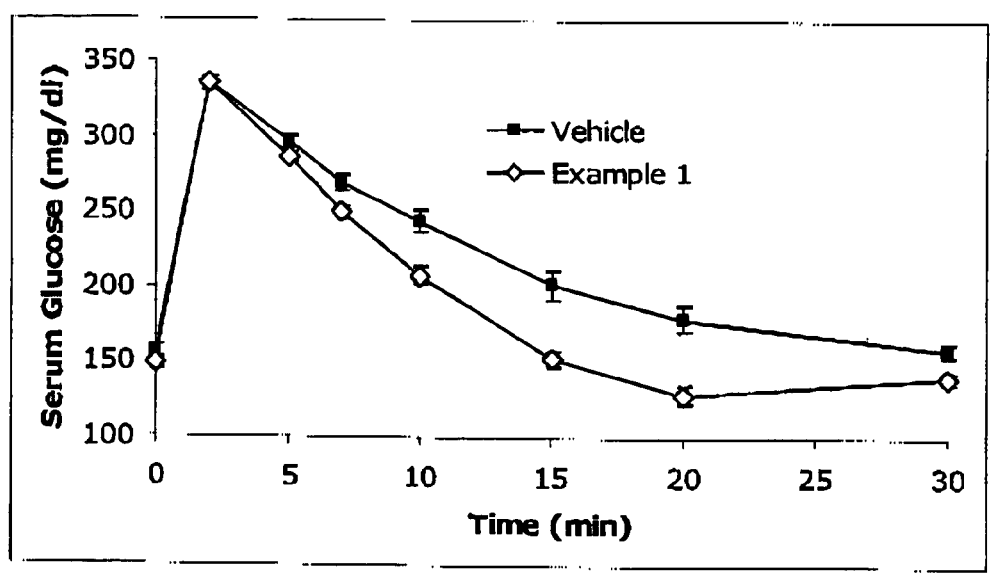
Figure 15:
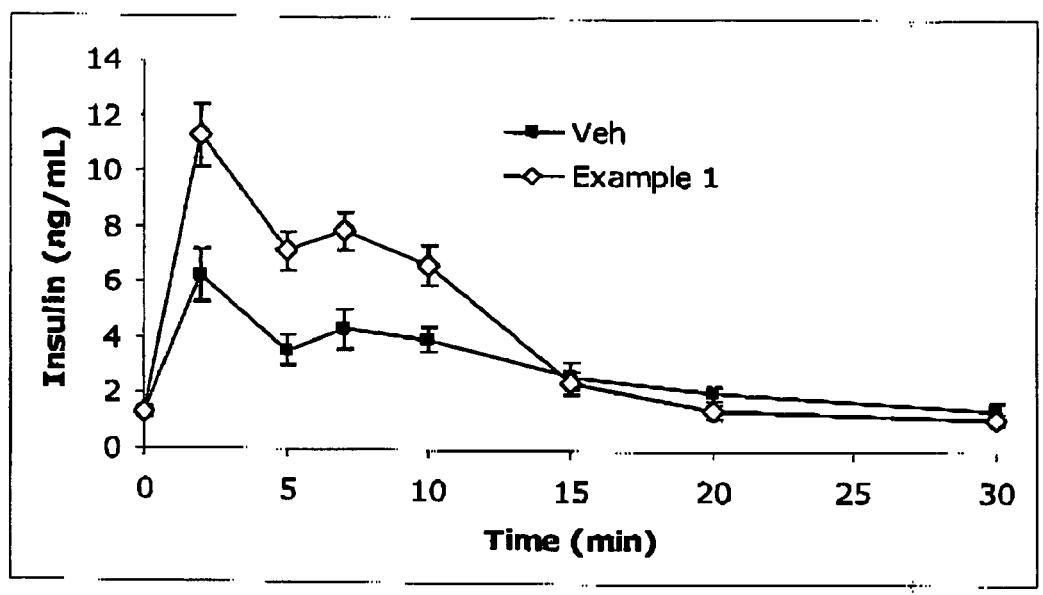

FIG. 14 and FIG. 15 show circulating plasma glucose and insulin concentrations at each time point throughout the intravenous glucose tolerance test. The data is represented as the average glucose and insulin levels±SEM for all animals in for the two treatment groups. The area under the glucose curve (AUC) was significantly reduced, and the rate of glucose elimination was significantly increased in animals treated with Example 1 compared to vehicle treated animals. The peak (2 minute) insulin response and the area under the insulin curve were significantly increased in Example 1 treated animals compared to vehicle.

These results illustrates that GPR119 agonists, here represented by Example 1, augments glucose stimulated insulin secretion and enhance glucose disposal during the intravenous glucose tolerance test.

GPR119 Agonists and Glucose Homeostasis

The Effect of a GPR119 Agonists on Oral Glucose Tolerance in Normal mice

Figure 16:
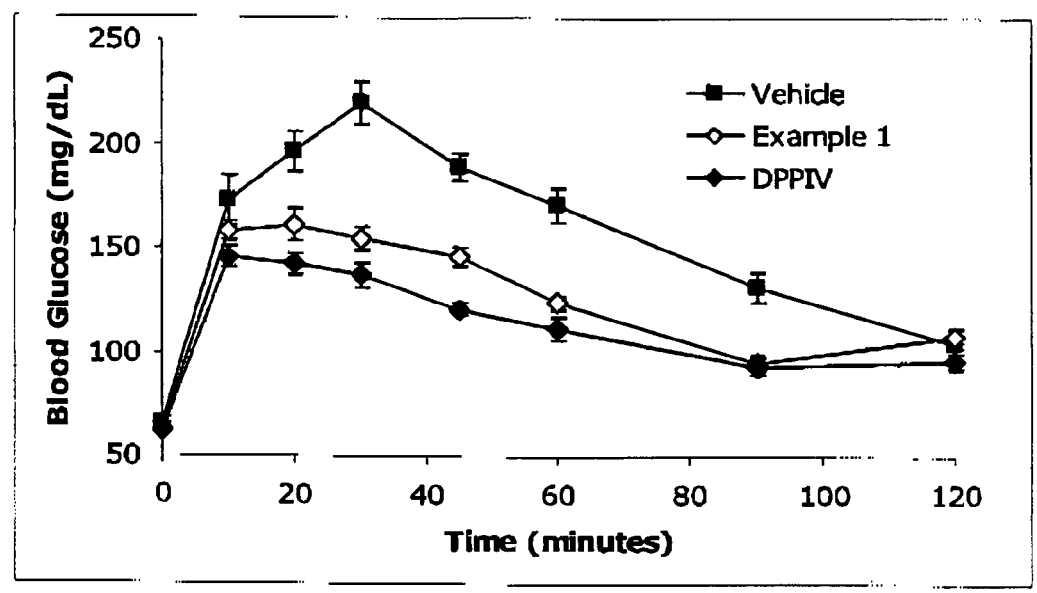

Nine weeks old male C57BL/6 mice (Taconic farms, USA) were fasted overnight and randomly assigned to three different treatment groups (n=9-10 per treatment arm) to receive vehicle (0.5% HPMC/0.1% Tween80), a GPR119 agonist (Example 1, 30 mg/kg) or a positive control (10 mg/kg), specifically a DPPIV inhibitor known to improve glucose tolerance in vivo by preventing degradation of the GLP-1 and GIP. Vehicle or compounds were delivered by oral gavage at a volume of 10 mL/kg, and the tip of tail was nicked using a scalpel to allow whole blood glucose measurements. One hour after administration of vehicle or test compounds, 2 g/kg of dextrose was administered by oral gavage. Whole blood glucose levels were determined from the abrasion at the tip of the tail at time points as indicated in FIG. 16 using a Glucometer (Freestyle, Therasense). At the end of the study the mice were sacrificed by cervical dislocation.

FIG. 16 shows the average whole blood glucose concentration±SEM for the animals in each treatment group. These results illustrate that GPR119 agonists, as demonstrated with Example 1, and the DPPIV compound significantly enhanced glucose disposal during the course of the oral glucose tolerance test in mice.

The Effect of a GPR119 Agonist on Oral Glucose Tolerance in Wild Type and GPR119 Knockout Mice Male transgenic wild type (WT) and GPR119 knock-out (KO) mice (Charles River Laboratories, USA), at an age of 12 weeks, were fasted overnight (approximately 15 hrs) then randomly grouped (n=8-10) to receive vehicle (0.5% HPMC/ 0.1% Tween80), a GPR119 agonist (30 mg/kg) or a positive control (10 mg/kg), the DPPIV inhibitor as described above. Vehicle or compounds were delivered orally by oral gavage at a volume of 10 mL/kg, and the tip of tail was nicked using a scalpel to allow whole blood glucose measurements. One hour after administration of vehicle or test compounds, dextrose was administered orally at 2 g/kg. Whole blood glucose levels were measured prior to, and 10, 20, 30, 45, 60, 90 and 120 min after the oral glucose load using a Glucometer (Freestyle, Therasense) from the tip of tail. At the end of the study the mice were sacrificed by cervical dislocation.

Figure 17:
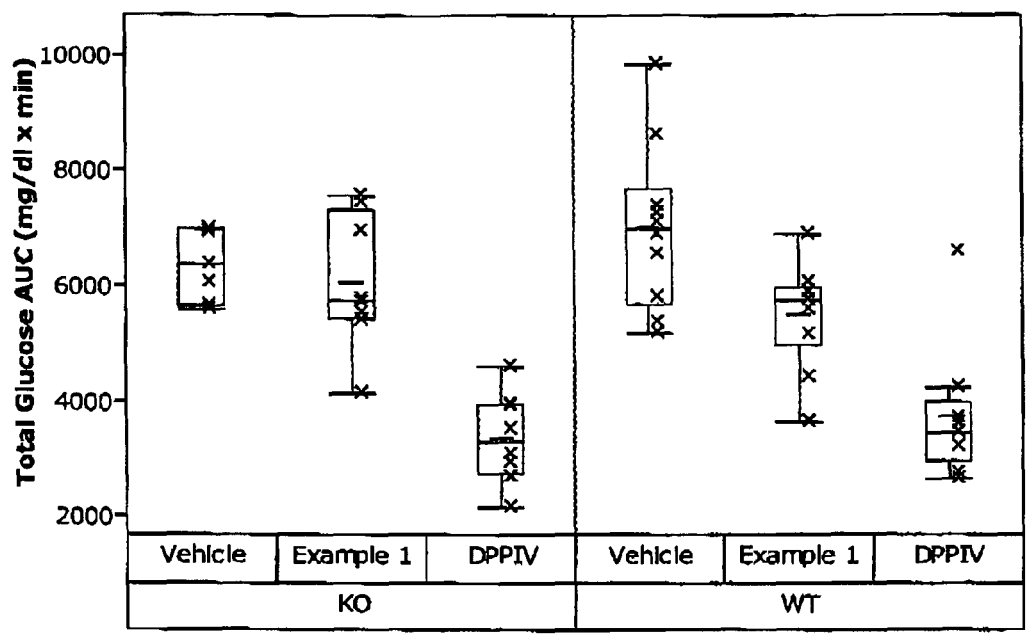

The glucose tolerance was calculated as the area under the glucose curve (AUC). Data is represented as box plots summarizing the distribution of data for each treatment group, as described above. Horizontal lines represent the mean data. FIG. 17 shows the total glucose AUC for each treatment group in WT and KO mice. Example 1 at 30 mg/kg, and the positive control (DPPIV) improved glucose tolerance as it reduced the total glucose AUC by 28%, and 47% respectively. In GPR119 KO mice Example 1 had no effect on glucose tolerance whereas DPPIV significantly reduced total glucose AUC by 45%.

These results demonstrate that GPR119 agonists, here illustrated by Example 1, improve glucose tolerance through interaction with the GPR119 receptor.

The Effect of a Gpr119 Agonist on Oral Glucose Tolerance in Rats

Figure 18:
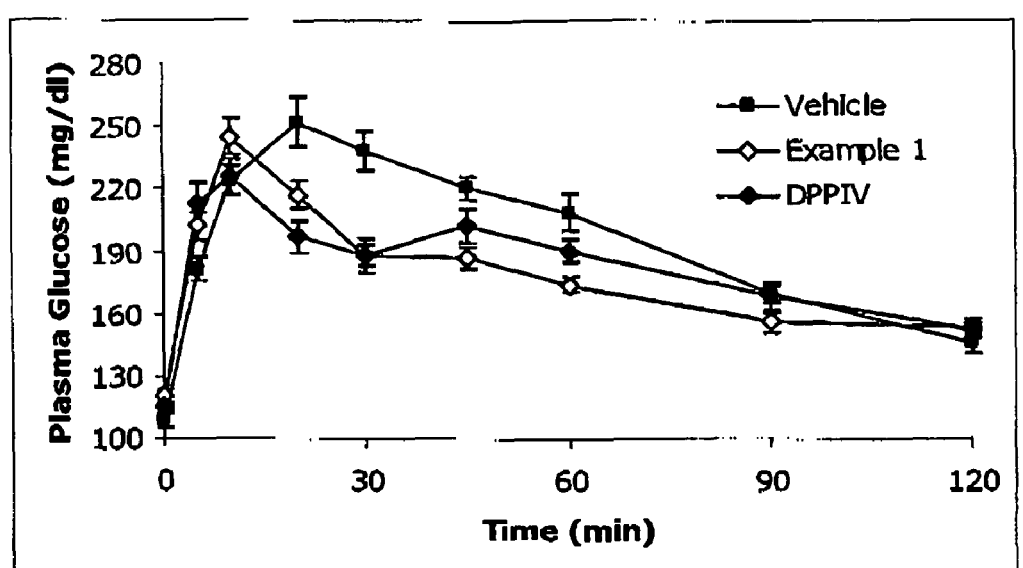

Eight weeks old male Sprague-Dawley rats had catheters surgically implanted into the jugular catheter vein and allowed to recover for one week. Food was removed in the afternoon the day before the experiment to fast animals overnight. The following morning animals were randomly assigned to treatment groups to receive vehicle (n=7) (0.5% HPMC/0.1% Tween80), a GPR119 agonist (Example 1, 10 mg/kg) or a positive control (10 mg/kg), namely a DPPIV inhibitor as described above. Vehicle and compounds were delivered by oral gavage at a volume of 10 mg/kg. Two and a half hours after administration of vehicle or GPR119 agonist and one hour after administration of DPPIV inhibitor, 2 g/kg dextrose was administered orally. Blood samples were collected at timepoints as indicated in FIG. 18, and placed in chilled $K_2$-EDTA containing tubes (Cat. #T-MQK, Terumo Medical Corp, Elkton Md.), supplemented with a DPP4 inhibitor and Aprotenin (Trasylol; Bayer Pharmaceuticals, West Haven, Conn.) yielding a final concentration of 30 µL and 250 KIU/ mL respectively. The tubes were immediately centrifuged, plasma collected for subsequent measurement of glucose and hormone levels and stored at −80° C. Plasma glucose, insulin and total GLP-1 levels were measured as described above.

Figure 19:
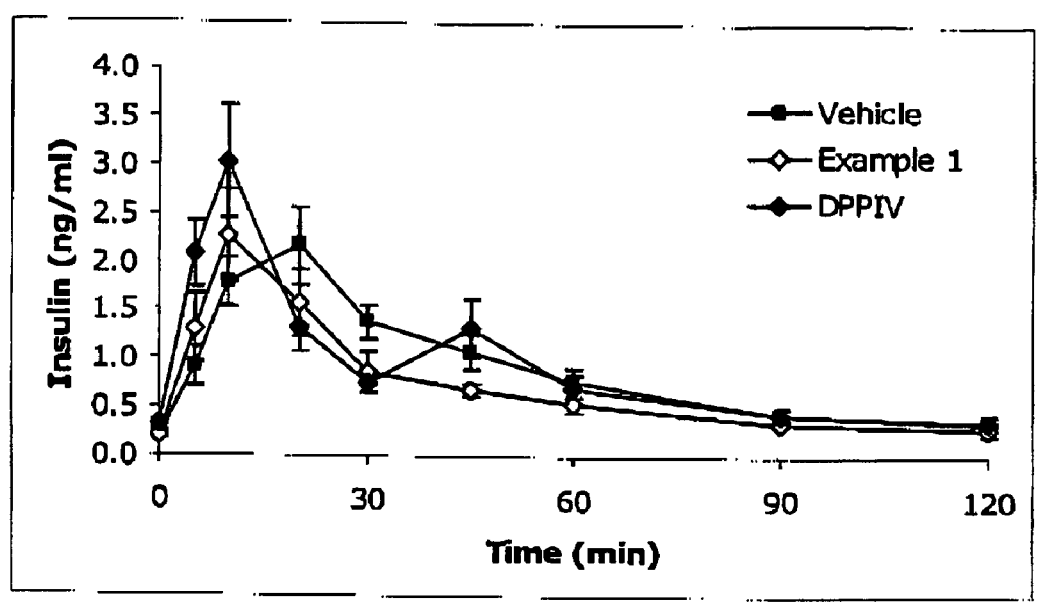
Figure 20:
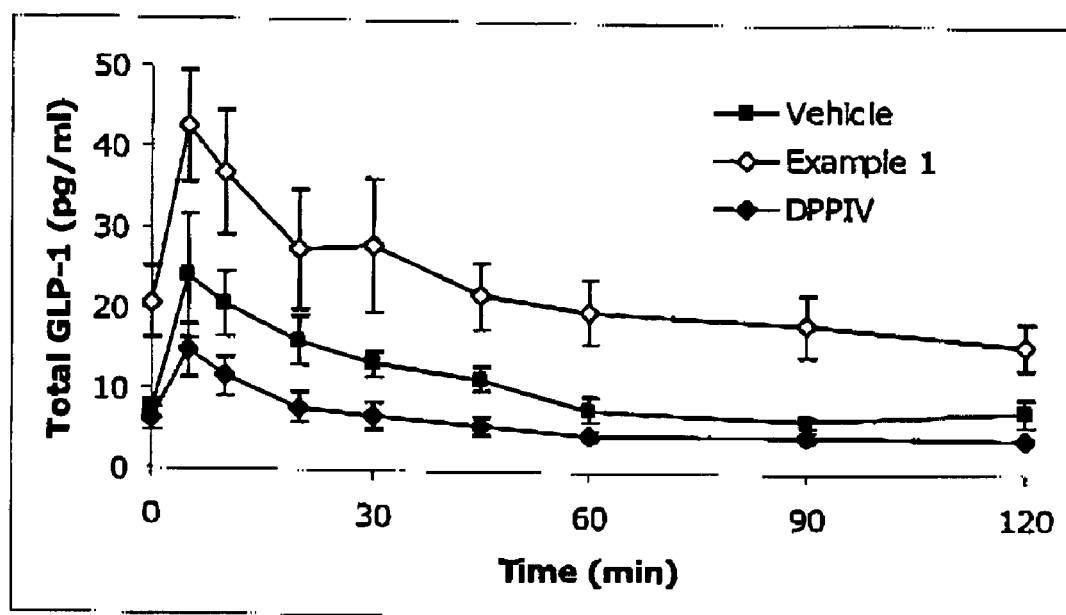

FIG. 18 shows the glucose concentration, FIG. 19 the insulin concentrations and FIG. 20 the total GLP-1 concentrations throughout the glucose tolerance test for the different treatment groups as indicated. The data is represents as mean values±SEM from all animals within each treatment group.

These results show that GPR119 agonists, as illustrated with Example 1, as well as the DPPIV inhibitor, significantly decreased the glucose excursion during the 120 minutes time course of the oral glucose tolerance test compared to vehicle. The total glucose area under the curve (AUC) was reduced by 38 and 24% respectively. Insulin AUC was not significantly different between the treatment groups. Both baseline total GLP-1 and the total GLP-1 AUC were significantly increased for the treatment group receiving the GPR119 agonist compared to vehicle and DPPIV treated animals.

These results illustrate that GPR119 agonists, as demonstrated with Example 1, improves glucose disposal during the course of an oral glucose tolerance test in rats. Furthermore, GPR119 agonists, here demonstrated with Example 1, increase the total GLP-1 levels independent of glucose prior to the oral glucose tolerance test, as well as augment the nutrient stimulated increase in total GLP-1 following the oral glucose load.

Insulin Sensitizing Effects of GPR119 Agonists
Whole Body Insulin Sensitivity Assessed by the Euglycemic Hyperinsulinemic Clamps In Vivo in Rats Male Sprague Dawley rats, weighing at 300-350 gram, had catheters surgically implanted into the jugular and femoral veins and allowed to recover for one week following the surgery. On the day before the experiment, food was removed in the afternoon to fast the animals overnight. The following morning animals were randomly assigned to two treatment groups, vehicle (n=7) and or 10 mg/kg of a GPR119 agonist (Example 1, n=9). Blood samples were collected from the jugular vein for baseline glucose measurements prior to oral administration of the respective treatment. The euglycemic hyperinsulinemic clamp was initiated approximately 90 minutes following oral administration of the respective treatments, by starting the constant insulin infusion at a rate of 1 mU/kg/min human insulin (Humulin, Eli Lilly and Company, Indianapolis, Id.) into the femoral vein of conscious animals. Whole blood glucose levels were measured every 10 minutes throughout the clamp. As the plasma glucose levels began to fall exogenous glucose infusion was started at a variable rate adjusted to achieve a stable plasma glucose level of 90-100 mg/dl. The glucose infusion rate required to maintain euglycemia was recorded throughout the experiment for each animal, and represents a measure of insulin sensitivity. Plasma glucose and human insulin levels were measured at the end of the clamp (at 180 min) as described above. At the end of the study the rats were sacrificed by an overdose of Nembutal.

Figure 21:
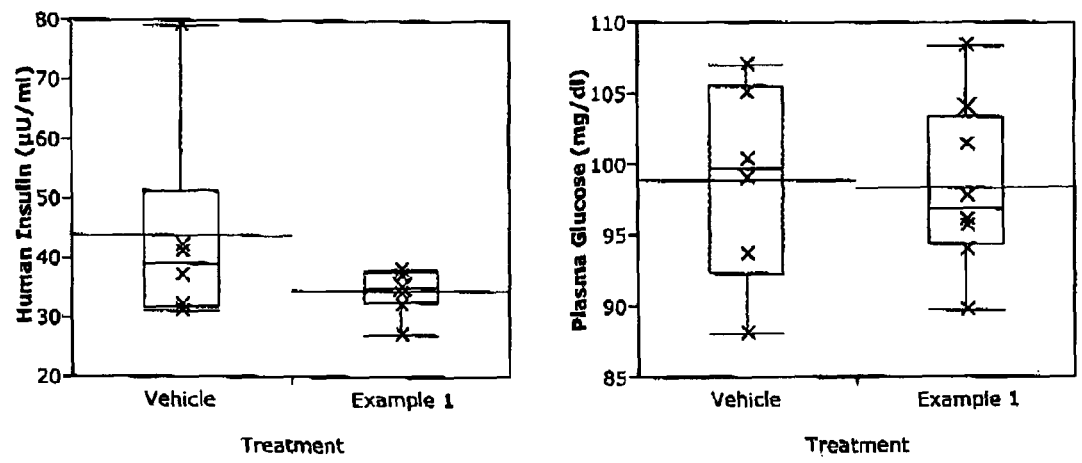
Figure 22:
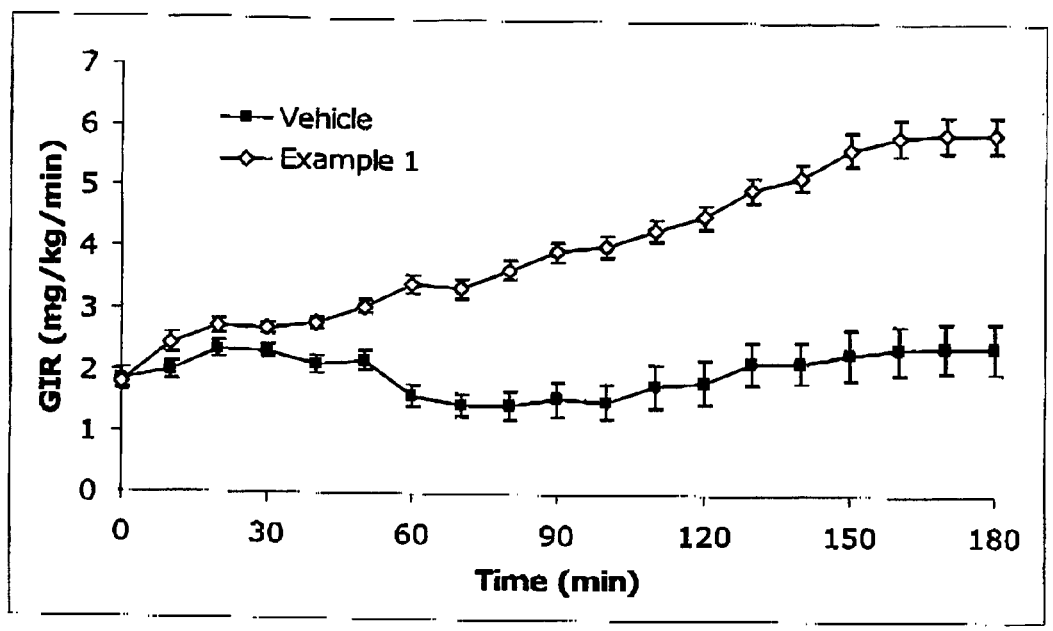

FIG. 21 shows the average human insulin levels and plasma glucose levels as measured at the end of the clamp for each treatment group. Data is represented as box plots summarizing the distribution of data for each treatment group, as described above. Horizontal lines represent the mean data. There was no significant difference in steady state insulin exposure or euglycemia between treatment groups. FIG. 22 shows the glucose infusion rates (GIR) required to maintain euglycemic in the two treatment groups throughout the clamp. The data is represented as mean GIR±SEM. At steady state, 180 minutes after starting the clamp, the glucose infusion rate required to maintain euglycemia in Example 1 treated animals were three times that of vehicle treated animals.

This data demonstrates that treatment with a GPR119 agonist, here illustrated with Example 1, enhances whole body insulin sensitivity in normal rats.

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A compound of Formula (I):

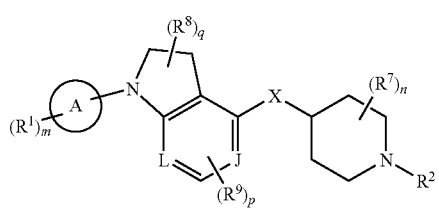

or a salt thereof, wherein
ring A is an aryl or heteroaryl;
m is 1, 2, or 3;
each $R^1$ independently is acyl; acylsulfonamide; acyloxy; $C_2$-$C_6$ alkenyl; $C_1$-$C_6$ alkoxy; $C_1$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio; $C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl; heteroaryl substituted with one or more $C_1$-$C_6$ alkyl, $C_1$-$C_6$ alkoxy, cyano, halogen, or $C_1$-$C_6$ haloalkyl; hydroxyl; nitro; sulfonamide; or thiol;
L and J each independently is CH or N;
n is 0, 1, 2, 3, or 4;
each $R^7$ independently is $C_1$-$C_6$ alkyl;
q is 0, 1, or 2;
each $R^8$ independently is $C_1$-$C_6$ alkyl, amino, $C_1$-$C_6$ alkylamino, $C_1$-$C_6$ dialkylamino, halogen, or $C_1$-$C_6$ haloalkyl;
p is 0, 1, or 2;
when p is 1 or 2, then $R^9$ is substituted from a carbon atom on the depicted ring;
each $R^9$ independently is $C_1$-$C_6$ alkyl, $C_1$-$C_6$ alkoxy, amino, $C_1$-$C_6$ alkylamino, $C_1$-$C_6$ dialkylamino, halogen, $C_1$-$C_6$ haloalkyl, or cyano;
X is —$NR^4$—, —O—, —S—, —S(O)—, or —S(O)$_2$—;
wherein $R^4$ is H or $C_1$-$C_6$ alkyl;
$R^2$ is —$Y_t$—$R^5$;
wherein Y is —C(O)—, —C(O)O—, —C(S)—, —C(S)S—, —C(S)O—, or —C(O)S—;
t is 0 or 1; and
$R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro.

2. The compound of claim 1 wherein when A is aryl then A is phenyl and when A is heteroaryl then A is pyrimidinyl or piperidinyl.

3. The compound of claim 1 wherein m is 1 or 2.

4. The compound of claim 1 wherein $R^1$ is $C_1$-$C_6$ alkylsulfonyl, cyano, halogen, or heteroaryl.

5. The compound of claim 1 wherein m is 1 and $R^1$ is $C_1$-$C_3$ alkylsulfonyl.

6. The compound of claim 1 wherein m is 2 and one $R^1$ is $C_1$-$C_3$ alkylsulfonyl and the other $R^1$ is halogen.

7. The compound of claim 6 wherein one $R^1$ is methylsulfonyl and one $R^1$ is fluorine.

8. The compound of claim 7 wherein the methylsulfonyl is located para to the depicted N atom and the fluorine is located ortho to the depicted N atom.

9. The compound of claim 1 wherein m is 2 and one $R^1$ is cyano and the other $R^1$ is halogen.

10. The compound of claim 1 wherein L and J are the same.

11. The compound of claim 1 wherein both L and J are N.

12. The compound of claim 1 wherein p is 0 or 1.

13. The compound of claim 1 wherein q is 0.

14. The compound of claim 1 wherein X is —O—.

15. The compound of claim 1 wherein t is 0.

16. The compound of claim 15 wherein $R^5$ is heteroaryl or heteroaryl substituted with one or more of $C_1$-$C_6$ alkyl, $C_1$-$C_6$ alkoxy, aryl, $C_1$-$C_6$ aralkyl, cyano, halogen, $C_1$-$C_6$ haloalkyl, heteroayrl, or heteroaralkyl.

17. The compound of claim 16 wherein the heteroaryl is pyrimidinyl or oxadiazolyl.

18. The compound of claim 1 wherein t is 1.

19. The compound of claim 18 wherein Y is —C(O)O—.

20. The compound of claim 19 wherein $R^5$ is $C_1$-$C_6$ alkyl; aryl; aryl substituted with one or more of $C_1$-$C_6$ alkyl, $C_1$-$C_6$ alkoxy, aryl, $C_1$-$C_6$ aralkyl, cyano, halogen, $C_1$-$C_6$ haloalkyl, heteroaryl, or heteroaralkyl; or $C_3$-$C_7$ cycloalkyl.

21. The compound of claim 20 wherein $R^5$ is $C_1$-$C_6$ alkyl.

22. A compound of Formula (II):

(II)

or a salt thereof, wherein
ring A is an aryl or heteroaryl;
m is 1, 2, or 3;
each $R^1$ independently is acyl; acylsulfonamide; acyloxy; $C_2$-$C_6$ alkenyl; $C_1$-$C_6$ alkoxy; $C_r$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio; $C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl substituted with one or more $C_1$-$C_6$ alkyl, $C_1$-$C_6$ alkoxy, cyano, halogen, or $C_1$-$C_6$ haloalkyl; hydroxyl; nitro; sulfonamide; or thiol;
n is 0, 1, 2, 3, or 4;
each $R^7$ independently is $C_1$-$C_6$ alkyl;
q is 0, 1, or 2;
each $R^8$ independently is $C_1$-$C_6$ alkyl, amino, $C_1$-$C_6$ alkylamino, $C_1$-$C_6$ dialkylamino, halogen, or $C_1$-$C_6$ haloalkyl;
p is 0, 1, or 2;
when p is 1 or 2, then $R^9$ is substituted from a carbon atom on the depicted ring;
each $R^9$ independently is $C_1$-$C_6$ alkyl, $C_1$-$C_6$ alkoxy, amino, $C_1$-$C_6$ alkylamino, $C_1$-$C_6$ dialkylamino, halogen, $C_1$-$C_6$ haloalkyl, or cyano;
X is —$NR^4$—, —O—, —S—, —S(O)—, or —$S(O)_2$—;
wherein $R^4$ is H or $C_1$-$C_6$ alkyl;
$R^2$ is —$Y_t$—$R^5$;
wherein Y is —C(O)—, —C(O)O—, —C(S)—, —C(S)S—, —C(S)O—, or —C(O)S—;
t is 0 or 1; and
$R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro.

23. A compound of Formula (III):

(III)

or a salt thereof, wherein
ring A is an aryl or heteroaryl;
m is 1, 2, or 3;
each $R^1$ independently is acyl; acylsulfonamide; acyloxy; $C_2$-$C_6$ alkenyl; $C_1$-$C_6$ alkoxy; $C_1$-$C_6$ alkoxycarbonyl; $C_1$-$C_6$ alkyl; $C_1$-$C_6$ alkylamino; $C_1$-$C_6$ alkylcarboxamide; $C_1$-$C_6$ alkylthiocarboxamide; $C_2$-$C_6$ alkynyl; $C_1$-$C_6$ alkyloxyphosphoryl; $C_1$-$C_6$ alkylsulfonamide; $C_1$-$C_6$ alkylsulfinyl; $C_1$-$C_6$ alkylsulfonyl; $C_1$-$C_6$ alkylthio;

$C_1$-$C_6$ alkylthioureyl; $C_1$-$C_6$ alkylureyl; amino; aryl; aryl substituted with one or more $C_1$-$C_6$ alkyl, $C_1$-$C_6$ alkoxy, cyano, halogen, or $C_1$-$C_6$ haloalkyl; carbamimidoyl; carboxamide; carboxy; cyano; $C_3$-$C_7$ cycloalkyl; $C_3$-$C_7$ cycloalkyl substituted with one or more $C_1$-$C_6$ alkyl, $C_1$-$C_6$ alkoxy, cyano, halogen, or $C_1$-$C_6$ haloalkyl; $C_1$-$C_6$ dialkylamino; $C_1$-$C_6$ dialkylcarboxamide; $C_1$-$C_6$ dialkyloxyphosphoryl; $C_1$-$C_6$ dialkylsulfonamide; $C_1$-$C_6$ dialkylthiocarboxamide; $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more $C_1$-$C_6$ alkyl, $C_1$-$C_6$ alkoxy, cyano, halogen, or $C_1$-$C_6$ haloalkyl; heteroaryl; heteroaryl substituted with one or more $C_1$-$C_6$ alkyl, $C_1$-$C_6$ alkoxy, cyano, halogen, or $C_1$-$C_6$ haloalkyl; hydroxyl; nitro; sulfonamide; or thiol;

X is —$NR^4$—, —O—, —S—, —S(O)—, or —$S(O)_2$—;

wherein $R^4$ is H or $C_1$-$C_6$ alkyl;

$R^2$ is —$Y_t$—$R^5$;

wherein Y is —C(O)—, —C(O)O—, —C(S)—, —C(S)S—, —C(S)O—, or —C(O)S—;

t is 0 or 1; and $R^5$ is hydrogen; acylalkylene; acylalkylene substituted with one or more $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_2$-$C_6$ alkenyl; $C_1$-$C_6$ alkoxyalkylene; $C_1$-$C_6$ alkyl; $C_1$-$C_6$ alkylamino; $C_2$-$C_6$ alkynyl; $C_1$-$C_6$ alkylcarboxamidealkylene; $C_1$-$C_6$ alkylsulfinyl; $C_1$-$C_6$ alkylsulfonyl; $C_1$-$C_6$ alkylsulfonamide; $C_1$-$C_6$ alkylsulfoximine; $C_1$-$C_6$ alkylthio; amino; aryl; aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkyl; aralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; aralkylcarboxamidealkylene; aralkylcarboxamidealkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; arylamino; arylamino substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; carbamimodoyl; cyano; $C_3$-$C_7$ cycloalkyl; $C_3$-$C_7$ cycloalkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ cycloalkylalkylene; $C_1$-$C_6$ cycloalkylalkylene substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; $C_1$-$C_6$ dialkylamino; diarylamino; $C_1$-$C_6$ dialkylcarboxamidealkylene; $C_1$-$C_6$ dialkylsulfonamide $C_1$-$C_6$ haloalkoxy; $C_1$-$C_6$ haloalkyl; $C_1$-$C_6$ haloalkylsulfinyl; $C_1$-$C_6$ haloalkylsulfonyl; $C_1$-$C_6$ haloalkylthio; halogen; heterocyclyl; heterocyclyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroaryl; heteroaryl substituted with one or more of $C_1$-$C_6$ alkyl, $C_1$-$C_6$ alkoxy, aryl, aryl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl, aralkyl, cyano, halogen, $C_1$-$C_6$ haloalkyl, heteroaryl, or heteroaralkyl; heteroaralkyl; heteroaralkyl substituted with one or more of $C_1$-$C_6$ alkyl, $C_1$-$C_6$ alkoxy, aryl, aralkyl, cyano, halogen, $C_1$-$C_6$ haloalkyl, heteroaryl, or heteroaralkyl; heteroarylamino; hydroxyl; or nitro.

24. A compound selected from:

1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

1,1-Dimethylethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

2,2-Dimethylpropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;

4-{[1-(5-Bromo-2-pyrimidinyl)-4-piperidinyl]oxy}-[2-fluoro-4-(methylsulfonyl)phenyl]-6,7-dihydro-5H-pyrrolo[2,3-d]pyrimidine;

7-[2-Fluoro-4-(methylsulfonyl)phenyl]-4-({1-[5-(2-methylpropyl)-2-pyrimidinyl]-4-piperidinyl}oxy)-6,7-dihydro-5H-pyrrolo[2,3-d]pyrimidine;

7-[2-Fluoro-4-(methylsulfonyl)phenyl]-4-{[1-(2-pyrimidinyl)-4-piperidinyl]oxy}-6,7-dihydro-5H-pyrrolo[2,3-d]pyrimidine;

4-{[1-(5-Ethyl-2-pyrimidinyl)-4-piperidinyl]oxy}-[2-fluoro-4-(methylsulfonyl)phenyl]-6,7-dihydro-5H-pyrrolo[2,3-d]pyrimidine;

7-[2-Fluoro-4-(methylsulfonyl)phenyl]-4-{[1-(5-fluoro-2-pyrimidinyl)-4-piperidinyl]oxy}-6,7-dihydro-5H-pyrrolo[2,3-d]pyrimidine;

1-Methylethyl 4-{[7-(4-cyano-2-fluorophenyl)-6,7-dihydro-5H-pyrrolo[2,3-d]pyrimidin-4-yl]oxy}-1-piperidinecarboxylate;

1-Methylethyl 4-({7-[2-fluoro-4-(1,3-thiazol-2-yl)phenyl]-6,7-dihydro-5H-pyrrolo[2,3-d]pyrimidin-4-yl}oxy)-1-piperidinecarboxylate;

1-Methylethyl 4-({7-[4-(methylsulfonyl)phenyl]-6,7-dihydro-5H-pyrrolo[2,3-d]pyrimidin-4-yl}thio)-1-piperidinecarboxylate;

1-Methylethyl 4-({7-[2-fluoro-4-(methylsulfonyl)phenyl]-6,7-dihydro-5H-pyrrolo[2,3-d]pyrimidin-4-yl}sulfonyl)-1-piperidinecarboxylate;

1,1-Dimethylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate;

1-Methylethyl 4-({7-[2-fluoro-4-(methylsulfonyl)phenyl]-2-methyl-6,7-dihydro-5H-pyrrolo[2,3-d]pyrimidin-4-yl}oxy)-1-piperidinecarboxylate;

7-[2-Fluoro-4-(methylsulfonyl)phenyl]-2-methyl-4-({1-[3-(1-methylethyl)-1,2,4-oxadiazol-5-yl]-4-piperidinyl}oxy)-6,7-dihydro-5H-pyrrolo[2,3-d]pyrimidine;

2,5-Difluoro-4-[4-({1-[3-(1-methylethyl)-1,2,4-oxadiazol-5-yl]-4-piperidinyl}oxy)-5,6-dihydro-7H-pyrrolo[2,3-d]pyrimidin-7-yl]benzonitrile;

7-[2-Fluoro-4-(methylsulfonyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

7-(4-Bromo-2,5-difluorophenyl)-4-({1-[3-(1-methylethyl)-1,2,4-oxadiazol-5-yl]-4-piperidinyl}oxy)-6,7-dihydro-5H-pyrrolo[2,3-d]pyrimidine;

1,1-Dimethylethyl 4-{[7-(4-bromo-2,5-difluorophenyl)-6,7-dihydro-5H-pyrrolo[2,3-d]pyrimidin-4-yl]oxy}-1-piperidinecarboxylate;

1,1-Dimethylethyl 4-({1-[4-(methylsulfonyl)phenyl]-2,3-dihydro-1H-indol-4-yl}oxy)-1-piperidinecarboxylate;

1-Methylethyl 4-({1-[4-(methylsulfonyl)phenyl]-2,3-dihydro-1H-indol-4-yl}oxy)-1-piperidinecarboxylate;

1-Methylethyl 4-{[1-(4-cyanophenyl)-2,3-dihydro-1H-indol-4-yl]oxy}-1-piperidinecarboxylate;

1-Methylethyl 4-({1-[4-(1,3-thiazol-2-yl)phenyl]-2,3-dihydro-1H-indol-4-yl}oxy)-1-piperidinecarboxylate;

1,1-Dimethylethyl 4-({1-[5-(methylsulfonyl)-2-pyrimidinyl]-2,3-dihydro-1H-indol-4-yl}oxy)-1-piperidinecarboxylate;
1-Methylethyl 4-({1-[5-(methylsulfonyl)-2-pyrimidinyl]-2,3-dihydro-1H-indol-4-yl}oxy)-1-piperidinecarboxylate;
1-Methylethyl 4-[(1-{4-[bis(butyloxy)phosphoryl]phenyl}-2,3-dihydro-1H-indol-4-yl)oxy]-1-piperidinecarboxylate;
4-Fluorophenyl 4-({1-[4-(methylsulfonyl)phenyl]-2,3-dihydro-1H-indol-4-yl}oxy)-1-piperidinecarboxylate;
1,1-Dimethylethyl 4-({1-[2-fluoro-4-(methylsulfonyl)phenyl]-2,3-dihydro-1H-indol-4-yl}oxy)-1-piperidinecarboxylate;
1-Methylethyl 4-({1-[2-fluoro-4-(methylsulfonyl)phenyl]-2,3-dihydro-1H-indol-4-yl}oxy)-1-piperidinecarboxylate;
(±)-1,1-Dimethylethyl 4-({1-[4-(methylsulfinyl)phenyl]-2,3-dihydro-1H-indol-4-yl}oxy)-1-piperidinecarboxylate;
(+)-1,1-Dimethylethyl 4-({1-[4-(methylsulfinyl)phenyl]-2,3-dihydro-1H-indol-4-yl}oxy)-1-piperidinecarboxylate;
(−)-1,1-Dimethylethyl 4-({1-[4-(methylsulfinyl)phenyl]-2,3-dihydro-1H-indol-4-yl}oxy)-1-piperidinecarboxylate;
1,1-Dimethylethyl 4-[(1-{4-[(ethyloxy)carbonyl]phenyl}-2,3-dihydro-1H-indol-4-yl)oxy]-1-piperidinecarboxylate;
4-{4-[(1-{[(1,1-Dimethylethyl)oxy]carbonyl}-4-piperidinyl)oxy]-2,3-dihydro-1H-indol-1-yl}benzoic acid;
1,1-Dimethylethyl 4-({1-[4-({[2-(methyloxy)ethyl]amino}carbonyl)phenyl]-2,3-dihydro-1H-indol-4-yl}oxy)-1-piperidinecarboxylate;
1,1-Dimethylethyl 4-[(1-{4-[(methylamino)carbonyl]phenyl}-2,3-dihydro-1H-indol-4-yl)oxy]-1-piperidinecarboxylate;
1,1-Dimethylethyl 4-{[1-(4-{[(3-hydroxypropyl)amino]carbonyl}phenyl)-2,3-dihydro-1H-indol-4-yl]oxy}-1-piperidinecarboxylate;
1,1-Dimethylethyl 4-{[1-(4-cyanophenyl)-2,3-dihydro-1H-indol-4-yl]oxy}-1-piperidinecarboxylate;
1,1-Dimethylethyl 4-{[1-(4-formylphenyl)-2,3-dihydro-1H-indol-4-yl]oxy}-1-piperidinecarboxylate;
1-[2-Fluoro-4-(methylsulfonyl)phenyl]-4-{[1-(2-pyrimidinyl)-4-piperidinyl]oxy}-2,3-dihydro-1H-indole;
4-{[1-(5-Fluoro-2-pyrimidinyl)-4-piperidinyl]oxy}-1-[4-(methylsulfonyl)phenyl]-2,3-dihydro-1H-indole;
1-[4-(Methylsulfonyl)phenyl]-4-{[1-(5-propyl-2-pyrimidinyl)-4-piperidinyl]oxy}-2,3-dihydro-1H-indole;
1-[4-(Methylsulfonyl)phenyl]-4-({1-[5-(phenylmethyl)-2-pyrimidinyl]-4-piperidinyl}oxy)-2,3-dihydro-1H-indole;
1-[4-(Methylsulfonyl)phenyl]-4-{[1-(5-phenyl-2-pyrimidinyl)-4-piperidinyl]oxy}-2,3-dihydro-1H-indole;
4-{[1-(5-Bromo-2-pyrimidinyl)-4-piperidinyl]oxy}-1-[4-(methylsulfonyl)phenyl]-2,3-dihydro-1H-indole;
2-[4-({1-[4-(Methylsulfonyl)phenyl]-2,3-dihydro-1H-indol-4-yl}oxy)-1-piperidinyl]-5-pyrimidinecarbonitrile;
4-{[1-(Cyclopentylacetyl)-4-piperidinyl]oxy}-1-[4-(methylsulfonyl)phenyl]-2,3-dihydro-1H-indole;
4-({1-[3-(1-Methylethyl)-1,2,4-oxadiazol-5-yl]-4-piperidinyl}oxy)-1-[4-(methylsulfonyl)phenyl]-2,3-dihydro-1H-indole;
1-Methylethyl 4-({1-[4-(3,5-dimethyl-4-isoxazolyl)phenyl]-2,3-dihydro-1H-indol-4-yl}oxy)-1-piperidinecarboxylate;
1-Methylethyl 4-({1-[4-(3-furanyl)phenyl]-2,3-dihydro-1H-indol-4-yl}oxy)-1-piperidinecarboxylate;
1-Methylethyl 4-({1-[4-(1-methyl-1H-pyrazol-4-yl)phenyl]-2,3-dihydro-1H-indol-4-yl}oxy)-1-piperidinecarboxylate;
(1R,2S,5R)-5-Methyl-2-(1-methylethyl)cyclohexyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
1-Methylethyl 4-({7-[4-(methylsulfonyl)phenyl]-6,7-dihydro-5H-pyrrolo[2,3-d]pyrimidin-4-yl}oxy)-1-piperidinecarboxylate;
1-Methylethyl 4-{[7-(4-cyanophenyl)-6,7-dihydro-5H-pyrrolo[2,3-d]pyrimidin-4-yl]oxy}-1-piperidinecarboxylate;
1-Methylethyl 4-({7-[2-fluoro-4-(1-methyl-1H-pyrrol-2-yl)phenyl]-6,7-dihydro-5H-pyrrolo[2,3-d]pyrimidin-4-yl}oxy)-1-piperidinecarboxylate;
(±)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;
(+)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;
(−)-1-Methylethyl 4-({7-[2-fluoro-4-(methylsulfonyl)phenyl]-6-methyl-6,7-dihydro-5H-pyrrolo[2,3-d]pyrimidin-4-yl}oxy)-1-piperidinecarboxylate;
Methyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
Ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
Propyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
n-Butyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
2-Fluoroethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
3-Chloropropyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
2-(Methyloxy)ethyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
2-Propen-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;
3-Buten-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;
2-Butyn-1-yl 4-({7-[2-fluoro-4-(methylsulfonyl)phenyl]-6,7-dihydro-5H-pyrrolo[2,3-d]pyrimidin-4-yl}oxy)-1-piperidinecarboxylate;
Pentyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
Hexyl 4-({7-[2-fluoro-4-(methylsulfonyl)phenyl]-6,7-dihydro-5H-pyrrolo[2,3-d]pyrimidin-4-yl}oxy)-1-piperidinecarboxylate;
1-Methylethyl 4-{[7-(2-methyl-3-pyridinyl)-6,7-dihydro-5H-pyrrolo[2,3-d]pyrimidin-4-yl]oxy}-1-piperidinecarboxylate;

1-Methylethyl 4-{[7-(4-cyano-3-fluorophenyl)-6,7-dihydro-5H-pyrrolo[2,3-d]pyrimidin-4-yl]oxy}-1-piperidinecarboxylate;
S-Ethyl 4-({7-[2-fluoro-4-(methylsulfonyl)phenyl]-6,7-dihydro-5H-pyrrolo[2,3-d]pyrimidin-4-yl}oxy)-1-piperidinecarbothioate;
S-Methyl 4-({7-[2-fluoro-4-(methylsulfonyl)phenyl]-6,7-dihydro-5H-pyrrolo[2,3-d]pyrimidin-4-yl}oxy)-1-piperidinecarbothioate;
S-(1-Methylethyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
S-(2-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
(±)-S-(1,2-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
(±)-S-(1-Methylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
S-(1,1-Dimethylpropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
(±)-S-(2-Methylbutyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
S-2-Propen-1-yl 4-({7-[2-fluoro-4-(methylsulfonyl)phenyl]-6,7-dihydro-5H-pyrrolo[2,3-d]pyrimidin-4-yl}oxy)-1-piperidinecarbothioate;
S-(3-Chloropropyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
S-Cyclopentyl 4-({7-[2-fluoro-4-(methylsulfonyl)phenyl]-6,7-dihydro-5H-pyrrolo[2,3-d]pyrimidin-4-yl}oxy)-1-piperidinecarbothioate;
S-Cyclohexyl 4-({7-[2-fluoro-4-(methylsulfonyl)phenyl]-6,7-dihydro-5H-pyrrolo[2,3-d]pyrimidin-4-yl}oxy)-1-piperidinecarbothioate;
S-(2,4-Difluorophenyl)4-({7-[2-fluoro-4-(methylsulfonyl)phenyl]-6,7-dihydro-5H-pyrrolo[2,3-d]pyrimidin-4-yl}oxy)-1-piperidinecarbothioate;
1-Methylethyl 4-({7-[2-fluoro-4-(methylsulfonyl)phenyl]-6,7-dihydro-5H-pyrrolo[2,3-d]pyrimidin-4-yl}oxy)-1-piperidinecarbodithioate;
2-Methylpropyl 4-({7-[2-fluoro-4-(methylsulfonyl)phenyl]-6,7-dihydro-5H-pyrrolo[2,3-d]pyrimidin-4-yl}oxy)-1-piperidinecarbodithioate;
Phenyl 4-({7-[2-fluoro-4-(methylsulfonyl)phenyl]-6,7-dihydro-5H-pyrrolo[2,3-d]pyrimidin-4-yl}oxy)-1-piperidinecarbodithioate;
7-[2-Fluoro-4-(methylsulfonyl)phenyl]-4-{[1-(2-pyridinylmethyl)-4-piperidinyl]oxy}-6,7-dihydro-5H-pyrrolo[2,3-d]pyrimidine trifluoroacetate;
N-(1,1-Dimethylethyl)-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate;
2-[4-({7-[2-Fluoro-4-(methylsulfonyl)phenyl]-6,7-dihydro-5H-pyrrolo[2,3-d]pyrimidin-4-yl}oxy)-1-piperidinyl]-1-[5-(2-pyridinyl)-2-thienyl]ethanone trifluoroacetate;
4-{[1-(Ethylsulfonyl)-4-piperidinyl]oxy}-7-[2-fluoro-4-(methylsulfonyl)phenyl]-6,7-dihydro-5H-pyrrolo[2,3-d]pyrimidine;
7-[2-Fluoro-4-(methylsulfonyl)phenyl]-4-({1-[(1-methylethyl)sulfonyl]-4-piperidinyl}oxy)-6,7-dihydro-5H-pyrrolo[2,3-d]pyrimidine;
4-({7-[2-Fluoro-4-(methylsulfonyl)phenyl]-6,7-dihydro-5H-pyrrolo[2,3-d]pyrimidin-4-yl}oxy)-N,N-dimethyl-1-piperidinesulfonamide;
N,N-Diethyl-2-[4-({7-[2-fluoro-4-(methylsulfonyl)phenyl]-6,7-dihydro-5H-pyrrolo[2,3-d]pyrimidin-4-yl}oxy)-1-piperidinyl]acetamide trifluoroacetate;
2-[4-({7-[2-Fluoro-4-(methylsulfonyl)phenyl]-6,7-dihydro-5H-pyrrolo[2,3-d]pyrimidin-4-yl}oxy)-1-piperidinyl]-N-(phenylmethyl)acetamide;
2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-methyl-2-thienyl)ethanone;
1-(5-Ethyl-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate;
1-(5-Chloro-2-thienyl)-2-[4-({7-[2-fluoro-4-(methylsulfonyl)phenyl]-6,7-dihydro-5H-pyrrolo[2,3-d]pyrimidin-4-yl}oxy)-1-piperidinyl]ethanone trifluoroacetate;
7-[2-Fluoro-4-(methylsulfonyl)phenyl]-4-{[1-({5-[4-(methyloxy)phenyl]-1,2,4-oxadiazol-3-yl}methyl)-4-piperidinyl]oxy}-6,7-dihydro-5H-pyrrolo[2,3-d]pyrimidine;
2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(1-methyl-1H-pyrrol-2-yl)ethanone;
2-[4-({7-[2-Fluoro-4-(methylsulfonyl)phenyl]-6,7-dihydro-5H-pyrrolo[2,3-d]pyrimidin-4-yl}oxy)-1-piperidinyl]-1-(5-phenyl-2-thienyl)ethanone;
7-[2-Fluoro-4-(methylsulfonyl)phenyl]-4-({1-[5-(1-methylethyl)-1,2,4-oxadiazol-3-yl]-4-piperidinyl}oxy)-6,7-dihydro-5H-pyrrolo[2,3-d]pyrimidine;
7-[2-Fluoro-4-(methylsulfonyl)phenyl]-4-{[1-(1,4,5,6-tetrahydro-2-pyrimidinyl)-4-piperidinyl]oxy}-6,7-dihydro-5H-pyrrolo[2,3-d]pyrimidine;
1-Methylethyl 4-[(7-{4-[(dimethylamino)sulfonyl]phenyl}-6,7-dihydro-5H-pyrrolo[2,3-d]pyrimidin-4-yl)oxy]-1-piperidinecarboxylate;
1-Methylethyl 4-{[7-(5-cyano-2-pyridinyl)-6,7-dihydro-5H-pyrrolo[2,3-d]pyrimidin-4-yl]oxy}-1-piperidinecarboxylate;
1-Methylethyl 4-{[7-(5-fluoro-2-pyridinyl)-6,7-dihydro-5H-pyrrolo[2,3-d]pyrimidin-4-yl]oxy}-1-piperidinecarboxylate;
1,1-Dimethylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate;
1-Methylethyl 4-({7-[2-fluoro-4-(methylsulfonyl)phenyl]-6,7-dihydro-5H-pyrrolo[2,3-d]pyrimidin-4-yl}amino)-1-piperidinecarboxylate trifluoroacetate;
1-Methylethyl 4-[{7-[2-fluoro-4-(methylsulfonyl)phenyl]-6,7-dihydro-5H-pyrrolo[2,3-d]pyrimidin-4-yl}(methyl)amino]-1-piperidinecarboxylate trifluoroacetate;
7-[2-Fluoro-4-(methylsulfonyl)phenyl]-N-[1-(2-fluoro-5-pyrimidinyl)-4-piperidinyl]-6,7-dihydro-5H-pyrrolo[2,3-d]pyrimidin-4-amine trifluoroacetate;
7-[2-Fluoro-4-(methylsulfonyl)phenyl]-4-{[1-(methylsulfonyl)-4-piperidinyl]oxy}-6,7-dihydro-5H-pyrrolo[2,3-d]pyrimidine trifluoroacetate;
(±)-1-Methylethyl 4-({7-[5-(methylsulfinyl)-2-pyridinyl]-6,7-dihydro-5H-pyrrolo[2,3-d]pyrimidin-4-yl}oxy)-1-piperidinecarboxylate hydrochloride;
1-Methylethyl 4-({7-[5-(methylsulfonyl)-2-pyridinyl]-6,7-dihydro-5H-pyrrolo[2,3-d]pyrimidin-4-yl}oxy)-1-piperidinecarboxylate hydrochloride;

1-Methylethyl 4-({7-[6-(methylthio)-3-pyridinyl]-6,7-dihydro-5H-pyrrolo[2,3-d]pyrimidin-4-yl}oxy)-1-piperidinecarboxylate;

(±)-1-Methylethyl 4-({7-[6-(methylsulfinyl)-3-pyridinyl]-6,7-dihydro-5H-pyrrolo[2,3-d]pyrimidin-4-yl}oxy)-1-piperidinecarboxylate hydrochloride;

1-Methylethyl 4-({7-[6-(methylsulfonyl)-3-pyridinyl]-6,7-dihydro-5H-pyrrolo[2,3-d]pyrimidin-4-yl}oxy)-1-piperidinecarboxylate hydrochloride;

1-Methylethyl 4-({7-[2-fluoro-4-(methylthio)phenyl]-6,7-dihydro-5H-pyrrolo[2,3-d]pyrimidin-4-yl}oxy)-1-piperidinecarboxylate;

(±)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

(R)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

(S)-1-Methylethyl 4-({7-[2-fluoro-4-(methylsulfinyl)phenyl]-6,7-dihydro-5H-pyrrolo[2,3-d]pyrimidin-4-yl}oxy)-1-piperidinecarboxylate;

7-[2-Fluoro-4-(methylthio)phenyl]-4-{[1-(5-fluoro-2-pyrimidinyl)-4-piperidinyl]oxy}-6,7-dihydro-5H-pyrrolo[2,3-d]pyrimidine;

(±)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

(R)-7-[2-fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

(S)-7-[2-Fluoro-4-(methylsulfinyl)phenyl]-4-{[1-(5-fluoro-2-pyrimidinyl)-4-piperidinyl]oxy}-6,7-dihydro-5H-pyrrolo[2,3-d]pyrimidine;

7-[2-Fluoro-4-(methylthio)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(±)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(R)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

(S)-7-[2-Fluoro-4-(methylsulfinyl)phenyl]-4-({1-[3-(1-methylethyl)-1,2,4-oxadiazol-5-yl]-4-piperidinyl}oxy)-6,7-dihydro-5H-pyrrolo[2,3-d]pyrimidine;

1-Methylethyl 4-({7-[4-(methylthio)phenyl]-6,7-dihydro-5H-pyrrolo[2,3-d]pyrimidin-4-yl}oxy)-1-piperidinecarboxylate;

(±)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

(+)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

(−)-1-Methylethyl 4-({7-[4-(methylsulfinyl)phenyl]-6,7-dihydro-5H-pyrrolo[2,3-d]pyrimidin-4-yl}oxy)-1-piperidinecarboxylate;

1-Methylethyl 4-({2-amino-7-[2-fluoro-4-(methylsulfonyl)phenyl]-6,7-dihydro-5H-pyrrolo[2,3-d]pyrimidin-4-yl}oxy)-1-piperidinecarboxylate;

1-Methylethyl 4-{[7-[2-fluoro-4-(methylsulfonyl)phenyl]-2-(methylamino)-6,7-dihydro-5H-pyrrolo[2,3-d]pyrimidin-4-yl]oxy}-1-piperidinecarboxylate;

7-(4-Bromo-2-fluorophenyl)-4-{[1-(5-fluoro-2-pyrimidinyl)-4-piperidinyl]oxy}-6,7-dihydro-5H-pyrrolo[2,3-d]pyrimidine;

3-Fluoro-4-(4-{[1-(5-fluoro-2-pyrimidinyl)-4-piperidinyl]oxy}-5,6-dihydro-7H-pyrrolo[2,3-d]pyrimidin-7-yl)benzonitrile;

3-Fluoro-4-[4-({1-[3-(1-methylethyl)-1,2,4-oxadiazol-5-yl]-4-piperidinyl}oxy)-5,6-dihydro-7H-pyrrolo[2,3-d]pyrimidin-7-yl]benzonitrile;

4-[4-({1-[3-(1-Methylethyl)-1,2,4-oxadiazol-5-yl]-4-piperidinyl}oxy)-5,6-dihydro-7H-pyrrolo[2,3-d]pyrimidin-7-yl]benzonitrile;

4-(4-{[1-(5-Fluoro-2-pyrimidinyl)-4-piperidinyl]oxy}-5,6-dihydro-7H-pyrrolo[2,3-d]pyrimidin-7-yl)benzonitrile;

4-{[1-(5-Fluoro-2-pyrimidinyl)-4-piperidinyl]oxy}-7-[4-(methylsulfonyl)phenyl]-6,7-dihydro-5H-pyrrolo[2,3-d]pyrimidine;

4-({1-[3-(1-Methylethyl)-1,2,4-oxadiazol-5-yl]-4-piperidinyl}oxy)-7-[4-(methylsulfonyl)phenyl]-6,7-dihydro-5H-pyrrolo[2,3-d]pyrimidine;

4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine;

(R)-4-({1-[3-(1-methylethyl)-1,2,4-oxadiazol-5-yl]-4-pipendinyl}oxy)-7-[4-(methylsulfinyl)phenyl]-6,7-dihydro-5H-pyrrolo[2,3-d]pyrimidine;

(S)-4-({1-[3-(1-Methylethyl)-1,2,4-oxadiazol-5-yl]-4-piperidinyl}oxy)-7-[4-(methylsulfinyl)phenyl]-6,7-dihydro-5H-pyrrolo[2,3-d]pyrimidine;

4-{[1-(5-fluoro-2-pyrimidinyl)-4-piperidinyl]oxy}-7-[4-(methylsulfinyl)phenyl]-6,7-dihydro-5H-pyrrolo[2,3-d]pyrimidine;

(R)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine;

(S)-4-{[1-(5-Fluoro-2-pyrimidinyl)-4-piperidinyl]oxy}-7-[4-(methylsulfinyl)phenyl]-6,7-dihydro-5H-pyrrolo[2,3-d]pyrimidine;

S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

(R)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

(S)-S-Ethyl 4-({7-[2-fluoro-4-(methylsulfinyl)phenyl]-6,7-dihydro-5H-pyrrolo[2,3-d]pyrimidin-4-yl}oxy)-1-piperidinecarbothioate;

1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

(S)-1-Methylethyl 4-({7-[2-fluoro-4-(S-methylsulfonimidoyl)phenyl]-6,7-dihydro-5H-pyrrolo[2,3-d]pyrimidin-4-yl}oxy)-1-piperidinecarboxylate;

1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(S)-1-Methylethyl 4-({7-[4-(S-methylsulfonimidoyl)phenyl]-6,7-dihydro-5H-pyrrolo[2,3-d]pyrimidin-4-yl}oxy)-1-piperidinecarboxylate;

(R)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate;

(S)-1-Methylethyl 4-({7-[2,5-difluoro-4-(methylsulfinyl)phenyl]-6,7-dihydro-5H-pyrrolo[2,3-d]pyrimidin-4-yl}oxy)-1-piperidinecarboxylate;

or a salt thereof.

25. A pharmaceutical composition comprising a compound as claimed in claim 1.

26. A method for the treatment of metabolic disorders or conditions comprising the administration of a compound according to claim 1 wherein the condition or disorder is selected from the group consisting of diabetes and obesity.

27. A method for the treatment of metabolic disorders or conditions comprising the administration of a compound of claim 22, wherein the condition or disorder is selected from the group consisting of diabetes and obesity.

28. A method for the treatment of metabolic disorders or conditions comprising the administration of a compound of claim 23, wherein the condition or disorder is selected from the group consisting of diabetes and obesity.

29. A method for the treatment of metabolic disorders or conditions comprising the administration of a compound of claim 24, wherein the condition or disorder is selected from the group consisting of diabetes and obesity.

30. A pharmaceutical composition comprising a compound as claimed in claim 22.

31. A pharmaceutical composition comprising a compound as claimed in claim 23.

32. A pharmaceutical composition comprising a compound as claimed in claim 24.

* * * * *